United States Patent
Bruce et al.

(10) Patent No.: US 7,994,203 B2
(45) Date of Patent: Aug. 9, 2011

(54) ORGANIC COMPOUNDS

(75) Inventors: Ian Bruce, Horsham (GB); Andrew James Culshaw, Horsham (GB); Nicholas James Devereux, Horsham (GB); François Gessier, Altkirch (FR); Jeffrey McKenna, Horsham (GB); James Neef, Horsham (GB); Helen Elizabeth Oakman, Horsham (GB)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 12/462,417

(22) Filed: Aug. 3, 2009

(65) Prior Publication Data

US 2010/0035874 A1 Feb. 11, 2010

(30) Foreign Application Priority Data

Aug. 6, 2008 (EP) ..................................... 08161930
Jan. 14, 2009 (EP) ..................................... 09150553

(51) Int. Cl.
*A61K 31/4162* (2006.01)
*C07D 489/04* (2006.01)

(52) U.S. Cl. ........................................ 514/375; 548/218

(58) Field of Classification Search .................... 548/218
See application file for complete search history.

(56) References Cited

U.S. PATENT DOCUMENTS

2002/0183375 A1  12/2002 Dubowchik

FOREIGN PATENT DOCUMENTS

WO    WO9631517 A1 * 10/1996

OTHER PUBLICATIONS

Isomers [online], [retrieved on Mar. 11, 2007]. Retrieved from internet, URL; http://chemed.chem.purdue.edu/genchem/topicreview/bp/Iorganic/isomers.html>.*
Cecil Textbook of Medicine, 20th edition (1996), vol. 2, pp. 2050-2057.*
Cecil Textbook of Medicine, 20th edition i1996), vol. 2, pp. 1992-1996.*
FDA mulls drug to slow late-stage Alzheimer's [online], [retrieved on Sep. 23, 2003]. Retrieved from the internet, URL; http:www.cnn com120031HEALTHIconditionslO91241alzheimers.drug.aplindex.html>.*
Cognitive disorder [online], [retrieved on Sep. 1, 2006]. Retrieved from the Internet, URL; http://en.wikipedia.org/wiki/Category:Cognitive_disorders>.*
Dementia [online], [retrieved on May 24, 2007]. Retrieved from the Internet, URL; http:llen.wikipedia.orglwikilDementia>.*
John Tellew, "Small Molecule Antagonists of the Corticotropin Releasing Factor (CRF) . . . " Current Topics in Medicinal Chemistry 8:506-520, 2008.
Meena Patel, "Synthesis of 4,5-Diaryl-1 H-pyrazole-3-ol Derivatives as Potential COX-2 Inhibitors" J. Org. Chem. 69:7058-7065, 2004.

* cited by examiner

*Primary Examiner* — Shawquia Young
(74) *Attorney, Agent, or Firm* — Michael G. Smith; Philippe Mueller

(57) ABSTRACT

There are described pyrazolo[5.1-b]oxazole derivatives useful as corticotropin releasing factor ($CRF_1$) receptor antagonists.

10 Claims, No Drawings

ORGANIC COMPOUNDS

FIELD OF THE INVENTION

The present invention relates to pyrazolo[5.1-b]oxazole derivatives their preparation, their use as pharmaceuticals and pharmaceutical compositions containing them. More particularly the present invention relates to their use as corticotropin releasing factor ($CRF_1$) receptor antagonists.

SUMMARY OF THE INVENTION

In a first aspect of the invention we provide a compound of formula I;

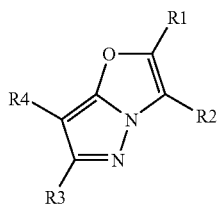

I in which $R^1$ and $R^3$, which may be the same or different, are each hydrogen, alkyl C1 to 6 or halo alkyl C1 to 6;

$R^2$ is phenyl, a 5- or 6-membered heteroaryl or a bicyclic heteroaryl system, each of which may optionally be substituted by one or more of alkyl C1 to 6, alkoxy C1 to 6, halo, haloalkyl C1 to 6, thioalkyl C1 to 6, —$NR^5R^6$, —CN, haloalkoxy C1 to 6, —$O(CH_2)_xO(CH_2)_y$—, aryl or -Het;

Het is a 5- or 6-membered heteroaryl or a 4, 5- or 6-membered heterocycle;

$R^4$ is alkylene C2 to 10, hydroxy alkyl C1 to 10, each of which may optionally be substituted by aryl, or is —$OR^7$, —$(CH_2)_mNR^8R^9$, —$COR^{10}$, a 5- or 6-membered heteroaryl or a 5- or 6-membered heterocycle, the 5- or 6-membered heteroaryl or 5- or 6-membered heterocycle being optionally substituted by one or more substituents selected from the group alkyl C1 to 10, haloalkyl C1 to 10, hydroxyalkyl C1 to 10, alkoxy(C1 to 3)alkyl(C1 to 3), halo, —$CO_2R^{19}$, —$CONR^{20}R^{21}$, aryl or a 5- or 6-membered heterocycle or heteroaryl;

$R^5$ and $R^6$, which may be the same or different, are each hydrogen or alkyl C1 to 6 or $R^5$ and $R^6$, together with the nitrogen to which they are attached, form an optionally substituted saturated or unsaturated cyclic group;

$R^7$ is alkyl C1 to 10, cycloalkyl C3 to 10, optionally fused to an aryl, alkyl(C1 to 6)-cycloalkyl(C3 to 6)-, hydroxy alkyl C1 to 10, hydroxyalkyl(C1 to 6)-(haloalkyl C1 to 6), alkyl (C1 to 6)-oxy-alkyl(C1 to 6), —$(CH_2)_qCOOR^{22}$ or a 5- or 6-membered heterocycle; each of which is optionally substituted by one or more of alkyl C1 to 10, alkoxy C1 to 10, hydroxyalkyl C1 to 10, aryl or a 5- or 6-membered heteroaryl, the aryl or a 5- or 6-membered heteroaryl being optionally substituted by alkyl C1 to 10;

$R^8$ and $R^9$, which may be the same or different, are each hydrogen, alkyl C1 to 10, halo alkyl C1 to 10, alkyl(C1 to 6)-oxy-alkyl(C1 to 6), —$COOR^{11}$, —$COR^{12}$ or arylalkyl C1 to 6 or together with the nitrogen to which they are attached $R^8$ and $R^9$ form a 5- or 6-membered heterocycle, optionally substituted by one or more of alkyl C1 to 6;

m is an integer 0 or 1;
q is an integer from 1 to 6;

x and y, which may be the same or different, are each an integer from 1 to 6;

$R^{10}$ is hydrogen, alkyl C1 to 6, —$NR^{13}R^{14}$, hydroxy or alkoxy C1 to 6;

$R^{12}$ is alkyl C1 to 10, aryl or is a 5 - or 6-membered unsaturated heterocyclic ring;

$R^{13}$ and $R^{14}$, which may be the same or different, are each alkyl C1 to 10, cycloalkyl C3 to 10, cycloalkyl(C3 to 6)alkyl(C1 to 6)-, alkoxy C1 to 10, haloalkyl C1 to 10, aryl, a 5- or 6-membered heterocycle or heteroaryl comprising 1, 2 or 3 heteroatoms; each of which may be optionally substituted by aryl or heteroaryl, or $R^{13}$ and $R^{14}$ together with the nitrogen to which they are attached form a 5- or 6-membered heterocycle comprising 1, 2 or 3 heteroatoms, which may optionally be fused to a phenyl group, said heterocycle and optionally fused phenyl group being optionally substituted by one or more of alkoxy C1 to 10;

$R^{22}$ is hydrogen or alkyl C1 to 6;

$R^{11}$ is alkyl C1 to 6 or aryl;

$R^{19}$ is hydrogen or alkyl C1 to 10;

$R^{20}$ and $R^{21}$, which may be the same or different, are each alkyl C1 to 10;

and isomers thereof, in free form or as a pharmaceutically acceptable salt.

For purposes of interpreting this specification, the following definitions will apply and whenever appropriate, terms used in the singular will also include the plural and vice versa.

As used herein, the term "alkyl" refers to a fully saturated, branched or unbranched hydrocarbon moiety, i.e. primary, secondary or tertiary alkyl or, where appropriate, cycloalkyl or alkyl substituted by cycloalkyl, they may also be saturated or unsaturated alkyl groups. Where not otherwise identified, preferably the alkyl comprises 1 to 20 carbon atoms, more preferably 1 to 16 carbon atoms, 1 to 10 carbon atoms, 1 to 7 carbon atoms, or 1 to 4 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, n-decyl and the like.

As used herein, the term "haloalkyl" refers to an alkyl as defined herein, that is substituted by one or more halo groups as defined herein. Preferably the haloalkyl can be monohaloalkyl, dihaloalkyl or polyhaloalkyl including perhaloalkyl. A monohaloalkyl can have one iodo, bromo, chloro or fluoro within the alkyl group. Dihaloalkyl and polyhaloalkyl groups can have two or more of the same halo atoms or a combination of different halo groups within the alkyl. Preferably, the polyhaloalkyl contains up to 12, or 10, or 8, or 6, or 4, or 3, or 2 halo groups. Non-limiting examples of haloalkyl include fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichloropropyl. A perhaloalkyl refers to an alkyl having all hydrogen atoms replaced with halo atoms.

As used herein, the term "alkoxy" refers to alkyl-O—, wherein alkyl is defined herein above. Representative examples of alkoxy include, but are not limited to, methoxy, ethoxy, propoxy, 2-propoxy, butoxy, tert-butoxy, pentyloxy, hexyloxy, cyclopropyloxy-, cyclohexyloxy- and the like. Preferably, alkoxy groups have about 1-7, more preferably about 1-4 carbons.

As used herein, the term "heterocyclic" or "heterocyclo" refers to an optionally substituted, saturated or unsaturated non-aromatic ring or ring system, e.g., which is a 4-, 5-, 6-, or 7-membered monocyclic, 7-, 8-, 9-, 10-, 11-, or 12-membered bicyclic or 10-, 11-, 12-, 13-, 14- or 15-membered tricyclic ring system and contains at least one heteroatom selected from O, S and N, where the N and S can also optionally be oxidized to various oxidation states. The heterocyclic group can be attached at a heteroatom or a carbon atom. The heterocyclyl can include fused or bridged rings as well as spirocyclic rings. Examples of heterocycles include tetrahydrofuran (THF), dihydrofuran, 1,4-dioxane, morpholine, 1,4-dithiane, piperazine, piperidine, 1,3-dioxolane, imidazolidine, imidazoline, pyrroline, pyrrolidine, tetrahydropyran, dihydropyran, oxathiolane, dithiolane, 1,3-dioxane, 1,3-dithiane, oxathiane, thiomorpholine, and the like.

The term substituted heterocycle further refers to heterocyclic groups as defined herein substituted with 1, 2 or 3 substituents selected from the groups consisting of the following:
(a) alkyl;
(b) hydroxy (or protected hydroxy);
(c) halo;
(d) haloalkyl;
(e) oxo, i.e., =O;
(f) amino, alkylamino or dialkylamino;
(g) alkoxy;
(h) cycloalkyl;
(i) carboxyl;
(j) heterocyclooxy, wherein heterocyclooxy denotes a heterocyclic group bonded through an oxygen bridge;
(k) alkyl-O—C(O)—;
(l) mercapto;
(m) nitro;
(n) cyano;
(o) sulfamoyl or sulfonamido;
(p) aryl;
(q) alkyl-C(O)—O—;
(r) aryl-C(O)—O—;
(s) aryl-S—;
(t) aryloxy;
(u) alkyl-S—;
(v) formyl, i.e., HC(O)—;
(w) carbamoyl;
(y) aryl-alkyl-; and
(z) aryl substituted with alkyl, cycloalkyl, alkoxy, hydroxy, amino, alkyl-C(O)—NH—, alkylamino, dialkylamino or halogen.

As used herein, the term "aryl" refers to an aromatic carbocyclic ring system containing 6 to 14 ring carbon atoms, which may be unsubstituted or substituted as defined.

As used herein, the term "aryloxy" refers to both an —O-aryl and an —O-heteroaryl group, wherein aryl and heteroaryl are defined herein.

As used herein, the term "heteroaryl" refers to a 5-14 membered monocyclic- or bicyclic- or polycyclic-aromatic ring system, having 1 to 8 heteroatoms selected from N, O or S. Preferably, the heteroaryl is a 5-10 or 5-7 membered ring system. Typical heteroaryl groups include 2- or 3-thienyl, 2- or 3-furyl, 2- or 3-pyrrolyl, 2-, 4-, or 5-imidazolyl, 3-, 4-, or 5-pyrazolyl, 2-, 4-, or 5-thiazolyl, 3-, 4-, or 5-isothiazolyl, 2-, 4-, or 5-oxazolyl, 3-, 4-, or 5-isoxazolyl, 3- or 5-1,2,4-triazolyl, 4- or 5-1,2,3-triazolyl, tetrazolyl, 2-, 3-, or 4-pyridyl, 3- or 4-pyridazinyl, 3-, 4-, or 5-pyrazinyl, 2-pyrazinyl, 2-, 4-, or 5-pyrimidinyl.

The term "heteroaryl" also refers to a group in which a heteroaromatic ring is fused to one or more aryl, cycloaliphatic, or heterocyclyl rings, where the radical or point of attachment is on the heteroaromatic ring. Nonlimiting examples include but are not limited to 1-, 2-, 3-, 5-, 6-, 7-, or 8-indolizinyl, 1-, 3-, 4-, 5-, 6-, or 7-isoindolyl, 2-, 3-, 4-, 5-, 6-, or 7-indolyl, 2-, 3-, 4-, 5-, 6-, or 7-indazolyl, 2-, 4-, 5-, 6-, 7-, or 8-purinyl, 1-, 2-, 3-, 4-, 6-, 7-, 8-, or 9-quinolizinyl, 2-, 3-, 4-, 5-, 6-, 7-, or 8-quinoliyl, 1-, 3-, 4-, 5-, 6-, 7-, or 8-isoquinolinyl, 1-, 4-, 5-, 6-, 7-, or 8-phthalazinyl, 2-, 3-, 4-, 5-, or 6-naphthyridinyl, 2-, 3-, 5-, 6-, 7-, or 8-quinazolinyl, 3-, 4-, 5-, 6-, 7-, or 8-cinnolinyl, 2-, 4-, 6-, or 7-pteridinyl, 1-, 2-, 3-, 4-, 5-, 6-, 7-, or 8-4aH carbazolyl, 1-, 2-, 3-, 4-, 5-, 6-, 7-, or 8-carbzaolyl, 1-, 3-, 4-, 5-, 6-, 7-, 8-, or 9-carbolinyl, 1-, 2-, 3-, 4-, 6-, 7-, 8-, 9-, or 10-phenanthridinyl, 1-, 2-, 3-, 4-, 5-, 6-, 7-, 8-, or 9-acridinyl, 1-, 2-, 4-, 5-, 6-, 7-, 8-, or 9-perimidinyl, 2-, 3-, 4-, 5-, 6-, 8-, 9-, or 10-phenathrolinyl, 1-, 2-, 3-, 4-, 6-, 7-, 8-, or 9-phenazinyl, 1-, 2-, 3-, 4-, 6-, 7-, 8-, 9-, or 10-phenothiazinyl, 1-, 2-, 3-, 4-, 6-, 7-, 8-, 9-, or 10-phenoxazinyl, 2-, 3-, 4-, 5-, 6-, or 1-, 3-, 4-, 5-, 6-, 7-, 8-, 9-, or 10-benzisoqinolinyl, 2-, 3-, 4, or thieno[2,3-b]furanyl, 2-, 3-, 5-, 6-, 7-, 8-, 9-, 10-, or 11-7H-pyrazino[2,3-c]carbazolyl,2-, 3-, 5-, 6-, or 7-2H-furo[3,2-b]-pyranyl, 2-, 3-, 4, 5-, 7-, or 8-5H-pyrido[2,3-d]-o-oxazinyl, 1-, 3-, or 5-1H-pyrazolo[4,3-d]-oxazolyl, 2-, 4-, or 54H-imidazo[4,5-d]thiazolyl, 3-, 5-, or 8-pyrazino[2,3-d]pyridazinyl, 2-, 3-, 5-, or 6-imidazo[2,1-b]thiazolyl, 1-, 3-, 6-, 7-, 8-, or 9-furo[3,4-c]cinnolinyl, 1-, 2-, 3-, 4-, 5-6-, 8-, 9-, 10, or 11-4H-pyrido[2,3-c]carbazolyl, 2-, 3-, 6-, or 7-imidazo[1,2-b][1,2,4]triazinyl, 7-benzo[b]thienyl, 2-, 4-, 5-, 6-, or 7-benzoxazolyl, 2-, 4-, 5-, 6-, or 7-benzimidazolyl, 2-, 4-, 5-, 6-, or 7-benzothiazolyl, 1-, 2-, 4-, 5-, 6-, 7-, 8-, or 9-benzoxapinyl, 2-, 4-, 5-, 6-, 7-, or 8-benzoxazinyl, 1-, 2-, 3-, 5-, 6-, 7-, 8-, 9-, 10-, or 11-1H-pyrrolo[1,2-b][2]benzazapinyl. Typical fused heteroaryl groups include, but are not limited to 2-, 3-, 4-, 5-, 6-, 7-, or 8-quinolinyl, 1-, 3-, 4-, 5-, 6-, 7-, or 8-isoquinolinyl, 2-, 3-, 4-, 5-, 6-, or 7-indolyl, 2-, 3-, 4-, 5-, 6-, or 7-benzo[b]thienyl, 2-, 4-, 5-, 6-, or 7-benzoxazolyl, 2-, 4-, 5-, 6-, or 7-benzimidazolyl, 2-, 4-, 5-, 6-, or 7-benzothiazolyl.

A heteroaryl group may be mono-, bi-, tri-, or polycyclic, preferably mono-, bi-, or tricyclic, more preferably mono- or bicyclic.

As used herein, the term "halogen" or "halo" refers to fluoro, chloro, bromo, and iodo.

Halo alkyl shall include mono- and poly-halogenated alkyl, e.g. mono-, di- or tri-substituted. When more than one halo atom is present they may be the same or different.

$R^1$ and $R^3$ are each preferably methyl.

$R^2$ is preferably phenyl, more preferably substituted phenyl, or a 5- or 6-membered unsaturated heterocyclic ring. A preferred substitution pattern is 2, 4-disubstituted or 2, 4, 6 trisubstituted. When $R^2$ is a 5- or 6-membered unsaturated heterocyclic ring, examples of such heterocycles include, pyridine, thiazole, thiophene and imidazole.

$R^4$ is preferably alkyl(C1 to 6)-oxy-alkyl(C1 to 6), heteroaryl, $(CH_2)_m NR^8 R^9$ or $—COR^{10}$. Thus, $R^4$ is preferably an amide, e.g. a —CON— amide or a —NCO— amide, an ether or a heteroaryl. When $R^4$ is a heteroaryl it may be a pyrazole, an imidazole or a triazole, each of which may be optionally substituted as hereinbefore described. In one aspect of the invention $R^4$ is an optionally substituted pyrazole. In another aspect of the invention $R^4$ is an optionally substituted triazole.

When $R^5$ and $R^6$ together form an optionally substituted saturated or unsaturated cyclic group it may be a 5- or 6-membered ring. When $R^5$ and $R^6$ together form an optionally substituted saturated cyclic group, the cyclic group may be piperidine, morpholine, piperazine or azetidine.

Specific compounds of formula I which may be mentioned include:
3-(2,4-Dichloro-phenyl)-6-ethyl-2-methyl-pyrazolo[5,1-b] oxazole-7-carboxylic acid cyclopropyl methyl-propyl-amide;

3-(2,4-Dichloro-phenyl)-2,6-dimethyl-pyrazolo[5,1-b]oxazole-7-carboxylic acid cyclopropyl methyl-propyl-amide;
3-(2,4-Dichloro-phenyl)-2,6-dimethyl-pyrazolo[5,1-b]oxazole-7-carboxylic acid diethylamide;
3-(2,4-Dichloro-phenyl)-2,6-dimethyl-pyrazolo[5,1-b]oxazole-7-carboxylic acid dipropylamide;
3-(2,4-Dimethyl-phenyl)-2,6-dimethyl-pyrazolo[5,1-b]oxazole-7-carboxylic acid dipropylamide;
3-(2,4-Dichloro-phenyl)-2,6-dimethyl-pyrazolo[5,1-b]oxazole-7-carboxylic acid propyl-(tetrahydro-pyran-4-yl)-amide;
3-(2,4-Dimethyl-phenyl)-6-methyl-pyrazolo[5,1-b]oxazole-7-carboxylic acid cyclopropyl methyl-propyl-amide;
3-(2,4-Dimethyl-phenyl)-2,6-dimethyl-pyrazolo[5,1-b]oxazole-7-carboxylic acid cyclopropyl methyl-propyl-amide;
3-(2,4-Dichloro-phenyl)-6-methyl-pyrazolo[5,1-b]oxazole-7-carboxylic acid dipropyl amide;
6-Methyl-3-(2,4,6-trimethyl-phenyl)-pyrazolo[5,1-b]oxazole-7-carboxylic acid dipropyl amide;
[3-(2,4-Dichloro-phenyl)-6-ethyl-2-methyl-pyrazolo[5,1-b]oxazol-7-yl]-pyrrolidin-1-yl-methanone;
3-(2,4-Dichloro-phenyl)-6-ethyl-2-methyl-pyrazolo[5,1-b]oxazole-7-carboxylic acid benzyl-methyl-amide;
[3-(2,4-Dichloro-phenyl)-6-ethyl-2-methyl-pyrazolo[5,1-b]oxazol-7-yl]-piperidin-1-yl-methanone;
3-(2,4-Dichloro-phenyl)-2,6-dimethyl-pyrazolo[5,1-b]oxazole-7-carboxylic acid cyclopropyl-(tetrahydro-pyran-4-yl)-amide;
[3-(2,4-Dichloro-phenyl)-6-ethyl-2-methyl-pyrazolo[5,1-b]oxazol-7-yl]-morpholin-4-yl-methanone;
3-(2,4-Dichloro-phenyl)-6-ethyl-2-methyl-pyrazolo[5,1-b]oxazole-7-carboxylic acid benzyl-ethyl-amide;
3-(2,4-Dichloro-phenyl)-6-ethyl-2-methyl-pyrazolo[5,1-b]oxazole-7-carboxylic acid ethyl-phenyl-amide;
3-(2,4-Dichloro-phenyl)-2,6-dimethyl-pyrazolo[5,1-b]oxazole-7-carboxylic acid benzyl-ethyl-amide;
[3-(2,4-Dichloro-phenyl)-2,6-dimethyl-pyrazolo[5,1-b]oxazol-7-yl]-piperidin-1-yl-methanone;
3-(2,4-Dichloro-phenyl)-2,6-dimethyl-pyrazolo[5,1-b]oxazole-7-carboxylic acid phenyl-propyl-amide;
[3-(2,4-Dichloro-phenyl)-2,6-dimethyl-pyrazolo[5,1-b]oxazol-7-yl]-(6,7-dimethoxy-3,4-dihydro-1H-isoquinolin-2-yl)-methanone;
[3-(2,4-Dichloro-phenyl)-2,6-dimethyl-pyrazolo[5,1-b]oxazol-7-yl]-(3,4-dihydro-1H-isoquinolin-2-yl)-methanone;
[3-(2,4-Dichloro-phenyl)-2,6-dimethyl-pyrazolo[5,1-b]oxazol-7-yl]-(3,4-dihydro-2H-quinolin-1-yl)-methanone;
3-(2,4-Dichloro-phenyl)-2,6-dimethyl-pyrazolo[5,1-b]oxazol-7-yl]-(2,3-dihydro-indol-1-yl)-methanone;
3-(2,4-Dichloro-phenyl)-2,6-dimethyl-pyrazolo[5,1-b]oxazole-7-carboxylic acid benzyl-(2,2,2-trifluoro-ethyl)-amide; (±)-3-(2,4-Dichloro-phenyl)-2,6-dimethyl-7-(1-phenyl-propoxy)-pyrazolo[5,1-b]oxazole;
3-(2,4-Dichloro-phenyl)-7-(1-ethyl-propoxy)-2,6-dimethyl-pyrazolo[5,1-b]oxazole;
3-(2,4-Dichloro-phenyl)-7-(1-methoxymethyl-butoxy)-2,6-dimethyl-pyrazolo[5,1-b]oxazole;
7-Benzyloxy-3-(2,4-dichloro-phenyl)-2,6-dimethyl-pyrazolo[5,1-b]oxazole;
3-(2,4-Dichloro-phenyl)-2,6-dimethyl-7-(1-propyl-butoxy)-pyrazolo[5,1-b]oxazole;
7-Cyclopentyloxy-3-(2,4-dichloro-phenyl)-2,6-dimethyl-pyrazolo[5,1-b]oxazole;
3-(2,4-Dichloro-phenyl)-7-(furan-2-ylmethoxy)-2,6-dimethyl-pyrazolo[5,1-b]oxazole;
3-(2,4-Dichloro-phenyl)-2,6-dimethyl-7-(tetrahydro-furan-3-yloxy)-pyrazolo[5,1-b]oxazole;
3-(2,4-Dichloro-phenyl)-2,6-dimethyl-7-(3-methyl-cyclopentyloxy)-pyrazolo[5,1-b]oxazole;
7-Cyclohexyloxy-3-(2,4-dichloro-phenyl)-2,6-dimethyl-pyrazolo[5,1-b]oxazole;
3-(2,4-Dichloro-phenyl)-2,6-dimethyl-7-(thiazol-4-yl-methoxy)-pyrazolo[5,1-b]oxazole;
3-(2,4-Dichloro-phenyl)-2,6-dimethyl-7-(thiophen-3-yl-methoxy)-pyrazolo[5,1-b]oxazole;
(±)-2-[3-(2,4-Dichloro-phenyl)-2,6-dimethyl-pyrazolo[5,1-b]oxazol-7-yloxy]-2-phenyl-ethanol;
3-(2,4-Dichloro-phenyl)-2,6-dimethyl-7-((R)-1-phenyl-ethoxy)-pyrazolo[5,1-b]oxazole;
3-(2,4-Dichloro-phenyl)-2,6-dimethyl-7-((S)-1-phenyl-ethoxy)-pyrazolo[5,1-b]oxazole;
3-(2,4-Dichloro-phenyl)-2,6-dimethyl-7-(2-methyl-benzyloxy)-pyrazolo[5,1-b]oxazole;
3-(2,4-Dichloro-phenyl)-2,6-dimethyl-7-(pyridin-2-yl-methoxy)-pyrazolo[5,1-b]oxazole;
3-(2,4-Dichloro-phenyl)-2,6-dimethyl-7-(pyridin-3-yl-methoxy)-pyrazolo[5,1-b]oxazole;
3-(2,4-Dichloro-phenyl)-7-(indan-1-yloxy)-2,6-dimethyl-pyrazolo[5,1-b]oxazole;
3-(2,4-Dichloro-phenyl)-2,6-dimethyl-7-(3-methyl-benzyloxy)-pyrazolo[5,1-b]oxazole;
3-(2,4-Dichloro-phenyl)-2,6-dimethyl-7-(pyridin-4-yl-methoxy)-pyrazolo[, 1-b]oxazole;
3-(2,4-Dichloro-phenyl)-2,6-dimethyl-7-(4-methyl-benzyloxy)-pyrazolo[5,1-b]oxazole;
(±)-3-(2,4-Dichloro-phenyl)-7-(1,2-dimethyl-propoxy)-2,6-dimethyl-pyrazolo[5,1-b]oxazole;
7-((S)-sec-Butoxy)-3-(2,4-dichloro-phenyl)-2,6-dimethyl-pyrazolo[5,1-b]oxazole;
3-(2,4-Dichloro-phenyl)-7-(furan-3-ylmethoxy)-2,6-dimethyl-pyrazolo[5,1-b]oxazole;
7-((R)-sec-Butoxy)-3-(2,4-dichloro-phenyl)-2,6-dimethyl-pyrazolo[5,1-b]oxazole;
7-Benzyloxy-3-(2,4-dichloro-phenyl)-6-ethyl-2-methyl-pyrazolo[5,1-b]oxazole;
7-(4-Chloro-benzyloxy)-3-(2,4-dichloro-phenyl)-2,6-dimethyl-pyrazolo[5,1-b]oxazole;
(±)-3-(2,4-Dichloro-phenyl)-2,6-dimethyl-7-(2-methyl-cyclopentyloxy)-pyrazolo[5,1-b]oxazole;
(±)-[3-(2,4-Dichloro-phenyl)-2,6-dimethyl-pyrazolo[5,1-b]oxazol-7-yloxy]-phenyl-acetic acid methyl ester;
3-(2,4-Dichloro-phenyl)-2,6-dimethyl-7-(1-methyl-1H-pyrazol-3-ylmethoxy)-pyrazolo[5,1-b]oxazole;
(±)-3-(2,4-Dichloro-phenyl)-7-(2-methoxy-1-methyl-ethoxy)-2,6-dimethyl-pyrazolo[5,1-b]oxazole;
2-[3-(2,4-Dichloro-phenyl)-2,6-dimethyl-pyrazolo[5,1-b]oxazol-7-yloxy]-2-phenyl-ethanol (Enantiomer 1);
2-[3-(2,4-Dichloro-phenyl)-2,6-dimethyl-pyrazolo[5,1-b]oxazol-7-yloxy]-2-phenyl-ethanol (Enantiomer 2);
2-[3-(2,4-Dichloro-phenyl)-2,6-dimethyl-pyrazolo[5,1-b]oxazol-7-yloxy]-3,3,3-trifluoro-propan-1-ol;
[3-(2,4-Dichloro-phenyl)-2,6-dimethyl-pyrazolo[5,1-b]oxazol-7-yl]-dipropyl-amine hydrochloride;
[3-(2,4-Dichloro-phenyl)-2,6-dimethyl-pyrazolo[5,1-b]oxazol-7-yl]-(1-propyl-butyl)-amine;
[3-(2,4-Dimethyl-phenyl)-2,6-dimethyl-pyrazolo[5,1-b]oxazol-7-yl]-(1-propyl-butyl)-amine;
[3-(2,4-Dichloro-phenyl)-2-ethyl-6-methyl-pyrazolo[5,1-b]oxazol-7-yl]-dipropyl-amine;
[3-(2,4-Bis-trifluoromethyl-phenyl)-2,6-dimethyl-pyrazolo[5,1-b]oxazol-7-yl]-dipropyl-amine;

[3-(2,4-Dichloro-phenyl)-6-isopropyl-2-methyl-pyrazolo[5,1-b]oxazol-7-yl]-dipropyl-amine;
[3-(2,4-Dichloro-phenyl)-2-methyl-6-trifluoromethyl-pyrazolo[5,1-b]oxazol-7-yl]-dipropyl-amine;
N-[3-(2,4-Dichloro-phenyl)-2,6-dimethyl-pyrazolo[5,1-b]oxazol-7-yl]-N-propyl-propionamide;
N-[3-(2,4-Dichloro-phenyl)-2,6-dimethyl-pyrazolo[5,1-b]oxazol-7-yl]-propionamide;
N-[3-(2,4-Dichloro-phenyl)-2,6-dimethyl-pyrazolo[5,1-b]oxazol-7-yl]-N-ethyl-propionamide;
N-[3-(2,4-Dichloro-phenyl)-2-ethyl-6-methyl-pyrazolo[5,1-b]oxazol-7-yl]-propionamide;
N-[3-(2,4-Dichloro-phenyl)-2,6-dimethyl-pyrazolo[5,1-b]oxazol-7-yl]-N-(2,2,2-trifluoro-ethyl)-propionamide;
Ethyl 3-(2,4-dichlorophenyl)-2,6-dimethylpyrazolo[5,1-b]oxazol-7-yl(propyl)carbamate;
N-(3-(2,4-dichlorophenyl)-2,6-dimethylpyrazolo[5,1-b]oxazol-7-yl)-N-propylacetamide;
N-(3-(2,4-dichlorophenyl)-2,6-dimethylpyrazolo[5,1-b]oxazol-7-yl)-N-propyliso butyramide;
N-[3-(2,4-Dichloro-phenyl)-2-ethyl-6-methyl-pyrazolo[5,1-b]oxazol-7-yl]-N-ethyl-propionamide;
N-(3-(2,4-dichlorophenyl)-2,6-dimethylpyrazolo[5,1-b]oxazol-7-yl)-N-propyl benzamide;
N-[3-(2,4-Dichloro-phenyl)-2-ethyl-6-methyl-pyrazolo[5,1-b]oxazol-7-yl]-N-(2,2,2-trifluoro-ethyl)-propionamide;
N-(3-(2,4-dichlorophenyl)-6-ethyl-2-methylpyrazolo[5,1-b]oxazol-7-yl)-N-propyl propionamide;
N-(3-(2,4-dichlorophenyl)-6-ethyl-2-methylpyrazolo[5,1-b]oxazol-7-yl)-N-ethyl propionamide;
N-(3-(2,4-dichlorophenyl)-6-ethyl-2-methylpyrazolo[5,1-b]oxazol-7-yl)-N-(2,2,2-trifluoroethyl) propionamide;
[3-(2,4-Dichloro-phenyl)-2-ethyl-6-methyl-pyrazolo[5,1-b]oxazol-7-ylmethyl]-dipropyl-amine;
[3-(2,4-Dimethyl-phenyl)-2,6-dimethyl-pyrazolo[5,1-b]oxazol-7-ylmethyl]-dipropyl-amine;
Bis-cyclopropylmethyl-[3-(2,4-dimethyl-phenyl)-2,6-dimethyl-pyrazolo[5,1-b]oxazol-7-yl methyl]-amine;
Cyclopropylmethyl-[3-(2,4-dichloro-phenyl)-2-methyl-pyrazolo[5,1-b]oxazol-7-yl methyl]-propyl-amine;
Cyclopropylmethyl-[3-(2,4-dimethyl-phenyl)-6-methyl-pyrazolo[5,1-b]oxazol-7-yl methyl]-propyl-amine;
Cyclopropylmethyl-[3-(2,4-dimethyl-phenyl)-2,6-dimethyl-pyrazolo[5,1-b]oxazol-7-yl methyl]-propyl-amine;
Cyclopropylmethyl-[3-(4-methoxy-2-methyl-phenyl)-2,6-dimethyl-pyrazolo[5,1-b]oxazol-7-ylmethyl]-propyl-amine;
[3-(2,4-Dichloro-phenyl)-2,6-dimethyl-pyrazolo[5,1-b]oxazol-7-ylmethyl]-dipropyl-amine;
[6-Methyl-3-(2,4,6-trimethyl-phenyl)-pyrazolo[5,1-b]oxazol-7-ylmethyl]-dipropyl-amine;
Cyclopropylmethyl-[3-(2,4-dichloro-phenyl)-2,6-dimethyl-pyrazolo[5,1-b]oxazol-7-ylmethyl]-propyl-amine;
Cyclobutylmethyl-[3-(2,4-dichloro-phenyl)-2,6-dimethyl-pyrazolo[5,1-b]oxazol-7-ylmethyl]-ethyl-amine;
Cyclobutylmethyl-[3-(2,4-dichloro-phenyl)-2,6-dimethyl-pyrazolo[5,1-b]oxazol-7-ylmethyl]-propyl-amine;
[3-(2,4-Dichloro-phenyl)-2,6-dimethyl-pyrazolo[5,1-b]oxazol-7-ylmethyl]-ethyl-(3,3,3-trifluoro-propyl)-amine;
[3-(2,4-Dichloro-phenyl)-2,6-dimethyl-pyrazolo[5,1-b]oxazol-7-ylmethyl]-propyl-(3,3,3-trifluoro-propyl)-amine;
Cyclopropylmethyl-[3-(2,4-dichloro-phenyl)-2,6-dimethyl-pyrazolo[5,1-b]oxazol-7-ylmethyl]-(2-methoxy-ethyl)-amine;
[2,6-Dimethyl-3-(2,4,6-trimethyl-phenyl)-pyrazolo[5,1-b]oxazol-7-ylmethyl]-dipropyl-amine;
Cyclopropylmethyl-[2,6-dimethyl-3-(2,4,6-trimethyl-phenyl)-pyrazolo[5,1-b]oxazol-7-yl methyl]-propyl-amine;
Cyclopropylmethyl-[3-(2,4-dichloro-phenyl)-2-ethyl-6-methyl-pyrazolo[5,1-b]oxazol-7-yl methyl]-propyl-amine;
(±)-7-(2-Ethyl-piperidin-1-ylmethyl)-2,6-dimethyl-3-(2,4,6-trimethyl-phenyl)-pyrazolo[5,1-b]oxazole;
2,6-Dimethyl-7-piperidin-1-ylmethyl-3-(2,4,6-trimethyl-phenyl)-pyrazolo[5,1-b]oxazole;
[3-(2-Chloro-4-methoxy-phenyl)-2,6-dimethyl-pyrazolo[5,1-b]oxazol-7-ylmethyl]-cyclopropyl methyl-propyl-amine;
[3-(4-Chloro-2-methyl-phenyl)-2,6-dimethyl-pyrazolo[5,1-b]oxazol-7-ylmethyl]-dipropyl-amine;
[3-(4-Chloro-2-methyl-phenyl)-2,6-dimethyl-pyrazolo[5,1-b]oxazol-7-ylmethyl]-cyclopropyl methyl-propyl-amine;
[3-(2-Chloro-4-methoxy-phenyl)-2,6-dimethyl-pyrazolo[5,1-b]oxazol-7-ylmethyl]-dipropyl-amine;
[3-(2-Chloro-4-methoxy-phenyl)-2,6-dimethyl-pyrazolo[5,1-b]oxazol-7-ylmethyl]-cyclopropyl methyl-propyl-amine;
[3-(2,4-Dichloro-phenyl)-6-ethyl-2-methyl-pyrazolo[5,1-b]oxazol-7-ylmethyl]-dipropyl-amine;
Cyclopropylmethyl-[3-(2,4-dichloro-phenyl)-6-ethyl-2-methyl-pyrazolo[5,1-b]oxazol-7-yl methyl]-propyl-amine;
[3-(2,4-Bis-trifluoromethyl-phenyl)-2,6-dimethyl-pyrazolo[5,1-b]oxazol-7-ylmethyl]-cyclo propylmethyl-propyl-amine;
[3-(6-Chloro-4-methyl-pyridin-3-yl)-2,6-dimethyl-pyrazolo[5,1-b]oxazol-7-ylmethyl]-cyclo propylmethyl-propyl-amine;
4-Chloro-5-{7-[(cyclopropylmethyl-propyl-amino)-methyl]-2,6-dimethyl-pyrazolo[5,1-b]oxazol-3-yl}-pyridin-2-yl)-dimethyl-amine;
Cyclopropylmethyl-[3-(2,4-dimethoxy-phenyl)-6-ethyl-2-methyl-pyrazolo[5,1-b]oxazol-7-yl methyl]-propyl-amine;
Cyclopropylmethyl-[3-(6-methoxy-4-methyl-pyridin-3-yl)-2,6-dimethyl-pyrazolo[5,1-b]oxazol-7-ylmethyl]-propyl-amine;
Cyclopropylmethyl-[3-(6-methoxy-2-methyl-pyridin-3-yl)-2,6-dimethyl-pyrazolo[5,1-b]oxazol-7-ylmethyl]-propyl-amine;
[3-(2,4-Dichloro-phenyl)-2,6-dimethyl-pyrazolo[5,1-b]oxazol-7-ylmethyl]-diethyl-amine;
Cyclopropylmethyl-[3-(2,4-dichloro-phenyl)-2-isopropyl-6-methyl-pyrazolo[5,1-b]oxazol-7-yl methyl]-propyl-amine;
[6-Cyclopropyl-3-(2,4-dichloro-phenyl)-2-methyl-pyrazolo[5,1-b]oxazol-7-ylmethyl]-cyclo propylmethyl-propyl-amine;
Cyclopropylmethyl-[3-(2,4-dimethoxy-phenyl)-2,6-dimethyl-pyrazolo[5,1-b]oxazol-7-yl methyl]-propyl-amine;
Cyclopropylmethyl-[3-(2,4-dichloro-phenyl)-6-methyl-2-propyl-pyrazolo[5,1-b]oxazol-7-yl methyl]-propyl-amine;
Cyclopropylmethyl-[3-(2,4-difluoro-phenyl)-2,6-dimethyl-pyrazolo[5,1-b]oxazol-7-ylmethyl]-propyl-amine;
[3-(2,4-Dichloro-phenyl)-6-methyl-pyrazolo[5,1-b]oxazol-7-ylmethyl]-dipropyl-amine;
Cyclopropylmethyl-[3-(2,4-dichloro-phenyl)-2-methyl-6-propyl-pyrazolo[5,1-b]oxazol-7-yl methyl]-propyl-amine;
[2-Butyl-3-(2,4-dichloro-phenyl)-6-methyl-pyrazolo[5,1-b]oxazol-7-ylmethyl]-cyclopropyl methyl-propyl-amine;
3-(6-Chloro-2-methyl-pyridin-3-yl)-2,6-dimethyl-pyrazolo[5,1-b]oxazol-7-ylmethyl]-cyclopropylmethyl-propyl-amine;

(5-{7-[(Cyclopropyl methyl-propyl-amino)-methyl]-2,6-dimethyl-pyrazolo[5,1-b]oxazol-3-yl}-6-methyl-pyridin-2-yl)-dimethyl-amine;

3-(2-Chloro-phenyl)-2,6-dimethyl-pyrazolo[5,1-b]oxazol-7-ylmethyl]-cyclopropyl methyl-propyl-amine;

[3-(4-Chloro-phenyl)-2,6-dimethyl-pyrazolo[5,1-b]oxazol-7-yl methyl]-cyclopropyl methyl-propyl-amine;

3-(2,4-Dichloro-phenyl)-7-(3,5-dimethyl-pyrazol-1-yl)-2,6-dimethyl-pyrazolo[5,1-b]oxazole;

3-(2,4-Dichloro-phenyl)-7-(3-trifluoromethyl-pyrazol-1-yl)-2,6-dimethyl-pyrazolo[5,1-b]oxazole;

3-(2,4-Dichloro-phenyl)-7-(3,5-dimethyl-pyrazol-1-yl)-6-ethyl-2-methyl-pyrazolo[5,1-b]oxazole;

3-(2,4-Dichloro-phenyl)-2,6-dimethyl-7-(3-methyl-5-trifluoromethyl-pyrazol-1-yl)-pyrazolo[5,1-b]oxazole;

3-(2,4-Dichloro-phenyl)-2,6-dimethyl-7-(3-thiazol-2-yl-pyrazol-1-yl)-pyrazolo[5,1-b]oxazole;

1-{1-[3-(2,4-Dichloro-phenyl)-2,6-dimethyl-pyrazolo[5,1-b]oxazol-7-yl]-1H-pyrazol-3-yl}-imidazolidin-2-one;

3-(2,4-Dichloro-phenyl)-2,6-dimethyl-7-(5-methyl-3-trifluoromethyl-pyrazol-1-yl)-pyrazolo[5,1-b]oxazole;

3-(2,4-Dichloro-phenyl)-7-(3,5-dimethyl-[1,2,4]triazol-1-yl)-2,6-dimethyl-pyrazolo[5,1-b]oxazole;

1-{1-[3-(2,4-Dichloro-phenyl)-2,6-dimethyl-pyrazolo[5,1-b]oxazol-7-yl]-5-methyl-1H-pyrazol-3-yl}-imidazolidin-2-one;

3-(2,4-Dichloro-phenyl)-7-(2,4-dimethyl-imidazol-1-yl)-2,6-dimethyl-pyrazolo[5,1-b]oxazole;

3-(2-Chloro-4-methoxy-phenyl)-7-(3,5-dimethyl-[1,2,4]triazol-1-yl)-2,6-dimethyl-pyrazolo[5,1-b]oxazole;

7-(3,5-Dimethyl-[1,2,4]triazol-1-yl)-3-(4-methoxy-2-methyl-phenyl)-2,6-dimethyl-pyrazolo[5,1-b]oxazole;

3-(2,4-Dichloro-phenyl)-7-(3,5-dimethyl-[1,2,4]triazol-1-yl)-2-ethyl-6-methyl-pyrazolo[5,1-b]oxazole;

2-[3-(2,4-Dichloro-phenyl)-2,6-dimethyl-pyrazolo[5,1-b]oxazol-7-yl]-5-methyl-2H-pyrazole-3-carboxylic acid ethyl ester;

1-[3-(2,4-Dichloro-phenyl)-2,6-dimethyl-pyrazolo[5,1-b]oxazol-7-yl]-5-methyl-1H-pyrazole-3-carboxylic acid ethyl ester;

3-(2,4-Dichloro-phenyl)-7-(3,5-dimethyl-[1,2,4]triazol-1-yl)-6-ethyl-2-methyl-pyrazolo[5,1-b]oxazole;

1-{1-[6-Ethyl-3-(4-methoxy-2-methyl-phenyl)-2-methyl-pyrazolo[5,1-b]oxazol-7-yl]-1H-pyrazol-3-yl}-imidazolidin-2-one;

{1-[3-(2-Chloro-4-methoxy-phenyl)-6-ethyl-2-methyl-pyrazolo[5,1-b]oxazol-7-yl]-1H-pyrazol-3-yl}-imidazolidin-2-one;

1-{1-[3-(4-Chloro-2-methyl-phenyl)-6-ethyl-2-methyl-pyrazolo[5,1-b]oxazol-7-yl]-1H-pyrazol-3-yl}-imidazolidin-2-one;

3-(2-Chloro-4-methoxy-phenyl)-6-ethyl-2-methyl-7-(5-methyl-3-trifluoromethyl-pyrazol-1-yl)-pyrazolo[5,1-b]oxazole;

3-(4-Chloro-2-methyl-phenyl)-6-ethyl-2-methyl-7-(5-methyl-3-trifluoromethyl-pyrazol-1-yl)-pyrazolo[5,1-b]oxazole;

3-(2-Chloro-4-methoxy-phenyl)-6-ethyl-2-methyl-7-(5-methyl-3-trifluoromethyl-pyrazol-1-yl)-pyrazolo[5,1-b]oxazole;

2-[3-(2,4-Dichloro-phenyl)-2,6-dimethyl-pyrazolo[5,1-b]oxazol-7-yl]-5-methyl-2H-pyrazole-3-carboxylic acid;

{2-[3-(2,4-Dichloro-phenyl)-2,6-dimethyl-pyrazolo[5,1-b]oxazol-7-yl]-5-methyl-2H-pyrazol-3-yl}-methanol;

{1-[3-(2,4-Dichloro-phenyl)-2,6-dimethyl-pyrazolo[5,1-b]oxazol-7-yl]-5-methyl-1H-pyrazol-3-yl}-methanol;

2-[3-(2,4-Dichloro-phenyl)-2,6-dimethyl-pyrazolo[5,1-b]oxazol-7-yl]-5-methyl-2H-pyrazole-3-carboxylic acid dimethylamide;

1-{1-[3-(2,4-Dichloro-phenyl)-6-ethyl-2-methyl-pyrazolo[5,1-b]oxazol-7-yl]-1H-pyrazol-3-yl}-imidazolidin-2-one;

3-(2,4-dichlorophenyl)-2-ethyl-6-methyl-7-(5-methyl-3-(trifluoromethyl)-1H-1,2,4-triazol-1-yl)pyrazolo[5,1-b]oxazole;

3-(4-methoxy-2-methylphenyl)-2,6-dimethyl-7-(5-methyl-3-(trifluoromethyl)-1H-1,2,4-triazol-1-yl)pyrazolo[5,1-b]oxazole;

3-(2,4-dichlorophenyl)-2,6-dimethyl-7-(5-methyl-3-(trifluoromethyl)-1H-1,2,4-triazol-1-yl) pyrazolo[5,1-b]oxazole;

3-(2-Chloro-4-methoxyphenyl)-2,6-dimethyl-7-(5-methyl-3-(trifluoromethyl)-1H-1,2,4-triazol-1-yl)pyrazolo[5,1-b]oxazole;

3-(2,4-Dimethoxy-phenyl)-7-(3,5-dimethyl-[1,2,4]triazol-1-yl)-2,6-dimethyl-pyrazolo[5,1-b]oxazole;

7-(3,5-Dimethyl-1H-1,2,4-triazol-1-yl)-2-ethyl-3-(4-methoxy-2-methylphenyl)-6-methyl pyrazolo[5,1-b]oxazole;

7-(3,5-Dimethyl-[1,2,4]triazol-1-yl)-3-[4-methoxy-2-(2-methoxy-ethoxy)-phenyl]-2,6-dimethyl-pyrazolo[5,1-b]oxazole;

2-Ethyl-3-(4-methoxy-2-methylphenyl)-6-methyl-7-(5-methyl-3-(trifluoromethyl)-1H-1,2,4-triazol-1-yl)pyrazolo[5,1-b]oxazole;

3-(2-Chloro-4-(1H-1,2,4-triazol-1-yl)phenyl)-7-(3,5-dimethyl-1H-1,2,4-triazol-1-yl)-2-ethyl-6-methylpyrazolo[5,1-b]oxazole;

7-(3,5-Dimethyl-[1,2,4]triazol-1-yl)-3-(4-methoxy-2,5-dimethyl-phenyl)-2,6-dimethyl-pyrazolo[5,1-b]oxazole;

4-(7-(3,5-Dimethyl-1H-1,2,4-triazol-1-yl)-2,6-dimethylpyrazolo[5,1-b]oxazol-3-yl)-3-methyl benzonitrile;

7-(3,5-Dimethyl-[1,2,4]triazol-1-yl)-3-(4-methoxy-2,3-dimethyl-phenyl)-2,6-dimethyl-pyrazolo[5,1-b]oxazole;

7-(3,5-Dimethyl-[1,2,4]triazol-1-yl)-2,6-dimethyl-3-(2-methyl-4-trifluoromethoxy-phenyl)-pyrazolo[5,1-b]oxazole;

3-(4-Bromo-2-methylphenyl)-7-(3,5-dimethyl-1H-1,2,4-triazol-1-yl)-2,6-dimethyl pyrazolo[5,1-b]oxazole;

3-(4-Bromo-2-chlorophenyl)-7-(3,5-dimethyl-1H-1,2,4-triazol-1-yl)-2,6-dimethyl-pyrazolo[5,1-b]oxazole;

3-(2,6-Dimethoxy-pyridin-3-yl)-7-(3,5-dimethyl-[1,2,4]triazol-1-yl)-2,6-dimethyl-pyrazolo[5,1-b]oxazole;

7-(3,5-Dimethyl-[1,2,4]triazol-1-yl)-3-(4-methoxy-2,6-dimethyl-phenyl)-2,6-dimethyl-pyrazolo[5,1-b]oxazole;

3-(5-Chloro-3-methyl-2-phenyl-3H-imidazol-4-yl)-7-(3,5-dimethyl-[1,2,4]triazol-1-yl)-2,6-dimethyl-pyrazolo[5,1-b]oxazole;

7-(3,5-dimethyl-1H-1,2,4-triazol-1-yl)-3-(2-methoxy-4-methylphenyl)-2,6-dimethyl pyrazolo[5,1-b]oxazole;

7-(3,5-dimethyl-1H-1,2,4-triazol-1-yl)-2,6-dimethyl-3-(7-methyl-2,3-dihydrobenzo[b][1,4]dioxin-6-yl)pyrazolo[5,1-b]oxazole;

7-(3,5-Dimethyl-[1,2,4]triazol-1-yl)-3-(2-methoxy-5-methyl-phenyl)-2,6-dimethyl-pyrazolo[5,1-b]oxazole;

7-(3,5-Dimethyl-[1,2,4]triazol-1-yl)-3-(6-methoxy-2-methyl-pyridin-3-yl)-2,6-dimethyl-pyrazolo[5,1-b]oxazole;

7-(3,5-Dimethyl-1H-1,2,4-triazol-1-yl)-3-(1,3-dimethyl-1H-indol-2-yl)-2,6-dimethyl pyrazolo[5,1-b]oxazole;

7-(3,5-Dimethyl-1H-1,2,4-triazol-1-yl)-3-(5-methoxy-2-methylphenyl)-2,6-dimethyl pyrazolo[5,1-b]oxazole;

3-(4-Cyclobutoxy-2-methylphenyl)-7-(3,5-dimethyl-1H-1,2,4-triazol-1-yl)-2,6-dimethyl pyrazolo[5,1-b]oxazole;

7-(3,5-Dimethyl-1H-1,2,4-triazol-1-yl)-3-(4-ethoxy-2-methylphenyl)-2,6-dimethyl pyrazolo[5,1-b]oxazole;

3-(6-Chloro-2-methyl-pyridin-3-yl)-7-(3,5-dimethyl-[1,2,4]triazol-1-yl)-2,6-dimethyl-pyrazolo[5,1-b]oxazole;

7-(3,5-Dimethyl-[1,2,4]triazol-1-yl)-2,6-dimethyl-3-(2-methyl-6-methylsulfanyl-pyridin-3-yl)-pyrazolo[5,1-b]oxazole;

7-(3,5-Dimethyl-1H-1,2,4-triazol-1-yl)-2,6-dimethyl-3-(2-methyl-4-(methylthio)phenyl)pyrazolo[5,1-b]oxazole;

3-(2,3-Dihydrobenzofuran-5-yl)-7-(3,5-dimethyl-1H-1,2,4-triazol-1-yl)-2,6-dimethyl pyrazolo[5,1-b]oxazole;

3-(2,4-Dichloro-phenyl)-2,6-dimethyl-7-(1-methylene-butyl)-pyrazolo[5,1-b]oxazole;

4-[3-(2,4-Dichloro-phenyl)-2,6-dimethyl-pyrazolo[5,1-b]oxazol-7-yl]-heptan-4-ol;

1-[3-(2,4-Dichloro-phenyl)-2,6-dimethyl-pyrazolo[5,1-b]oxazol-7-yl]-ethanol;

[3-(2,4-Dichloro-phenyl)-2,6-dimethyl-pyrazolo[5,1-b]oxazol-7-yl]-phenyl-methanol;

7-((E)-But-1-enyl)-3-(2,4-dichloro-phenyl)-2,6-dimethyl-pyrazolo[5,1-b]oxazole;

3-(2,4-Dichloro-phenyl)-7-[1-eth-(Z)-ylidene-butyl]-2,6-dimethyl-pyrazolo[5,1-b]oxazole;

3-(2,4-Dichloro-phenyl)-2,6-dimethyl-7-(1-methylene-butyl)-pyrazolo[5,1-b]oxazole;

7-(3,5-Dimethyl-[1,2,4]triazol-1-yl)-2,6-dimethyl-3-(2-methyl-4-pyrazol-1-yl-phenyl)-pyrazolo[5,1-b]oxazole;

7-(3,5-Dimethyl-[1,2,4]triazol-1-yl)-2,6-dimethyl-3-(2-methyl-4-trideuteriomethoxy-phenyl)-pyrazolo[5,1-b]oxazole;

3-(4-(1H-imidazol-1-yl)-2-methylphenyl)-7-(3,5-dimethyl-1H-1,2,4-triazol-1-yl)-2,6-dimethyl pyrazolo[5,1-b]oxazole; and 3-(Benzofuran-5-yl)-7-(3,5-dimethyl-1H-1,2,4-triazol-1-yl)-2,6-dimethylpyrazolo[5,1-b]oxazole;

and isomers thereof, in free form or as a pharmaceutically acceptable salt.

Another aspect of this invention relates to the fact that the compounds of formula I and their pharmaceutically acceptable salts have beneficial pharmacological activity and, therefore, are useful as pharmaceuticals.

Therefore, according to a further aspect of the invention we provide a compound of formula I as hereinbefore described as a medicament. More particularly, we provide a compound of formula I as hereinbefore described as a corticotropin releasing factor ($CRF_1$) receptor antagonist.

According to a further aspect of the invention we provide the use of a compound of formula I as hereinbefore described in the manufacture of a medicament. More particularly, we provide the use as hereinbefore described in the manufacture of a medicament for a corticotropin releasing factor ($CRF_1$) receptor antagonist.

Furthermore it has now been found that the compounds of formula I, or a salt thereof, behave as CRF, receptor antagonists.

The CRF-1 or CRF-2a receptor activity of the agents of the invention has been determined in vitro in the following way:

Chinese hamster ovary (CHO) cells expressing either the human recombinant CRF-1 or CRF-2a receptors (Chen et al., Proc Natl Acad Sci USA 90, 8967-8971, 1993; Liaw et al., Endocrinology 137, 72-77, 1996) are propagated in Dulbecco's modified Eagle medium supplemented with 10% foetal calf serum, non-essential amino acids, 100 U/ml penicillin, 100 mg/l streptomycin and 1 g/l geneticin (G418). For cyclic AMP determinations the Homogeneous Time-Resolved Fluoresce (HTRF) cAMP dynamic 2 kit (Cishbio International, France) was used as per manufacturers' instructions. CHO cells, previously cryopreserved, were thawed, centrifuged for 7 mins at 1200 rpm and resuspended in serum free media, then pipetted out onto clear bottomed black tissue culture treated 384-well microtitre plates (Corning Inc, US) at 2,000 cells per well. Compounds of the invention, prepared in DMSO, and subsequently diluted 50 fold in assay buffer (1× Hanks balanced salt solution, 0.2% (w/v) bovine serum albumin, 1.7 mM isobutylmethylxanthine and 10 mM Hepes, pH7.4) are then added onto the cell containing plate where a further 2 fold dilution is performed and incubated for 15 min. Following incubation, buffer containing a 5 times final concentration of agonist is added to the plate and incubated for 30 min. Finally, d2 dye labelled cAMP and cryptate labeled anti-cAMP antibody, both made in lysis buffer, are added to the plate followed by a settling period of 1 hour. During the settling period cAMP produced by the cells competes with the d2 labelled cAMP for the anti-cAMP cryptate. The plate is read on the Pherastar (BMG, Germany). Increasing levels of endogenous cAMP produced by cells can be followed by a decrease of fluorescent signal and vice versa. Values represented by a change in arbitrary fluorescence units are converted into cAMP concentrations by use of a standard curve the reagents for which are supplied with the kit. Antagonist dose response curves (1 nM-3 µM) are constructed in the presence of 1 nM CRF. IC50 values of antagonists are calculated by fitting the percent inhibition of the effect of CRF by increasing concentrations of the antagonists. The fit is performed using the nonlinear logistic function of the Activitybase software package v 5.4.5.27 (IDBS, UK).

In this test, the agents of the invention show CRF, antagonistic activity with IC50 CRF, values of about 1 nM to 30 µM, preferably 1 nM to 10 µM.

Compounds of the invention are useful in the treatment of any state with increased endogenous level of CRF (corticotropin releasing factor) or in which the HPA (hypothalamic pituitary axis) is disregulated, or of various diseases induced or facilitated by CRF.

Compounds of the invention are in particular useful in the treatment or prevention of gastrointestinal disorders including irritable bowel syndrome with or without diarrhea, inflammatory bowel diseases, post-operative ileus, reflux disease and infectious diarrhea.

Compounds of the invention are also in particular useful in the treatment or prevention of major depressive disorders including bipolar depression, unipolar depression, single or recurrent major depressive episodes with or without psychotic features, catatonic features, melancholic features, atypical features or postpartum onset, the treatment of anxiety and the treatment of panic disorders. Other mood disorders encompassed within the term major depressive disorders include fatigue syndrome and dysthymic disorder with early or late onset and with or without atypical features, neurotic depression, post traumatic stress disorders, post operative stress and social phobia; dementia of the Alzheimer's type, with early or late onset, with depressed mood; vascular dementia with depressed mood; mood disorders induced by alcohol, amphetamines, cocaine, hallucinogens, inhalants, opioids, phencyclidine, sedatives, hypnotics, anxiolytics and other substances; schizoaffective disorder of the depressed type; and adjustment disorder with depressed mood. Major depressive disorders may also result from a general medical condition including, but not limited to, myocardial infarction, diabetes, miscarriage or abortion, etc.

Compounds of the invention are also useful in the treatment or prevention of schizophrenic disorders including paranoid schizophrenia, disorganised schizophrenia, catatonic schizophrenia, undifferentiated schizophrenia, residual schizophrenia.

Compounds of the invention are also useful in the treatment or prevention of neurodegenerative diseases such as Alzheimer's disease, Parkinson's disease, Huntington's disease, senile dementia of the Alzheimer's type, and multiinfarct dementia.

Compounds of the invention are useful as analgesics. In particular they are useful in the treatment of traumatic pain such as postoperative pain; traumatic avulsion pain such as brachial plexus; chronic pain such as arthritic pain such as occurring in osteo-, rheumatoid or psoriatic arthritis; neuropathic pain such as post-herpetic neuralgia, trigeminal neuralgia, segmental or intercostal neuralgia, fibromyalgia, causalgia, peripheral neuropathy, diabetic neuropathy, chemotherapy-induced neuropathy, AIDS related neuropathy, occipital neuralgia, geniculate neuralgia, glossopharyngeal neuralgia, reflex sympathetic dystrophy, phantom limb pain; various forms of headache such as migraine, acute or chronic tension headache, temporomandibular pain, maxillary sinus pain, cluster headache; odontalgia; cancer pain; pain of visceral origin; gastrointestinal pain; nerve entrapment pain; sport's injury pain; dysmennorrhoea; menstrual pain; meningitis; arachnoiditis; musculoskeletal pain; low back pain e.g. spinal stenosis; prolapsed disc; sciatica; angina; ankylosing spondyolitis; gout; burns; scar pain; itch; and thalamic pain such as post stroke thalamic pain.

Compounds of the invention are also useful for the treatment of dysfunction of appetite and food intake and in circumstances such as anorexia, anorexia nervosa, bulimia, obesity and metabolic syndrome.

Compounds of the invention are also useful in the treatment of sleep disorders including dysomnia, insomnia, sleep apnea, narcolepsy, and circadian rhythmic disorders.

Compounds of the invention are also useful in the treatment or prevention of cognitive disorders. Cognitive disorders include dementia, amnestic disorders and cognitive disorders not otherwise specified.

Furthermore compounds of the invention are also useful as memory and/or cognition enhancers in healthy humans with no cognitive and/or memory deficit.

Compounds of the invention are also useful in the treatment of tolerance to and dependence on a number of substances. For example, they are useful in the treatment of dependence on nicotine, alcohol, caffeine, phencyclidine (phencyclidine like compounds), or in the treatment of tolerance to and dependence on opiates (e.g. cannabis, heroin, morphine) or benzodiazepines; in the treatment of cocaine, sedative ipnotic, amphetamine or amphetamine-related drugs (e.g. dextroamphetamine, methylamphetamine) addiction or a combination thereof.

Compounds of the invention are also useful as anti-inflammatory agents. In particular they are useful in the treatment of inflammation in asthma, influenza, chronic bronchitis and rheumatoid arthritis; in the treatment of inflammatory diseases of the gastrointestinal tract such as Crohn's disease, ulcerative colitis, postoperative gastric ileus (POI), inflammatory bowel disease (IBD) and non-steroidal anti-inflammatory drug induced damage; inflammatory diseases of the skin such as herpes and eczema; inflammatory diseases of the bladder such as cystitis and urge incontinence; and eye and dental inflammation.

Compounds of the invention are also useful the treatment of fertility problems, sexual dysfunctions and pre-term birth and non-inflammatory urogenital disorders such as overactive bladder and related urinary incontinence.

Compounds of the invention are also useful in the treatment of allergic disorders, in particular allergic disorders of the skin such as urticaria, and allergic disorders of the airways such as rhinitis.

Compounds of the invention are also useful the treatment of mast cell activation disorders such as mastocytosis.

Compounds of the invention are also useful the treatment of Cushing's syndrome induced by drugs such as steroids or cancer such as pituitary adenoma.

Compounds of the invention are also useful in the treatment of emesis, i.e. nausea, retching and vomiting. Emesis includes acute emesis, delayed emesis and anticipatory emesis. The compounds of the invention are useful in the treatment of emesis however induced. For example, emesis may be induced by drugs such as cancer chemotherapeutic agents such as alkylating agents, e.g. cyclophosphamide, carmustine, lomustine and chlorambucil; cytotoxic antibiotics, e.g. dactinomycin, doxorubicin, mitomycin-C and bleomycin; anti-metabolites, e.g. cytarabine, methotrexate and 5-fluorouracil; vinca alkaloids, e.g. etoposide, vinblastine and vincristine; and others such as cisplatin, dacarbazine, procarbazine and hydroxyurea; and combinations thereof; radiation sickness; radiation therapy, e.g. irradiation of the thorax or abdomen, such as in the treatment of cancer; poisons; toxins such as toxins caused by metabolic disorders or by infection, e.g. gastritis, or released during bacterial or viral gastrointestinal infection; pregnancy; vestibular disorders, such as motion sickness, vertigo, dizziness and Meniere's disease; post-operative sickness; gastrointestinal obstruction; reduced gastrointestinal motility; visceral pain, e.g. myocardial infarction or peritonitis; migraine; increased intercranial pressure; decreased intercranial pressure (e.g. altitude sickness); opioid analgesics, such as morphine; and gastro-oesophageal reflux disease, acid indigestion, over-indulgence of food or drink, acid stomach, sour stomach, regurgitation, heartburn, such as episodic heartburn, nocturnal heartburn, and meal-induced heartburn and dyspepsia.

Compounds of the invention are of particular use in the treatment of gastrointestinal disorders such as irritable bowel syndrome; skin disorders such as psoriasis, pruritis and sunburn; vasospastic diseases such as angina, vascular headache and Reynaud's disease; cerebral ischeamia such as cerebral vasospasm following subarachnoid haemorrhage; fibrosing and collagen diseases such as scleroderma and eosinophilic fascioliasis; disorders related to immune enhancement or suppression such as systemic lupus erythematosus and rheumatic diseases such as fibrositis; and cough.

Compounds of the invention are useful for the treatment of neurotoxic injury which follows cerebral stroke, thromboembolic stroke, hemorrhagic stroke, cerebral ischemia, cerebral vasospam, hypoglycemia, hypoxia, anoxia, perinatal asphyxia cardiac arrest.

The utility of the agents of the invention in the above indicated diseases could be confirmed in a range of standard tests. (1) The anxiolytic activity of the agents of the invention can be confirmed in the mouse elevated plus-maze [see for example Rodgers R. J., Behavioural Pharmacology 8: 477-496 (1997) where the relevance of the elevated plus-maze is discussed on p. 486; for the method, see Rodgers R. J. et al. Ethology and Psychopharmacology (Eds S J Cooper and C A Hendrie), pp 9-44 (1994), J. Wiley, Chichester]. (2) The analgesic activity of the agents of the invention can be confirmed in rat visceral hyperalgesia models following colorectal distension [see for example Schwetz I, Am J Physiology 286: G683-G691 (2004); for the method, see Ness T. J., Brain Research 450:153-169 (1988)]. (3) The anti-diarrheal activity of the agents of the invention can be confirmed in rat defecation models during stress or CRF challenge [see for example Maillot C., Gastroenterology 119:1569-1579 (2002)].

In these tests, the agents of the invention show anxiolytic-like, visceral analgesic and anti-diarrheal effects following oral administration of 0.1 to 30 mg/kg.

For the above-mentioned indications, the appropriate dosage will of course vary depending upon, for example, the compound employed, the host, the mode of administration and the nature and severity of the condition being treated. However, in general, satisfactory results in animals are indicated to be obtained at a daily dosage of from about 0.1 to about 100 mg/kg, preferably from about 1 to about 30 mg/kg animal body weight. In larger mammals, for example humans, an indicated daily dosage is in the range from about 1 to about 500 mg, preferably from about 1 to about 100 mg of an agent of the invention, conveniently administered, for example, in divided doses up to three times a day or in sustained release form.

The agents of the invention may be administered by any conventional route, in particular enterally, preferably orally, for example in the form of tablets or capsules, or parenterally, for example in the form of injectable solutions or suspensions.

In accordance with the foregoing, the present invention also provides an agent of the invention, for use as a pharmaceutical, e.g. for the treatment of diseases induced or facilitated by CRF, such as these indicated above.

Therefore, according to a further aspect of the invention we provide a compound of formula I, or a salt thereof, for the treatment or alleviation of treatment of any state with increased endogenous level of CRF or in which the HPA (hypothalamic pituitary axis) is disregulated, or of various diseases induced or facilitated by CRF.

The agents of the invention can be administered in vivo either alone or in combination with other pharmaceutical agents, e.g. agents effective in the treatment of diseases and conditions in which an increased endogenous level of CRF plays a role or is implicated. A suitable combination consists of a compound of the present invention with one or more compounds selected from the group consisting of dopamine D2 receptor antagonists, serotonin 5-HT4 receptor agonists, serotonin 5-HT3 receptor agonists, serotonin 5-HT3 receptor antagonists, CCK1 receptor antagonists, motilin receptor agonists, μ-opioid receptor antagonists, opioid receptor agonists and opiates, other CRF-1 receptor antagonists, glutamate receptor antagonists, neurokinin receptor antagonists, histamine H2 receptor antagonists, histamine H4 receptor antagonists, proton pump inhibitors, chloride channel activators, guanylate cyclase-c activators, muscarinic receptor antagonists, antispasmodics, stimulant laxatives, osmotic laxatives, faecal softeners, absorbents and fibre supplements, antacids, GI relaxants, bismuth compounds, vanilloid receptor antagonists, anticonvulsants, NSAIDS, COX-2 inhibitors, GABAb receptor modulators, CB receptor ligands, calcium channel blockers, sodium channel blockers, tricyclic antidepressants, serotonin and noradrenaline re-uptake inhibitors, benzodiazepines, alpha-2 receptor agonists and ghrelin receptor agonists.

More specifically, a compound of the present invention may be administered as a combination with one or more compounds selected from the group consisting of dopamine D2 receptor antagonists, such as, chlorpromazine, prochlorperazine, haloperidol, alizapride, domperidone, metoclopramide and itopride; serotonin 5-HT4 receptor agonists, such as, cisapride, cinitapride, mosapride, renzapride, prucalopride, tegaserod, velusetrag, ATI-7505 and compounds described in WO 2005068461, US 2005228014, WO 2005080389, US 2006100426, US 2006100236, US 2006135764, US 2005277671, WO 2005092882, WO 2005073222, JP 2005104896, JP 2005082508, WO 2005021539, JP 2004277319, JP 2004277318, WO 2004026869, EP 1362857, WO 2006108127, US 20060183901, WO 2006127815, US 20060276482, WO 2007005951, WO 2007010390, WO 2007005951, WO 2007048643, WO 2007096352, WO 2007068739 and WO 20070117796; serotonin 5-HT3 receptor agonists, such as, pumesotrag and compounds described in WO 2007004041; serotonin 5-HT3 receptor antagonists, such as, alosetron, cilansetron, ramosetron, azasetron, ondansetron, granisetron, tropisetron, DDP225 and compounds described in WO 2006183769, WO 2006105117 and WO 2007004041; CCK1 receptor antagonists, such as, JNJ-17156516, devazepide, loxiglumide and dexloxiglumide; motilin receptor agonists, such as, motilin, atilmotin, erythromycin, alemcinal, mitemcinal, KOS-2187, 1-[4-(3-fluoro-phenylamino)-piperidin-1-yl]-2-[4-((S)-3-methyl-piperazin-1-ylmethyl)-phenyl]-ethanone and compounds described in WO 2005060693, WO 2006127252, WO 2007007018, WO 2007012479 and WO 2008000729; m-opioid receptor antagonists, such as, naxolone, alvimopan, methylnaltrexone and compounds described in US 20050203123, US 2006063792, WO 2007050802, US 2007103187, WO 2009029252, WO 2009029256, WO 2009029257 and WO 2009029253; opioid receptor agonists and opiates, such as, morphine, buprenorphine, diamorphine, dihydrocodeine, fentanyl, pethidine, asimadoline, loperamide and codeine; CRF-1 receptor antagonists, such as, GSK876008, pexacerfont and compounds described in WO 2004069257, WO 9940089, U.S. Pat. No. 6,844,351, WO 2005013997, WO 2005014557, WO 2005023806, WO 2005026126, WO 2005028480, WO 005044793, WO 2005051954, WO 2005051954, WO 2005115399, WO 2005028480, WO 2005023806, WO 2006044958, WO 2006044821 and US 20060211710; glutamate receptor antagonists, such as, AZD9272, AZD2066, AFQ056, ADX48621 and compounds described in WO 9902497, WO 2000020001, WO 200304758 and WO 2005030723, WO 2005077345, US 2006009443, EP 1716152, WO 2005080397, US 2006019997, WO 2005066155, WO 2005082884, WO 2005044266, WO 2005077373, EP 1713791, EP 1720860, WO 2005080379, EP 1716130, US 2006235024, WO 2005080363 WO 2006114264, WO 2006114260, WO 2006089700, WO 2006114262, WO 2006123257, US 2005272779, WO 2006048771, WO 2006123249, US 2006009477, WO 2006014185, EP 1723144, US 2006025414, US 2006004021, US 2006160857, WO 2006074884, WO 2006129199, WO 2006123244, WO 2006123255, WO 2007040982, WO 2007023290, WO 2007023242, WO 2007050050, WO 2007039781, WO 2007039782 and WO 2007023245; neurokinin receptor antagonists, such as, taletant, osanetant, casopitant, nepadutrent, saredutant, DNK-333, SLV-317, SLV321, SLV317 and compounds described in EP 96-810237, WO 2006137790, WO 2006137791, WO 2006094934, WO 2007037742 and WO 2007037743; histamine H2 receptor antagonists, such as, famotidine, cimetidine, ranitidine and nizatidine; histamine H4 receptor antagonists, such as, JNJ7777120, JNJ10191584 and compounds described in US 2006111416, WO 2006050965, WO 2005092066, WO 2005054239 US 2005070550, US 2005070527, EP 1505064, WO 2007090852, WO 2007090853, WO 2007090854, US 20070232616, US 20070238771, WO 2007117399, WO 2007031529 and WO 2007072163; proton pump inhibitors, such as, omeprazole, lansoprazole, rabeprazole, tentoprazole, pantoprazole, esomeprazole, revaprazan, soraprazan and AGN201904; chloride channel activators, such as, lubiprostone; guanylate cyclase-2c activators, such as, linaclotide, guanilib, guanylin, uroguanylin and compounds described in WO 2005087797, WO 2005016244, WO 2007022531, WO 2007101158, WO 2007101161 and U.S. Pat. No. 7,041,786; muscarinic receptor antagonists, such as, darifenacin, solifenacin, atropine, dicycloverine, hycosine butyl bromide, propantheline, oxybutinin, cimetropium bromide and pinaverium bromide; antispasmodics, such as, mebeverine, octylonium bromide, trimebutine, tiropramide, alverine and peppermint oil; stimulant laxatives, such as, bisacodyl; osmotic laxatives, such as, activated charcoal with sorbitol, lactulose, magnesium hydroxide and phosphate buffered saline; faecal softeners, such as, senna concentrate, liquid paraffin and arachis oil; absorbents and fibre supplements; bulk fibre laxatives such as bran, methylcellulose, ispaghula husk and sterculia; antacids, such as, aluminium, magnesium and calcium antacids, simeticone and alginate containing preparations; GI relaxants, such as, cholestyramine resin; bismuth compounds, such as, bismuth subsalicylate; vanilloid receptor antagonists, such as, SB705498, ABT-102, AZD1386, GRC-6211, MK-2295 and compounds described in WO 2002076946, WO 2004033435, WO 2005121116, WO 2005120510, WO 2006006740, WO 2006006741, WO 2006010445, WO 2006016218, US 2006058308, WO 2006033620, WO 2006038871, US 2006084640, US 2006089360, WO 2006058338, WO 2006063178, US 2006128689, WO 2006062981, WO 2006065646, WO 2006068618, WO 2006068592, WO 2006068593, WO 2006076646, US 2006160872, WO 200608082, US 2006183745, WO 2006095263, WO 2006102645, WO 2006100520, US 2006241296, WO 2006122200, WO 2006120481, WO 2006122250, DE 102005044814, WO 2006122772, WO 2006122777, WO 2006124753, WO 2006122799, WO 2006122770, WO 2006122769, WO 2006136245, WO 2007030761, US 20070088072, US 20070088073, US 20070105920, WO 2007042906, WO 2007045462, WO 2007050732; anticonvulsants, such as, carbemazepine, oxcarbemazepine, lamotrigine, gabapentin and pregabalin; NSAIDS, such as, aspirin, acetometaphen, ibuprofen, diclofenac, naproxen, flurbiprofen, indomethacin, piroxicam, ketoprofen, sulindac and diflunisal; COX-2 inhibitors, such as, celecoxib, rofecoxib, lumiracoxib, valdecoxib, etoricoxib and compounds described in WO 2004048314; GABAb receptor modulators, such as, racemic and (R)-baclofen, AZD3355, XP19986 and compounds described in WO 2006001750 and WO 2004000856; CB receptor ligands, such as, dronabinol, nabilone, cannabidiol, rimonabant and compounds described in WO 2002042248 and WO 2003066603; calcium channel blockers, such as, ziconotide, AGI0-003, PD-217014 and compounds described in WO 2006038594, WO 2006030211 and WO 2005068448; sodium channel blockers, such as, lamotrigine and compounds described in WO 2006023757, WO 2005097136, JP 2005206590 and WO 2005047270; tricyclic antidepressants, such as, clomipramine, amoxapine, nortripyline, amitriptyline, imipramine, desipramine, doxepin, trimipramine and protripyline; serotonin and noradrenaline re-uptake inhibitors, such as, milnacipran, desvenlafaxine, sibutramine, duloxetine, fluoxetine, paroxetine, citalopram, sertraline and fluvoxamine; benzodiazepines, such as, levotofisopam, diazepam, lorazepam, clonazepam and alprazolam; alpha-2 receptor agonists, such as, clonidine, tizanidine and guanfacine; ghrelin receptor agonists, such as, ghrelin, ibutamoren, capromorelin, tabimorelin, ipamorelin, 2-Methylalanyl-N-[1(R)-formamido-2-(1H-indol-3-yl)ethyl]-D-tryptophanamide, TZP-101, TZP-102, LY-444711, EX-1314 and compounds described in U.S. Pat. No. 6,525,203, US 20050154043, WO 2005097788, WO 2006036932, WO 2006135860, US 20060079562, WO 2006010629, WO 2006009674, WO 2006009645, US 20070021331, WO 2007020013, US 20070037857, WO 2007014258, WO 2007113202, WO 2007118852, US 20080194672, US 20080051383 and US 20080051383; corticosteroids, such as, hydrocortisone, cortisone, dexamethasone, betamethasone, beclomethasone, prednisolone, 6-methylprednisolone, budesonide, mometasone furoate, ciclesonide, fluticasone propionate and fluticasone furoate; aminosalicylates, such as, mesalazine, ipsalazide, olsalazine and balsalazide; immunomodulators, such as, azathioprine, 6-mercaptopurine, methotrexate, mycophenolate mofetil, ciclosporin and tacrolimus; PDE4 inhibitors, such as, tetomilast, cilomilast, roflumilast and arofylline; antibiotics, such as, metronidazole, ornidazole and ciprofloxacin; anti-adhesion molecule agents, such as, natalizumab and MLN02; anti IL-2 agents, such as, daclizumab and basilixumab; anti CD-3 agents, such as, visilizumab; and anti-TNF agents, such as, infliximab, adalimumab, fontolizumab and certolizumab pegol; psychiatric medications comprising compounds selected from the group consisting of agomelatine, azapirones, alprazolam, amitriptyline, aniracetam, acetyl-L-carnitine, aripiprazol, acetophenazine, benzodiazepines, barbiturate, buspirone, bupropione, chlordiazepoxide, chlorazepate, clonazepam, chlorpromazine, clozapine, CX614, CX516, chlorprothixene, diphenhydramine hydroxyzine, demoxepam, diazepam, droperidol, duloxetine, donezepil, doxepine, desipramine, flurazepam, fluphenazine, fluoxetine, flupentixol, gabapentin, melatonin, ginkgo-derived compounds, galantamine, haloperidol, Hydergine (ergoloid mesylates), huperzine, isocarboxazid, imipramine, lorazepam, loxapine, meprobamate, medazepam, moclobemide, molindone, maprotiline, modafinil, memantine, methylphenicate, mesoridazine, methotrimeprazine, nortriptyline, naproxen, oxazepam, oxiracetam, olanzapine, prazepam, paroxetine, phenelzine, pipotiazine, perphenazine, promazine, pimozide, PDE4 inhibitors, quazepam, quetiapine, reboxetine, rivastigmine, prochlorperazine, risperidone, sertraline, sertindole, temazepam, triazolam, tranylcypromine, tomoxetine, thiotixene, trifluoperazine, thioridazine, zolpidem and ziprasidone.

A preferred group of compounds which may be mentioned are compounds of formula II;

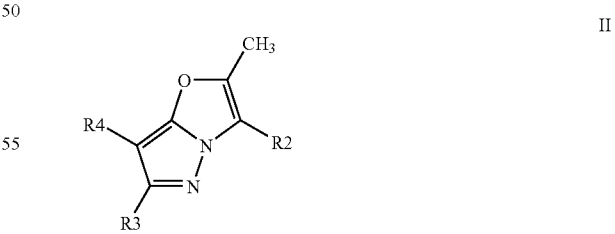

in which $R^2$, $R^3$ and $R^4$ are each as hereinbefore defined;

and isomers thereof, in free form or as a pharmaceutically acceptable salt.

An alternative preferred group of compounds which may be mentioned are compounds of formula III;

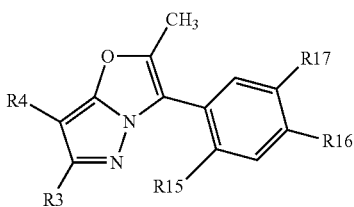

III in which $R^1$, $R^3$ and $R^4$ are each as hereinbefore defined;

$R^{15}$ and $R^{16}$, which may be the same or different, are each alkyl C1 to 6, alkoxy C1 to 6, halo, haloalkyl C1 to 6, haloalkoxy C1 to 6 or —$NR^5R^6$; and $R^{17}$ is hydrogen, alkyl C1 to 6, alkoxy C1 to 6, halo, haloalkyl C1 to 6, haloalkoxy C1 to 6 or —$NR^5R^6$;

$R^5$ and $R^6$ are each as hereinbefore as defined;

and isomers thereof;

in free form or as a pharmaceutically acceptable salt.

$R^{15}$ and $R^{16}$ may be the same, such as $R^{15}$ and $R^{16}$ are both halo, e.g. —Cl.

Alternatively, $R^{15}$, $R^{16}$ and $R^{17}$ may be selected from alkyl C1 to 6, e.g. methyl, and alkoxy C1 to 6, e.g. methoxy.

An alternative preferred group of compounds which may be mentioned are compounds of formula IV;

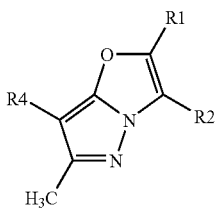

IV in which $R^1$, $R^2$ and $R^4$ are each as hereinbefore defined;

in free form or as a pharmaceutically acceptable salt.

In another aspect of the invention we provide a group of compounds which may be mentioned are compounds of formula V;

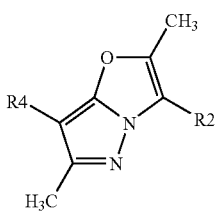

V in which $R^2$ and $R^4$ are each as hereinbefore defined;

and isomers thereof;

in free form or as a pharmaceutically acceptable salt.

In another aspect of the invention we provide a group of compounds which are compounds of formula I;

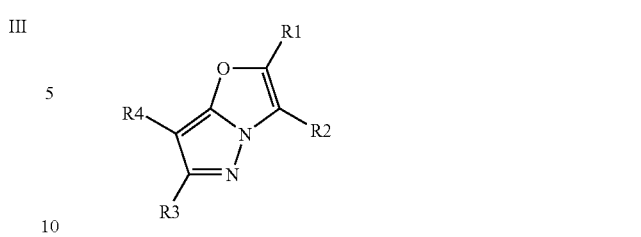

I in which $R^4$ is a 5- or 6-membered heteroaryl being optionally substituted by one or more substituents selected from the group alkyl C1 to 10, haloalkyl C1 to 10, hydroxyalkyl C1 to 10, alkoxy(C1 to 3)alkyl(C1 to 3), —$CO_2R^{19}$, —$CONR^{20}R^{21}$, or a 5- or 6-membered heterocycle or heteroaryl; and $R^1$, $R^2$, $R^3$, $R^{19}$, $R^{20}$ and $R^{21}$ are each as hereinbefore defined;

and isomers thereof;

in free form or as a pharmaceutically acceptable salt.

In a particular aspect of the invention we provide a group of compounds which may be mentioned which are compounds of formula I;

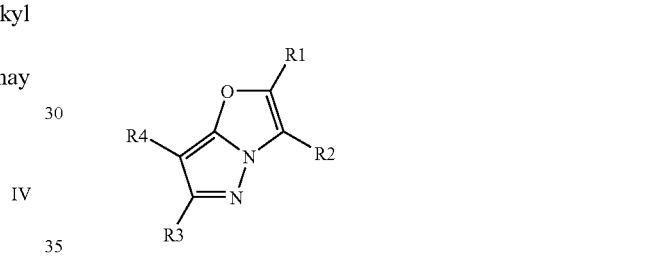

I in which $R^4$ is a triazole being optionally substituted by one or more substituents selected from the group alkyl C1 to 10, haloalkyl C1 to 10, hydroxyalkyl C1 to 10, alkoxy(C1 to 3)alkyl(C1 to 3), —$CO_2R^{19}$, —$CONR^{20}R^{21}$, or a 5- or 6-membered heterocycle or heteroaryl; and $R^1$, $R^2$, $R^3$, $R^{19}$, $R^{20}$ and $R^{21}$ are each as hereinbefore defined;

and isomers thereof;

in free form or as a pharmaceutically acceptable salt.

Acid addition salts may be produced from the free bases in known manner, and vice-versa.

Compounds of the present invention are either obtained in the free form, as a salt thereof, or as prodrug derivatives thereof.

As used herein, the term "pharmaceutically acceptable salt" refers to salts that retain the biological effectiveness and properties of the compounds of this invention and, which are not biologically or otherwise undesirable. In many cases, the compounds of the present invention are capable of forming acid and/or base salts by virtue of the presence of amino and/or carboxyl groups or groups similar thereto. Pharmaceutically acceptable acid addition salts can be formed with inorganic acids and organic acids, e.g., acetate, aspartate, benzoate, besylate, bicarbonate/carbonate, bisulphate/sulphate, borate, camsylate, citrate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulphate, naphthylate, 2-napsylate, nicotinate, nitrate, orotate, oxalate, palmitate, pamoate, phosphate/hydrogen phosphate/dihydrogen phosphate, saccharate, stearate, succinate, tartrate, tosylate and trifluoroacetate salts. Inorganic acids from which salts can be derived include, for example, hydrochloric acid, hydrobromic acid, sulfuric acid, nitric acid, phosphoric acid, and the like. Organic acids from which salts can be derived include, for example, acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like. Pharmaceutically acceptable base addition salts can be formed with inorganic and organic bases. Inorganic bases from which salts can be derived include, for example, sodium, potassium, lithium, ammonium, calcium, magnesium, iron, zinc, copper, manganese, aluminum, and the like; particularly preferred are the ammonium, potassium, sodium, calcium and magnesium salts. Organic bases from which salts can be derived include, for example, primary, secondary, and tertiary amines, substituted amines including naturally occurring substituted amines, cyclic amines, basic ion exchange resins, and the like, specifically such as isopropylamine, trimethylamine, diethylamine, triethylamine, tripropylamine, and ethanolamine. The pharmaceutically acceptable salts of the present invention can be synthesized from a parent compound, a basic or acidic moiety, by conventional chemical methods. Generally, such salts can be prepared by reacting free acid forms of these compounds with a stoichiometric amount of the appropriate base (such as Na, Ca, Mg, or K hydroxide, carbonate, bicarbonate, or the like), or by reacting free base forms of these compounds with a stoichiometric amount of the appropriate acid. Such reactions are typically carried out in water or in an organic solvent, or in a mixture of the two. Generally, non-aqueous media like ether, ethyl acetate, ethanol, isopropanol, or acetonitrile are preferred, where practicable. Lists of additional suitable salts can be found, e.g., in "Remington's Pharmaceutical Sciences", 20th ed., Mack Publishing Company, Easton, Pa., (1985); and in "Handbook of Pharmaceutical Salts: Properties, Selection, and Use" by Stahl and Wermuth (Wiley-VCH, Weinheim, Germany, 2002).

A prodrug is a compound which is converted to a therapeutically active compound after administration. For example, conversion may occur by hydrolysis of an ester group or some other biologically labile group. Prodrug preparation is well known in the art. For example "Prodrugs and Drug Delivery Systems," which is a chapter in Richard B. Silverman, *Organic Chemistry of Drug Design and Drug Action,* 2d Ed., Elsevier Academic Press: Amsterdam, 2004, pp. 496-557, provides further detail on the subject.

As used herein, the term "isomers" refers to different compounds that have the same molecular formula but differ in arrangement and configuration of the atoms. Also as used herein, the term "an optical isomer" or "a stereoisomer" refers to any of the various stereo isomeric configurations which may exist for a given compound of the present invention and includes geometric isomers. It is understood that a substituent may be attached at a chiral center of a carbon atom. Therefore, the invention includes enantiomers, diastereomers or racemates of the compound. "Enantiomers" are a pair of stereoisomers that are non-superimposable mirror images of each other. A 1:1 mixture of a pair of enantiomers is a "racemic" mixture. The term is used to designate a racemic mixture where appropriate. "Diastereoisomers" are stereoisomers that have at least two asymmetric atoms, but which are not mirror-images of each other. The absolute stereochemistry is specified according to the Cahn-Ingold-Prelog R-S system. When a compound is a pure enantiomer the stereochemistry at each chiral carbon may be specified by either R or S. Resolved compounds whose absolute configuration is unknown can be designated (+) or (−) depending on the direction (dextro- or levorotatory) which they rotate plane polarized light at the wavelength of the sodium D line. Certain of the compounds described herein contain one or more asymmetric centers and may thus give rise to enantiomers, diastereomers, and other stereoisomeric forms that may be defined, in terms of absolute stereochemistry, as (R)— or (S)—. The present invention is meant to include all such possible isomers, including racemic mixtures, optically pure forms and intermediate mixtures. Optically active (R)— and (S)-isomers may be prepared using chiral synthons or chiral reagents, or resolved using conventional techniques. If the compound contains a double bond, the substituent may be E or Z configuration. If the compound contains a disubstituted cycloalkyl, the cycloalkyl substituent may have a cis- or trans-configuration. All tautomeric forms are also intended to be included.

Compounds of formula (I) in optically pure form, where appropriate, can be obtained from the corresponding racemates according to well-known procedures, e.g., HPLC with chiral matrix. Alternatively, optically pure starting materials can be used.

Stereoisomeric mixtures, e.g., mixtures of diastereomers, can be separated into their corresponding isomers in a manner known per se by means of suitable separation methods. Diastereomeric mixtures, e.g., may be separated into their individual diastereomers by means of fractionated crystallisation, chromatography, solvent distribution and similar procedures. This separation may take place either at the level of a starting compound or in a compound of formula (I) itself. Enantiomers may be separated through the formation of diastereomeric salts, e.g., by salt formation with an enantiomer-pure chiral acid, or by means of chromatography, e.g., by HPLC, using chromatographic substrates with chiral ligands.

As used herein, the term "isomers" refers to different compounds that have the same molecular formula but differ in arrangement and configuration of the atoms. Also as used herein, the term "an optical isomer" or "a stereoisomer" refers to any of the various stereo isomeric configurations which may exist for a given compound of the present invention and includes geometric isomers. It is understood that a substituent may be attached at a chiral center of a carbon atom. Therefore, the invention includes enantiomers, diastereomers or racemates of the compound. "Enantiomers" are a pair of stereoisomers that are non-superimposable mirror images of each other. A 1:1 mixture of a pair of enantiomers is a "racemic" mixture. The term is used to designate a racemic mixture where appropriate. "Diastereoisomers" are stereoisomers that have at least two asymmetric atoms, but which are not mirror-images of each other. The absolute stereochemistry is specified according to the Cahn-Ingold-Prelog R-S system. When a compound is a pure enantiomer the stereochemistry at each chiral carbon may be specified by either R or S. Resolved compounds whose absolute configuration is unknown can be designated (+) or (−) depending on the direction (dextro- or levorotatory) which they rotate plane polarized light at the wavelength of the sodium D line. Certain of the compounds described herein contain one or more asymmetric centers and may thus give rise to enantiomers, diastereomers, and other stereoisomeric forms that may be defined, in terms of absolute stereochemistry, as (R)— or (S)—. The present invention is meant to include all such possible isomers, including racemic mixtures, optically pure forms and intermediate mixtures. Optically active (R)— and (S)-isomers may be prepared using chiral synthons or chiral reagents, or resolved using conventional techniques. If the compound contains a double bond, the substituent may be E or Z configuration. If the compound contains a disubstituted cycloalkyl, the cycloalkyl substituent may have a cis- or trans-configuration. All tautomeric forms are also intended to be included.

Any asymmetric atom (e.g., carbon or the like) of the compound(s) of the present invention can be present in racemic or enantiomerically enriched, for example the (R)—, (S)—or (R,S)-configuration. In certain embodiments, each asymmetric atom has at least 50% enantiomeric excess, at least 60% enantiomeric excess, at least 70% enantiomeric excess, at least 80% enantiomeric excess, at least 90% enantiomeric excess, at least 95% enantiomeric excess, or at least 99% enantiomeric excess in the (R)— or (S)-configuration. Substituents at atoms with unsaturated bonds may, if possible, be present in cis-(Z)- or trans-(E)-form.

Accordingly, as used herein a compound of the present invention can be in the form of one of the possible isomers, rotamers, atropisomers, tautomers or mixtures thereof, for example, as substantially pure geometric (cis or trans) isomers, diastereomers, optical isomers (antipodes), racemates or mixtures thereof.

Any resulting mixtures of isomers can be separated on the basis of the physicochemical differences of the constituents, into the pure or substantially pure geometric or optical isomers, diastereomers, racemates, for example, by chromatography and/or fractional crystallization.

Any resulting racemates of final products or intermediates can be resolved into the optical antipodes by known methods, e.g., by separation of the diastereomeric salts thereof, obtained with an optically active acid or base, and liberating the optically active acidic or basic compound. In particular, a basic moiety may thus be employed to resolve the compounds of the present invention into their optical antipodes, e.g., by fractional crystallization of a salt formed with an optically active acid, e.g., tartaric acid, dibenzoyl tartaric acid, diacetyl tartaric acid, di-O,O'-p-toluoyl tartaric acid, mandelic acid, malic acid or camphor-10-sulfonic acid. Racemic products can also be resolved by chiral chromatography, e.g., high pressure liquid chromatography (HPLC) using a chiral adsorbent.

According to a further aspect of the invention we provide a method of treatment or alleviation of any state with increased endogenous level of CRF or in which the HPA (hypothalamic pituitary axis) is disregulated, or of various diseases induced or facilitated by CRF which comprises administering to a mammal a therapeutically effective amount of a compound of formula I, or a salt thereof, as hereinbefore described.

We further provide a pharmaceutical composition comprising a compound of formula I as hereinbefore described, in free form or in pharmaceutically acceptable salt form, in association with a pharmaceutically acceptable adjuvant, diluent or carrier.

The pharmaceutical composition can be formulated for particular routes of administration such as oral administration, parenteral administration, and rectal administration, etc. In addition, the pharmaceutical compositions of the present invention can be made up in a solid form including capsules, tablets, pills, granules, powders or suppositories, or in a liquid form including solutions, suspensions or emulsions. The pharmaceutical compositions can be subjected to conventional pharmaceutical operations such as sterilization and/or can contain conventional inert diluents, lubricating agents, or buffering agents, as well as adjuvants, such as preservatives, stabilizers, wetting agents, emulsifers and buffers etc. Typically, the pharmaceutical compositions are tablets and gelatin capsules comprising the active ingredient together with
 a) diluents, e.g., lactose, dextrose, sucrose, mannitol, sorbitol, cellulose and/or glycine;
 b) lubricants, e.g., silica, talcum, stearic acid, its magnesium or calcium salt and/or polyethyleneglycol; for tablets also
 c) binders, e.g., magnesium aluminum silicate, starch paste, gelatin, tragacanth, methylcellulose, sodium carboxymethylcellulose and/or polyvinylpyrrolidone; if desired
 d) disintegrants, e.g., starches, agar, alginic acid or its sodium salt, or effervescent mixtures; and/or
 e) absorbents, colorants, flavors and sweeteners.

Tablets may be either film coated or enteric coated according to methods known in the art.

Suitable compositions for oral administration include an effective amount of a compound of the invention in the form of tablets, lozenges, aqueous or oily suspensions, dispersible powders or granules, emulsion, hard or soft capsules, or syrups or elixirs. Compositions intended for oral use are prepared according to any method known in the art for the manufacture of pharmaceutical compositions and such compositions can contain one or more agents selected from the group consisting of sweetening agents, flavoring agents, coloring agents and preserving agents in order to provide pharmaceutically elegant and palatable preparations. Tablets contain the active ingredient in admixture with nontoxic pharmaceutically acceptable excipients which are suitable for the manufacture of tablets. These excipients are, for example, inert diluents, such as calcium carbonate, sodium carbonate, lactose, calcium phosphate or sodium phosphate; granulating and disintegrating agents, for example, corn starch, or alginic acid; binding agents, for example, starch, gelatin or acacia; and lubricating agents, for example magnesium stearate, stearic acid or talc. The tablets are uncoated or coated by known techniques to delay disintegration and absorption in the gastrointestinal tract and thereby provide a sustained action over a longer period. For example, a time delay material such as glyceryl monostearate or glyceryl distearate can be employed. Formulations for oral use can be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example, peanut oil, liquid paraffin or olive oil.

Certain injectable compositions are aqueous isotonic solutions or suspensions, and suppositories are advantageously prepared from fatty emulsions or suspensions. Said compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. Said compositions are prepared according to conventional mixing, granulating or coating methods, respectively, and contain about 0.1-75%, or contain about 1-50%, of the active ingredient.

Suitable compositions for transdermal application include an effective amount of a compound of the invention with carrier. Carriers include absorbable pharmacologically acceptable solvents to assist passage through the skin of the host. For example, transdermal devices are in the form of a bandage comprising a backing member, a reservoir containing the compound optionally with carriers, optionally a rate controlling barrier to deliver the compound of the skin of the host at a controlled and predetermined rate over a prolonged period of time, and means to secure the device to the skin.

Suitable compositions for topical application, e.g., to the skin and eyes, include aqueous solutions, suspensions, ointments, creams, gels or sprayable formulations, e.g., for delivery by aerosol or the like. Such topical delivery systems will in particular be appropriate for dermal application, e.g., for the treatment of skin cancer, e.g. for prophylactic use in sun creams, lotions, sprays and the like. They are thus particularly suited for use in topical, including cosmetic, formulations well-known in the art. Such may contain solubilizers, stabilizers, tonicity enhancing agents, buffers and preservatives.

As used herein a topical application may also pertain to an inhalation or to an intranasal application. They are conveniently delivered in the form of a dry powder (either alone, as a mixture, for example a dry blend with lactose, or a mixed component particle, for example with phospholipids) from a dry powder inhaler or an aerosol spray presentation from a pressurised container, pump, spray, atomizer or nebuliser, with or without the use of a suitable propellant.

The pharmaceutical composition or combination of the present invention can be in unit dosage of about 1-1000 mg of active ingredient(s) for a subject of about 50-70 kg, or about 1-500 mg or about 1-250 mg or about 1-150 mg or about 0.5-100 mg, or about 1-50 mg of active ingredients. The therapeutically effective dosage of a compound, the pharmaceutical composition, or the combinations thereof, is dependent on the species of the subject, the body weight, age and individual condition, the disorder or disease or the severity thereof being treated. A physician, clinician or veterinarian of ordinary skill can readily determine the effective amount of each of the active ingredients necessary to prevent, treat or inhibit the progress of the disorder or disease.

The above-cited dosage properties are demonstrable in vitro and in vivo tests using advantageously mammals, e.g., mice, rats, dogs, monkeys or isolated organs, tissues and preparations thereof. The compounds of the present invention can be applied in vitro in the form of solutions, e.g., preferably aqueous solutions, and in vivo either enterally, parenterally, advantageously intravenously, e.g., as a suspension or in aqueous solution. The dosage in vitro may range between about $10^{-3}$ molar and $10^{-9}$ molar concentrations. A therapeutically effective amount in vivo may range depending on the route of administration, between about 0.1-500 mg/kg, or between about 1-100 mg/kg.

The activity of a compound according to the present invention can be assessed by the following in vitro & in vivo methods.

As used herein, the term "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, binders, excipients, disintegration agents, lubricants, sweetening agents, flavoring agents, dyes, such like materials and combinations thereof, as would be known to one of ordinary skill in the art (see, for example, Remington's Pharmaceutical Sciences, 18th Ed. Mack Printing Company, 1990, pp. 1289-1329). Except insofar as any conventional carrier is incompatible with the active ingredient, its use in the therapeutic or pharmaceutical compositions is contemplated.

The term "a therapeutically effective amount" of a compound of the present invention refers to an amount of the compound of the present invention that will elicit the biological or medical response of a subject, for example, reduction or inhibition of an enzyme or a protein activity, or ameliorate symptoms, alleviate conditions, slow or delay disease progression, or prevent a disease, etc. In one non-limiting embodiment, the term "a therapeutically effective amount" refers to the amount of the compound of the present invention that, when administered to a subject, is effective to (1) at least partially alleviating, inhibiting, preventing and/or ameliorating a condition, or a disorder or a disease (i) mediated by CRF, or (ii) associated with CRF activity, or (iii) characterized by abnormal activity of CRF; or (2) reducing or inhibiting the activity of CRF; or (3) reducing or inhibiting the expression of CRF. In another non-limiting embodiment, the term "a therapeutically effective amount" refers to the amount of the compound of the present invention that, when administered to a cell, or a tissue, or a non-cellular biological material, or a medium, is effective to at least partially reducing or inhibiting the activity of CRF; or at least partially reducing or inhibiting the expression of CRF. The meaning of the term "a therapeutically effective amount" as illustrated in the above embodiment for CRF also applies by the same means to any other relevant proteins/peptides/enzymes.

As used herein, the term "subject" refers to an animal. Preferably, the animal is a mammal. A subject also refers to for example, primates (e.g., humans), cows, sheep, goats, horses, dogs, cats, rabbits, rats, mice, fish, birds and the like. In a preferred embodiment, the subject is a human.

As used herein, the term "inhibition" or "inhibiting" refers to the reduction or suppression of a given condition, symptom, or disorder, or disease, or a significant decrease in the baseline activity of a biological activity or process.

As used herein, the term "treating" or "treatment" of any disease or disorder refers in one embodiment, to ameliorating the disease or disorder (i.e., slowing or arresting or reducing the development of the disease or at least one of the clinical symptoms thereof). In another embodiment "treating" or "treatment" refers to alleviating or ameliorating at least one physical parameter including those which may not be discernible by the patient. In yet another embodiment, "treating" or "treatment" refers to modulating the disease or disorder, either physically, (e.g., stabilization of a discernible symptom), physiologically, (e.g., stabilization of a physical parameter), or both. In yet another embodiment, "treating" or "treatment" refers to preventing or delaying the onset or development or progression of the disease or disorder.

As used herein, the term "a," "an," "the" and similar terms used in the context of the present invention (especially in the context of the claims) are to be construed to cover both the singular and plural unless otherwise indicated herein or clearly contradicted by the context.

All methods described herein can be performed in any suitable order unless otherwise indicated herein or otherwise clearly contradicted by context. The use of any and all examples, or exemplary language (e.g. "such as") provided herein is intended merely to better illuminate the invention and does not pose a limitation on the scope of the invention otherwise claimed.

Compounds of the present invention are either obtained in the free form, as a salt thereof, or as prodrug derivatives thereof.

When both a basic group and an acid group are present in the same molecule, the compounds of the present invention may also form internal salts, e.g., zwitterionic molecules.

The present invention also provides pro-drugs of the compounds of the present invention that converts in vivo to the compounds of the present invention. A pro-drug is an active or inactive compound that is modified chemically through in vivo physiological action, such as hydrolysis, metabolism and the like, into a compound of this invention following administration of the prodrug to a subject. The suitability and techniques involved in making and using pro-drugs are well known by those skilled in the art. Prodrugs can be conceptually divided into two non-exclusive categories, bioprecursor prodrugs and carrier prodrugs. See *The Practice of Medicinal Chemistry*, Ch. 31-32 (Ed. Wermuth, Academic Press, San Diego, Calif., 2001). Generally, bioprecursor prodrugs are compounds, which are inactive or have low activity compared to the corresponding active drug compound, that contain one or more protective groups and are converted to an active form by metabolism or solvolysis. Both the active drug form and any released metabolic products should have acceptably low toxicity.

Carrier prodrugs are drug compounds that contain a transport moiety, e.g., that improve uptake and/or localized delivery to a site(s) of action. Desirably for such a carrier prodrug, the linkage between the drug moiety and the transport moiety is a covalent bond, the prodrug is inactive or less active than the drug compound, and any released transport moiety is acceptably non-toxic. For prodrugs where the transport moiety is intended to enhance uptake, typically the release of the transport moiety should be rapid. In other cases, it is desirable to utilize a moiety that provides slow release, e.g., certain polymers or other moieties, such as cyclodextrins. Carrier prodrugs can, for example, be used to improve one or more of the following properties: increased lipophilicity, increased duration of pharmacological effects, increased site-specificity, decreased toxicity and adverse reactions, and/or improvement in drug formulation (e.g., stability, water solubility, suppression of an undesirable organoleptic or physiochemical property). For example, lipophilicity can be increased by esterification of (a) hydroxyl groups with lipophilic carboxylic acids (e.g., a carboxylic acid having at least one lipophilic moiety), or (b) carboxylic acid groups with lipophilic alcohols (e.g., an alcohol having at least one lipophilic moiety, for example aliphatic alcohols).

Exemplary prodrugs are, e.g., esters of free carboxylic acids and S-acyl derivatives of thiols and O-acyl derivatives of alcohols or phenols, wherein acyl has a meaning as defined herein. Preferred are pharmaceutically acceptable ester derivatives convertible by solvolysis under physiological conditions to the parent carboxylic acid, e.g., lower alkyl esters, cycloalkyl esters, lower alkenyl esters, benzyl esters, mono- or di-substituted lower alkyl esters, such as the α-(amino, mono- or di-lower alkylamino, carboxy, lower alkoxycarbonyl)-lower alkyl esters, the α-(lower alkanoyloxy, lower alkoxycarbonyl or di-lower alkylaminocarbonyl)-lower alkyl esters, such as the pivaloyloxymethyl ester and the like conventionally used in the art. In addition, amines have been masked as arylcarbonyloxymethyl substituted derivatives which are cleaved by esterases in vivo releasing the free drug and formaldehyde (Bundgaard, *J. Med. Chem.* 2503 (1989)). Moreover, drugs containing an acidic NH group, such as imidazole, imide, indole and the like, have been masked with N-acyloxymethyl groups (Bundgaard, *Design of Prodrugs*, Elsevier (1985)). Hydroxy groups have been masked as esters and ethers. EP 039,051 (Sloan and Little) discloses Mannich-base hydroxamic acid prodrugs, their preparation and use.

Furthermore, the compounds of the present invention, including their salts, can also be obtained in the form of their hydrates, or include other solvents used for their crystallization.

The present invention includes all pharmaceutically acceptable isotopically-labeled compounds of the invention, i.e. compounds of formula (I), wherein (1) one or more atoms are replaced by atoms having the same atomic number, but an atomic mass or mass number different from the atomic mass or mass number usually found in nature, and/or (2) the isotopic ratio of one or more atoms is different from the naturally occurring ratio.

Examples of isotopes suitable for inclusion in the compounds of the invention comprises isotopes of hydrogen, such as $^2$H and $^3$H, carbon, such as $^{11}$C, $^{13}$C and $^{14}$C, chlorine, such as $^{36}$Cl, fluorine, such as $^{18}$F, iodine, such as $^{123}$I and $^{125}$I, nitrogen, such as $^{13}$N and $^{15}$N, oxygen, such as $^{15}$O, $^{17}$O and $^{18}$O, phosphorus, such as $^{32}$P, and sulphur, such as $^{35}$S.

Certain isotopically-labeled compounds of formula (I), for example, those incorporating a radioactive isotope, are useful in drug and/or substrate tissue distribution studies. The radioactive isotopes tritium, i.e. $^3$H, and carbon-14, i.e. $^{14}$C, are particularly useful for this purpose in view of their ease of incorporation and ready means of detection.

Substitution with heavier isotopes such as deuterium, i.e. $^2$H, may afford certain therapeutic advantages resulting from greater metabolic stability, for example, increased in vivo half-life or reduced dosage requirements, and hence may be preferred in some circumstances.

Substitution with positron emitting isotopes, such as $^{11}$C, $^{18}$F, $^{15}$O and $^{13}$N, can be useful in Positron Emission Topography (PET) studies for examining substrate receptor occupancy.

Isotopically-labeled compounds of formula (I) can generally be prepared by conventional techniques known to those skilled in the art or by processes analogous to those described in the accompanying Examples and Preparations using an appropriate isotopically-labeled reagents in place of the non-labeled reagent previously employed.

Pharmaceutically acceptable solvates in accordance with the invention include those wherein the solvent of crystallization may be isotopically substituted, e.g. $D_2O$, $d_6$-acetone, d6-DMSO.

Compounds of the invention, i.e. compounds of formula I that contain groups capable of acting as donors and/or acceptors for hydrogen bonds may be capable of forming co-crystals with suitable co-crystal formers. These co-crystals may be prepared from compounds of formula I by known co-crystal forming procedures. Such procedures include grinding, heating, co-subliming, co-melting, or contacting in solution compounds of formula I with the co-crystal former under crystallization conditions and isolating co-crystals thereby formed. Suitable co-crystal formers include those described in WO 2004/078163. Hence the invention further provides co-crystals comprising a compound of formula I.

The pharmaceutical compositions for separate administration of the combination partners and for the administration in a fixed combination, i.e., a single galenical composition comprising at least two combination partners, according to the invention can be prepared in a manner known per se and are those suitable for enteral, such as oral or rectal, and parenteral administration to mammals, including man, comprising a therapeutically effective amount of at least one pharmacologically active combination partner alone or in combination with one or more pharmaceutically acceptable carriers, especially suitable for enteral or parenteral application.

Pharmaceutical compositions contain, e.g., from about 0.1% to about 99.9%, preferably from about 20% to about 60%, of the active ingredients. Pharmaceutical preparations for the combination therapy for enteral or parenteral administration are, e.g., those in unit dosage form, such as tablets including sugar-coated tablets, capsules, suppositories and ampoules. These are prepared in a manner known, per se, e.g., by means of conventional mixing, granulating, sugar-coating, dissolving or lyophilizing processes. It will be appreciated that the unit content of a combination partner contained in an individual dose of each dosage form need not in itself constitute an effective amount since the necessary effective amount can be reached by administration of a plurality of dosage units.

The present invention includes all pharmaceutically acceptable isotopically-labelled compounds of formula (I) wherein one or more atoms are replaced by atoms having the same atomic number, but an atomic mass or mass number different from the atomic mass or mass number usually found in nature.

Examples of isotopes suitable for inclusion in the compounds of the invention include isotopes of hydrogen, such as 2H and 3H, carbon, such as 11C, 13C and 14C, chlorine, such as 36Cl, fluorine, such as 18F, iodine, such as 123I and 125I, nitrogen, such as 13N and 15N, oxygen, such as 15O, 17O and 18O, phosphorus, such as 32P, and sulphur, such as 35S.

Substitution with heavier isotopes such as deuterium, i.e. 2H, may afford certain therapeutic advantages resulting from greater metabolic stability, for example, increased in vivo half-life or reduced dosage requirements, and hence may be preferred in some circumstances.

Isotopically-labeled compounds of formula (I) can generally be prepared by conventional techniques known to those skilled in the art or by processes analogous to those described in the accompanying Examples and Preparations using an appropriate isotopically-labeled reagents in place of the non-labeled reagent previously employed.

According to an additional aspect of the invention we provide a process for the manufacture of a compound of formula I as hereinbefore described which comprises one or more of the following steps;

(i) the condensation of a compound of formula VI;

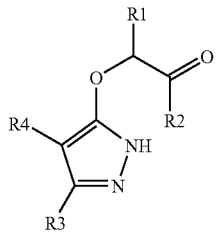

VI in which $R^1$, $R^2$, $R^3$ and $R^4$ are each as hereinbefore defined;

(ii) reacting a compound of formula VII;

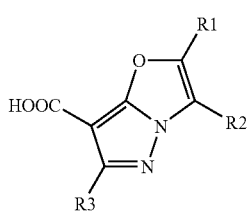

VII in which $R^1$, $R^2$ and $R^3$ are each as hereinbefore defined; with a compound of formula VIII

  NHR$^{13}$R$^{14}$    VIII in which $R^{13}$ and $R^{14}$ are each as hereinbefore defined;

(iii) reacting a compound of formula IX;

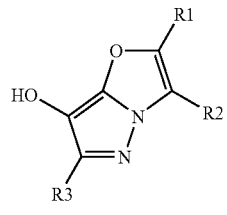

IX in which $R^1$, $R^2$ and $R^3$ are each as hereinbefore defined; with a compound of formula X

 R$^7$OH    X in which $R^7$ is as hereinbefore defined;

(iv) reducing a compound of formula XI;

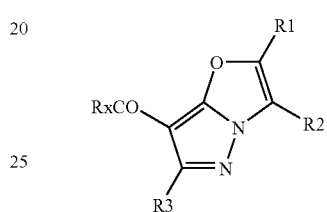

XI in which $R^1$, $R^2$ and $R^3$ are each as hereinbefore defined; and $R^x$ is alkyl C1 to 5;

(v) reacting a compound of formula XII;

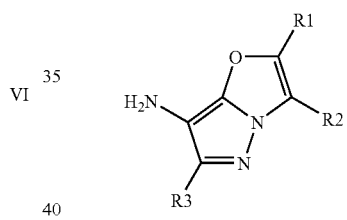

XII in which $R^1$, $R^2$ and $R^3$ are each as hereinbefore defined; with a compound of formula XIII or XIV;

 R$^{12}$CHO    XIII

 R$^{17}$COR$^{18}$    XIV in which $R^{12}$ is as hereinbefore defined; and
$R^{17}$ and $R^{18}$, which may be the same or different, are each alkyl C1 to 6; or (vi) reacting a compound of formula XV;

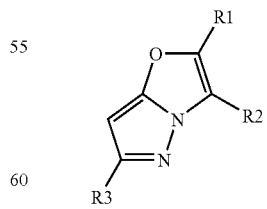

XV in which $R^1$, $R^2$ and $R^3$ are each as hereinbefore defined; with a compound of formula XVI;

 R$^8$R$^9$NH    XVI in which $R^8$ and $R^9$ are as hereinbefore defined.

In any additional process steps, carried out as desired, functional groups of the starting compounds which should not take part in the reaction may be present in unprotected form or may be protected e.g., by one or more of the protecting groups mentioned below. The protecting groups are then wholly- or partly-removed according to one of the methods described there.

The protecting groups may already be present in precursors and should protect the functional groups concerned against unwanted secondary reactions. It is a characteristic of protecting groups that they lend themselves readily, i.e., without undesired secondary reactions, to removal, typically by solvolysis, reduction, photolysis or also by enzyme activity, e.g., under conditions analogous to physiological conditions, and that they are not present in the end-products. The skilled artisan knows, or can easily establish, which protecting groups are suitable with the reactions mentioned hereinabove and hereinafter.

The protection of such functional groups by protecting groups, the protecting groups themselves, and their removal reactions are described, e.g., in standard reference works, such as J. F. W. McOmie, *Protective Groups in Organic Chemistry*, Plenum Press, London and NY (1973); T. W. Greene, *Protective Groups in Organic Synthesis*, Wiley, N.Y. (1981); *The Peptides*; Volume 3, E. Gross and J Meienhofer, Eds., Academic Press, London and NY (1981); *Methoden der organischen Chemie* (*Methods of organic chemistry*), Houben Weyl, 4$^{th}$ Edition, Volume 15/1, Georg Thieme Verlag, Stuttgart (1974); H. D. Jakubke and H. Jescheit, *Aminosauren, Peptide, Proteine* (*Amino acids, peptides, proteins*), Verlag Chemie, Weinheim, Deerfield Beach, and Basel (1982); and Jochen Lehmann, *Chemie der Kohlenhydrate: Monosaccharide und Derivate* (*Chemistry of carbohydrates monosaccharides and derivates*) Georg Thieme Verlag., Stuttgart (1974).

All process steps described herein can be carried out under known reaction conditions, preferably under those specifically mentioned, in the absence of or usually in the presence of solvents or diluents, preferably such as are inert to the reagents used and able to dissolve these, in the absence or presence of catalysts, condensing agents or neutralizing agents, e.g., ion exchangers, typically cation exchangers, e.g., in the H+ form, depending on the type of reaction and/or reactants at reduced, normal or elevated temperature, e.g., in the range from −100° C. to about 190° C., preferably from about −80° C. to about 150° C., e.g., at −80° C. to 60° C., at room temperature, at −20° C. to 40° C. or at the boiling point of the solvent used, under atmospheric pressure or in a closed vessel, where appropriate under pressure, and/or in an inert atmosphere, e.g., under argon or nitrogen.

The invention further includes any variant of the present processes, in which an intermediate product obtainable at any stage thereof is used as starting material and the remaining steps are carried out, or in which the starting materials are formed in situ under the reaction conditions, or in which the reaction components are used in the form of their salts or optically pure antipodes.

Compounds of the invention and intermediates can also be converted into each other according to methods generally known per se.

Certain of the intermediates used in the processes as hereinbefore described are novel per se. Therefore, according to a further aspect of the invention we provide a compound of formula VI;

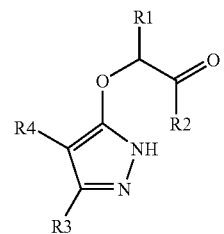

VI in which $R^1$, $R^2$, $R^3$ and $R^4$ are each as hereinbefore defined; a compound of formula VII;

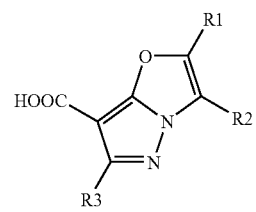

VII in which $R^1$, $R^2$ and $R^3$ are each as hereinbefore defined; a compound of formula IX;

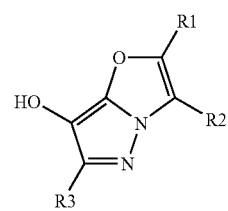

IX in which $R^1$, $R^2$ and $R^3$ are each as hereinbefore defined; reducing a compound of formula XI;

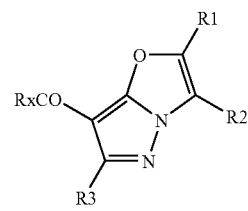

XI in which $R^1$, $R^2$ and $R^3$ are each as hereinbefore defined; and $R^x$ is alkyl C1 to 5;

a compound of formula XII;

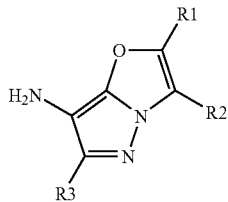

XII in which $R^1$, $R^2$ and $R^3$ are each as hereinbefore defined;
a compound of formula XV; and

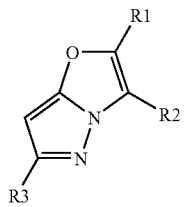

XV in which $R^1$, $R^2$ and $R^3$ are each as hereinbefore defined.

Compounds of formula I may be prepared by the general reactions (it should be noted that the group R referred to in the reaction sequences below are for illustrative purposes only and do not precisely correspond to the R groups hereinbefore defined).

Referring to the examples that follow, compounds of the preferred embodiments are synthesized using the methods described herein, or other methods, which are known in the art.

It should be understood that the organic compounds according to the preferred embodiments may exhibit the phenomenon of tautomerism. As the chemical structures within this specification can only represent one of the possible tautomeric forms, it should be understood that the preferred embodiments encompasses any tautomeric form of the drawn structure.

It is understood that the invention is not limited to the embodiments set forth herein for illustration, but embraces all such forms thereof as come within the scope of the above disclosure.

EXPERIMENTAL DETAILS

General Methods $^1$H-NMR: Run on either Bruker Ultrashield™ 400 (400 MHz) spectrometer or are run on open access Bruker AVANCE 400 NMR spectrometers using ICON-NMR. Spectra are measured at 298K and are referenced using the solvent peak, chemical shifts (δ-values) are reported in ppm, coupling constants (J) are given in Hz, spectra splitting pattern are designated as singlet (s), doublet (d), triplet (t), quadruplet (q), multiplet or more overlapping signals (m), broad signal (br), solvent is given in parentheses.

MS: These are either Agilent 1100 HPLC/Micromass Platform Mass Spectrometer combinations or Waters Acquity UPLC with SQD Mass Spectrometer or Waters Alliance HT HPLC system equipped with a MS detector Waters MicromassZQ or Waters Micromass Plattform LCZ system. Mass spectra are run on LCMS systems using electrospray ionization. [M+H]$^+$ refers to mono-isotopic molecular weights.

HPLC: Waters Alliance HPLC system, retention times for system A ($^A$t$_{Ret}$) are reported in min, linear gradient 5-100% CH$_3$CN and H$_2$O (0.1% TFA) in 4 min+0.5 min 100% CH$_3$CN, PDA MaxPlot detection (210.0 nm to 400.0 nm), flow rate 3 ml/min at 35° C., the column is a Sunfire™ C18, 4.6×20 mm, 3.5 µm.

prep-HPLC: Waters HPLC prep-system, UV detector Waters 2487 Dual λ Absorbance Detector or MS detector Waters micromassZQ, reversed phase column SunFire™ Prep, C18 OBD, 100×30 mm, 5 µm, or 100×19 mm, 5 µm, gradient elution (CH$_3$CN/water with 0.1% TFA), generally product obtained as a TFA salt after lyophilization.

TLC: Precoated silica gel 60 F$_{254}$ glass plates (Merck), visualization by UV light (254 nm).

The various starting materials, intermediates, and compounds of the preferred embodiments may be isolated and purified, where appropriate, using conventional techniques such as precipitation, filtration, crystallization, evaporation, distillation, and chromatography. Unless otherwise stated, all starting materials are obtained from commercial suppliers and used without further purification. Salts may be prepared from compounds by known salt-forming procedures.

The following examples are intended to illustrate the invention and are not to be construed as being limitations thereon. Temperatures are given in degrees centigrade. If not mentioned otherwise, all evaporations are performed under reduced pressure, preferably between about 15 mm Hg and 100 mm Hg (=20-133 mbar). The structure of final products, intermediates and starting materials is confirmed by standard analytical methods, e.g., spectroscopic characteristics, e.g., MS, NMR. Abbreviations used are those conventional in the art.

Abbreviations

NMP N-methylpyrrolidine
THF tetrahydrofuran
MeOH methanol
DCM dichloromethane
EtOAc ethyl acetate
EtOH ethanol
LCMS liquid chromatographic mass spectroscopy
TEA triethylamine
TFA trifluoroacetic acid
HPLC high performance liquid chromatography
CDI carbonyl diimidazole
bp boiling point
DCE 1,2-dichloroethane
DCM dichloromethane
DEAD Diethyl azodicarboxylate
DIPEA N,N-diisopropylethylamine
DIBAL-H Diisobutylaluminium hydride
DMF N,N-dimethylformamide
DMSO dimethylsulfoxide
eq. equivalent
h hour
HATU O-(7-azabenzotriazol-1-yl)-N,N,N',N'-tetramethyluronium hexafluorophosphate
HPLC high pressure liquid chromatography
min minute
MS mass spectroscopy
MeI methyl iodide
NBS N-bromosuccinimide
NMM N-methylmorpholine
NMR nuclear magnetic resonance
O/N overnight
R$_F$ retention factor
RT room temperature
TBME tert-butyl-methylether
TLC thin layer chromatography
prep-HPLC preparative high pressure liquid chromatography

Example 1.0

3-(2,4-Dichloro-phenyl)-6-ethyl-2-methyl-pyrazolo[5,1-b]oxazole-7-carboxylic acid cyclopropylmethyl-propyl-amide

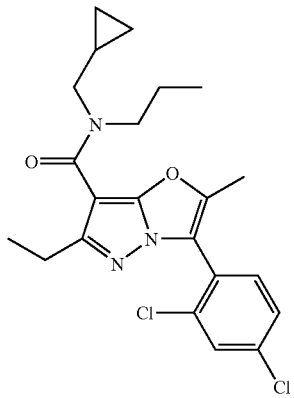

The following Schemes, Tables and protocols describe the preparation of intermediates and subsequently final compounds. The compounds and procedures outlined are meant to be illustrative and not exhaustive:

Preparation of Final Compounds

To a stirred solution of 3-(2,4-dichloro-phenyl)-6-ethyl-2methyl-pyrazolo[5,1-b]oxazole-7-carboxylic acid (Intermediate IA) (37 mg, 0.11 mmol, 1 eq.) in DMF (0.8 ml) is successively added cyclopropylmethyl-propylamine (0.017 ml, 0.12 mmol, 1.1 eq.), DIPEA (0.038 ml, 0.22 mmol, 2 eq.) and HATU (46 mg, 0.12 mmol, 1.1 eq.) at RT. The reaction mixture is heated at 50° C. for 2 h then poured into EtOAc and washed with $K_2CO_3$ 2M in water (2×). The organic layer is dried over $Na_2SO_4$, filtered and concentrated to dryness and the resulting crude residue is purified by column chromatography ($SiO_2$; gradient elution iso-hexane/EtOAc 6:1 to 1:1) to yield the title compound as a yellow oil. MS: m/z 434.3 $[M+H]^+$; $^1H$ NMR (400 MHz, DMSO-$d_6$) δ 7.90 (1H, d), 7.73 (1H, d), 7.65 (1H, dd), 3.46 (2H, t), 3.30 (2H, s), 2.70 (2H, q), 2.34 (3H, s), 1.60 (2H, m), 1.11 (3H, t), 1.02 (1H, m), 0.63 (3H, m), 0.48 (2H, m), 0.20 (2H, m).

The compounds of the following tabulated Examples are prepared by a similar method to that of Example 1 using the appropriate pyrazolo oxazole carboxylic acid starting materials and amine.

TABLE 1

| Ex. | Structure | $[M + H]^+$ | Name |
|---|---|---|---|
| 1.1 | 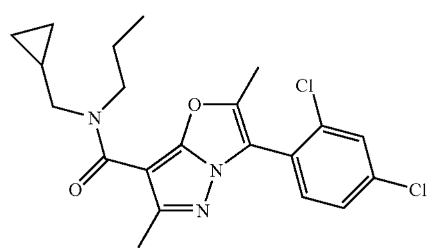 | 420.3 | 3-(2,4-Dichloro-phenyl)-2,6-dimethyl-pyrazolo[5,1-b]oxazole-7-carboxylic acid cyclopropylmethyl-propyl-amide |
| 1.2 | 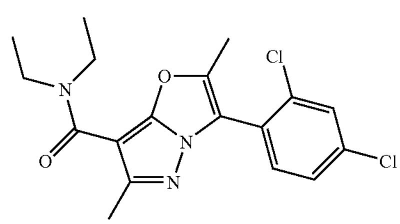 | 380.1 | 3-(2,4-Dichloro-phenyl)-2,6-dimethyl-pyrazolo[5,1-b]oxazole-7-carboxylic acid diethylamide |
| 1.3 | 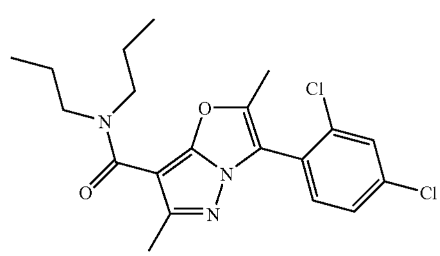 | 480.3 | 3-(2,4-Dichloro-phenyl)-2,6-dimethyl-pyrazolo[5,1-b]oxazole-7-carboxylic acid dipropylamide |

TABLE 1-continued

| Ex. | Structure | [M + H]+ | Name |
|---|---|---|---|
| 1.4 | 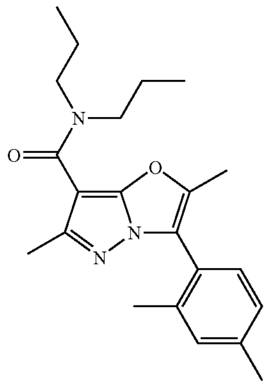 | 368.4 | 3-(2,4-Dimethyl-phenyl)-2,6-dimethyl-pyrazolo[5,1-b]oxazole-7-carboxylic acid dipropylamide |
| 1.5 | 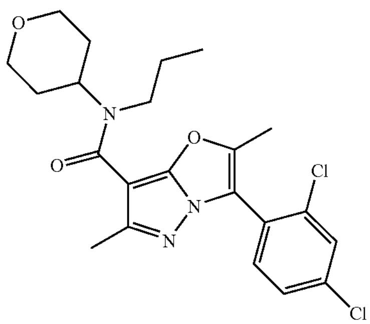 | 450.3 | 3-(2,4-Dichloro-phenyl)-2,6-dimethyl-pyrazolo[5,1-b]oxazole-7-carboxylic acid propyl-(tetrahydro-pyran-4-yl)-amide |
| 1.6 | 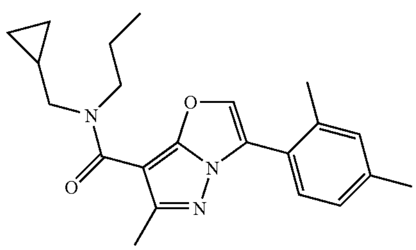 | 366.5 | 3-(2,4-Dimethyl-phenyl)-6-methyl-pyrazolo[5,1-b]oxazole-7-carboxylic acid cyclopropylmethyl-propyl-amide |
| 1.7 | 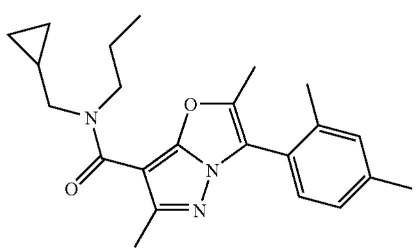 | 380.4 | 3-(2,4-Dimethyl-phenyl)-2,6-dimethyl-pyrazolo[5,1-b]oxazole-7-carboxylic acid cyclopropylmethyl-propyl-amide |
| 1.8 | 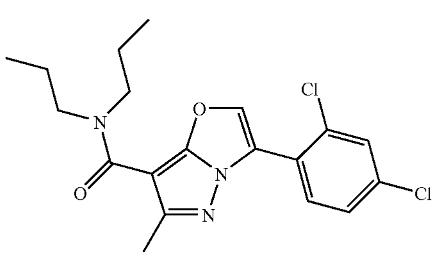 | 394.2 | 3-(2,4-Dichloro-phenyl)-6-methyl-pyrazolo[5,1-b]oxazole-7-carboxylic acid dipropylamide |

TABLE 1-continued

| Ex. | Structure | [M + H]+ | Name |
|---|---|---|---|
| 1.9 | 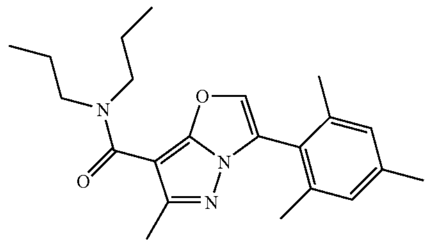 | 368.3 | 6-Methyl-3-(2,4,6-trimethyl-phenyl)-pyrazolo[5,1-b]oxazole-7-carboxylic acid dipropylamide |
| 1.10 | 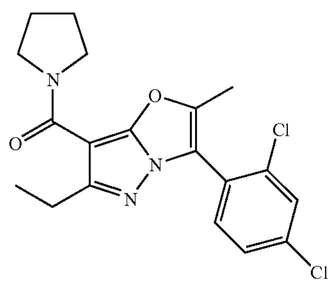 | 392.2 | [3-(2,4-Dichloro-phenyl)-6-ethyl-2-methyl-pyrazolo[5,1-b]oxazol-7-yl]-pyrrolidin-1-yl-methanone |
| 1.11 | 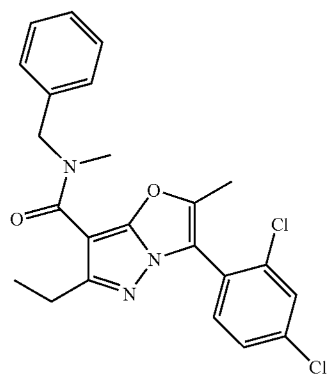 | 442.3 | 3-(2,4-Dichloro-phenyl)-6-ethyl-2-methyl-pyrazolo[5,1-b]oxazole-7-carboxylic acid benzyl-methyl amide |
| 1.12 | 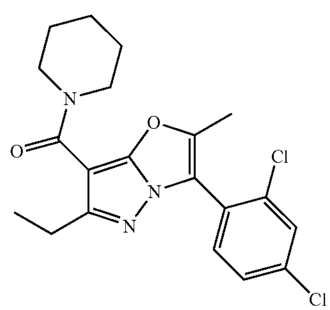 | 406.3 | [3-(2,4-Dichloro-phenyl)-6-ethyl-2-methyl-pyrazolo[5,1-b]oxazol-7-yl]-piperidin-1-yl-methanone |
| 1.13 | 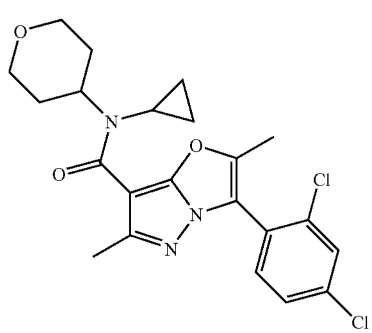 | 448.0 | 3-(2,4-Dichloro-phenyl)-2,6-dimethyl-pyrazolo[5,1-b]oxazole-7-carboxylic acid cyclopropyl-(tetrahydro-pyran-4-yl)-amide |

TABLE 1-continued

| Ex. | Structure | [M + H]+ | Name |
|---|---|---|---|
| 1.14 | 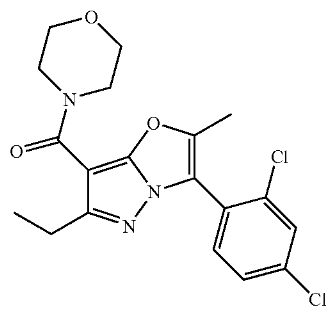 | 408.2 | [3-(2,4-Dichloro-phenyl)-6-ethyl-2-methyl-pyrazolo[5,1-b]oxazol-7-yl]-morpholin-4-yl-methanone |
| 1.15 | 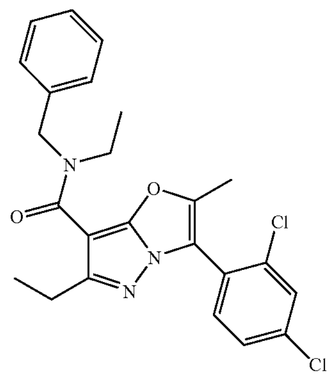 | 456.3 | 3-(2,4-Dichloro-phenyl)-6-ethyl-2-methyl-pyrazolo[5,1-b]oxazole-7-carboxylic acid benzyl-ethyl-amide |
| 1.16 | 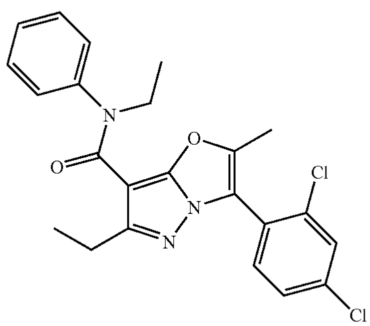 | 442.2 | 3-(2,4-Dichloro-phenyl)-6-ethyl-2-methyl-pyrazolo[5,1-b]oxazole-7-carboxylic acid ethyl-phenyl-amide |
| 1.17 | 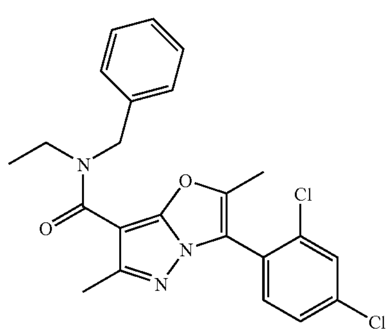 | 442.0 | 3-(2,4-Dichloro-phenyl)-2,6-dimethyl-pyrazolo[5,1-b]oxazole-7-carboxylic acid benzyl-ethyl-amide |
| 1.18 | 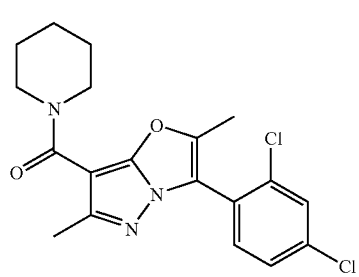 | 392.0 | [3-(2,4-Dichloro-phenyl)-2,6-dimethyl-pyrazolo[5,1-b]oxazol-7-yl]-piperidin-1-yl-methanone |

TABLE 1-continued

| Ex. | Structure | [M + H]+ | Name |
|---|---|---|---|
| 1.19 | 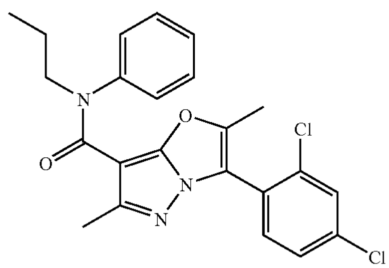 | 442.0 | 3-(2,4-Dichloro-phenyl)-2,6-dimethyl-pyrazolo[5,1-b]oxazole-7-carboxylic acid phenyl-propyl-amide |
| 1.20 | 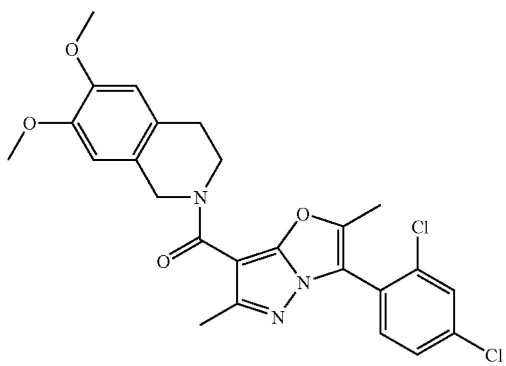 | 500.0 | [3-(2,4-Dichloro-phenyl)-2,6-dimethyl-pyrazolo[5,1-b]oxazol-7-yl]-(6,7-dimethoxy-3,4-dihydro-1H-isoquinolin-2-yl)-methanone |
| 1.21 | 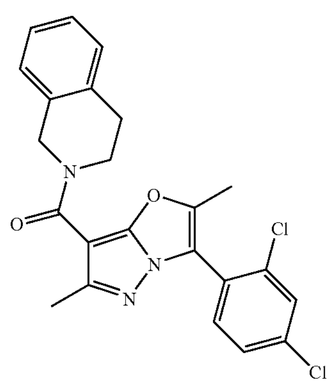 | 440.0 | [3-(2,4-Dichloro-phenyl)-2,6-dimethyl-pyrazolo[5,1-b]oxazol-7-yl]-(3,4-dihydro-1H-isoquinolin-2-yl)-methanone |
| 1.22 | 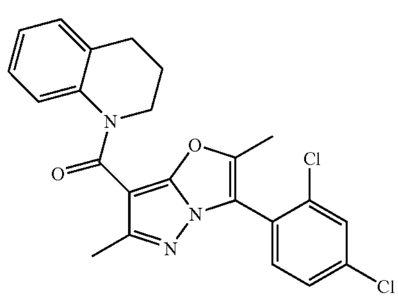 | 440.0 | [3-(2,4-Dichloro-phenyl)-2,6-dimethyl-pyrazolo[5,1-b]oxazol-7-yl]-(3,4-dihydro-2H-quinolin-1-yl)-methanone |
| 1.23 | 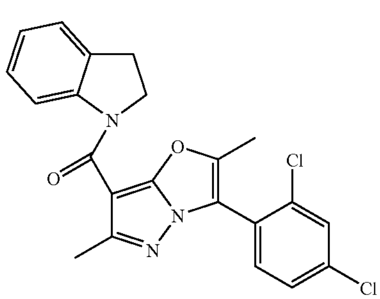 | 426.0 | 3-(2,4-Dichloro-phenyl)-2,6-dimethyl-pyrazolo[5,1-b]oxazol-7-yl]-(2,3-dihydro-indol-1-yl)-methanone |

| Ex. | Structure | [M + H]+ | Name |
|---|---|---|---|
| 1.24 | 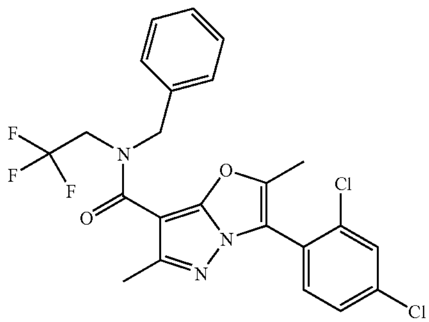 | 496.0 | 3-(2,4-Dichloro-phenyl)-2,6-dimethyl-pyrazolo[5,1-b]oxazole-7-carboxylic acid benzyl-(2,2,2-trifluoro-ethyl)-amide |

Example 2.1

(±)-3-(2,4-Dichloro-phenyl)-2,6-dimethyl-7-(1-phenyl-propoxy)-pyrazolo[5,1-b]oxazole

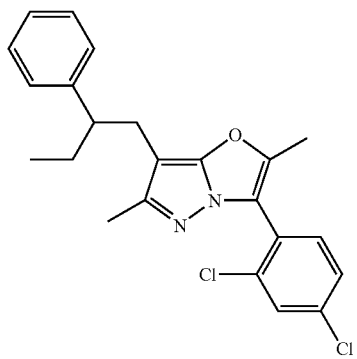

To a stirring solution of triphenylphosphine (66.2 mg, 0.252 mmol) in THF (1.683 ml) under $N_2$ at RT is added DEAD (0.040 ml, 0.252 mmol) followed by triethylamine (0.035 ml, 0.252 mmol), 1-phenyl-1-propanol (0.035 ml, 0.252 mmol) and 3-(2,4-dichloro-phenyl)-2,6-dimethyl-pyrazolo[5,1-b]oxazol-7-ol (Intermediate IC) (50 mg, 0.168 mmol). The reaction mixture is stirred overnight and then added to sat. ammonium chloride (50 ml). The mixture is extracted with EtOAc (60 ml) and the combined organic phases are washed with brine, dried over $MgSO_4$ and concentrated in vacuo. The crude product is purified by ISCO combiflash chromatography, eluting with 0 to 100% (iso-hexane/EtOAc) on a 12 g SiO2-column to give the title compound as a solid; MS: m/z 415.21 [M+H]+; $^1$H NMR (400 MHz, CDCl$_3$) δ 7.52 (2H, m), 7.35 (6H, m), 4.58 (1H, t), 2.25 (3H, s), 2.20 (3H, s), 2.15 (1H, m), 1.94 (1H, m), 1.05 (3H, t).

Example 2.2

3-(2,4-Dichloro-phenyl)-7-(1-ethyl-propoxy)-2,6-dimethyl-pyrazolo[5,1-b]oxazole1

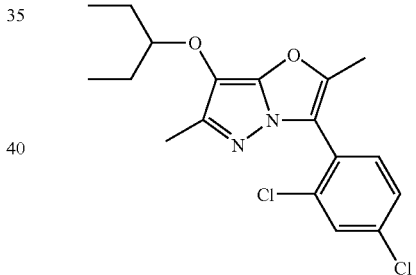

A solution of 3-(2,4-dichloro-phenyl)-2,6-dimethyl-pyrazolo[5,1-b]oxazol-7-ol (Intermediate IC) (40 mg, 0.135 mmol), cesium carbonate (52.6 mg, 0.162 mmol) and 3-bromopentane (0.020 ml, 0.162 mmol) in DMF (1.346 ml) is stirred at 75° C. for 2 hours. The reaction mixture is poured into sat. NaHCO$_3$ (25 ml) and the product extracted into EtOAc (35 ml) (brine is used to aid separation of the phases). The organic portion is separated and washed with brine, dried over MgSO$_4$ and concentrated in vacuo. The crude product is purified by ISCO combiflash chromatography, eluting with 0 to 100% (iso-hexane/EtOAc) on a 4 g SiO2-column to give the title compound as a yellow solid; MS: m/z 367.13 [M+H]+; $^1$H NMR 400.13 MHz (CDCl3)–7.60 (1H, s), 7.48 (2H, d), 7.40 (2H, dd), 3.79 (1H, m), 2.32 (3H, s), 2.30 (3H, s), 1.70 (4H, m), 1.04 (6H, t).

Example 2.3

3-(2,4-Dichloro-phenyl)-7-(1-methoxymethyl-butoxy)-2,6-dimethyl-pyrazolo[5,1-b]oxazole

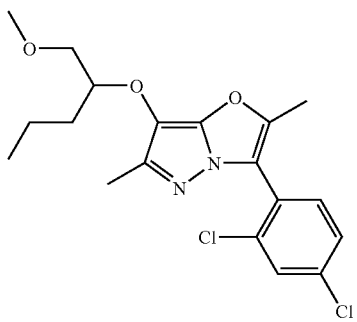

Step 1: 2-[3-(2,4-Dichloro-phenyl)-2,6-dimethyl-pyrazolo[5,1-b]oxazol-7-yloxy]-pentanoic acid ethyl ester:

A solution of 3-(2,4-dichloro-phenyl)-2,6-dimethyl-pyrazolo[5,1-b]oxazol-7-ol (Intermediate IC) (100 mg, 0.337 mmol), cesium carbonate (132 mg, 0.404 mmol) and ethyl 2-bromovalerate (0.069 ml, 0.404 mmol) in DMF (3.365 ml) is stirred at 45° C. for 2 hours. The reaction mixture is poured into sat NaHCO$_3$ (50 ml) and the product is extracted with EtOAc (2×50 ml) (brine is used to aid the phase separation). The combined organic extracts are washed with brine, dried over MgSO$_4$ and concentrated in vacuo. Purification of the resultant oil by ISCO combiflash chromatography, eluting with 0 to 100% (iso-hexane/EtOAc) on a 12 g SiO2-column affords the title compound as a solid; MS: m/z 425.21 [M+H]$^+$.

Step 2: (±)-2-[3-(2,4-Dichloro-phenyl)-2,6-dimethyl-pyrazolo[5,1-b]oxazol-7-yloxy]-pentan-1-ol;

To a cooled (0° C.), stirring solution of 2-[3-(2,4-dichloro-phenyl)-2,6-dimethyl-pyrazolo[5,1-b]oxazol-7-yloxy]-pentanoic acid ethyl ester (85 mg, 0.200 mmol) in THF (2.0 ml) at is added DIBAL-H (0.400 ml, 0.400 mmol). The reaction mixture is warmed to RT and stirred for 2 hours. The mixture is added to sat. ammonium chloride (50 ml) and the product is extracted into EtOAc (2×50 ml). The combined organics are washed with brine, dried over MgSO$_4$ and concentrated in vacuo. The crude product is purified by ISCO combiflash chromatography, eluting with 0 to 100% (iso-hexane/EtOAc) on a 12 g SiO2-column to yield the title compound as a white solid; MS: m/z 385.13 [M+H]$^+$.

Step 3: (±)-3-(2,4-Dichloro-phenyl)-7-(1-methoxymethyl-butoxy)-2,6-dimethyl-pyrazolo[5,1-b]oxazole:

To a stirring solution of (±)-2-[3-(2,4-dichloro-phenyl)-2,6-dimethyl-pyrazolo[5,1-b]oxazol-7-yloxy]-pentan-1-ol (60 mg, 0.157 mmol) in THF (1.565 ml) at RT is added NaH (6.26 mg, 0.157 mmol). After 10 mins MeI (10.77 μl, 0.172 mmol) is added and the reaction mixture is stirred for a further 3 hours. An additional 1.1eq of MeI (10.77 μl, 0.172 mmol) is added and reaction continued for 1 hour whereupon it is added to sat. ammonium chloride (50 ml) and the product extracted into EtOAc (60 ml). The organics are washed with brine, dried over MgSO$_4$ and concentrated in vacuo. The crude reaction products are purified by ISCO combiflash chromatography, eluting with 0 to 100% (iso-hexane/EtOAc) on a 12 g SiO2-column to give (±)-3-(2,4-Dichloro-phenyl)-7-(1-methoxymethyl-butoxy)-2,6-dimethyl-pyrazolo[5,1-b]oxazole as a solid; MS: m/z 397.20 [M+H]$^+$; $^1$H NMR (400 MHz, CDCl$_3$) δ 7.58 (2H, m), 7.41 (1H, dd), 4.03 (1H, m), 3.58 (2H, m), 3.44 (3H, s), 2.33 (3H, s), 2.30 (3H, s), 1.76 (2H, m), 1.57 (2H, m), 1.00 (3H, t).

The racemic (±)-3-(2,4-dichloro-phenyl)-7-(1-methoxymethyl-butoxy)-2,6-dimethyl-pyrazolo[5,1-b]oxazole are separated into its composite enantiomers by SFC using the following method:
Mobile Phase: 10% EtOH 0.1% DEA/75% CO$_2$
Column: Chiralpak AD-H, 250×10 mm id, 5 μm
Detection: UV @ 220 nm
Flow rate: 10 ml/min
Sample concentration: 20 mg in 1.5 ml EtOH
Injection volume: 200 μl The examples shown in the following table are prepared according to the procedures of Examples 2.1, 2.2 or 2.3 using the appropriate starting compounds, the methods of preparation of which are described hereinafter or are commercially available.

TABLE 2

| Ex. | Structure | [M + H]$^+$ | Name |
|---|---|---|---|
| 2.4 | 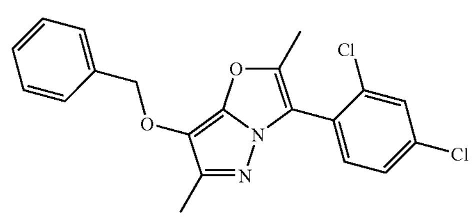 | 387.12 | 7-Benzyloxy-3-(2,4-dichloro-phenyl)-2,6-dimethyl-pyrazolo[5,1-b]oxazole |
| 2.5 | 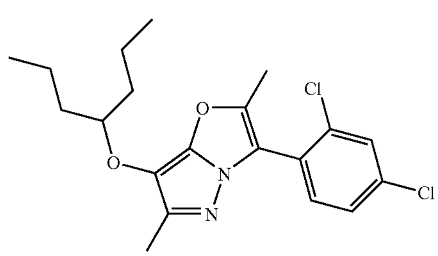 | 395.2 | 3-(2,4-Dichloro-phenyl)-2,6-dimethyl-7-(1-propyl-butoxy)-pyrazolo[5,1-b]oxazole |

TABLE 2-continued

| Ex. | Structure | [M + H]+ | Name |
|---|---|---|---|
| 2.6 | 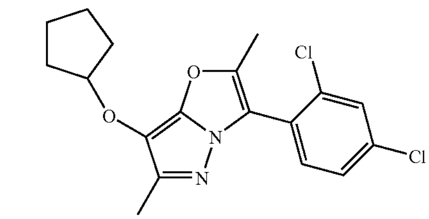 | 365.1 | 7-Cyclopentyloxy-3-(2,4-dichloro-phenyl)-2,6-dimethyl-pyrazolo[5,1-b]oxazole |
| 2.7 | 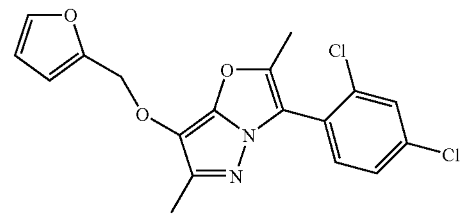 | 377.14 | 3-(2,4-Dichloro-phenyl)-7-(furan-2-ylmethoxy)-2,6-dimethyl-pyrazolo[5,1-b]oxazole |
| 2.8 | 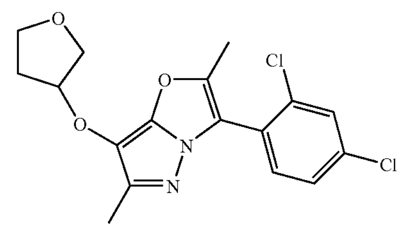 | 367.14 | 3-(2,4-Dichloro-phenyl)-2,6-dimethyl-7-(tetrahydro-furan-3-yloxy)-pyrazolo[5,1-b]oxazole |
| 2.9 | 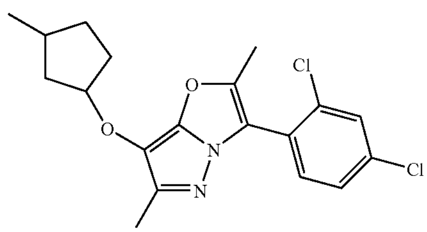 | 379.18 | 3-(2,4-Dichloro-phenyl)-2,6-dimethyl-7-(3-methyl-cyclopentyloxy)-pyrazolo[5,1-b]oxazole |
| 2.10 | 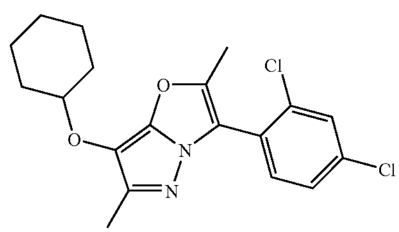 | 379.22 | 7-Cyclohexyloxy-3-(2,4-dichloro-phenyl)-2,6-dimethyl-pyrazolo[5,1-b]oxazole |
| 2.11 | 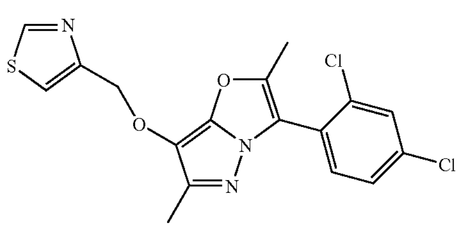 | 394.16 | 3-(2,4-Dichloro-phenyl)-2,6-dimethyl-7-(thiazol-4-ylmethoxy)-pyrazolo[5,1-b]oxazole |
| 2.12 | 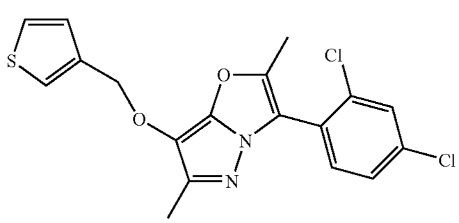 | 393.18 | 3-(2,4-Dichloro-phenyl)-2,6-dimethyl-7-(thiophen-3-ylmethoxy)-pyrazolo[5,1-b]oxazole |

TABLE 2-continued

| Ex. | Structure | [M + H]+ | Name |
|---|---|---|---|
| 2.13 | 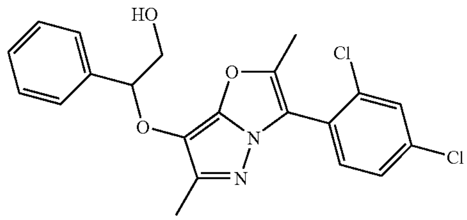 | 417.31 | (±)-2-[3-(2,4-Dichloro-phenyl)-2,6-dimethyl-pyrazolo[5,1-b]oxazol-7-yloxy]-2-phenyl-ethanol |
| 2.14 | 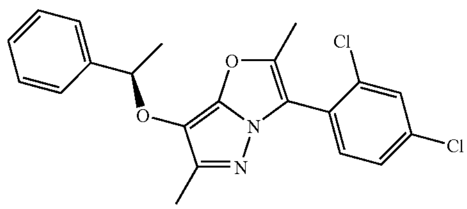 | 401.21 | 3-(2,4-Dichloro-phenyl)-2,6-dimethyl-7-((R)-1-phenyl-ethoxy)-pyrazolo[5,1-b]oxazole |
| 2.15 | 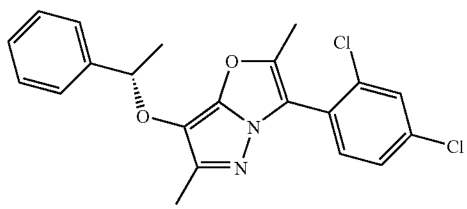 | 401.21 | 3-(2,4-Dichloro-phenyl)-2,6-dimethyl-7-((S)-1-phenyl-ethoxy)-pyrazolo[5,1-b]oxazole |
| 2.16 | 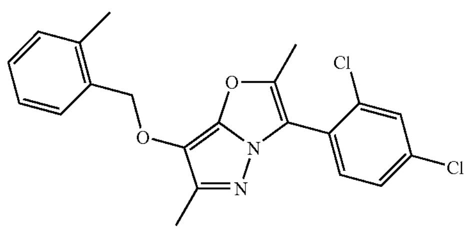 | 401.22 | 3-(2,4-Dichloro-phenyl)-2,6-dimethyl-7-(2-methyl-benzyloxy)-pyrazolo[5,1-b]oxazole |
| 2.17 | 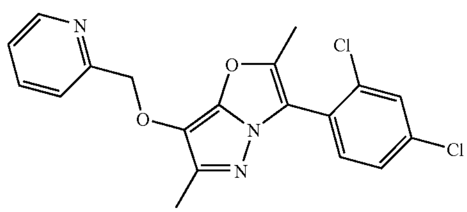 | 388.15 | 3-(2,4-Dichloro-phenyl)-2,6-dimethyl-7-(pyridin-2-ylmethoxy)-pyrazolo[5,1-b]oxazole |
| 2.18 | 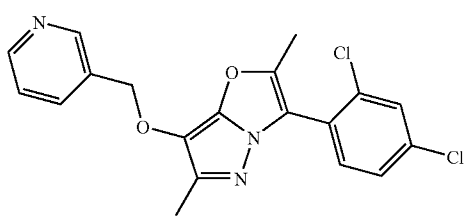 | 388.18 | 3-(2,4-Dichloro-phenyl)-2,6-dimethyl-7-(pyridin-3-ylmethoxy)-pyrazolo[5,1-b]oxazole |
| 2.19 | 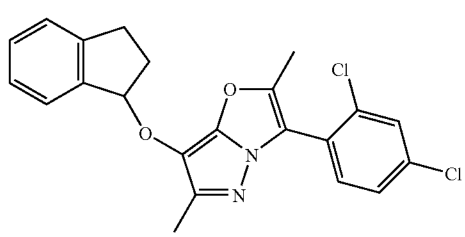 | 413.26 | 3-(2,4-Dichloro-phenyl)-7-(indan-1-yloxy)-2,6-dimethyl-pyrazolo[5,1-b]oxazole |

TABLE 2-continued

| Ex. | Structure | [M + H]+ | Name |
|---|---|---|---|
| 2.20 | 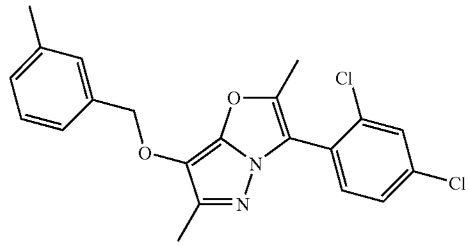 | 401.23 | 3-(2,4-Dichloro-phenyl)-2,6-dimethyl-7-(3-methyl-benzyloxy)-pyrazolo[5,1-b]oxazole |
| 2.21 | 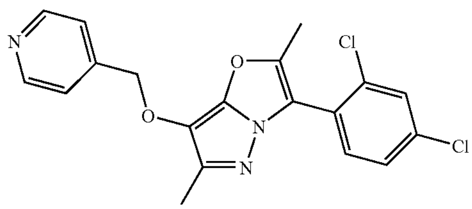 | 388.17 | 3-(2,4-Dichloro-phenyl)-2,6-dimethyl-7-(pyridin-4-ylmethoxy)-pyrazolo[5,1-b]oxazole |
| 2.22 | 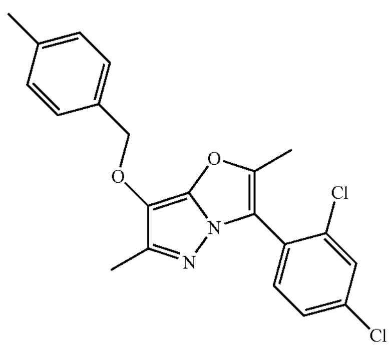 | 401.23 | 3-(2,4-Dichloro-phenyl)-2,6-dimethyl-7-(4-methyl-benzyloxy)-pyrazolo[5,1-b]oxazole |
| 2.23 | 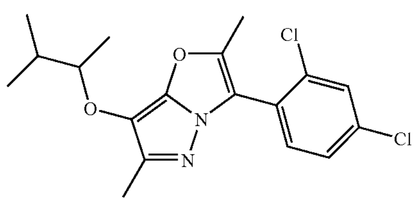 | 367.18 | (±)-3-(2,4-Dichloro-phenyl)-7-(1,2-dimethyl-propoxy)-2,6-dimethyl-pyrazolo[5,1-b]oxazole |
| 2.24 | 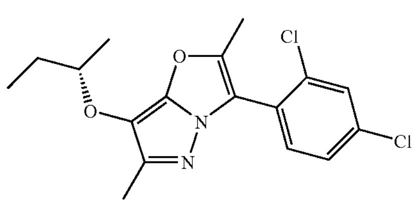 | 353.12 | 7-((S)-sec-Butoxy)-3-(2,4-dichloro-phenyl)-2,6-dimethyl-pyrazolo[5,1-b]oxazole |
| 2.25 | 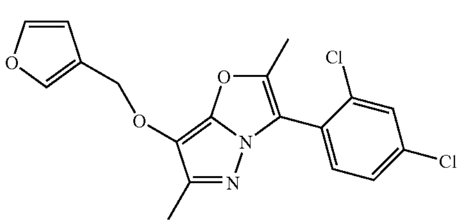 | 377.13 | 3-(2,4-Dichloro-phenyl)-7-(furan-3-ylmethoxy)-2,6-dimethyl-pyrazolo[5,1-b]oxazole |

TABLE 2-continued

| Ex. | Structure | [M + H]+ | Name |
|---|---|---|---|
| 2.26 | 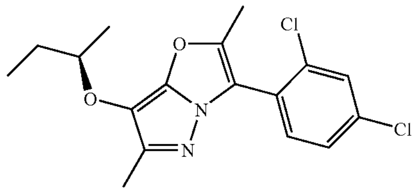 | 353.13 | 7-((R)-sec-Butoxy)-3-(2,4-dichloro-phenyl)-2,6-dimethyl-pyrazolo[5,1-b]oxazole |
| 2.27 | 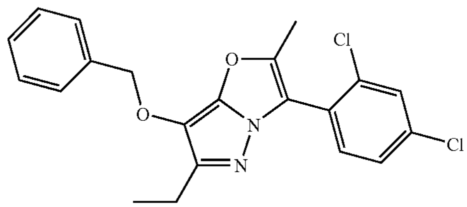 | 401.24 | 7-Benzyloxy-3-(2,4-dichloro-phenyl)-6-ethyl-2-methyl-pyrazolo[5,1-b]oxazole |
| 2.28 | 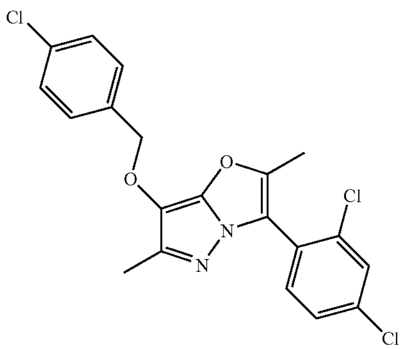 | 421.21 | 7-(4-Chloro-benzyloxy)-3-(2,4-dichloro-phenyl)-2,6-dimethyl-pyrazolo[5,1-b]oxazole |
| 2.29 | 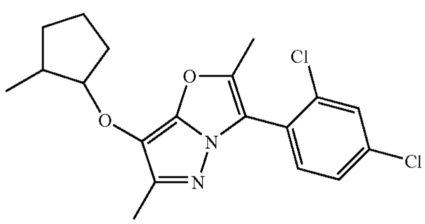 | 379.18 | (±)-3-(2,4-Dichloro-phenyl)-2,6-dimethyl-7-(2-methyl-cyclopentyloxy)-pyrazolo[5,1-b]oxazole |
| 2.30 | 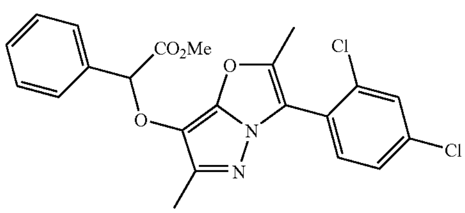 | 445.23 | (±)-[3-(2,4-Dichloro-phenyl)-2,6-dimethyl-pyrazolo[5,1-b]oxazol-7-yloxy]-phenyl-acetic acid methyl ester |
| 2.31 | 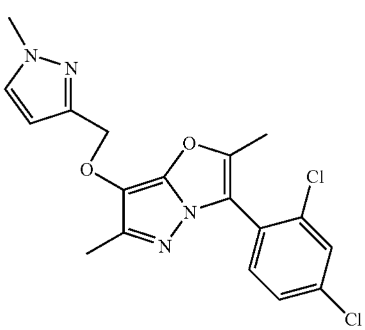 | 391.27 | 3-(2,4-Dichloro-phenyl)-2,6-dimethyl-7-(1-methyl-1H-pyrazol-3-ylmethoxy)-pyrazolo[5,1-b]oxazole |

TABLE 2-continued

| Ex. | Structure | [M + H]+ | Name |
|---|---|---|---|
| 2.32 | 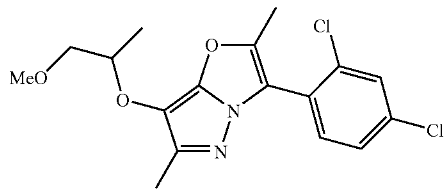 | 369.15 | (±)-3-(2,4-Dichloro-phenyl)-7-(2-methoxy-1-methyl-ethoxy)-2,6-dimethyl-pyrazolo[5,1-b]oxazole |
| 2.33 | 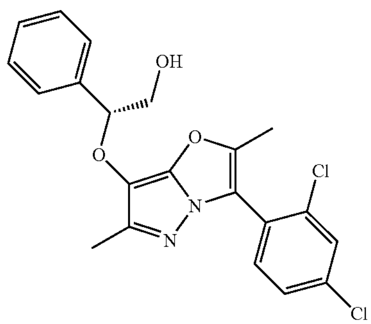 | 417.28 | Enantiomer 1 2-[3-(2,4-Dichloro-phenyl)-2,6-dimethyl-pyrazolo[5,1-b]oxazol-7-yloxy]-2-phenyl-ethanol |
| 2.34 | 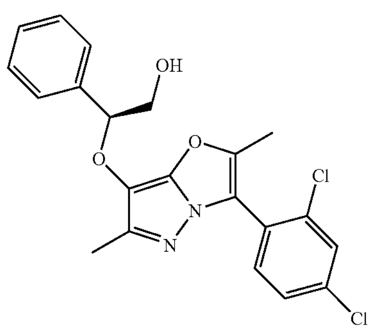 | 417.27 | Enantiomer 2 2-[3-(2,4-Dichloro-phenyl)-2,6-dimethyl-pyrazolo[5,1-b]oxazol-7-yloxy]-2-phenyl-ethanol |
| 2.35 | 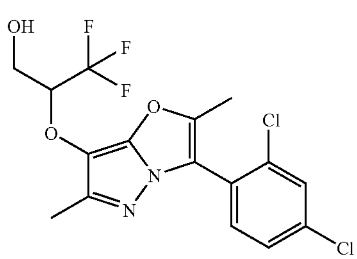 | 409.0 | 2-[3-(2,4-Dichloro-phenyl)-2,6-dimethyl-pyrazolo[5,1-b]oxazol-7-yloxy]-3,3,3-trifluoro-propan-1-ol |

Example 3.1

[3-(2,4-Dichloro-phenyl)-2,6-dimethyl-pyrazolo[5,1b]oxazol-7-yl]dipropyl-amine hydrochloride

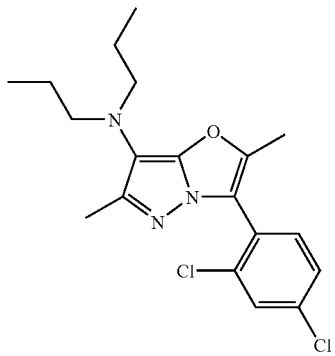

To a mixture of 3-(2,4-dichloro-phenyl)-2,6-dimethyl-pyrazolo[5,1-b]oxazol-7-ylamine (Intermediate ID) (0.296 g, 1.00 mmol), propionaldehyde (0.220 ml, 3.00 mmol) and AcOH (0.285 ml, 5.00 mmol) in 1,2-dichloroethane (10 ml) is added NaBH(OAc)$_3$ (0.848 g, 4.00 mmol) at RT. The reaction mixture is stirred for 4 h and then partitioned between EtOAc (80 ml) and NaHCO$_3$ (50 ml). The organic phase is dried (Na$_2$SO$_4$) and evaporated in vacuo to give the crude product. Purification by chromatography on silica eluting with EtOAc: iso-hexane (1:10) affords the title compound as a white solid; MS: m/z 380.20 [M+H]$^+$ $^1$H NMR (400 MHz, DMSO-d$_6$) δ 7.88 (1H, d), 7.71 (1H, d), 7.62 (1H, dd), 2.81 (4H, t), 2.30 (3H, s), 2.14 (3H, s), 1.35 (4H, m), 0.86 (6H, t).

The examples shown in the following table are prepared according to the procedure Example 3.1 using the appropriate starting compounds, the methods of preparation of which are described hereinafter or are commercially available.

TABLE 3

| Ex. | Structure | [M + H]$^+$ | Name |
|---|---|---|---|
| 3.2 | 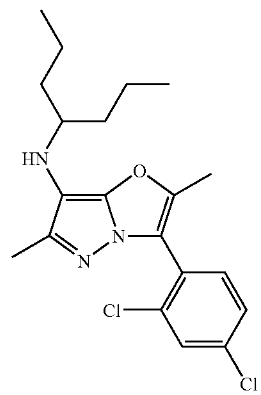 | 394.2 | [3-(2,4-Dichloro-phenyl)-2,6-dimethyl-pyrazolo[5,1-b]oxazol-7-yl]-(1-propyl-butyl)-amine |
| 3.3 | 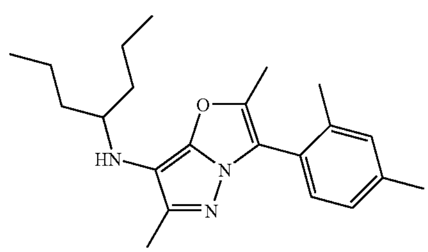 | 354.5 | [3-(2,4-Dimethyl-phenyl)-2,6-dimethyl-pyrazolo[5,1-b]oxazol-7-yl]-(1-propyl-butyl)-amine |
| 3.4 | 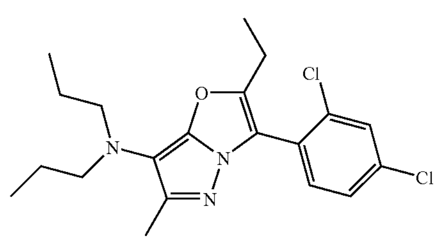 | 394.24 | [3-(2,4-Dichloro-phenyl)-2-ethyl-6-methyl-pyrazolo[5,1-b]oxazol-7-yl]-dipropyl-amine |

TABLE 3-continued

| Ex. | Structure | [M + H]⁺ | Name |
|---|---|---|---|
| 3.5 | 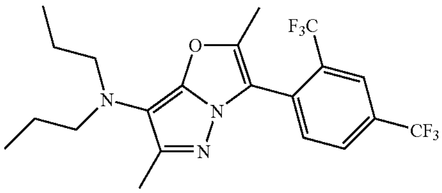 | 448.3 | [3-(2,4-Bis-trifluoromethyl-phenyl)-2,6-dimethyl-pyrazolo[5,1-b]oxazol-7-yl]-dipropyl-amine |
| 3.6 | 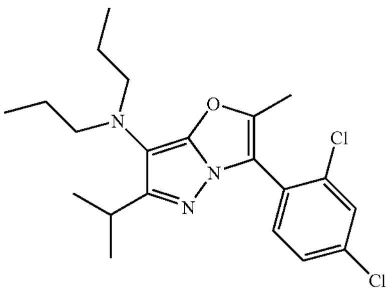 | 408.3 | [3-(2,4-Dichloro-phenyl)-6-isopropyl-2-methyl-pyrazolo[5,1-b]oxazol-7-yl]-dipropyl-amine |
| 3.7 | 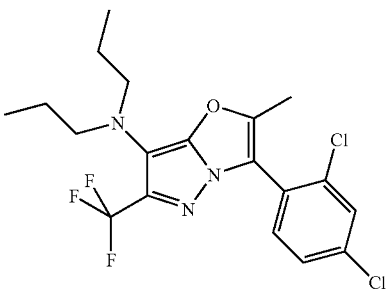 | 434.1 | [3-(2,4-Dichloro-phenyl)-2-methyl-6-trifluoromethyl-pyrazolo[5,1-b]oxazol-7-yl]-dipropyl-amine |

Example 4.0

N-[3-(2,4-Dichloro-phenyl)-2,6-dimethyl-pyrazolo[5,1-b]oxazol-7-yl]-N-propyl-propionamide

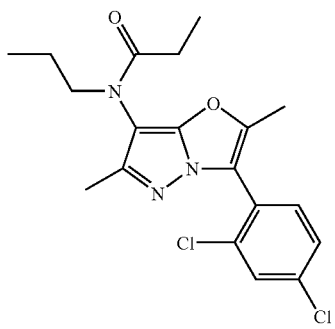

To a stirring solution of 3-(2,4-dichloro-phenyl)-2,6-dimethyl-pyrazolo[5,1-b]oxazol-7-ylamine (Intermediate ID) (150 mg, 0.51 mmol), glacial acetic acid (0.03 ml, 0.51 mmol) and sodium triacetoxyborohydride (150 mg, 0.71 mmol) in 1,2-dichloroethane (2 ml) is added propionaldehyde (0.037 ml, 0.51 mmol): the reaction mixture is stirred at RT for 22 h. Propionyl chloride (0.044 ml, 0.51 mmol) and DMAP (0.037 g, 0.31 mmol) are added and the reaction maintained at RT for 16 hours. The reaction mixture is filtered and following silica gel chromatography (iso-hexane/EtOAc gradient elution of 0-60%) the crude product is isolated as a semi-solid. Following a second chromatography (SiO₂, iso-hexane/EtOAc gradient of 0-40%) the desired N-[3-(2,4-dichloro-phenyl)-2,6-dimethyl-pyrazolo[5,1-b]oxazol-7-yl]-N-propyl-propionamide is isolated; MS: m/z 394.2 [M+H]⁺¹H NMR (400 MHz, DMSO-d₆) δ 7.90 (1H, d), 7.75 (1H, d), 7.64 (1H, dd), 3.79 (1H, br s), 3.18 (1H, br s), 2.33 (3H, s), 2.12 (3H, s), 2.04 (2H, q), 1.45 (2H, m), 0.92 (3H, t), 0.85 (3H, t).

Alternatively, Example 4.0 can be prepared according to the following procedure:

Step 1: N-(3-(2,4-Dichlorophenyl)-2,6-dimethylpyrazolo[5,1-b]oxazol-7-yl)propionamide To a suspension of 3-(2,4-dichloro-phenyl)-2,6-dimethyl-pyrazolo[5,1-b]oxazol-7-ylamine (Intermediate ID) (500 mg, 1.503 mmol) in DCM (10 ml) under N₂ is added triethylamine (0.461 ml, 3.31 mmol) followed by propionyl chloride (0.144 ml, 1.654 mmol) at 0° C. After 2 hr, the reaction mixture is diluted with DCM (50 ml) and washed with 1M HCl, NaHCO₃, Brine, dried (MgSO₄) and evaporated down to give a pink solid. This is then triturated with Et₂O to give the title compound as an off white solid. MS: n/z 351.9[M+H]⁺

Step 2: N-[3-(2,4-Dichloro-phenyl)-2,6-dimethyl-pyrazolo[5,1-b]oxazol-7-yl]-N-propyl-propionamide N-(3-(2,4-Dichlorophenyl)-2,6-dimethylpyrazolo[5,1-b]oxazol-7-yl) propionamide (634 mg, 1.800 mmol) is suspended in dry DMF (20 ml) and treated with NaH (60% in oil) (86 mg, 2.160 mmol) under N₂ at RT. The mixture is stirred at RT for 10 minutes before cooling to 0° C. in an ice bath. 1-Iodopropane (0.263 ml, 2.70 mmol) is added dropwise and the reaction mixture is stirred at 0° C. for 1 hr. The solvent is removed in vacuo and the resulting residue is dissolved in EtOAc and washed with 1M NaOH, 1M HCl, H₂O, brine, dried (MgSO₄) and evaporated down to give a brown oil. Purification by chromatography on silica eluting with 0% to 50% EtOAc/iso-hexane affords the title compound as a clear oil; MS: m/z 394.1 [M+H]⁺

The examples shown in the following table are prepared according to the procedures of Example 4.0 using the appropriate starting compounds, the methods of preparation of which are described hereinafter or are commercially available.

TABLE 4A

| Ex. | Structure | [M + H]⁺ | Name |
|---|---|---|---|
| 4.1 | 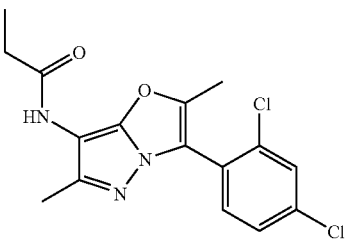 | 351.9 | N-[3-(2,4-Dichloro-phenyl)-2,6-dimethyl-pyrazolo[5,1-b]oxazol-7-yl]-propionamide |
| 4.2 | 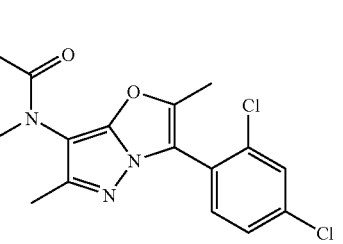 | 380.0 | N-[3-(2,4-Dichloro-phenyl)-2,6-dimethyl-pyrazolo[5,1-b]oxazol-7-yl]-N-ethyl-propionamide |
| 4.3 | 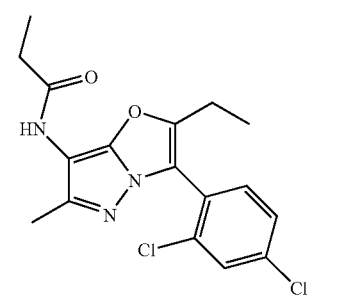 | 366.0 | N-[3-(2,4-Dichloro-phenyl)-2-ethyl-6-methyl-pyrazolo[5,1-b]oxazol-7-yl]-propionamide |
| 4.4 | 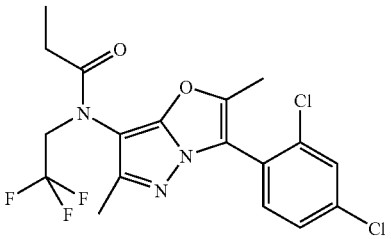 | 434.0 | N-[3-(2,4-Dichloro-phenyl)-2,6-dimethyl-pyrazolo[5,1-b]oxazol-7-yl]-N-(2,2,2-trifluoro-ethyl)-propionamide |
| 4.5 | 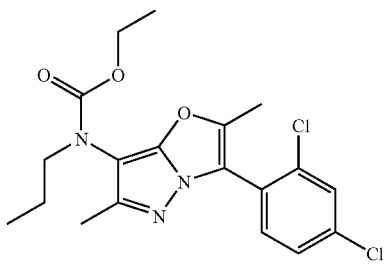 | 410.1 | Ethyl 3-(2,4-dichlorophenyl)-2,6-dimethylpyrazolo[5,1-b]oxazol-7-yl(propyl)carbamate |

TABLE 4A-continued

| Ex. | Structure | [M + H]+ | Name |
|---|---|---|---|
| 4.6 | 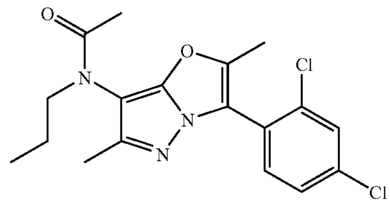 | 380 | N-(3-(2,4-dichlorophenyl)-2,6-dimethylpyrazolo[5,1-b]oxazol-7-yl)-N-propylacetamide |
| 4.7 | 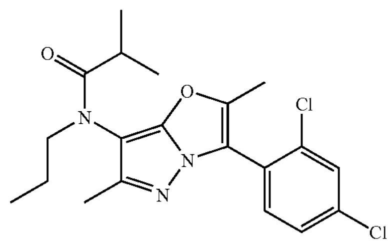 | 408.1 | N-(3-(2,4-dichlorophenyl)-2,6-dimethylpyrazolo[5,1-b]oxazol-7-yl)-N-propylisobutyramide |
| 4.8 | 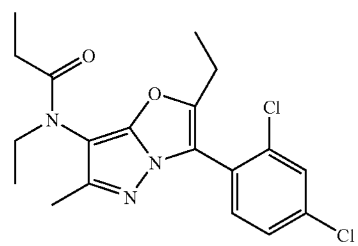 | 394.1 | N-[3-(2,4-Dichloro-phenyl)-2-ethyl-6-methyl-pyrazolo[5,1-b]oxazol-7-yl]-N-ethyl-propionamide |
| 4.9 | 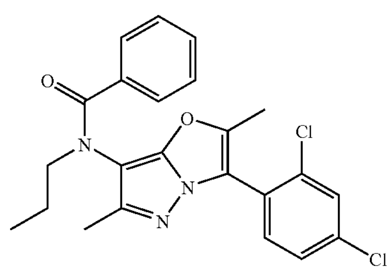 | 442 | N-(3-(2,4-dichlorophenyl)-2,6-dimethylpyrazolo[5,1-b]oxazol-7-yl)-N-propylbenzamide |
| 4.10 | 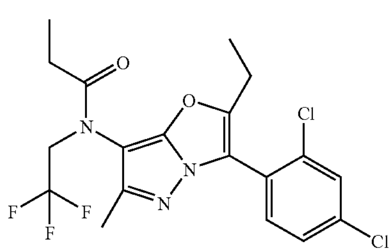 | 448 | N-[3-(2,4-Dichloro-phenyl)-2-ethyl-6-methyl-pyrazolo[5,1-b]oxazol-7-yl]-N-(2,2,2-trifluoro-ethyl)-propionamide |
| 4.11 | 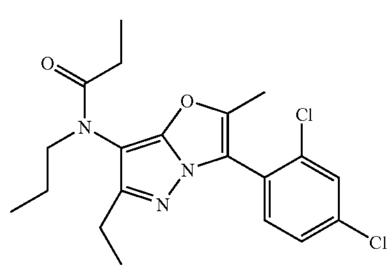 | 408 | N-(3-(2,4-dichlorophenyl)-6-ethyl-2-methylpyrazolo[5,1-b]oxazol-7-yl)-N-propylpropionamide |

TABLE 4A-continued

| Ex. | Structure | [M + H]⁺ | Name |
|---|---|---|---|
| 4.12 | 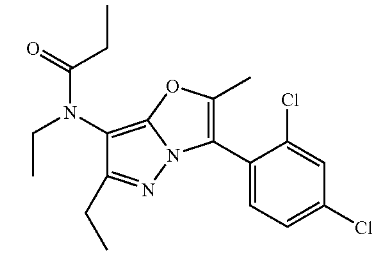 | 394 | N-(3-(2,4-dichlorophenyl)-6-ethyl-2-methylpyrazolo[5,1-b]oxazol-7-yl)-N-ethylpropionamide |
| 4.13 | 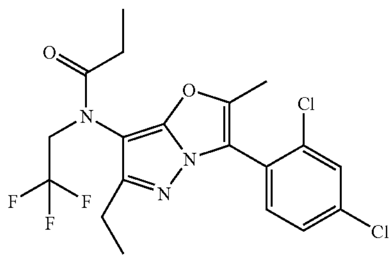 | 448 | N-(3-(2,4-dichlorophenyl)-6-ethyl-2-methylpyrazolo[5,1-b]oxazol-7-yl)-N-(2,2,2-trifluoroethyl)propionamide |

Example 5.1

[3-(2,4-Dichloro-phenyl)-2-ethyl-6-methyl-pyrazolo[5,1-b]oxazol-7-ylmethyl]-dipropyl-amine

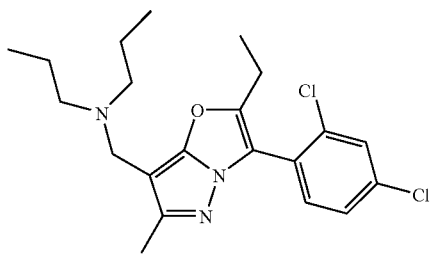

To a solution of 3-(2,4-dichloro-phenyl)-2-ethyl-6-methyl-pyrazolo[5,1-b]oxazole (Intermediate HO)(30 mg, 0.10 mmol, 1 eq.) and dipropylamine (0.042 ml, 0.31 mmol, 3 eq.) in AcOH (0.3 ml) is added formaldehyde (36.5% in water, 0.025 ml, 0.31 mmol, 3 eq.) at RT. The reaction mixture is heated at 50° C. for 2 h then cooled to RT and directly subjected to purification by reverse phase prep-HPLC (Waters system) to yield the title compound (TFA salt) as a colourless resin. HPLC: $^A t_{Ret}$=1.89; MS: m/z 408.1 [M+H]⁺; ¹H NMR (400 MHz, DMSO-d₆) δ 0.96 (t, 6H), 1.22 (t, 3H), 1.73-1.83 (m, 4H), 2.30 (s, 3H), 2.68 (q, 2H), 2.96-3.05 (m, 4H), 4.34 (m, 2H), 7.68 (m, 2H), 7.93 (m, 1H).

The examples shown in the following table are prepared according to the procedure of Example 5.1 using the appropriate starting compounds, the methods of preparation of which are described hereinafter or are commercially available.

It is also possible to prepare this class of analogs from the appropriate amide derivative (see Table 1) using 1.0M BH₃ in THF between 0° C. and 40° C. or by way of a two-step process using an amine in AcOH, with formaldehyde followed by a reductive amination of the derived compound in DCM using the appropriate aldehyde, AcOH and NaBH(OAc)₃.

TABLE 4

| Ex. | Structure | [M + H]⁺ | Name |
|---|---|---|---|
| 5.2 | 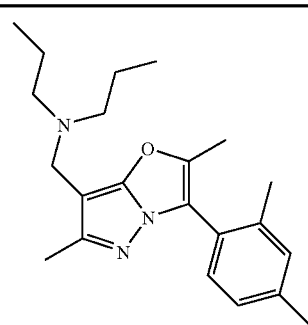 | 354.4 | [3-(2,4-Dimethyl-phenyl)-2,6-dimethyl-pyrazolo[5,1-b]oxazol-7-ylmethyl]-dipropyl-amine |

TABLE 4-continued

| Ex. | Structure | [M + H]+ | Name |
|---|---|---|---|
| 5.3 | 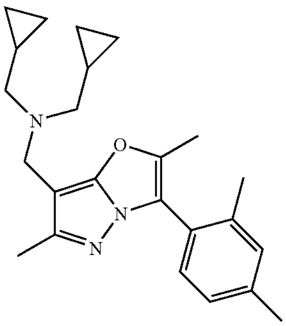 | 378.2 | Bis-cyclopropylmethyl-[3-(2,4-dimethyl-phenyl)-2,6-dimethyl-pyrazolo[5,1-b]oxazol-7-ylmethyl]-amine |
| 5.4 | 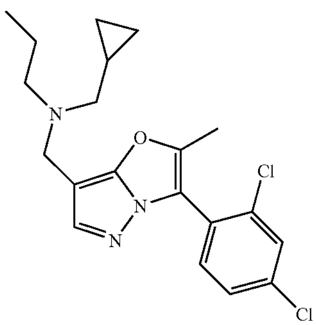 | 392.3 | Cyclopropylmethyl-[3-(2,4-dichloro-phenyl)-2-methyl-pyrazolo[5,1-b]oxazol-7-ylmethyl]-propyl-amine |
| 5.5 | 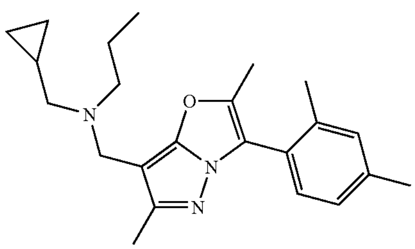 | 354.4 | Cyclopropylmethyl-[3-(2,4-dimethyl-phenyl)-6-methyl-pyrazolo[5,1-b]oxazol-7-ylmethyl]-propyl-amine |
| 5.6 | 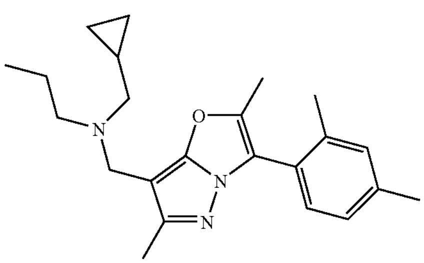 | 366.4 | Cyclopropylmethyl-[3-(2,4-dimethyl-phenyl)-2,6-dimethyl-pyrazolo[5,1-b]oxazol-7-ylmethyl]-propyl-amine |
| 5.7 | 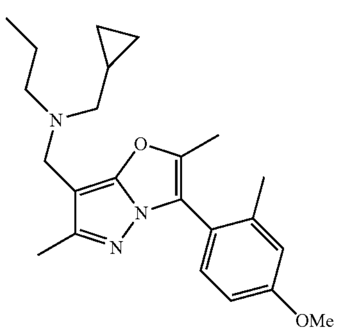 | 382.3 | Cyclopropylmethyl-[3-(4-methoxy-2-methyl-phenyl)-2,6-dimethyl-pyrazolo[5,1-b]oxazol-7-ylmethyl]-propyl-amine |

TABLE 4-continued

| Ex. | Structure | [M + H]+ | Name |
|---|---|---|---|
| 5.8 | 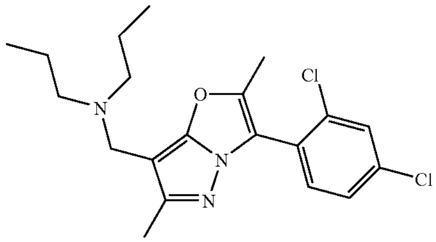 | 394.3 | [3-(2,4-Dichloro-phenyl)-2,6-dimethyl-pyrazolo[5,1-b]oxazol-7-ylmethyl]-dipropyl-amine |
| 5.9 | 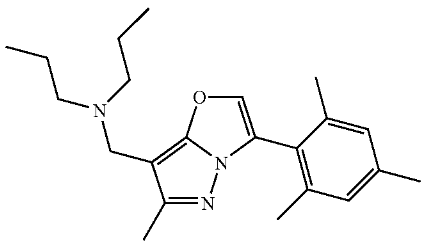 | 354.4 | [6-Methyl-3-(2,4,6-trimethyl-phenyl)-pyrazolo[5,1-b]oxazol-7-ylmethyl]-dipropyl-amine |
| 5.10 | 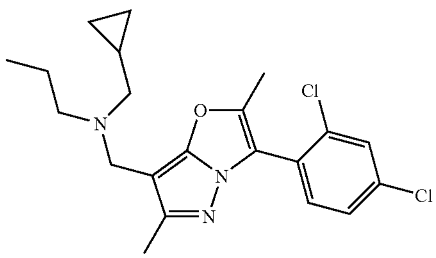 | 406.1 | Cyclopropylmethyl-[3-(2,4-dichloro-phenyl)-2,6-dimethyl-pyrazolo[5,1-b]oxazol-7-ylmethyl]-propyl-amine |
| 5.11 | 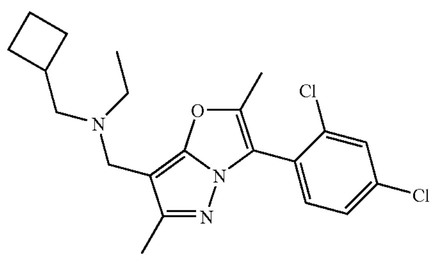 | 406.1 | Cyclobutylmethyl-[3-(2,4-dichloro-phenyl)-2,6-dimethyl-pyrazolo[5,1-b]oxazol-7-ylmethyl]-ethyl-amine |
| 5.12 | 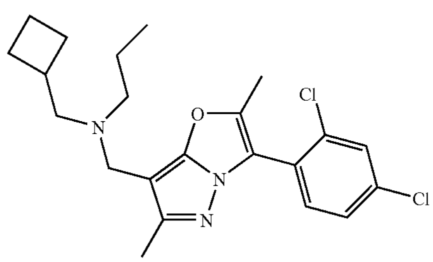 | 420.1 | Cyclobutylmethyl-[3-(2,4-dichloro-phenyl)-2,6-dimethyl-pyrazolo[5,1-b]oxazol-7-ylmethyl]-propyl-amine |
| 5.13 | 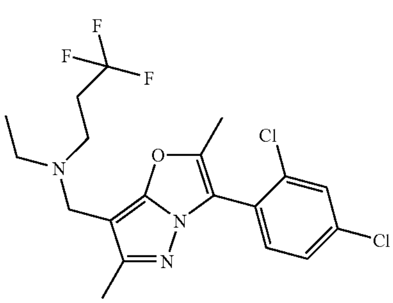 | 433.8 | [3-(2,4-Dichloro-phenyl)-2,6-dimethyl-pyrazolo[5,1-b]oxazol-7-ylmethyl]-ethyl-(3,3,3-trifluoro-propyl)-amine |

TABLE 4-continued

| Ex. | Structure | [M + H]+ | Name |
|---|---|---|---|
| 5.14 | 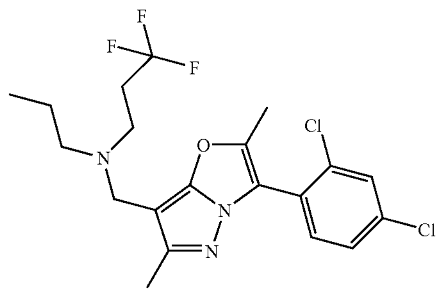 | 448.0 | [3-(2,4-Dichloro-phenyl)-2,6-dimethyl-pyrazolo[5,1-b]oxazol-7-ylmethyl]-propyl-(3,3,3-trifluoro-propyl)-amine |
| 5.15 | 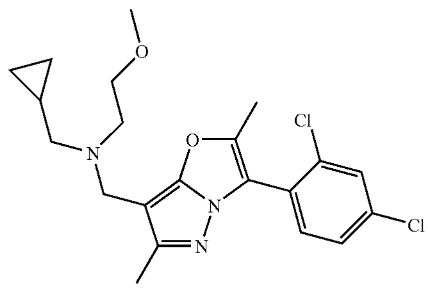 | 422.1 | Cyclopropylmethyl-[3-(2,4-dichloro-phenyl)-2,6-dimethyl-pyrazolo[5,1-b]oxazol-7-ylmethyl]-(2-methoxy-ethyl)-amine |
| 5.16 | 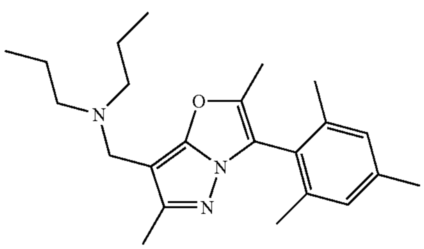 | 368.4 | [2,6-Dimethyl-3-(2,4,6-trimethyl-phenyl)-pyrazolo[5,1-b]oxazol-7-ylmethyl]-dipropyl-amine |
| 5.17 | 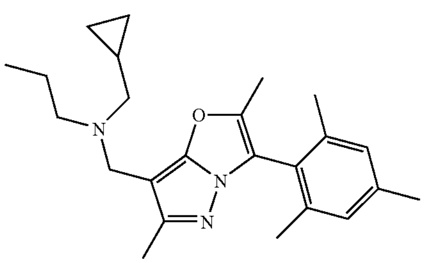 | 380.2 | Cyclopropylmethyl-[2,6-dimethyl-3-(2,4,6-trimethyl-phenyl)-pyrazolo[5,1-b]oxazol-7-ylmethyl]-propyl-amine |
| 5.18 | 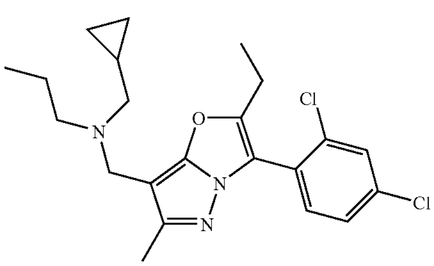 | 420.1 | Cyclopropylmethyl-[3-(2,4-dichloro-phenyl)-2-ethyl-6-methyl-pyrazolo[5,1-b]oxazol-7-ylmethyl]-propyl-amine |
| 5.19 | 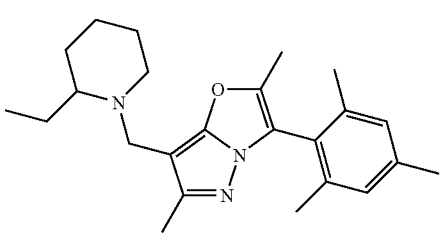 | 380.2 | (±)-7-(2-Ethyl-piperidin-1-ylmethyl)-2,6-dimethyl-3-(2,4,6-trimethyl-phenyl)-pyrazolo[5,1-b]oxazole |

TABLE 4-continued

| Ex. | Structure | [M + H]+ | Name |
|---|---|---|---|
| 5.20 | 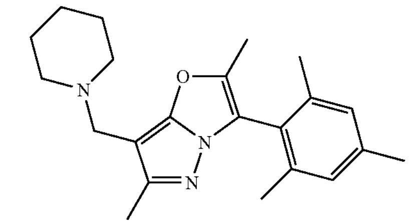 | 352.2 | 2,6-Dimethyl-7-piperidin-1-ylmethyl-3-(2,4,6-trimethyl-phenyl)-pyrazolo[5,1-b]oxazole |
| 5.21 | 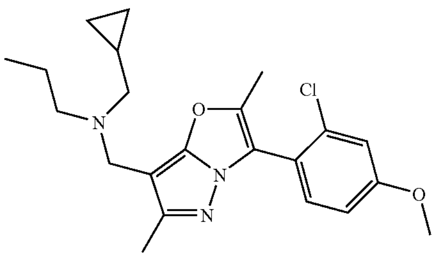 | 402.1 | [3-(2-Chloro-4-methoxy-phenyl)-2,6-dimethyl-pyrazolo[5,1-b]oxazol-7-ylmethyl]-cyclopropylmethyl-propyl-amine |
| 5.22 | 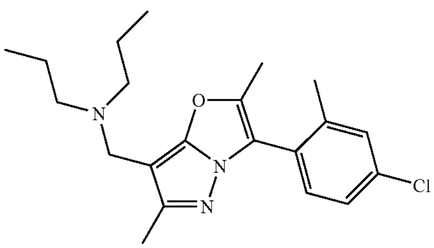 | 374.1 | [3-(4-Chloro-2-methyl-phenyl)-2,6-dimethyl-pyrazolo[5,1-b]oxazol-7-ylmethyl]-dipropyl-amine |
| 5.23 | 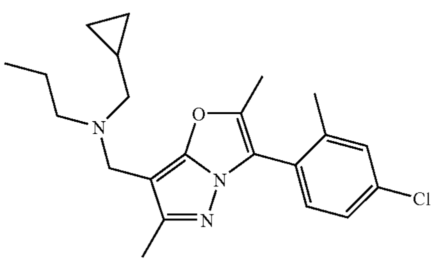 | 386.1 | [3-(4-Chloro-2-methyl-phenyl)-2,6-dimethyl-pyrazolo[5,1-b]oxazol-7-ylmethyl]-cyclopropylmethyl-propyl-amine |
| 5.24 | 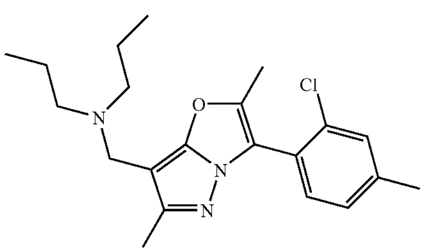 | 374.1 | [3-(2-Chloro-4-methyl-phenyl)-2,6-dimethyl-pyrazolo[5,1-b]oxazol-7-ylmethyl]-dipropyl-amine |
| 5.25 | 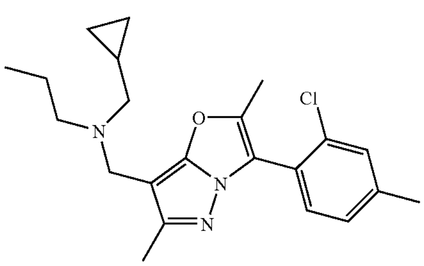 | 386.1 | [3-(2-Chloro-4-methyl-phenyl)-2,6-dimethyl-pyrazolo[5,1-b]oxazol-7-ylmethyl]-cyclopropylmethyl-propyl-amine |

TABLE 4-continued

| Ex. | Structure | [M + H]+ | Name |
|---|---|---|---|
| 5.26 | 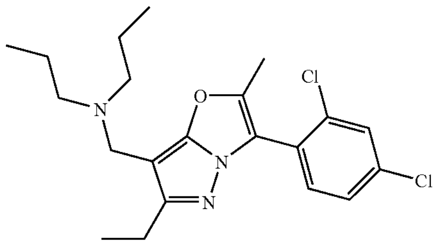 | 408.1 | [3-(2,4-Dichloro-phenyl)-6-ethyl-2-methyl-pyrazolo[5,1-b]oxazol-7-ylmethyl]-dipropyl-amine |
| 5.27 | 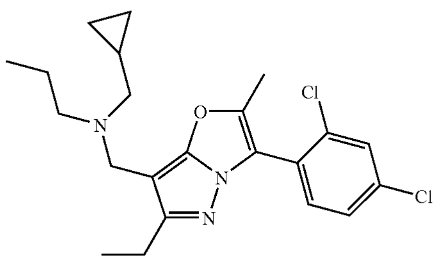 | 420.1 | Cyclopropylmethyl-[3-(2,4-dichloro-phenyl)-6-ethyl-2-methyl-pyrazolo[5,1-b]oxazol-7-ylmethyl]-propyl-amine |
| 5.28 | 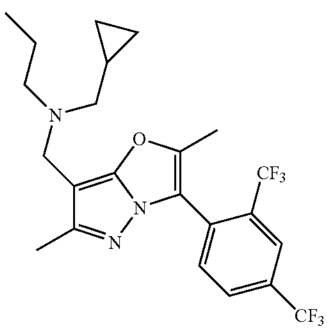 | 474.3 | [3-(2,4-Bis-trifluoromethyl-phenyl)-2,6-dimethyl-pyrazolo[5,1-b]oxazol-7-ylmethyl]-cyclopropylmethyl-propyl-amine |
| 5.29 | 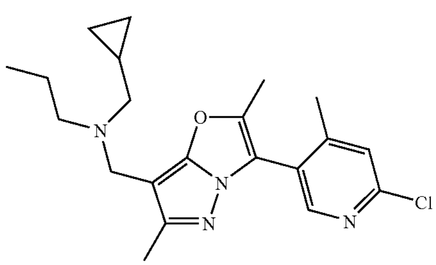 | 387.1 | [3-(6-Chloro-4-methyl-pyridin-3-yl)-2,6-dimethyl-pyrazolo[5,1-b]oxazol-7-ylmethyl]-cyclopropylmethyl-propyl-amine |
| 5.30 | 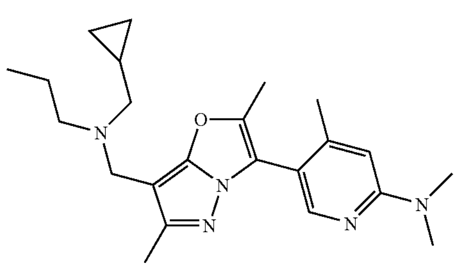 | 396.2 | 4-Chloro-5-{7-[(cyclopropylmethyl-propyl-amino)-methyl]-2,6-dimethyl-pyrazolo[5,1-b]oxazol-3-yl}-pyridin-2-yl)-dimethyl-amine |

TABLE 4-continued

| Ex. | Structure | [M + H]+ | Name |
| --- | --- | --- | --- |
| 5.31 | 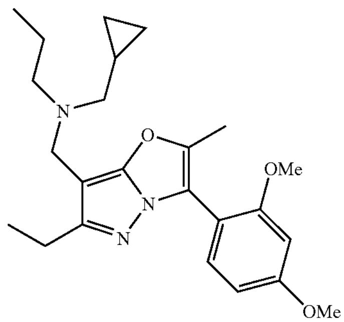 | 412.4 | Cyclopropylmethyl-[3-(2,4-dimethoxy-phenyl)-6-ethyl-2-methyl-pyrazolo[5,1-b]oxazol-7-ylmethyl]-propyl-amine |
| 5.32 | 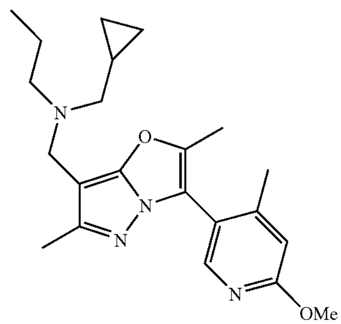 | 383.3 | Cyclopropylmethyl-[3-(6-methoxy-4-methyl-pyridin-3-yl)-2,6-dimethyl-pyrazolo[5,1-b]oxazol-7-ylmethyl]-propyl-amine |
| 5.33 | 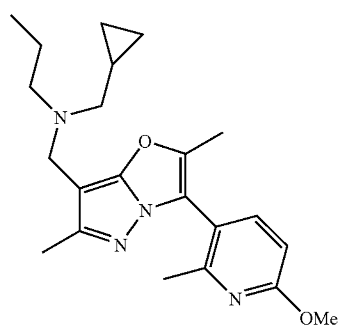 | 383.3 | Cyclopropylmethyl-[3-(6-methoxy-2-methyl-pyridin-3-yl)-2,6-dimethyl-pyrazolo[5,1-b]oxazol-7-ylmethyl]-propyl-amine |
| 5.34 | 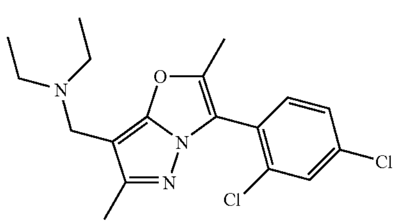 | 366.1 | [3-(2,4-Dichloro-phenyl)-2,6-dimethyl-pyrazolo[5,1-b]oxazol-7-ylmethyl]-diethyl-amine |
| 5.35 | 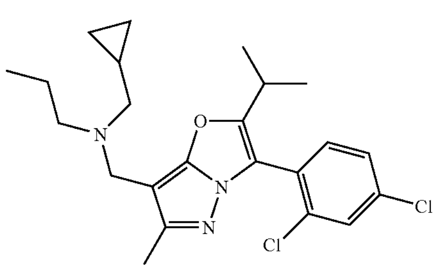 | 434.3 | Cyclopropylmethyl-[3-(2,4-dichloro-phenyl)-2-isopropyl-6-methyl-pyrazolo[5,1-b]oxazol-7-ylmethyl]-propyl-amine |

TABLE 4-continued

| Ex. | Structure | [M + H]+ | Name |
| --- | --- | --- | --- |
| 5.36 | 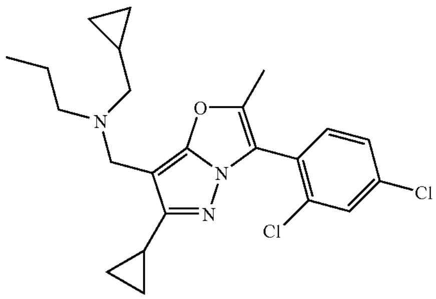 | 432.3 | [6-Cyclopropyl-3-(2,4-dichloro-phenyl)-2-methyl-pyrazolo[5,1-b]oxazol-7-ylmethyl]-cyclopropylmethyl-propyl-amine |
| 5.37 | 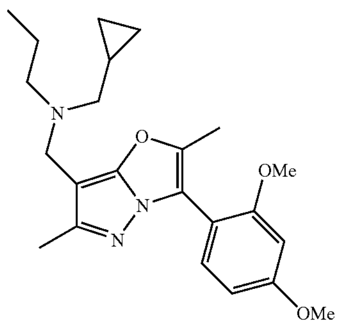 | 398.3 | Cyclopropylmethyl-[3-(2,4-dimethoxy-phenyl)-2,6-dimethyl-pyrazolo[5,1-b]oxazol-7-ylmethyl]-propyl-amine |
| 5.38 | 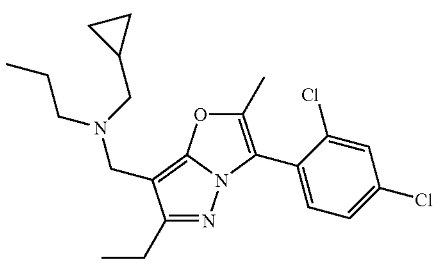 | 434.3 | Cyclopropylmethyl-[3-(2,4-dichloro-phenyl)-6-methyl-2-propyl-pyrazolo[5,1-b]oxazol-7-ylmethyl]-propyl-amine |
| 5.39 | 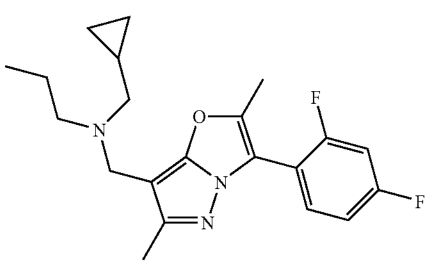 | 374.2 | Cyclopropylmethyl-[3-(2,4-difluoro-phenyl)-2,6-dimethyl-pyrazolo[5,1-b]oxazol-7-ylmethyl]-propyl-amine |
| 5.40 | 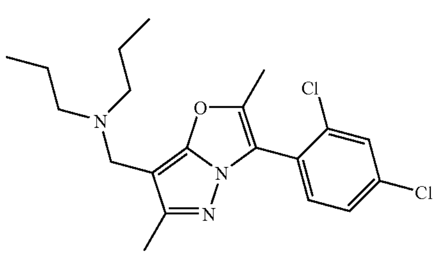 | 380.2 | [3-(2,4-Dichloro-phenyl)-6-methyl-pyrazolo[5,1-b]oxazol-7-ylmethyl]-dipropyl-amine |

TABLE 4-continued

| Ex. | Structure | [M + H]+ | Name |
|---|---|---|---|
| 5.41 | 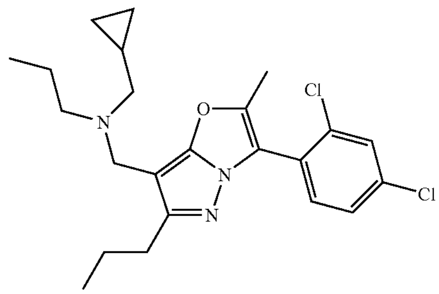 | 434.3 | Cyclopropylmethyl-[3-(2,4-dichloro-phenyl)-2-methyl-6-propyl-pyrazolo[5,1-b]oxazol-7-ylmethyl]-propyl-amine |
| 5.42 | 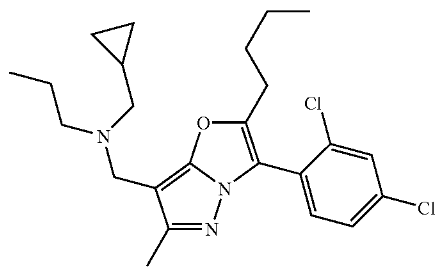 | 448.3 | [2-Butyl-3-(2,4-dichloro-phenyl)-6-methyl-pyrazolo[5,1-b]oxazol-7-ylmethyl]-cyclopropylmethyl-propyl-amine |
| 5.43 | 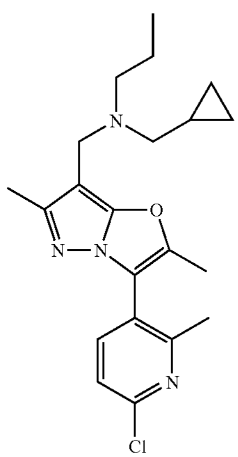 | 387.4 | 3-(6-Chloro-2-methyl-pyridin-3-yl)-2,6-dimethyl-pyrazolo[5,1-b]oxazol-7-ylmethyl]-cyclopropylmethyl-propyl-amine |
| 5.44 | 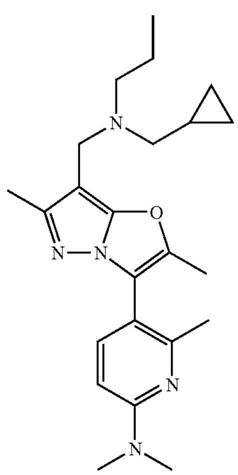 | 396.4 | (5-{7-[(Cyclopropyl methyl-propyl-amino)-methyl]-2,6-dimethyl-pyrazolo[5,1-b]oxazol-3-yl}-6-methyl-pyridin-2-yl)-dimethyl-amine |

TABLE 4-continued

| Ex. | Structure | [M + H]+ | Name |
|---|---|---|---|
| 5.45 | 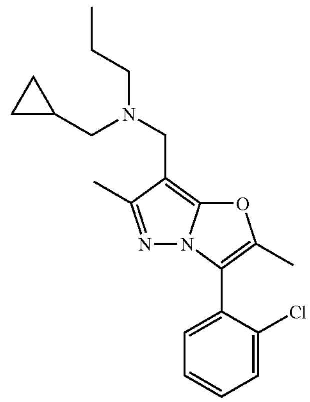 | 372.0 | [3-(2-Chloro-phenyl)-2,6-dimethyl-pyrazolo[5,1-b]oxazol-7-ylmethyl]-cyclopropyl methyl-propyl-amine |
| 5.46 | 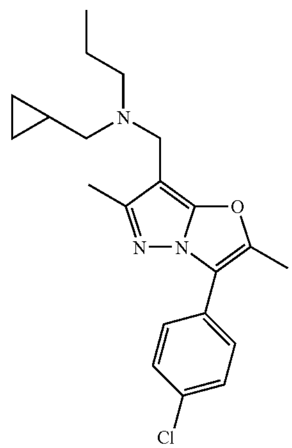 | 372.1 | [3-(4-Chloro-phenyl)-2,6-dimethyl-pyrazolo[5,1-b]oxazol-7-yl methyl]-cyclopropyl methyl-propyl-amine |

Example 6.1

3-(2,4-Dichloro-phenyl)-7-($3,5$-dimethyl-pyrazol-1-yl)-2,6-dimethyl-pyrazolo[5,1-b]oxazole

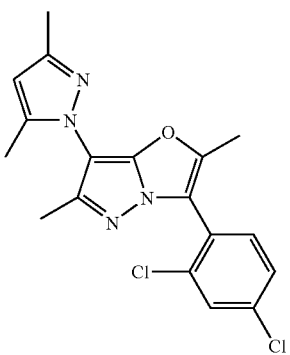

N'-[3-(2,4-Dichloro-phenyl)-2,6-dimethyl-pyrazolo[5,1-b]oxazol-7-yl]-N'-tert-butoxy carbonyl-hydrazinecarboxylic acid tert-butyl ester (Intermediate JA) (50 mg, 0.098 mmol), acetylacetone (0.514 ml, 4.99 mmol) and AcOH (5 ml) are stirred at 85° C. for 54 hours. The reaction is allowed to cool to RT and added to water (50 ml). The product is extracted into EtOAc (2×50 ml) and the combined organics are washed with brine, dried over MgSO$_4$ and concentrated in vacuo. The crude product is purified by ISCO combiflash chromatography, eluting with 0 to 100% (iso-hexane/EtOAc) on a 12 g SiO$_2$-column. The resulting gum is crystallised by dissolving in hot EtOAc, adding iso-hexane and scratching and allowing to cool at 0° C. over night. The title compound 3-(2,4-dichloro-phenyl)-7-(3,5-dimethyl-pyrazol-1-yl)-2,6-dimethyl-pyrazolo[5,1-b]oxazole is isolated as a yellow solid; MS: m/z 375.12 [M+H]+; $^1$H NMR (400.13 MHz (CDCl3) δ 7.60 (2H, m), 7.44 (1H, d), 6.01 (1H, s), 2.38 (3H, s), 2.33 (3H, s), 2.27 (3H, s), 2.22 (3H, s)

Example 6.2

3-(2,4-Dichloro-phenyl)-7-(3-trifluoromethyl-pyrazol-1-yl)-2,6-dimethyl-pyrazolo[5,1-b]oxazole

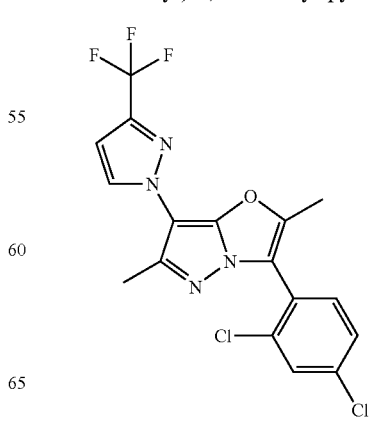

Step 1: 1-(2,4-Dichloro-phenyl)-2-(5'-methyl-3-trifluoromethyl-2'H-[1,4']bipyrazolyl-3'-yloxy)-propan-1-one To a stirred solution of 5'-methyl-3-trifluoromethyl-2'H-[1,4']bipyrazolyl-3'-ol (Intermediate KA)(270 mg, 1.163 mmol) and cesium carbonate (379 mg, 1.163 mmol) in DMF (2.684 ml) at 50° C. is added 2-bromo-1-(2,4-dichloro-phenyl)-propan-1-one (Intermediate AA) (328 mg, 1.163 mmol) slowly in DMF (1.789 ml). The reaction is stirred at 50° C. for 1 hour before cooling to RT. 2M $Na_2CO_3$ (100 ml) is added and the crude product is extracted with EtOAc (2×100 ml). The organic phases are combined, washed with brine, dried over $MgSO_4$ and concentrated in vacuo. The crude product is purified by ISCO combiflash chromatography, eluting with 0 to 100% (iso-hexane/EtOAc) on a 24 g $SiO_2$ column to give the title compound as a light brown oil; MS: m/z 433.24 $[M+H]^+$ Step 2: 3-(2,4-Dichloro-phenyl)-7-(3-trifluoromethyl-pyrazol-1-yl)-2,6-dimethyl-pyrazolo[5,1-b]oxazole:

1-(2,4-Dichloro-phenyl)-2-(5'-methyl-3-trifluoromethyl-2'H-[1,4']bipyrazolyl-3'-yloxy)-propan-1-one (150 mg, 0.346 mmol) is dissolved in 1,2-dichloroethane (1.39 ml) and titanium tetrachloride (0.046 ml, 0.416 mmol) is added; the reaction mixture is stirred at 85° C. under $N_2$ for 3 hours. The reaction mixture is allowed to cool to RT and quenched with sat. ammonium chloride then added to a further 50 ml solution of ammonium chloride. The crude product is extracted with EtOAc (2×50 ml). The combined organics are washed with water, brine, dried over $MgSO_4$ and concentrated in vacuo. Purification of the crude product by ISCO combiflash chromatography, eluting with 0 to 100% (EtOAc/Iso-hexane) on a 24 g SiO2-column afford the title compound as a solid MS: m/z 415.25 $[M+H]^+$; $^1H$ NMR (400.13 MHz ($CDCl_3$) δ 7.69 (1H, dd), 7.60 (1H, d), 7.54 (1H, d), 7.43 (1H, dd), 6.72 (1H, d), 2.37 (3H, s), 2.35 (3H, s).

Example 6.8

3-(2,4-Dichloro-phenyl)-7-(3,5-dimethyl-[1,2,4]triazol-1-yl)-2,6-dimethyl-pyrazolo[5,1-b]oxazole Step 1: 1-(2,4-Dichlorophenyl)-2-(4-(3,5-dimethyl-1H-1,2,4-triazol-1-yl)-3-methyl-1H-pyrazol-5-yloxy)propan-1-one To a stirring solution of 4-(3,5-dimethyl-[1,2,4]triazol-1-yl)-5-methyl-2H-pyrazol-3-ol (Intermediate KF) (97 mg, 0.502 mmol) and cesium carbonate (164 mg, 0.502 mmol) in DMF (1.158 ml) at 50° C. is added 2-bromo-1-(2,4-dichlorophenyl)-propan-1-one (Intermediate AA) (142 mg, 0.502 mmol) in DMF (0.772 ml). The reaction mixture is stirred under $N_2$ at 50° C. for 1.5 hours and then left to stand @ RT overnight. The resulting suspension is filtered and the filtrate is concentrated in vacuo. Purification by trituration from EtOAc affords the title product; MS: m/z 394.0 $[M+H]^+$ Step 2: 3-(2,4-Dichlorophenyl)-7-(3,5-dimethyl-1H-1,2,4-triazol-1-yl)-2,6-dimethyl pyrazolo[5,1-b]oxazole To a dispersion of 1-(2,4-dichlorophenyl)-2-(4-(3,5-dimethyl-1H-1,2,4-triazol-1-yl)-3-methyl-1H-pyrazol-5-yloxy)propan-1-one (120 mg, 0.304 mmol) in 1,2-dichloroethane (1.217 ml) is added titanium tetrachloride (0.080 ml, 0.73 mmol). The reaction mixture is heated at 85° C. for 4 hours and then left at RT overnight. The mixture is quenched carefully with sat. $NH_4Cl$ (50 ml) and extracted with EtOAc (2×50 ml). The combined organic extracts are washed with brine, dried over $MgSO_4$ and concentrated in vacuo to afford a white solid. Purification by recrystallisation from EtOAc (~3 ml) yields the title compound as a white crystalline solid; MS: m/z 376.0 $[M+H]^+$. $^1H$ NMR (400 MHz, DMSO-d6) δ 7.95 (1H, d), 7.77 (1H, d), 7.69 (1H, d), 2.38 (3H, s), 2.30 (3H, s), 2.28 (3H, s), 2.12 (3H, s).

Example 6.12

7-(3,5-Dimethyl-[1,2,4]triazol-1-yl)-3-(4-methoxy-2-methyl-phenyl)-2,6-dimethyl-pyrazolo[5,1-b]oxazole Step 1: 2-[4-(3,5-Dimethyl-[1,2,4]triazol-1-yl)-5-methyl-2H-pyrazol-3-yloxy]-1-(4-methoxy-2-methyl-phenyl)-propan-1-one:

To a suspension of 4-(3,5-dimethyl-[1,2,4]triazol-1-yl)-5-methyl-2H-pyrazol-3-ol (Intermediate KF) (1.127 g, 5.83 mmol) in dry DMF (80 ml) is added silver carbonate (1.609 g, 5.83 mmol) and the mixture is heated at 50° C. After 10 minutes a solution of 2-bromo-1-(4-methoxy-2-methyl-phenyl)-propan-1-one (1.5 g, 5.83 mmol) {prepared from 1-(4-methoxy-2-methyl-phenyl)-propan-1-one (Intermediate C) analogously to 2-bromo-1-(2,4-dichloro-phenyl)-propan-1-one (Intermediate AA)} in dry DMF (20 ml) is added in a dropwise manner. The resulting mixture is stirred at 50° C. for 1 hr, before cooling to RT whereupon it is filtered to remove the inorganic material. The filtrate is evaporated in vacuo to give a green/brown solid and partitioned between $DCM/H_2O$. The mixture is extracted with DCM (2×150 ml) and the combined organic extracts are dried ($MgSO_4$) and concentrated in vacuo to afford an orange solid. The crude product is purified by chromatography (on silica gel) eluting with 100% DCM followed by 2% MeOH/DCM to give the title compound as a pale yellow crystalline solid; MS: m/z 370.1 $[M+H]^+$. $^1H$ NMR (400 MHz, DMSO-$d_6$) δ 12.1 (1H, d), 7.95 (1H, d), 6.88 (2H, m), 5.89 (1H, q), 3.82 (3H, s), 2.39 (3H, s), 2.25 (3H, s), 2.23 (3H, s), 2.04 (3H, s), 1.37 (3H, d).

Step 2: 7-(3,5-Dimethyl-[1,2,4]triazol-1-yl)-3-(4-methoxy-2-methyl-phenyl)-2,6-dimethyl-pyrazolo[5,1-b]oxazole To a dispersion of 2-[4-(3,5-dimethyl-[1,2,4]triazol-1-yl)-5-methyl-2H-pyrazol-3-yloxy]-1-(4-methoxy-2-methyl-phenyl)-propan-1-one (0.905 g, 2.45 mmol) in 1,2-dichloroethane (20 ml) is added titanium tetrachloride (0.675 ml, 6.12 mmol). The reaction mixture is heated to 85° C. for 2.5 hours and then left at RT overnight. The mixture is quenched carefully with sat. $NH_4Cl$ (50 ml) and extracted with EtOAc (2×50 ml). The combined organic extracts are washed with $NaHCO_3$ (50 ml), brine, dried over $MgSO_4$ and concentrated in vacuo to afford a dark brown oil. The crude oil is then taken up in 10% $Et_2O$/iso-hexane (50 ml) and the brown solution is sonicated: no precipitation occurred immediately, but after 2 hours large crystals form. The solid is collected and washed with iso-hexane to give a cream coloured solid. Purification of this solid by recrystallisation from hot $Et_2O$ (~40 ml) yields the title compound as tan crystals; MS: m/z=352.1 $[M+H]^+$. $^1H$ NMR (400 MHz, DMSO-$d_6$) δ 7.39 (1H, d), 7.01 (1H, d), 6.94 (1H, dd), 3.83 (3H, s), 2.30 (6H, s), 2.26 (6H, s), 2.11 (3H, s).

The examples shown in the following table are prepared according to the procedures of Example 6.1, 6.2, 6.8 and 6.12 using the appropriate starting compounds, the methods of preparation of which are described hereinafter or are commercially available.

TABLE 5

| Ex. | Structure | [M + H]+ | Name |
|---|---|---|---|
| 6.3 | 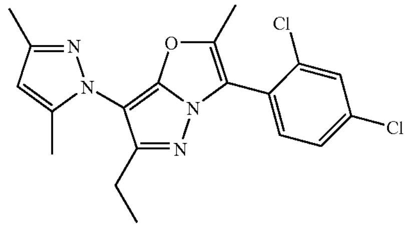 | 389.14 | 3-(2,4-Dichloro-phenyl)-7-(3,5-dimethyl-pyrazol-1-yl)-6-ethyl-2-methyl-pyrazolo[5,1-b]oxazole |
| 6.4 | 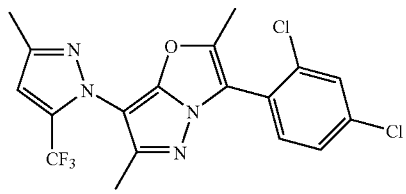 | 429.24 | 3-(2,4-Dichloro-phenyl)-2,6-dimethyl-7-(3-methyl-5-trifluoromethyl-pyrazol-1-yl)-pyrazolo[5,1-b]oxazole |
| 6.5 | 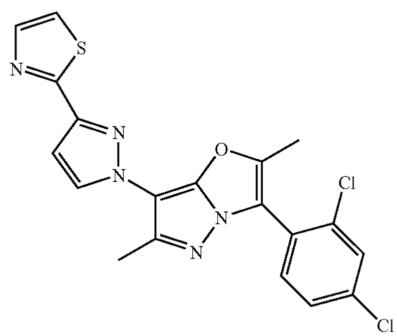 | 430.21 | 3-(2,4-Dichloro-phenyl)-2,6-dimethyl-7-(3-thiazol-2-yl-pyrazol-1-yl)-pyrazolo[5,1-b]oxazole |
| 6.6 | 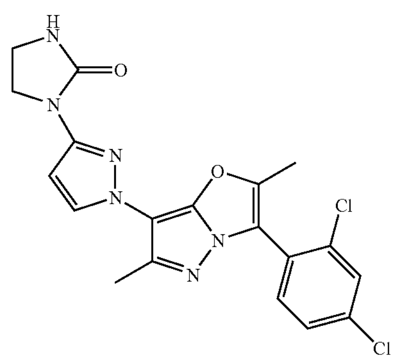 | 431.28 | 1-{1-[3-(2,4-Dichloro-phenyl)-2,6-dimethyl-pyrazolo[5,1-b]oxazol-7-yl]-1H-pyrazol-3-yl}-imidazolidin-2-one |
| 6.7 | 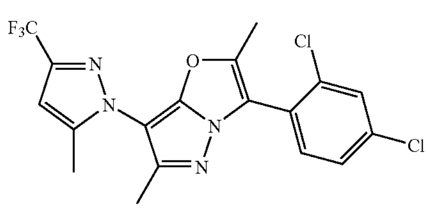 | 429.27 | 3-(2,4-Dichloro-phenyl)-2,6-dimethyl-7-(5-methyl-3-trifluoromethyl-pyrazol-1-yl)-pyrazolo[5,1-b]oxazole |
| 6.8 | 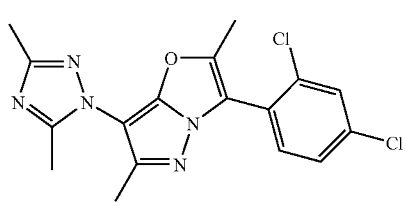 | 376.0 | 3-(2,4-Dichloro-phenyl)-7-(3,5-dimethyl-[1,2,4]triazol-1-yl)-2,6-dimethyl-pyrazolo[5,1-b]oxazole |

TABLE 5-continued

| Ex. | Structure | [M + H]⁺ | Name |
|---|---|---|---|
| 6.9 | 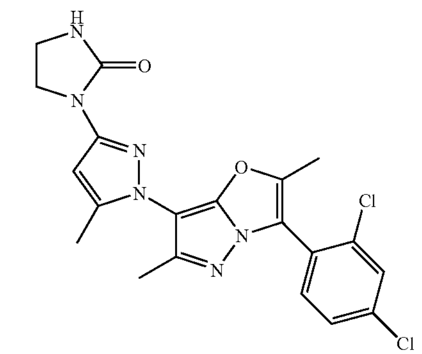 | 445.0 | 1-{1-[3-(2,4-Dichloro-phenyl)-2,6-dimethyl-pyrazolo[5,1-b]oxazol-7-yl]-5-methyl-1H-pyrazol-3-yl)-imidazolidin-2-one |
| 6.10 | 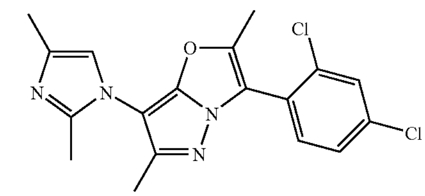 | 375.0 | 3-(2,4-Dichloro-phenyl)-7-(2,4-dimethyl-imidazol-1-yl)-2,6-dimethyl-pyrazolo[5,1-b]oxazole |
| 6.11 | 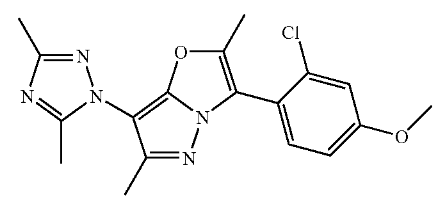 | 372.1 | 3-(2-Chloro-4-methoxy-phenyl)-7-(3,5-dimethyl-[1,2,4]triazol-1-yl)-2,6-dimethyl-pyrazolo[5,1-b]oxazole |
| 6.12 | 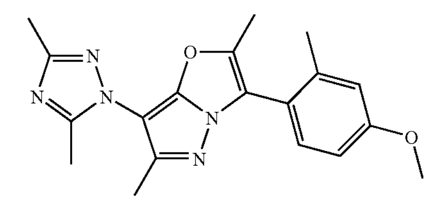 | 352.1 | 7-(3,5-Dimethyl-[1,2,4]triazol-1-yl)-3-(4-methoxy-2-methyl-phenyl)-2,6-dimethyl-pyrazolo[5,1-b]oxazole |
| 6.13 | 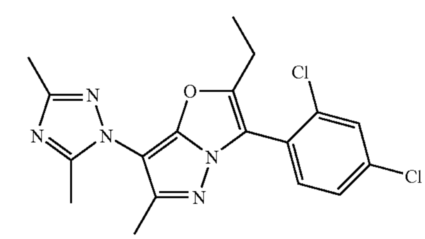 | 390.0 | 3-(2,4-Dichloro-phenyl)-7-(3,5-dimethyl-[1,2,4]triazol-1-yl)-2-ethyl-6-methyl-pyrazolo[5,1-b]oxazole |
| 6.14 | 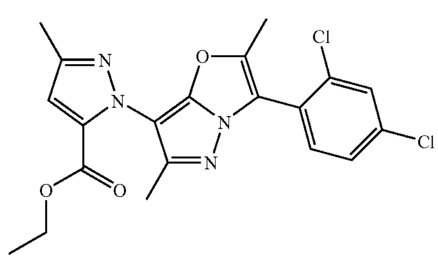 | 433.0 | 2-[3-(2,4-Dichloro-phenyl)-2,6-dimethyl-pyrazolo[5,1-b]oxazol-7-yl]-5-methyl-2H-pyrazole-3-carboxylic acid ethyl ester |

TABLE 5-continued

| Ex. | Structure | [M + H]⁺ | Name |
|---|---|---|---|
| 6.15 | 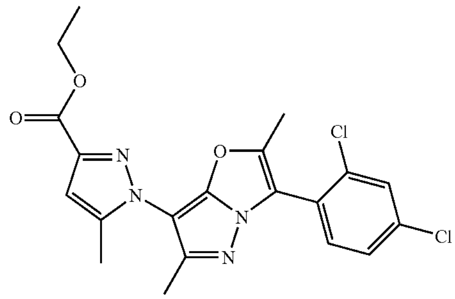 | 433.0 | 1-[3-(2,4-Dichloro-phenyl)-2,6-dimethyl-pyrazolo[5,1-b]oxazol-7-yl]-5-methyl-1H-pyrazole-3-carboxylic acid ethyl ester |
| 6.16 | 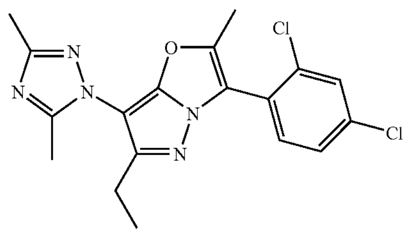 | 390.0 | 3-(2,4-Dichloro-phenyl)-7-(3,5-dimethyl-[1,2,4]triazol-1-yl)-6-ethyl-2-methyl-pyrazolo[5,1-b]oxazole |
| 6.17 | 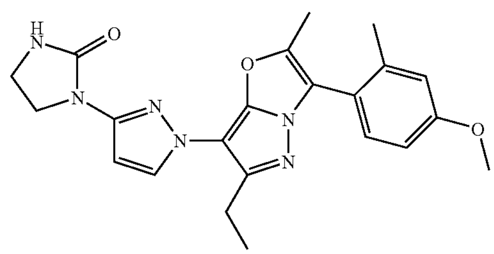 | 421.1 | 1-{1-[6-Ethyl-3-(4-methoxy-2-methyl-phenyl)-2-methyl-pyrazolo[5,1-b]oxazol-7-yl]-1H-pyrazol-3-yl}-imidazolidin-2-one |
| 6.18 | 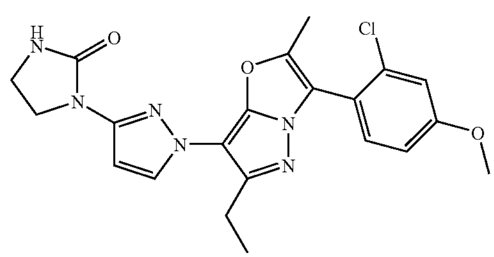 | 441.1 | 1-{1-[3-(2-Chloro-4-methoxy-phenyl)-6-ethyl-2-methyl-pyrazolo[5,1-b]oxazol-7-yl]-1H-pyrazol-3-yl}-imidazolidin-2-one |
| 6.19 | 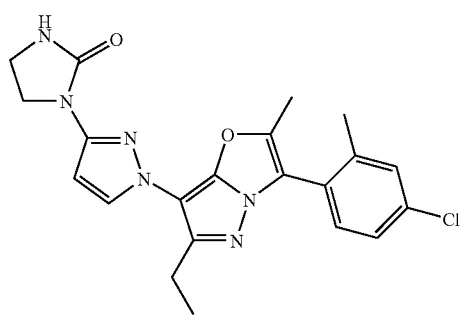 | 421.1 | 1-{1-[3-(4-Chloro-2-methyl-phenyl)-6-ethyl-2-methyl-pyrazolo[5,1-b]oxazol-7-yl]-1H-pyrazol-3-yl}-imidazolidin-2-one |

TABLE 5-continued

| Ex. | Structure | [M + H]⁺ | Name |
|---|---|---|---|
| 6.20 | 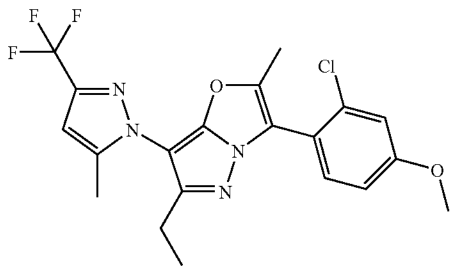 | 439.1 | 3-(2-Chloro-4-methoxy-phenyl)-6-ethyl-2-methyl-7-(5-methyl-3-trifluoromethyl-pyrazol-1-yl)-pyrazolo[5,1-b]oxazole |
| 6.21 | 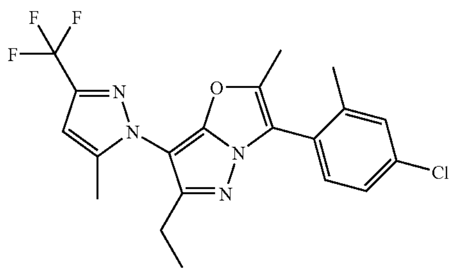 | 423.1 | 3-(4-Chloro-2-methyl-phenyl)-6-ethyl-2-methyl-7-(5-methyl-3-trifluoromethyl-pyrazol-1-yl)-pyrazolo[5,1-b]oxazole |
| 6.22 | 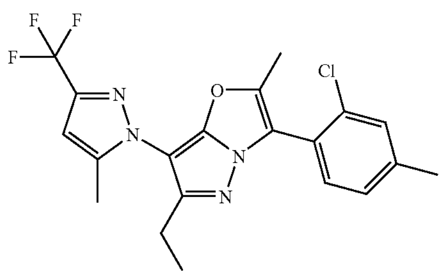 | 423.1 | 3-(2-Chloro-4-methyl-phenyl)-6-ethyl-2-methyl-7-(5-methyl-3-trifluoromethyl-pyrazol-1-yl)-pyrazolo[5,1-b]oxazole |
| 6.23 | 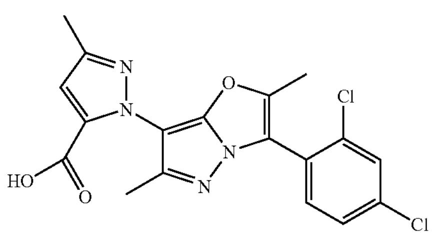 | 405.0 | 2-[3-(2,4-Dichloro-phenyl)-2,6-dimethyl-pyrazolo[5,1-b]oxazol-7-yl]-5-methyl-2H-pyrazole-3-carboxylic acid |
| 6.24 | 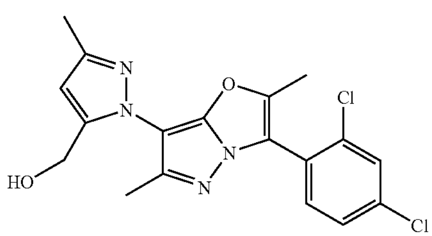 | 391.0 | {2-[3-(2,4-Dichloro-phenyl)-2,6-dimethyl-pyrazolo[5,1-b]oxazol-7-yl]-5-methyl-2H-pyrazol-3-yl}-methanol |
| 6.25 | 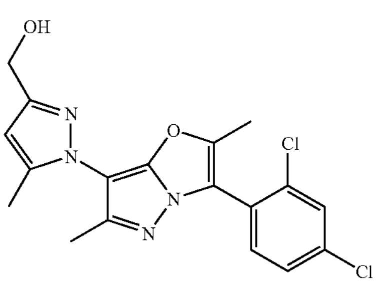 | 391.0 | {1-[3-(2,4-Dichloro-phenyl)-2,6-dimethyl-pyrazolo[5,1-b]oxazol-7-yl]-5-methyl-1H-pyrazol-3-yl}-methanol |

TABLE 5-continued

| Ex. | Structure | [M + H]+ | Name |
|---|---|---|---|
| 6.26 | 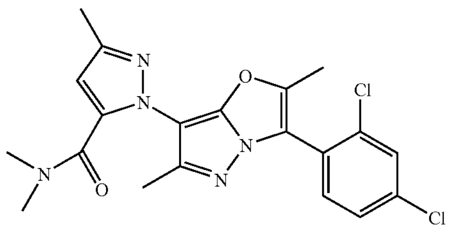 | 432.0 | 2-[3-(2,4-Dichloro-phenyl)-2,6-dimethyl-pyrazolo[5,1-b]oxazol-7-yl]-5-methyl-2H-pyrazole-3-carboxylic acid dimethylamide |
| 6.27 | 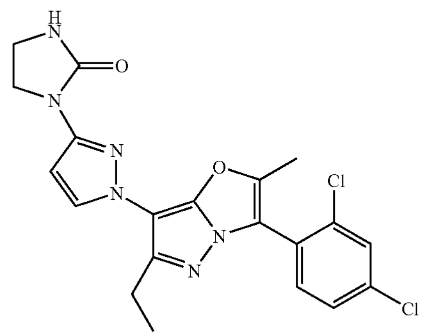 | 445.0 | 1-{1-[3-(2,4-Dichloro-phenyl)-6-ethyl-2-methyl-pyrazolo[5,1-b]oxazol-7-yl]-1H-pyrazol-3-yl}-imidazolidin-2-one |
| 6.28 | 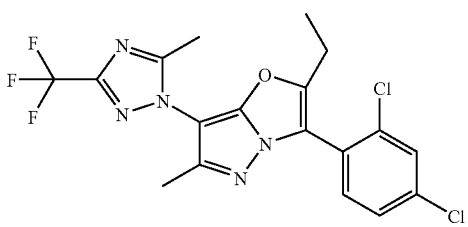 | 444 | 3-(2,4-dichlorophenyl)-2-ethyl-6-methyl-7-(5-methyl-3-(trifluoromethyl)-1H-1,2,4-triazol-1-yl)pyrazolo[5,1-b]oxazole |
| 6.29 | 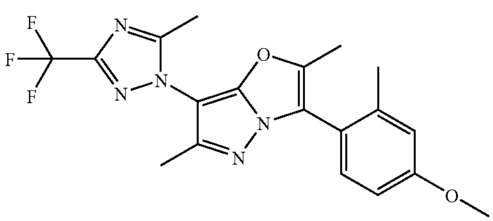 | 446 | 3-(4-methoxy-2-methylphenyl)-2,6-dimethyl-7-(5-methyl-3-(trifluoromethyl)-1H-1,2,4-triazol-1-yl)pyrazolo[5,1-b]oxazole |
| 6.30 | 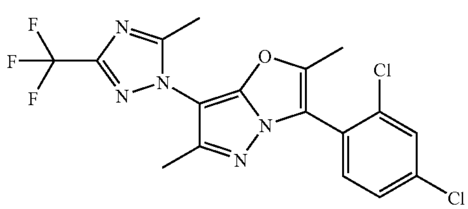 | 430 | 3-(2,4-dichlorophenyl)-2,6-dimethyl-7-(5-methyl-3-(trifluoromethyl)-1H-1,2,4-triazol-1-yl)pyrazolo[5,1-b]oxazole |
| 6.31 | 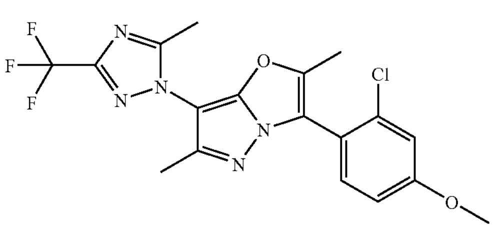 | 426 | 3-(2-Chloro-4-methoxyphenyl)-2,6-dimethyl-7-(5-methyl-3-(trifluoromethyl)-1H-1,2,4-triazol-1-yl)pyrazolo[5,1-b]oxazole |

TABLE 5-continued

| Ex. | Structure | [M + H]+ | Name |
|---|---|---|---|
| 6.32 | 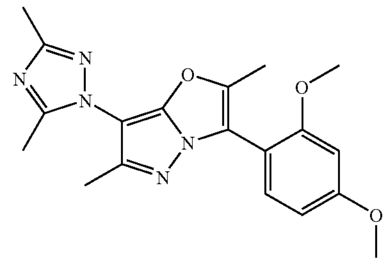 | 368.3 | 3-(2,4-Dimethoxy-phenyl)-7-(3,5-dimethyl-[1,2,4]triazol-1-yl)-2,6-dimethyl-pyrazolo[5,1-b]oxazole |
| 6.33 | 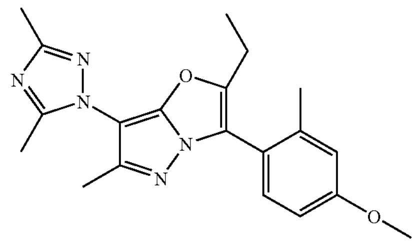 | 366.3 | 7-(3,5-Dimethyl-1H-1,2,4-triazol-1-yl)-2-ethyl-3-(4-methoxy-2-methylphenyl)-6-methylpyrazolo[5,1-b]oxazole |
| 6.34 | 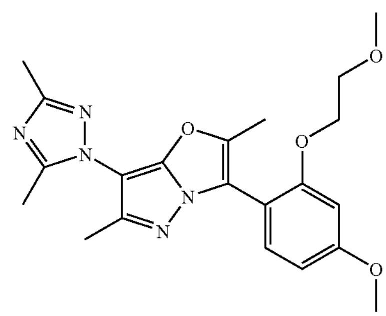 | 412.3 | 7-(3,5-Dimethyl-[1,2,4]triazol-1-yl)-3-[4-methoxy-2-(2-methoxy-ethoxy)-phenyl]-2,6-dimethyl-pyrazolo[5,1-b]oxazole |
| 6.35 | 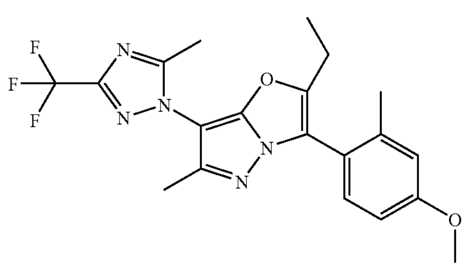 | 420.2 | 2-Ethyl-3-(4-methoxy-2-methylphenyl)-6-methyl-7-(5-methyl-3-(trifluoromethyl)-1H-1,2,4-triazol-1-yl)pyrazolo[5,1-b]oxazole |
| 6.36 | 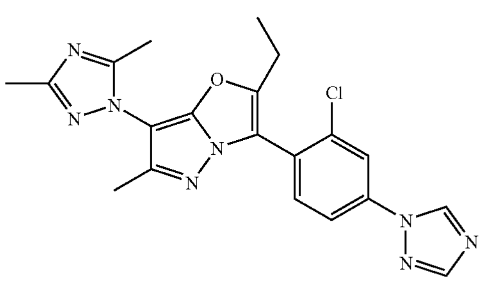 | 423.2 | 3-(2-Chloro-4-(1H-1,2,4-triazol-1-yl)phenyl)-7-(3,5-dimethyl-1H-1,2,4-triazol-1-yl)-2-ethyl-6-methylpyrazolo[5,1-b]oxazole |

TABLE 5-continued

| Ex. | Structure | [M + H]⁺ | Name |
|---|---|---|---|
| 6.37 | 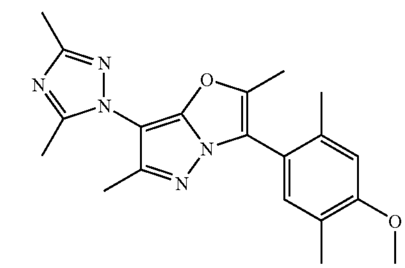 | 366.3 | 7-(3,5-Dimethyl-[1,2,4]triazol-1-yl)-3-(4-methoxy-2,5-dimethyl-phenyl)-2,6-dimethyl-pyrazolo[5,1-b]oxazole |
| 6.38 | 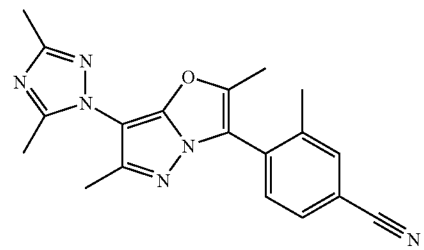 | 347.3 | 4-(7-(3,5-Dimethyl-1H-1,2,4-triazol-1-yl)-2,6-dimethylpyrazolo[5,1-b]oxazol-3-yl)-3-methylbenzonitrile |
| 6.39 | 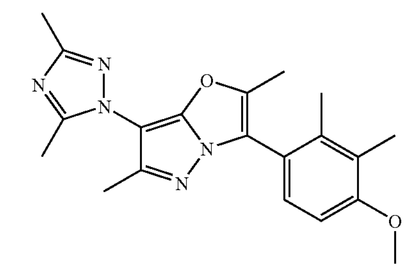 | 366.3 | 7-(3,5-Dimethyl-[1,2,4]triazol-1-yl)-3-(4-methoxy-2,3-dimethyl-phenyl)-2,6-dimethyl-pyrazolo[5,1-b]oxazole |
| 6.40 | 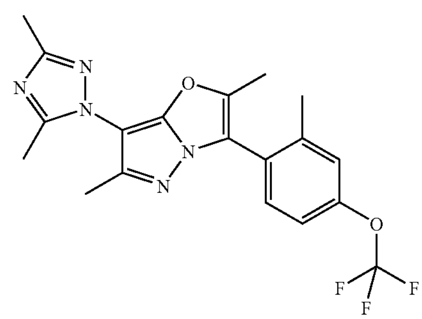 | 406.3 | 7-(3,5-Dimethyl-[1,2,4]triazol-1-yl)-2,6-dimethyl-3-(2-methyl-4-trifluoromethoxy-phenyl)-pyrazolo[5,1-b]oxazole |
| 6.41 | 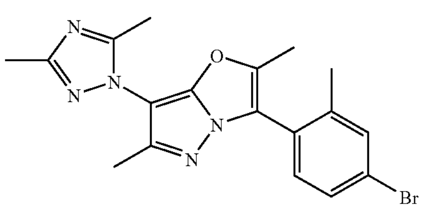 | 402.1 | 3-(4-Bromo-2-methylphenyl)-7-(3,5-dimethyl-1H-1,2,4-triazol-1-yl)-2,6-dimethylpyrazolo[5,1-b]oxazole |
| 6.42 | 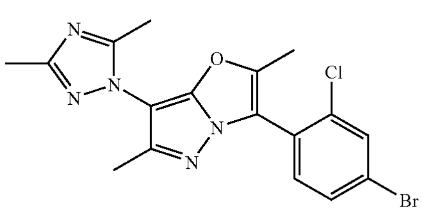 | 420.1 | 3-(4-Bromo-2-chlorophenyl)-7-(3,5-dimethyl-1H-1,2,4-triazol-1-yl)-2,6-dimethylpyrazolo[5,1-b]oxazole |

TABLE 5-continued

| Ex. | Structure | [M + H]+ | Name |
|---|---|---|---|
| 6.43 | 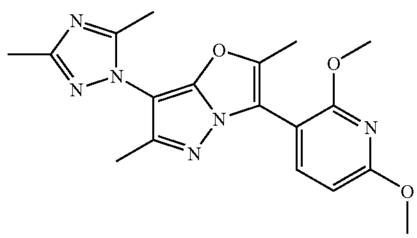 | 370.2 | 3-(2,6-Dimethoxy-pyridin-3-yl)-7-(3,5-dimethyl-[1,2,4]triazol-1-yl)-2,6-dimethyl-pyrazolo[5,1-b]oxazole |
| 6.44 | 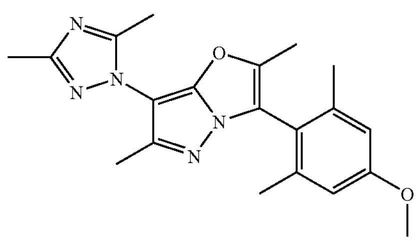 | 366.3 | 7-(3,5-Dimethyl-[1,2,4]triazol-1-yl)-3-(4-methoxy-2,6-dimethyl-phenyl)-2,6-dimethyl-pyrazolo[5,1-b]oxazole |
| 6.45 | 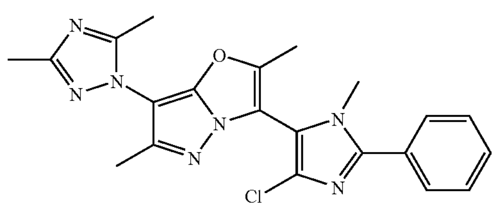 | 422.2 | 3-(5-Chloro-3-methyl-2-phenyl-3H-imidazol-4-yl)-7-(3,5-dimethyl-[1,2,4]triazol-1-yl)-2,6-dimethyl-pyrazolo[5,1-b]oxazole |
| 6.46 | 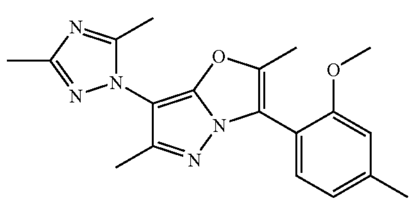 | 352.2 | 7-(3,5-dimethyl-1H-1,2,4-triazol-1-yl)-3-(2-methoxy-4-methylphenyl)-2,6-dimethylpyrazolo[5,1-b]oxazole |
| 6.47 | 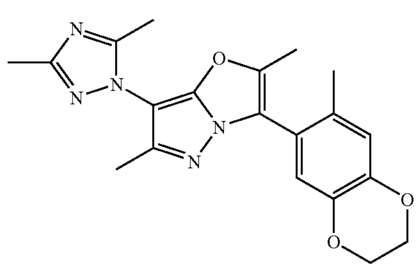 | 380.1 | 7-(3,5-dimethyl-1H-1,2,4-triazol-1-yl)-2,6-dimethyl-3-(7-methyl-2,3-dihydrobenzo[b][1,4]dioxin-6-yl)pyrazolo[5,1-b]oxazole |
| 6.48 | 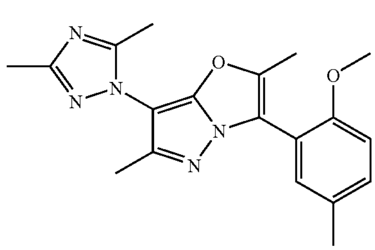 | 352.2 | 7-(3,5-Dimethyl-[1,2,4]triazol-1-yl)-3-(2-methoxy-5-methyl-phenyl)-2,6-dimethyl-pyrazolo[5,1-b]oxazole |

TABLE 5-continued

| Ex. | Structure | [M + H]+ | Name |
|---|---|---|---|
| 6.49 | 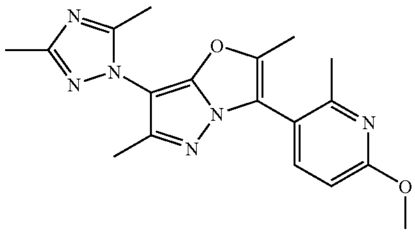 | 353.1 | 7-(3,5-Dimethyl-[1,2,4]triazol-1-yl)-3-(6-methoxy-2-methyl-pyridin-3-yl)-2,6-dimethyl-pyrazolo[5,1-b]oxazole |
| 6.50 | 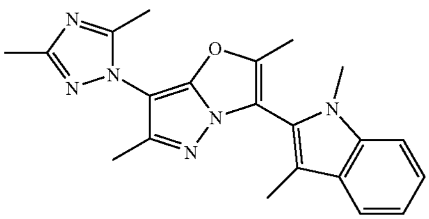 | 375.2 | 7-(3,5-Dimethyl-1H-1,2,4-triazol-1-yl)-3-(1,3-dimethyl-1H-indol-2-yl)-2,6-dimethylpyrazolo[5,1-b]oxazole |
| 6.51 | 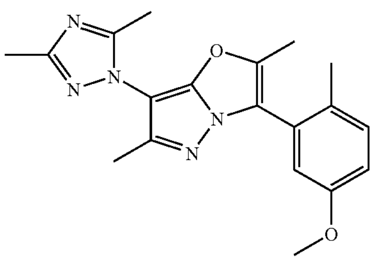 | 352.2 | 7-(3,5-Dimethyl-1H-1,2,4-triazol-1-yl)-3-(5-methoxy-2-methylphenyl)-2,6-dimethylpyrazolo[5,1-b]oxazole |
| 6.52 | 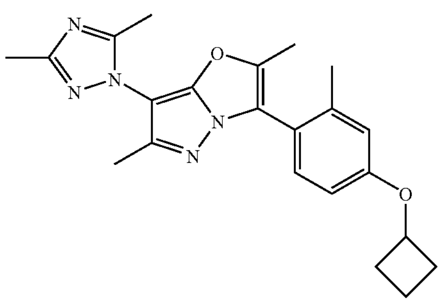 | 392.2 | 3-(4-Cyclobutoxy-2-methylphenyl)-7-(3,5-dimethyl-1H-1,2,4-triazol-1-yl)-2,6-dimethyl pyrazolo[5,1-b]oxazole |
| 6.53 | 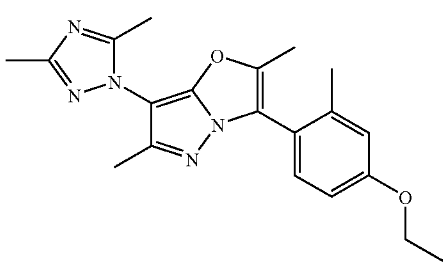 | 366.2 | 7-(3,5-Dimethyl-1H-1,2,4-triazol-1-yl)-3-(4-ethoxy-2-methylphenyl)-2,6-dimethylpyrazolo[5,1-b]oxazole |
| 6.54 | 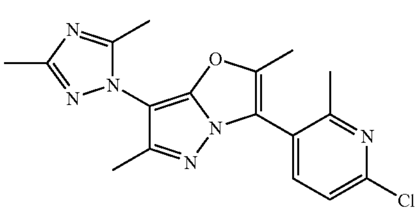 | 357.1 | 3-(6-Chloro-2-methyl-pyridin-3-yl)-7-(3,5-dimethyl-[1,2,4]triazol-1-yl)-2,6-dimethyl-pyrazolo[5,1-b]oxazole |

TABLE 5-continued

| Ex. | Structure | [M + H]⁺ | Name |
|---|---|---|---|
| 6.55 | 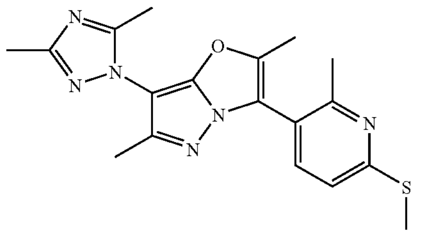 | 369.2 | 7-(3,5-Dimethyl-[1,2,4]triazol-1-yl)-2,6-dimethyl-3-(2-methyl-6-methylsulfanyl-pyridin-3-yl)-pyrazolo[5,1-b]oxazole |
| 6.56 | 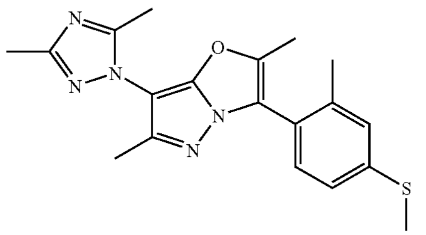 | 368.1 | 7-(3,5-Dimethyl-1H-1,2,4-triazol-1-yl)-2,6-dimethyl-3-(2-methyl-4-(methyltbio)phenyl)pyrazolo[5,1-b]oxazole |
| 6.57 | 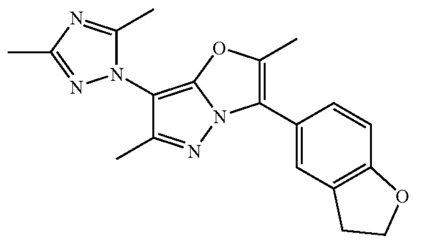 | 350.2 | 3-(2,3-Dihydrobenzofuran-5-yl)-7-(3,5-dimethyl-1H-1,2,4-triazol-1-yl)-2,6-dimethylpyrazolo[5,1-b]oxazole |

Example 6.5

7-(3,5-Dimethyl-[1,2,4]triazol-1-yl)-2,6-dimethyl-3-(2-methyl-6-methylsulfanyl-pyridin-3-yl)-pyrazolo[S5,1-b]oxazole To a stirred solution of 3-(6-Chloro-2-methyl-pyridin-3-yl)-7-(3,5-dimethyl-[1,2,4]triazol-1-yl)-2,6-dimethyl-pyrazolo[5,1-b]oxazole (Example 6.54) 100 mg, 0.280 mmol) in DMF (5 ml) is added sodium methanethiolate (39.3 mg, 0.561 mmol) and the contents heated to 70° C. for 3 hrs. After this time the contents are cooled to RT and sat NaHCO₃ is added and the contents extracted into EtOAc. The organic moiety is separated and washed with H₂O, brine, dried (MgSO₄) and evaporated to give a brown solid. The crude material is triturated with Et₂O to give the product as a white solid. MS m/z=369.2 [M+H]⁺; ¹H NMR 400.13 MHz (CDCl₃) –7.5 (1H, d), 7.2 (1H, d), 2.6 (3H, s), 2.5 (3H, s), 2.45 (6H, m), 2.35 (3H, s), 2.25 (3H, s).

Example 7.1

3-(2,4-Dichloro-phenyl)-2,6-dimethyl-7-(1-methyl-ene-butyl)-pyrazolo[5,1-b]oxazole

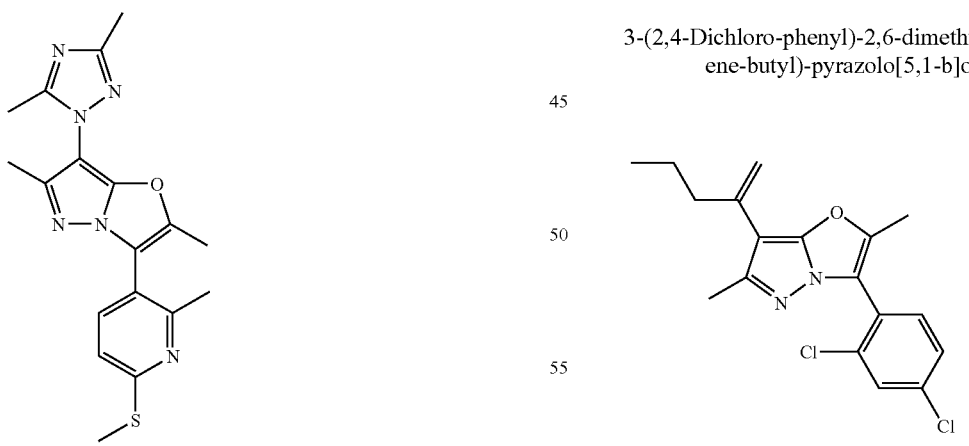

Step 1: 1-[3-(2,4-Dichloro-phenyl)-2,6-dimethyl-pyrazolo[5,1-b]oxazol-7-yl]-butan-1-ol:

To a stirred solution of 3-(2,4-dichloro-phenyl)-2,6-dimethyl-pyrazolo[S,1-b]oxazole-7-carbaldehyde (Intermediate IC, step 1) (0.900 g, 2.91 mmol) in THF (20 ml) at 0° C. is added propylmagnesium chloride (2.0 M in Et₂O) (1.601 ml, 3.20 mmol). The reaction mixture is stirred for 1 hour at 0° C. then allowed to warm to RT. The mixture is stirred for 5 minutes before quenching with NH₄Cl (sat. aq.) (3 ml). The reaction mixture is partitioned between EtOAc (100 ml) and H₂O (100 ml) and extracted with EtOAc (3×50 ml). The combined organic extracts are washed with brine (2×75 ml), dried Na₂SO₄, filtered and concentrated in vacuo. The crude product is crystallized from hot EtOAc (5 ml)/iso-hexane (30 ml) to yield the title compound as a white solid; MS: m/z 353.09 [M+H]⁺

Step 2: 1-[3-(2,4-Dichloro-phenyl)-2,6-dimethyl-pyrazolo[5,1-b]oxazol-7-yl]-butan-1-one:

To a solution 1-[3-(2,4-dichloro-phenyl)-2,6-dimethyl-pyrazolo[5,1-b]oxazol-7-yl]-butan-1-ol (0.700 g, 1.982 mmol) in CHCl₃ (15 ml) is added manganese dioxide (3.45 g, 39.6 mmol); the reaction mixture is heated to 60° C. for 18 hours and filtered through Celite® (filter material) 521, washing through with chloroform (75 ml). The solvent is removed in vacuo to yield the title compound as a white solid; MS: m/z 351.04 [M+H]⁺

Step 3: 3-(2,4-Dichloro-phenyl)-2,6-dimethyl-7-(1-methylene-butyl)-pyrazolo[5,1-b]oxazole:

To a suspension of methyltriphenylphosphonium bromide (0.814 g, 2.278 mmol) in THF (8 ml) is added 1.0M NaH-MDS (in THF) (2.278 ml, 2.278 mmol) generating a yellow reaction mixture. After stirring at RT for 10 minutes, 1-[3-(2,4-dichloro-phenyl)-2,6-dimethyl-pyrazolo[5,1-b]oxazol-7-yl]-butan-1-one (0.400 g, 1.139 mmol) is added and the reaction mixture is stirred at RT for 16 hours: a tan solution turning brown O/N. The reaction is quenched with ammonium chloride (sat. aq. 2 ml). The reaction mixture is partitioned between EtOAc (50 ml) and H₂O (50 ml) and extracted with EtOAc (3×20 ml). The combined organic extracts are washed with brine (1×50 ml), dried Na₂SO₄, filtered and concentrated in vacuo. The resulting residue is purified via Flashmaster SiO₂ 150 ml/50 g column eluting with 12:1 Iso-hexane/EtOAc to yield the title compound as a white crystalline solid; MS: 349.08 [M+H]⁺; 1H NMR (400 MHz, DMSO-d6) δ 7.77 (1H, d), 7.59 (1H, d), 7.51 (1H, dd), 4.94 (1H, d), 4.85 (1H, d), 2.30 (3H, t), 2.18 (3H, s), 2.14 (3H, s), 1.35 (2H, m), 0.79 (3H, t).

The examples shown in the following table are prepared according to the procedures of Example 7.1 using the appropriate starting compounds, the methods of preparation of which are described hereinafter or are commercially available.

TABLE 6

| Ex. | Structure | ¹H NMR or [M + H]⁺ | Name |
|---|---|---|---|
| 7.2 | 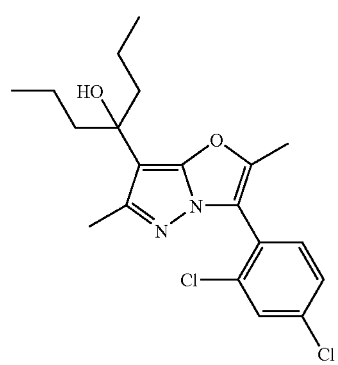 | (400 MHz, DMSO-d₆) δ 7.89 (1 H, d, J 2.1), 7.71 (1 H, d, J 8.3), 7.63 (1 H, dd, J 8.3, 2.1), 4.51 (1 H, s), 2.30 (3 H, s), 2.28 (3 H, s), 1.73 (4 H, m), 1.27 (4 H, m), 0.87 (6 H, m) | 4-[3-(2,4-Dichloro-phenyl)-2,6-dimethyl-pyrazolo[5,1-b]oxazol-7-yl]-heptan-4-ol |
| 7.3 | 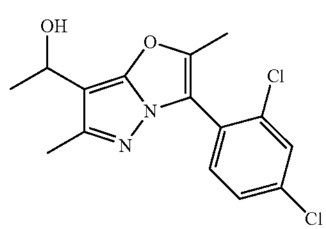 | 325.13 | 1-[3-(2,4-Dichloro-phenyl)-2,6-dimethyl-pyrazolo[5,1-b]oxazol-7-yl]-ethanol |
| 7.4 | 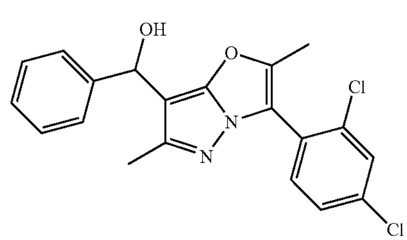 | 387.1 | [3-(2,4-Dichloro-phenyl)-2,6-dimethyl-pyrazolo[5,1-b]oxazol-7-yl]-phenyl-methanol |

TABLE 6-continued

| Ex. | Structure | ¹H NMR or [M + H]⁺ | Name |
|---|---|---|---|
| 7.5 | 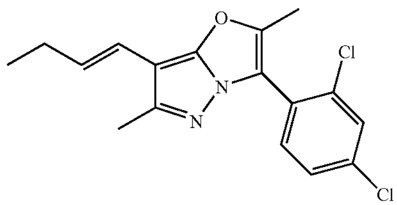 | 335.10 | 7-((E)-But-1-enyl)-3-(2,4-dichloro-phenyl)-2,6-dimethyl-pyrazolo[5,1-b]oxazole |
| 7.6 | 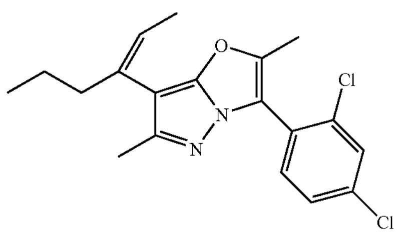 | 363.11 | 3-(2,4-Dichloro-phenyl)-7-[1-eth-(Z)-ylidene-butyl]-2,6-dimethyl-pyrazolo[5,1-b]oxazole |

Example 8

3-(2,4-Dichloro-phenyl)-2,6-dimethyl-7-(1-methyl-ene-butyl)-pyrazolo[5,1-b]oxazole

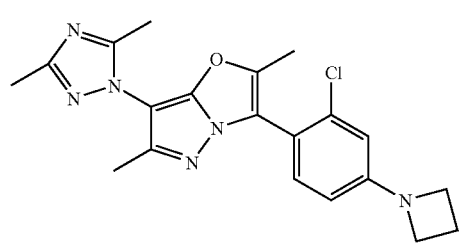

3-(4-Bromo-2-chlorophenyl)-7-(3,5-dimethyl-1H-1,2,4-triazol-1-yl)-2,6-dimethyl pyrazolo[5,1-b]oxazole (Ex. 6.42) (50 mg, 0.119 mmol), azetidine (16 µl, 0.237 mmol), cesium carbonate (116 mg, 0.237 mmol ), xantphos (23 mg, 0.039 mmol) and palladium acetate (9 mg, 0.039 mmol) are dissolved in 1,4-dioxane (1 ml). The reaction mixture is stirred for 30 mins at 120° C. in the microwave and then diluted with ethyl acetate. The mixture is filtered through Celite® (filter material) and the filtrate is concentrated in vacuo. The crude product is purified by chromatography on silica, eluting with 50-100% ethyl acetate/iso-hexane to afford the title product; MS: m/z 397.2 [M+H]⁺; 1H NMR (400 MHz, CDCl₃) δ 7.28 (1H, d), 6.45 (1H, s), 6.34 (1H, d), 3.88 (4H, t), 2.29-2.39 (8H, m), 2.25 (3H, s), 2.16 (3H, s).

Example 9

7-(3,5-Dimethyl-[1,2,4]-triazol-1-yl)-2,6-dimethyl-3-(2-methyl-4-pyrazol-1-yl-phenyl)-pyrazolo[5,1-b]oxazole

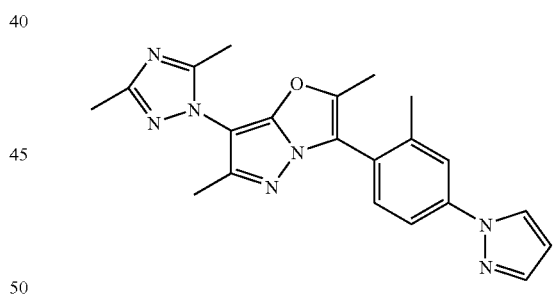

An oven dried flask is charged with 3-(4-bromo-2-methylphenyl)-7-(3,5-dimethyl-1H-1,2,4-triazol-1-yl)-2,6-dimethylpyrazolo[5,1-b]oxazole (Ex. 6.41)(50 mg, 0.125 mmol), 1H-pyrazole (25 mg, 0.37 mmol), (E)-2-hydroxybenzaldehyde oxime (6 mg, 0.05 mmol), copper (I) oxide (2 mg, 0.012 mmol) and cesium carbonate (163 mg, 0.5 mmol) followed by anhydrous acetonitrile (0.5 ml). The reaction mixture is degassed several times then heated at 82° C. under nitrogen. After 3 days the mixture is absorbed onto silica and purification by chromatography on silica gel, eluting with ethyl acetate to afford the product as a colourless gum. Trituation with diethyl ether-hexane yields the title compound as a white solid. MS m/z 388.3 [M+H]⁺; ¹H NMR (400 MHz, CDCl₃) δ 2.25 (3H, s), 2.37 (3H, s), 2.42 (9H, m), 6.50 (1H, m), 7.45 (2H, d), 7.65 (2H, d), 7.75 (2H, s), 7.98 (1H, s).

Example 10

7-(3,5-Dimethyl-[1,2,4]triazol-1-yl)-2,6-dimethyl-3-(2-methyl-4-trideuteriomethoxy-phenyl)-pyrazolo[5,1-b]oxazole

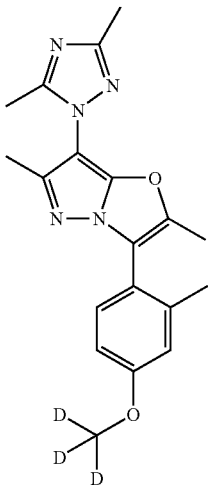

Step 1: 4-(7-(3,5-dimethyl-1H-1,2,4-triazol-1-yl)-2,6-dimethylpyrazolo[5,1-b]oxazol-3-yl)-3-methylphenol 7-(3,5-Dimethyl-[1,2,4]triazol-1-yl)-3-(4-methoxy-2-methyl-phenyl)-2,6-dimethyl-pyrazolo[5,1-b]oxazole (Ex. 6.12) (100 mg, 0.285 mmol) is dissolved in dry DCM (5 ml). The contents are flushed with $N_2$ and to this solution is added boron tribromide (1.423 ml, 1.423 mmol) dropwise at RT. After approximately 30 mins, the reaction is quenched by careful addition of $H_2O$. The mixture is transferred to a separating funnel and extracted with DCM (50 ml). The organic portion is separated and washed with 1M HCl, 1M NaOH, brine, dried ($MgSO_4$) and evaporated in vacuo to give a brown solid. Trituration with EtOAc affords the title compound as an off white solid. MS m/z 338.2 [M+H]$^+$; $^1$H NMR (400 MHz, DMSO-d6) δ 7.25 (d, 1H), 6.8 (s, 1H), 6.75 (d, 1H), 2.35 (s, 3H), 2.30 (s, 6H), 2.2 (s, 3H), 2.15 (s, 3H).

Step 2: 7-(3,5-Dimethyl-[1,2,4]triazol-1-yl)-2,6-dimethyl-3-(2-methyl-4-trideuterio methoxy-phenyl)-pyrazolo [5,1-b]oxazole

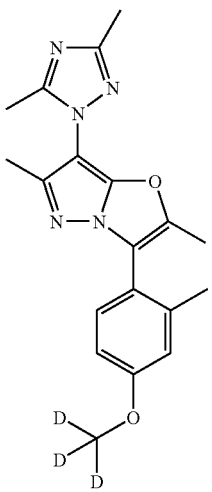

A solution of 4-(7-(3,5-dimethyl-1H-1,2,4-triazol-1-yl)-2,6-dimethylpyrazolo[5,1-b]oxazol-3-yl)-3-methylphenol (56 mg, 0.166 mmol) in dry DMF (2 ml) is treated with cesium carbonate (81 mg, 0.249 mmol) followed by D3-iodomethane (36.1 mg, 0.249 mmol) in dry DMF (1 ml). The resulting mixture is heated to 50° C. and stirred vigorously overnight. After cooling to RT, the mixture is partitioned between EtOAc and water. The organic portion is washed with brine, dried ($MgSO_4$) and concentrated in vacuo to give a brown oil. Purification by chromatography on silica (10 g) eluting with 100% EtOAc affords the product as a straw coloured oil. MS m/z 355.2 [M+H]$^+$; $^1$H NMR (400 MHz, CDCl$_3$) δ 7.3 (m, 2H), 7.85 (d, 1H), 2.45 (s, 3H), 2.40 (s, 3H), 2.3 (ds, 6H), 2.25 (s, 3H).

Example 11

3-(4-(1H-imidazol-1-yl)-2-methylphenyl)-7-(3,5-dimethyl-1H-1,2,4-triazol-1-yl)-2,6-dimethylpyrazolo[5,1-b]oxazole 3-(4-Bromo-2-methylphenyl)-7-(3,5-dimethyl-1H-1,2,4-triazol-1-yl)-2,6-dimethyl pyrazolo[5,1-b]oxazole (Ex. 6.41) (40 mg, 0.100 mmol), 4,7-dimethoxy-1,10-phenanthroline (24.01 mg, 0.100 mmol), 1H-imidazole (8.16 mg, 0.120 mmol), $Cu_2O$ (0.715 mg, 5.00 μmol) and $Cs_2CO_3$ (45.6 mg, 0.140 mmol) are added to NMP (2 ml) and stirred at 110° C. for 5 days.

LCMS 3 hrs: AcqC0028449. The reaction mixture is diluted with DCM and run through a Celite® plug (filter material). The mixture is reduced under vacuum and partitioned between water/EtOAc. The organic portions are washed with sat. $NaHCO_3$, water and brine, dried ($MgSO_4$) and concentrated in vacuo to give an orange oil. The oil is taken up in DCM and run through a 12 g ISCO column (silica), eluting with MeOH/DCM to afford the title product as an orange oil MS m/z 388.2 [M+H]$^+$.

Example 12

3-(Benzofuran-5-yl)-7-(3,5-dimethyl-1H-1,2,4-triazol-1-yl)-2,6-dimethylpyrazolo[5,1-b]oxazole Step 1: N-Methoxy-N-methylbenzofuran-5-carboxamide Benzofuran-5-carbonyl chloride (1 g, 5.54 mmol) in dry DCM (40 ml) is treated with N,O-dimethylhydroxylamine.HCl (0.594 g, 6.09 mmol) followed by triethylamine (1.930 ml, 13.84 mmol). After stirring at RT overnight, the mixture is diluted with DCM and washed with $H_2O$, 1M HCl, 1M NaOH, brine, dried ($MgSO_4$) and evaporated down to give a brown oil which is used without further purification; MS: m/z 206.1 [M+H]$^+$ Step 2: 1-(Benzofuran-5-yl)propan-1-one An ice-cooled mixture comprising N-methoxy-N-methyl-benzofuran-5-carboxamide (1 g, 4.87 mmol) in dry ether (20 ml) under $N_2$ is treated dropwise with ethylmagnesium bromide (2.437 ml, 7.31 mmol). After stirring for 30 mins the mixture is allowed to warm to RT. The reaction is quenched by careful addition of $NH_4Cl$ followed by 1M HCl and the contents are transferred to a separating funnel. The mixture is extracted with EtOAc and the organic portion is washed with 1M NaOH, brine, dried (MgSO4), evaporated down to give a light brown oil, which began to crystallise on standing. Purification by chromatography on silica eluting with 25% EtOAc/iso-Hex affords the title compound as a white crystalline solid. $^1$H NMR (400 MHz, CDCl$_3$) δ 8.2 (d, 1H), 7.9 (d, 1H), 7.6 (d, 1H), 7.45 (d, 1H), 6.8 (d, 1H), 3.0 (q, 2H), 1.2 (t, 3H).

Step 3: 1-(Benzofuran-5-yl)-2-bromopropan-1-one

To an oven dried roundbottom flask is added 1-(benzofuran-5-yl)propan-1-one (160 mg, 0.919 mmol) and dissolved in dry THF (5 ml). The flask is then cycled through a vacuum/N2 protocol and then cooled under $N_2$ to −78° C. using dry ice/acetone. At this temperature, lithium bis(trimethylsilyl)amide (1M in hexanes) (1.378 ml, 1.378 mmol) is added and stirring continues for ~30 mins. After this time, NBS (180 mg, 1.010 mmol) in THF (5 ml) is then added dropwise keeping the temp below −60° C. The mixture is left to warm to RT and stirring continued for ~5 hr. After this time, LCMS looked to show ~50% conversion to product. The raection is quenched by addition of $NH_4Cl$ and allowed to warm to RT. The contents are transferred to a separating funnel and extracted into EtOAc. The organic portion is washed with $NaHCO_3$, water, brine, dried ($MgSO_4$) and evaporated to give a clear oil. Purification by chromatography on silica gel (20 g) eluting with 100% iso-hexane followed by 5% EtOAc/iHex affords the title product as a clear oil. MS: m/z 253 $[M+H]^+$.

Step 4: 3-(Benzofuran-5-yl)-7-(3,5-dimethyl-1H-1,2,4-triazol-1-yl)-2,6-dimethylpyrazolo[5,1-b]oxazole The title compound is prepared from 1-(benzofuran-5-yl)-2-bromopropan-1-one (step 3) and 4-(3,5-dimethyl-[1,2,4]triazol-1-yl)-5-methyl-2H-pyrazol-3-ol (Intermediate KF) analogously to Example 6.2. MS: m/z 348.1 $[M+H]^+$.

$^1$H NMR (400 MHz, CDCl$_3$) δ 8.15 (d, 1H), 7.7 (m, 3H), 6.9 (d, 1H), 2.6 (s, 3H), 2.45 (m, 6H), 2.3 (s, 3H).

Preparation of Intermediate Compounds

Intermediate AA

2-Bromo-1-(2,4-dichloro-phenyl)-propan-1-one

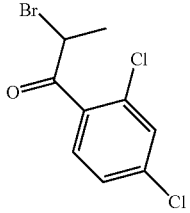

To a suspension of copper(II) bromide (18.30 g, 82 mmol) in EtOAc (40 ml) is added $^{2,4}$-dichloropropiophenone (8.32 g, 41.0 mmol) in CHCl$_3$ (40 ml). The reaction mixture is heated at reflux for 16 hours and then filtered (to remove white Cu(I)Br). The solvent removed in vacuo to yield an amber oil. This is dissolved in EtOAc and passed through a SiO$_2$ cartridge (25 g), the solvent removed in vacuo to yield 2-bromo-1-(2,4-dichloro-phenyl)-propan-1-one as a pale yellow oil; $^1$H NMR (400 MHz, CDCl$_3$) δ 7.51 (1H, d, J 8.3), 7.47 (1H, d, J 1.9), 7.36 (1H, dd, J 8.3, 1.9), 5.24 (1H, q, J 6.6), 1.92 (3H, d, J 6.6).

Intermediate AB-AD

These compounds namely,

2-Bromo-1-(2,4-dichloro-phenyl)-butan-1-one (Int. AB),

2-Bromo-1-(4-methoxy-2-methyl-phenyl)-propan-1-one (Int. AC) and

2-Bromo-1-(2,4-dimethoxy-phenyl)-propan-1-one (Int. AD), are prepared analogously to $^2$-bromo-1-(2,4-dichloro-phenyl)-propan-1-one (Intermediate AA) by replacing 2,4-dichloropropiophenone with the appropriate starting compound.

Intermediate BA

2-Bromo-1-(2,4-methyl-phenyl)-propan-1-one

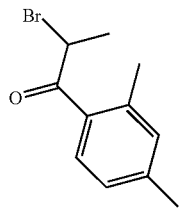

A mixture of m-xylene (3 ml, 24.0 mmol, 1 eq.) and 2-bromopropionyl bromide (2.70 ml, 25.5 mmol, 1.05 eq.) is slowly added to a well stirred suspension of AlCl$_3$ (5.18 g, 38.9 mmol, 1.6 eq.) in CS$_2$ (30 ml) at RT. The reaction mixture is stirred for 30 min then poured into ice water (200 ml) and extracted with Et$_2$O (100 ml). The organic layer is separated, washed successively with HCl 2M in water, Na$_2$CO$_3$ 2M in water, brine, dried over Na$_2$SO$_4$, filtered, and evaporated to yield the title compound as a light yellow oil which is used without further purification. HPLC: $^A$t$_{Ref}$=2.64; MS: m/z 241.2 $[M+H]^+$; $^1$H NMR (400 MHz, DMSO-d$_6$) δ 1.75 (d, J 6.6, 3H), 2.33 (s, 3H), 2.38 (s, 3H), 5.69 (q, J 6.6, 1H), 7.13-7.17 (m, 2H), 7.77 (d, J 7.6 Hz, 1H).

Intermediate BB

2-Bromo-1-(2-chloro-4-methoxy-phenyl)-propan-1-one

To a cooled (0° C.) stirring suspension of aluminum chloride (10.89 g, 82 mmol) in DCE (700 ml) is added 2-bromopropionyl bromide (8.66 ml, 82 mmol) followed by 3-chloroanisol (10 ml, 82 mmol) dropwise (rapidly) maintaining the temperature below 5° C. The reaction mixture is stirred at 0° C. for 10 min and RT for 3 hours. The mixture is poured into ice/water (1000 ml) containing 90 ml of 5M HCl. The organic phase is separated and the aqueous portion is washed with DCM (500 ml). The organic extracts are combined, washed with brine, dried (MgSO4) and concentrated in vacuo. Purification of the crude product by chromatography on silica eluting with 2.5% incraesing to 5% TBME/Hex increasing up to 5% affords the title product. MS: m/z 278.9 $[M+H]^+$ Intermediate C 1-(4-Methoxy-2-methyl-phenyl)-propan-1-one

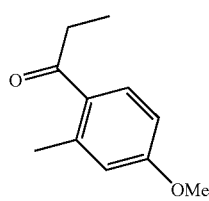

To a stirred suspension of samarium (598 mg, 3.97 mmol) in CH$_3$CN is added iodine (3.0 g, 11.9 mmol, 3 eq.) and the mixture is stirred at RT for 2 hrs. 1-Methoxy-3-methylbenzene (500 μL, 3.97 mmol, 1 eq) is added followed by the dropwise addition of propionyl chloride (3472 μL, 39.7 mmol). After stirring at RT for 1 hr, the reaction is quenched with water (5 ml) and extracted with EtOAc (2×50 ml). The combined organic extracts are washed with Na$_2$CO$_3$ (2M, 50 ml), sat Na$_2$S$_2$O$_4$ (4×50 ml), water and brine, dried over MgSO$_4$ and concentrated under reduced pressure. The resulting crude residue is purified by column chromatography on silica gel eluting with 10% EtOAc/iso-hexane to yield 1-(4-methoxy-2-methyl-phenyl)-propan-1-one as a clear oil; m/z 179.16 [M+H]$^+$. Alternatively, intermediate C can be made by an analogous process to that for intermediate DA below.

Intermediate DA

2-Bromo-1-(6-methoxy-4-methyl-pyridin-3-yl)-propan-1-one

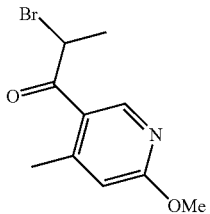

Step 1: 1-(6-Methoxy-4-methyl-pyridin-3-yl)-propan-1-ol:

To a cooled (−10° C.) solution of iPrMgCl (2.0M in THF, 619 ul, 1.24 mmol, 0.5 eq) in THF (5 ml) at is added n-BuLi (2.5M in hexanes, 990 ul, 2.47 mmol, 1 eq) and the mixture stirred at this temperature for 15 mins. This mixture is treated with a solution of 5-bromo-2-methoxy-4-methyl-pyridine (500 mg, 2.47 mmol) in THF (5 ml) and allowed to stir at −10° C. for 30 mins. After this time, propionaldehyde (0.324 ml, 4.45 mmol, 1.8 eq) is added and the contents left stirring for 2 hrs. The reaction is quenched with acetic acid (500 ul). The mixture is partitioned between EtOAc (100 ml) and Na$_2$CO$_3$ (2M, 50 ml) and the organic layer is separated, washed successively with 2M Na$_2$CO$_3$, water and brine, dried over MgSO$_4$, filtered, and evaporated to yield the title compound as a clear oil. The crude 1-(6-methoxy-4-methyl-pyridin-3-yl)-propan-1-ol is used without further purification. MS: m/z 182.1 [M+H]$^+$.

Step 2: 1-(6-Methoxy-4-methyl-pyridin-3-yl)-propan-1-one

To a stirred solution of 1-(6-methoxy-4-methyl-pyridin-3-yl)-propan-1-ol (445 mg, 2.45 mmol, 1 eq.) in CHCl$_3$ (10 ml) is added activated manganese dioxide (4.3 g, 49 mmol, 20 eq.) in one portion at RT. The reaction mixture is heated at reflux for 48 h. After cooling to RT, the mixture is filtered through Celite® (filter material) and concentrated under reduced pressure. The resulting crude residue is purified by column chromatography on silica gel eluting with 10% EtOAc/iso-hexane to yield 1-(6-methoxy-4-methyl-pyridin-3-yl)-propan-1-one as a white solid. MS: m/z 180.1 [M+H]$^+$; $^1$H NMR (400 MHz, CDCl$_3$) δ 1.2 (t, 3H), 2.55 (s, 3H), 2.95 (q, 2H), 4.00 (s, 3H), 6.60 (s, 1H), 8.65 (s, 1H).

Step 3: 2-Bromo-1-(6-methoxy-4-methyl-pyridin-3-yl)-propan-1-one:

To a stirred suspension of copper (II) bromide (499 mg, 2.23 mmol, 2 eq.) in EtOAc is added HBr (33% in acetic acid, 0.368 ml, 2.25 mmol, 2 eq.) followed by 1-(6-methoxy-4-methyl-pyridin-3-yl)-propan-1-ol (200 mg, 1.12 mmol, 1 eq.). The mixture is heated at 70° C. for 12 hrs. After cooling to RT the mixture is poured into 2M Na$_2$CO$_3$ (50 ml) and extracted with EtOAc (2×50 ml). The combined extracts are washed successively with 2M Na$_2$CO$_3$, water and brine, dried over MgSO$_4$, filtered, and concentrated under reduced pressure. The resulting crude residue is purified by column chromatography on silica gel eluting with 10% EtOAc/iso-hexane to yield 2-bromo-1-(6-methoxy-4-methyl-pyridin-3-yl)-propan-1-one as a clear oil. MS: m/z 257.9 [M+H]$^+$; $^1$H NMR (400 MHz, CDCl$_3$) δ 1.90 (d, 3H), 2.50 (s, 3H), 4.0 (s, 3H), 2.33 (s, 3H), 5.20 (q, 1H), 6.65 (s, 1H), 8.65 (s, 1H).

Intermediate DB

2-Bromo-1-(4-methoxy-2-methyl-phenyl)-butan-1-one

This compound is prepared from 1-bromo-4-methoxy-2-methylbenzene analogously to 2-bromo-1-(6-methoxy-4-methyl-pyridin-3-yl)-propan-1-one (Intermediate DA) by replacing propionaldehyde with butyraldehyde. MS: m/z 273 [M+H]$^+$ Intermediate DC 2-Bromo-1-(2,6-dimethoxy-pyridin-3-yl)-propan-1-one This compound is prepared analogously to 2-bromo-1-(6-methoxy-4-methyl-pyridin-3-yl)-propan-1-one (Intermediate DA) by replacing 5-bromo-2-methoxy-4-methyl-pyridine with the appropriate starting compound. MS: m/z 274 [M+H]$^+$ Intermediate DD 2-Bromo-1-(4-methoxy-2,6-dimethyl-phenyl)-propan-1-one This compound is prepared analogously to 2-bromo-1-(6-methoxy-4-methyl-pyridin-3-yl)-propan-1-one (Intermediate DA) by replacing 5-bromo-2-methoxy-4-methyl-pyridine with the appropriate starting compound. MS: m/z 271 [M+H]$^+$ Intermediate E 2-Bromo-1-(6-methoxy-2-methyl-pyridin-3-yl)-propan-1-one

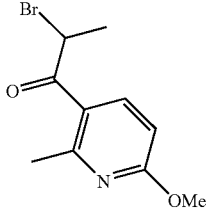

This compound is prepared from 3-bromo-6-methoxy-2-methylpyridine analogously to Intermediate DA. The oxidation step (2) is carried out using the following procedure:

A solution of 1-(6-methoxy-2-methyl-pyridin-3-yl)-propan-1-ol (1.15 g, 6.35 mmol) in DCM (20 ml) is treated with Dess-Martin periodinane (2.96 g, 6.98 mmol) and the resulting suspension stirred at RT overnight. The reaction mixture is diluted with DCM (80 ml) and sat NaHCO$_3$ (50 ml) added. The organic layer is separated and washed with H$_2$O (20 ml), brine (20 ml), dried (MgSO$_4$) and concentrated in vacuo. The resulting residue is purified by chromatography on silica gel (2×70 ml) using 50% EtOAc/iso-hexane to give 1-(6-methoxy-2-methyl-pyridin-3-yl)-propan-1-one as a white solid. MS: m/z 180.2 [M+H]$^+$.

Bromination of 1-(6-methoxy-2-methyl-pyridin-3-yl)-propan-1-one is conducted analogously to yield 2-bromo-1-(6-methoxy-2-methyl-pyridin-3-yl)-propan-1-one; MS: m/z 258.1 [M+H]$^+$.

Intermediate F

2-Bromo-1-(2,4-Dichloro-phenyl)-3-methyl-butan-1-one

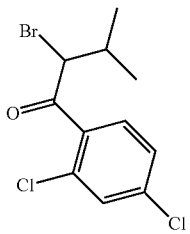

Step 1: 1-(2,4-Dichloro-phenyl)-3-methyl-butan-1-ol:

To a cooled (0° C.) stirred solution of 2,4-dichlorobenzaldehyde (2 g, 11.43 mmol) in THF (50 ml) under N$_2$ is added isobutyllithium (7.86 ml, 12.57 mmol) slowly and the reaction is stirred at RT over the weekend. The reaction mixture is added to sat. ammonium chloride (100 ml) and extracted with EtOAc (140 ml). The organic portion is washed with brine, dried over MgSO$_4$ and concentrated in vacuo. The crude product is purified by chromatography on silica (70 g/150 ml silica-column) eluting with 10% EtOAc/iso-hexane to give (2,4-dichloro-phenyl)-3-methyl-butan-1-ol as a yellow oil; $^1$H NMR (400 MHz, CDCl$_3$) δ 7.53 (1H, d, J 8.3), 7.36 (1H, d, J 2.0), 7.29 (1H, dd, J 8.3, 2.0), 5.18 (1H, dd, J 9.2, 3.7), 1.88 (1H, m), 1.61 (1H, ddd, 14.0, 9.2, 4.7), 1.52 (1H, ddd, 14.0, 9.1, 3.7), 1.03 (3H, d, J 6.6), 0.99 (3H, d, J 6.6).

Step 2: 1-(2,4-Dichloro-phenyl)-3-methyl-butan-1-one:

1-(2,4-Dichloro-phenyl)-3-methyl-butan-1-ol (600 mg, 2.57 mmol) and Dess-Martin periodinane (1092 mg, 2.57 mmol) in DCM (25 ml) is stirred at RT for 2 hours. The reaction mixture is added to EtOAc (200 ml) and washed with sat. sodium metabisulfite (200 ml), sat. NaHCO$_3$ (200 ml), brine, dried over MgSO$_4$ and concentrated in vacuo. The crude product is purified using an ISCO combiflash chromatography, eluting with 0 to 100% (EtOAc/iso-hexane) on a 40 g silica-column to give 1-(2,4-Dichloro-phenyl)-3-methyl-butan-1-one as a yellow oil; $^1$H NMR (400 MHz, CDCl$_3$) δ 7.45 (1H, d, J 1.9), 7.42 (1H, d, J 8.3), 7.32 (1H, dd, J 8.3, 1.9), 2.83 (2H, d, J 6.9), 2.25 (1H, sept, J 6.7), 1.00 (6H, d, J 6.7).

Step 3: 2-Bromo-1-(2,4-Dichloro-phenyl)-3-methyl-butan-1-one

To a stirring mixture of copper(II) bromide (773 mg, 3.46 mmol), in EtOAc (1.7 ml) at 60° C. is added a solution of 1-(2,4-Dichloro-phenyl)-3-methyl-butan-1-one (0.400 mg, 1.73 mmol) in CHCl$_3$ (1.7 ml) portion wise. The reaction is stirred for 2 hours at reflux and thereafter overnight at ambient temperature. The reaction mixture is filtered and the residue is washed with DCM (90 ml). The combined organic phase is washed with water (50 ml), brine, dried over Na$_2$SO$_4$ and concentrated in vacuo to yield 2-bromo-1-(2,4-dichloro-phenyl)-3-methyl-butan-1-one as a brown oil; $^1$H NMR (400 MHz, CDCl$_3$) δ 7.51 (1H, d, J 8.3), 7.47 (1H, d, J 1.9), 7.35 (1H, dd, J 8.3, 1.9), 4.97 (1H, d, J 7.5), 2.45 (1H, m), 1.18 (3H, d, J 7.6), 1.14 (3H, d, J 7.6).

Intermediate GA 1-(2,4-Dichloro-phenyl)-pentan-1-one

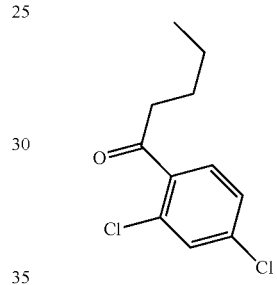

To a stirring hazy solution of 2,4-dichloro-N-methoxy-N-methylbenzenecarboxamide (1 g, 4.27 mmol), in THF (20 ml) is added BuLi (2.051 ml, 5.13 mmol) in portions. The reaction is stirred for 4 hours at RT and the partitioned between 1M HCl (100 ml) and EtOAc (140 ml). The organic portion is washed with brine, dried over Na$_2$SO$_4$, and concentrated in vacuo. The crude product is purified by ISCO combiflash chromatography eluting with 0 to 100% EtOAc/iso-hexane on a 40 g silica-column to yield 1-(2,4-dichloro-phenyl)-pentan-1-one as a brown oil; $^1$H NMR (400 MHz, CDCl$_3$) δ 7.45 (1H, d, J 2.0), 7.43 (1H, d, J 7.3), 7.32 (1H, dd, J 7.3, 2.0), 2.94 (2H, t, J 7.4), 1.70 (2H, m), 1.40 (2H, m), 0.95 (3H, t, J 7.3).

Intermediate GB

2-Bromo-1-(6-chloro-4-methyl-pyridin-3-yl)-propan-1-one

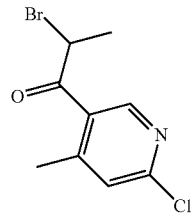

To 1-(6-chloro-4-methyl-pyridin-3-yl)-propan-1-one (0.25 g, 1.36 mmol) in DCM (6 ml) is added tetrabutylammonium tribromide (0.656 g, 1.36 mmol). The resulting orange solution is stirred at RT for 2 h (after 1 h a precipitate is observed). The reaction mixture is diluted with DCM and then quenched with water. The organic phase is separated and washed with water, dried over $Na_2SO_4$, filtered and evaporated. The crude product is purified on silica gel, using Heptane/EtOAc 99:1 to 80/20 gradient elution over 20 min to afford the title compound as a yellow oil; MS: m/z 261.9 $[M+H]^+$.

Alternatively, the title compound can be prepared using the following protocol adapted from J. Med. Chem. 1991, 34, 2736-2746

1-(6-Chloro-4-methyl-pyridin-3-yl)-propan-1-one (100 mg, 0.545 mmol) is dissolved in hydrobromic acid (48%) (2 ml, 17.68 mmol); to this is then added bromine (0.031 ml, 0.599 mmol) dropwise and the resulting orange solution stirred at RT. After 4 hours, further 0.2 eq (5 ul) of bromine is added and the reaction is left stirring O/N at RT. The reaction mixture is basified by careful addition of 2M $Na_2CO_3$ (5 ml) and then extracted into EtOAc (2×25 ml). The combined organic phase is washed with $H_2O$, brine, dried ($MgSO_4$) and evaporated to give a clear oil. The crude material is chromatographed on silica gel (20 g) eluting with (10% EtOAc/iso-hexane) to give the desired compound; MS: m/z 262.1 $[M+H]^+$; $^1H$ NMR (400 MHz, $CDCl_3$) δ 7.9 (d, 1H), 7.3 (d, 1H), 5.1 (q, 1H), 2.7 (s, 3H), 1.9 (d, 3H).

Intermediate GC

2-Bromo-1-(6-chloro-2-methyl-pyridin-3-yl)-propan-1-one

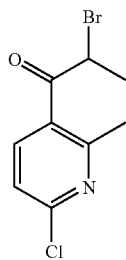

The title compound is prepared analogously to 2-bromo-1-(6-chloro-4-methyl-pyridin-3-yl)-propan-1-one using the appropriate starting compound; MS: m/z 264.0 $[M+H]^+$ Intermediate H 3-(2,4-Dichloro-phenyl)-6-ethyl-2-methyl-pyrazolo[5,1-b]oxazole

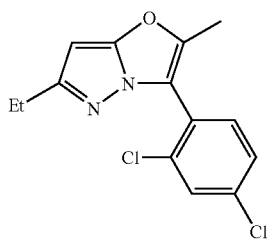

Step 1: 5-Ethyl-2H-pyrazol-3-ol:

To a ice/water cooled solution of ethyl 3-oxovalerate (10.81 g, 75.0 mmol) in ethanol (30 ml) is added via syringe hydrazine monohydrate (4.01 ml, 82 mmol) over a period of 1 minute: exothermic (internal T: 0° C. to peak T: 24° C.) which is reached after 5 minutes. At this time point, a white precipitate is observed and the cooling bath removed. The reaction mixture is stirred at RT for 2 hours. The reaction mixture is diluted with diethyl ether (100 ml). The resulting suspension is filtered, the solid washed with $Et_2O$ (100 ml) and dried in vacuo at 50° C. overnight to yield 5-Ethyl-2H-pyrazol-3-ol as a white solid; $^1H$ NMR (400 MHz, DMSO-$d_6$) δ 11.0 (1H, br s), 5.23 (1H, s), 2.45 (2H, q, J 7.6), 1.12 (3H, t, J 7.6).

Step 2: 1-(2,4-Dichloro-phenyl)-2-(5-ethyl-2H-pyrazol-3-yloxy)-propan-1-one:

To a solution of 5-ethyl-2H-pyrazol-3-ol (4.40 g, 39.2 mmol) in DMF (40 ml) is added cesium carbonate (13.42 g, 41.2 mmol) and the reaction mixture is heated to 50° C. After 5 minutes, 2-bromo-1-(2,4-dichloro-phenyl)-propan-1-one (Intermediate AA) (11.62 g, 41.2 mmol) in DMF (60 ml) is added slowly (addition time 10 minutes, initially yellow) and the reaction is stirred for a further 45 minutes giving a tan solution which is allowed to cool to RT. The reaction mixture is partitioned between EtOAc (150 ml) and 1N $Na_2CO_3$ (400 ml) and extracted with EtOAc (4×75 ml). The combined organic extracts are washed with $H_2O$ (1×200 ml) and brine (250 ml), dried ($Na_2SO_4$), filtered and concentrated in vacuo to yield a brown oil. The residue is pre-absorbed (dissolved in dichloromethane) onto silica gel and purified via Flashmaster ($SiO_2$ 340 g Snap cartridge column) eluting with 4:1 iso-hexane/EtOAc to 2:1 iso-hexane/EtOAc to yield the title compound as a pale yellow solid MS: m/z 313.12 $[M+H]^+$ Step 3: 3-(2,4-Dichloro-phenyl)-6-ethyl-2-methyl-pyrazolo[5,1-b]oxazole To a pale yellow solution of 1-(2,4-dichloro-phenyl)-2-(5-ethyl-2H-pyrazol-3-yloxy)-propan-1-one (9.00 g, 28.7 mmol) in 1,2-dichloroethane (125 ml) is slowly added via syringe titanium tetrachloride (3.80 ml, 34.5 mmol) generating a dark red solution. The reaction mixture is heated at 80° C. for 3 hours and allowed to cool to RT. The reaction mixture is poured slowly into $NH_4Cl$ (200 ml) and basified (pH 8) using $Na_2CO_3$ (200 ml). EtOAc (300 ml) is added and the biphasic solution is filtered through Celite® 521 (filter material) to remove titanium salts. The solution is extracted with EtOAc (3×75 ml) and the combined organics washed with $H_2O$ (1×100 ml), and brine (100 ml), dried ($Na_2SO_4$), filtered and concentrated in vacuo to yield an amber solid. The residue is crystallized from hot EtOAc/iso-hexane (1:5, 30 ml) to yield white solid: The mother liquor is purified using a Flashmaster ($SiO_2$ 150 ml/70 g column) eluting with 3:1 iso-hexane/EtOAc to yield a yellow solid which is crystallized from hot EtOAc/iso-hexane (1:8, 30 ml) to yield the title compound as a pale yellow solid; MS: m/z 295.15 $[M+H]^+$ The pyrazolo[5,1-b]oxazoles shown in the following Table are prepared analogously to Intermediate H using the appropriate α-bromo-ketone, the preparations of which are described herein before.

TABLE 7

| Ex. | Structure | [M + H]+ | Name |
|---|---|---|---|
| HA | 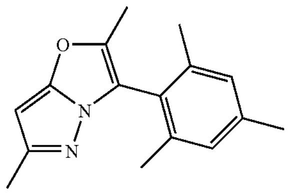 | 255.1 | 2,6-Dimethyl-3-(2,4,6-trimethyl-phenyl)-pyrazolo[5,1-b]oxazole |
| HB | 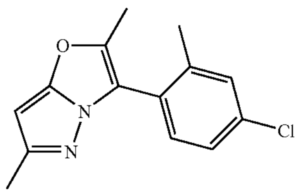 | 261.0 | 3-(4-Chloro-2-methyl-phenyl)-2,6-dimethyl-pyrazolo[5,1-b]oxazole |
| HC | 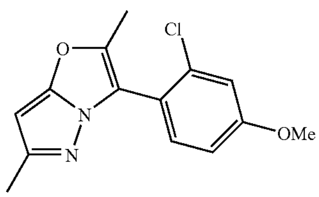 | 277.0 | 3-(2-Chloro-4-methoxy-phenyl)-2,6-dimethyl-pyrazolo[5,1-b]oxazole |
| HD | 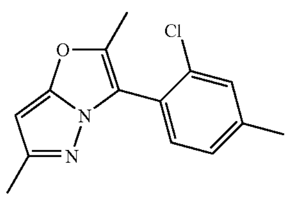 | 261.0 | 3-(4-Chloro-4-methyl-phenyl)-2,6-dimethyl-pyrazolo[5,1-b]oxazole |
| HE | 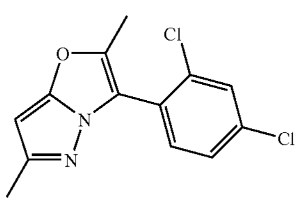 | 281.2 | 3-(2,4-Dichloro-phenyl)-2,6-dimethyl-pyrazolo[5,1-b]oxazole |
| HF | 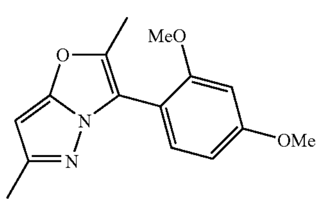 | 273.2 | 3-(2,4-Dimethoxy-phenyl)-2,6-dimethyl-pyrazolo[5,1-b]oxazole |
| HG | 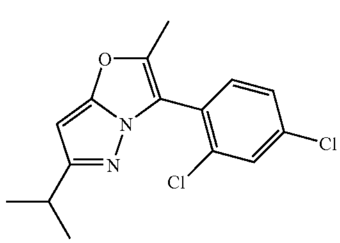 | 309.2 | 3-(2,4-Dichloro-phenyl)-6-isopropyl-2-methyl pyrazolo[5,1-b]oxazole |

TABLE 7-continued

| Ex. | Structure | [M + H]+ | Name |
|---|---|---|---|
| HH | 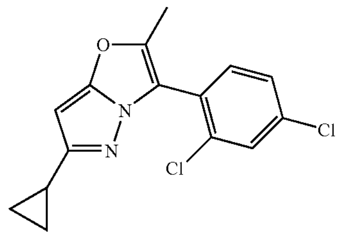 | 307.2 | 6-Cyclopropyl-3-(2,4-dichloro-phenyl)-2-methyl-pyrazolo[5,1-b]oxazole |
| HI | 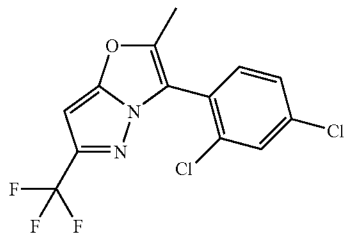 | 334.9 | 3-(2,4-Dichloro-phenyl)-2-methyl-6-trifluoromethyl-pyrazolo[5,1-b]oxazole |
| HJ | 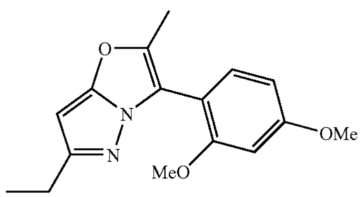 | 287.3 | 3-(2,4-Dimethoxy-phenyl)-6-ethyl-2-methyl-pyrazolo[5,1-b]oxazole |
| HK | 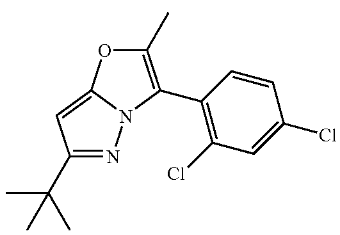 | 323.2 | 6-tert-Butyl-3-(2,4-dichloro-phenyl)-2-methyl-pyrazolo[5,1-b]oxazole |
| HL | 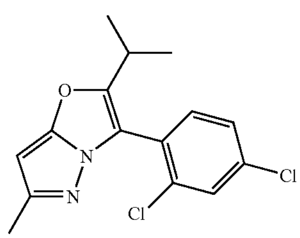 | 309.2 | 3-(2,4-Dichloro-phenyl)-2-isopropyl-6-methyl-pyrazolo[5,1-b]oxazole |
| HM | 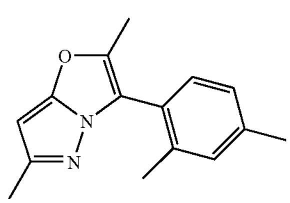 | 241.2 | 3-(2,4-Dimethyl-phenyl)-2,6-dimethyl-pyrazolo[5,1-b]oxazole |
| HN | 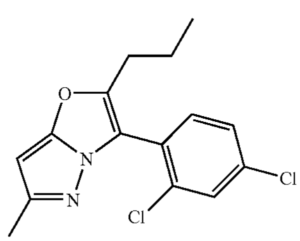 | 309.1 | 3-(2,4-Dichloro-phenyl)-6-methyl-2-propyl-pyrazolo[5,1-b]oxazole |

TABLE 7-continued

| Ex. | Structure | [M + H]+ | Name |
|---|---|---|---|
| HO | 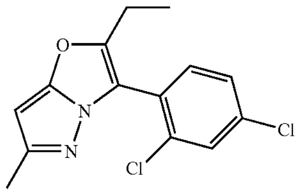 | 295.2 | 3-(2,4-Dichloro-phenyl)-2-ethyl-6-methyl-pyrazolo[5,1-b]oxazole |
| HP | 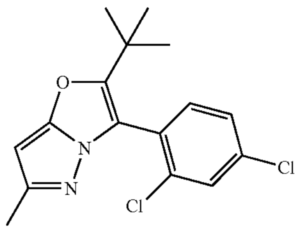 | 323.2 | 2-Butyl-3-(2,4-dichloro-phenyl)-6-methyl-pyrazolo[5,1-b]oxazole |
| HQ | 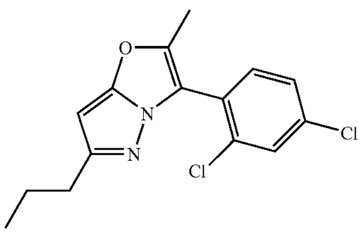 | 309.2 | 3-(2,4-Dichloro-phenyl)-2-methyl-6-propyl-pyrazolo[5,1-b]oxazole |
| HR | 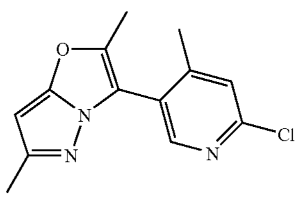 | 262.0 | 3-(6-Chloro-4-methyl-pyridin-2-yl)-2,6-dimethyl-pyrazolo[5,1-b]oxazole |
| HS | 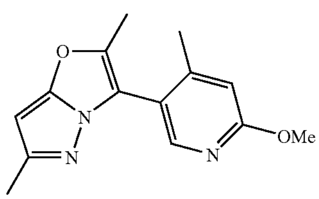 | 258.2 | 3-(6-Methoxy-4-methyl-pyridin-3-yl)-2,6-dimethyl-pyrazolo[5,1-b]oxazole |
| HT | 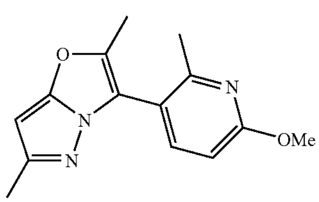 | 258.2 | 3-(6-Methoxy-2-methyl-pyridin-3-yl)-2,6-dimethyl-pyrazolo[5,1-b]oxazole |
| HU | 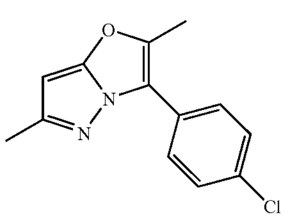 | 246.9 | 3-(4-Chloro-phenyl)-2,6-dimethyl-pyrazolo[5,1-b]oxazole |

TABLE 7-continued

| Ex. | Structure | [M + H]+ | Name |
|---|---|---|---|
| HV | 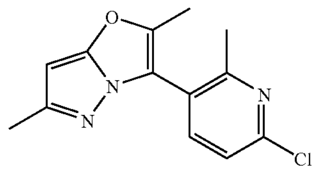 | 262.0 | 3-(6-Chloro-2-methyl-pyridin-3-yl)-2,6-dimethyl-pyrazolo[5,1-b]oxazole |
| HW | 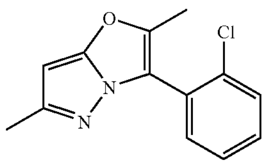 | 246.9 | 3-(2-Chloro-phenyl)-2,6-dimethyl-pyrazolo[5,1-b]oxazole |

Intermediate IA 3-(2,4-Dichloro-phenyl)-6-ethyl-2-methyl-pyrazolo[5.1-b]oxazole-7-carboxylic acid

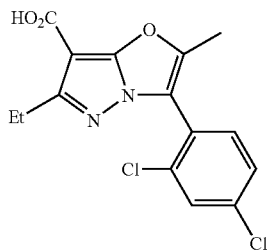

Step 1: Diethyl propionylmalonate:

This compound is prepared according to the procedure of Jung, J. C. et al. Synthetic Communications, 32, 24, 3767, 2002.

To a stirred suspension of magnesium ethoxide (3.56 g, 31.2 mmol) in anhydrous toluene (10 ml) at RT is added a solution of diethyl malonate (5 g, 31.2 mmol) in toluene (40 ml). The mixture is stirred at 50° C. for 2.5 hrs (until all the solid dissolved) then cooled to 8-10° C. (note: solidification occurs at 5° C.). To this solution is added slowly propionyl chloride (2.7 ml, 31.2 mmol). The reaction mixture is warmed to ambient temperature and stirring continues for 2 hrs. The reaction mixture is cooled to 5-10° C. and treated with 1M HCl (approx. 35 ml, 1.1 equiv.) to adjust the pH to approx. 1-3. The mixture is allowed to warm to RT and treated with sat. aq. NaHCO₃ to give a pH of 6-7. The layers are separated and the organic layer is washed with brine, dried (Na₂SO₃) and concentrated in vacuo to afford the title compound as a viscous orange oil; $^1$H NMR (400 MHz, CDCl₃) δ [13.45 (s) and 4.47 (s) combined 1H], 4.15-4.30 (4H, m), [2.66 (q, J 7.2) and 2.48 (q, J 7.5) combined 2H], 1.30 (6H, m), [1.21 (t, J 7.5) and 1.12 (t, J 7.2) combined 3H].

Step 2: 3-Ethyl-5-hydroxy-1H-pyrazole-4-carboxylic acid ethyl ester:

To diethyl propionylmalonate (3.63 g, 16.8 mmol) in glacial acetic acid (8 ml) at RT, is added hydrazine hydrate (55% hydrazine, 1.4 ml, 25.2 mmol). The reaction mixture is heated at 100° C. for 2 hrs and allowed to cool to ambient temperature whereupon crystallization occurs. The mixture is diluted with diethyl ether (approx. 25 ml) and stirred for 20 minutes and filtered to obtain the title compound as a white solid. This is washed with diethyl ether and dried in vacuo. A second crop of product is obtained by cooling the filtrate liquor, the precipitated solid is washed with diethyl ether and dried in vacuo. $^1$H NMR (400 MHz, DMSO-d₆) δ 12.0 (1H, br s), 9.8 (1H, br s), 4.16 (2H, q, J 7.1), 2.73 (2H, q, J 7.5), 1.24 (3H, t, J 7.1), 1.14 (3H, t, J 7.5).

Step 3: 5-[2-(2,4-Dichloro-phenyl)-1-methyl-2-oxo-ethoxy]-3-ethyl-1H-pyrazole-4-carboxylic acid ethyl ester:

To a stirred solution of 3-ethyl-5-hydroxy-1H-pyrazole-4-carboxylic acid ethyl ester (1.5 g, 8.14 mmol) in DMF (10 ml) is added K₂CO₃ (1.15 g, 8.14 mmol). The mixture is heated to 50° C. and treated with a solution of 2-bromo-1-(2,4-dichloro-phenyl)-propan-1-one (Intermediate AA) (2.53 g, 8.96 mmol) in DMF (10 ml). Stirring continues at 50° C. for 1 hour and after cooling to RT, the reaction mixture is poured into water (300 ml, pre-cooled to 10-15° C.) which is subsequently allowed to reach ambient temperature over 3 h (with stirring). The resulting suspension is filtered, washed with water and the solid dried in vacuo overnight. The resultant crude product is triturated in diethyl ether (approx. 15 ml) for 20 mins. then dried in vacuo to yield 5-[2-(2,4-dichloro-phenyl)-1-methyl-2-oxo-ethoxy]-3-ethyl-1H-pyrazole-4-carboxylic acid ethyl ester: yield: MS: m/z 385.13 [M+H]+

Step 4: 3-(2,4-Dichloro-phenyl)-6-ethyl-2-methyl-pyrazolo[5,1-b]oxazole-7-carboxylic acid ethyl ester To a stirred solution 5-[2-(2,4-dichloro-phenyl)-1-methyl-2-oxo-ethoxy]-3-ethyl-1H-pyrazole-4-carboxylic acid ethyl ester (2.48 g, 6.44 mmol) in 1,2-dichloroethane (40 ml) at RT is added TiCl₄ (0.86 ml, 7.73 mmol). The reaction mixture is heated to 80° C. for 2 hrs. On cooling, the mixture is poured into a stirred sat. aq. NH₄Cl (150 ml), (stirring continued for 5-10 mins following addition). Celite® (filter material) is added to this mixture and then filtered through a Celite® bed. The filter-cake is washed with EtOAc (30 ml) and the filtrate is extracted with EtOAc (approx. 90 ml). The combined organics are washed with 2N Na₂CO₃ (30 ml), brine and dried with sodium sulphate. On evaporation the resultant solid residue is triturated in 3/1 v/v iso-hexane/diethyl ether (15 ml) at RT for ½ h; the solid is filtered and dried in vacuo to give the title compound as a white solid yield: MS: m/z 367.20 [M+H]+

Step 5: 3-(2,4-Dichloro-phenyl)-6-ethyl-2-methyl-pyrazolo[5,1-b]oxazole-7-carboxylic acid A suspension containing 3-(2,4-dichloro-phenyl)-6-ethyl-2-methyl-pyrazolo[5,1-b]oxazole-7-carboxylic acid ethyl ester (1.80 g, 4.90 mmol) and lithium hydroxide monohydrate (1.0 g, 24.51 mmol) is heated at 70° C. in a 3/1 mixture of methanol/water (32 ml) for 2 hrs. The resulting solution is cooled to RT, diluted with water (60 ml) and glacial acetic acid added (approx. 3 ml) to adjust the pH to 4-5. The resultant suspension is stirred for 1 h and filtered and washed with water. The product is dried in vacuo at 50° C.; MS: m/z 339.03 [M+H]+

Intermediate IB 3-(2,4-Dimethyl-phenyl)-2,6-dimethyl-pyrazolo[5,1-b]oxazole-7-carboxylic acid

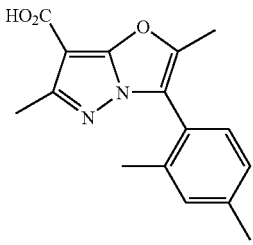

Step 1: 5-Methyl-3-oxo-2,3-dihydro-1H-pyrazole-4-carboxylic acid ethyl ester:

To a stirred solution of diethyl acetylmalonate (20 g, 89.0 mmol) in EtOH (180 ml) is added hydrazine mono-hydrochloride (7.54 g, 107.0 mmol, 1.2 eq.) in one portion at RT. The reaction mixture is heated at reflux for 3 h then filtered hot. The filtrate is cooled to RT and concentrated under reduced pressure. The resulting crude residue is purified by Combi-Flash Companion™ (Isco Inc.) column chromatography (SiO$_2$; gradient elution, DCM/[DCM/MeOH 9:1] 95:5→1:9]) to yield the title compound as a white solid. TLC: R$_F$=0.21 (DCM/MeOH 92.5:7.5); HPLC: $^A$t$_{Ret}$=0.75; MS: m/z 171.2 [M+H]$^+$; $^1$H NMR (400 MHz, DMSO-d$_6$) δ 1.24 (t, J 7.1, 3H), 2.30 (s, 3H), 4.15 (q, J 7.1, 2H).

Step 2: 3-[2-(2,4-Dimethyl-phenyl)-1-methyl-2-oxo-ethoxy]-5-methyl-1H-pyrazole-4-carboxylic acid ethyl ester:

To a well stirred mixture of 5-methyl-3-oxo-2,3-dihydro-1H-pyrazole4-carboxylic acid ethyl ester (200 mg, 1.18 mmol, 1 eq.) and K$_2$CO$_3$ (179 mg, 1.29 mmol, 1.1 eq.) in DMF (5 ml) is added dropwise a solution of 2-bromo-1-(2,4-dimethyl-phenyl)-propan-1-one (Intermediate BA) (298 mg, 1.23 mmol, 1.05 eq.) in DMF (2.5 ml) at 50° C. After the addition, the reaction mixture is further stirred at 50° C. for 1 h then poured into water (50 ml) and extracted with EtOAc (2×25 ml). The combined organic fractions are dried over Na$_2$SO$_4$, filtered and concentrated to dryness under reduced pressure. The resulting crude residue is purified by Combi-Flash Companion™ (Isco Inc.) column chromatography (SiO$_2$; gradient elution, [iso-hexane/DCM 1:1]/TBME 95:5→7:3) to yield the title compound as a white solid. TLC: R$_F$=0.74 (iso-hexane/DCM/TBME 1:1:2); HPLC: $^A$t$_{Ret}$=2.30; MS: m/z 331.3 [M+H]$^+$; $^1$H NMR (400 MHz, DMSO-d$_6$) δ 1.24 (t, J 7.1, 3H), 1.43 (d, J 6.8, 3H), 2.31 (s, 6H), 2.33 (s, 3H), 4.15 (m, 2H), 5.75 (q, J 6.8, 1H), 7.13 (m, 2H), 7.83 (m, 1H), 12.24 (br. s., 1H).

Step 3: 3-(2,4-dimethyl-phenyl)-2,6-dimethyl-pyrazolo[5,1-b]oxazole-7-carboxylic acid ethyl ester:

A mixture of 3-[2-(2,4-dimethyl-phenyl)-1-methyl-2-oxo-ethoxy]-5-methyl-1H-pyrazole-4-carboxylic acid ethyl ester (273 mg, 0.83 mmol), para-toluenesulfonic acid mono-hydrate (160 mg, 0.83 mmol) in toluene (15 ml) and AcOH (5 ml) is refluxed for 3 days. The reaction mixture is concentrated in vacuo and the residue is dissolved in EtOAc (40 ml). The organic solution is washed successively with Na$_2$CO$_3$ 2M in water (2×20 ml) and brine (20 ml), dried over Na$_2$SO$_4$, filtered and concentrated to dryness. The resulting crude residue is purified by Combi-Flash Companion™ (Isco Inc.) column chromatography (SiO$_2$; gradient elution, iso-hexane/TBME 98:2→7:3) to yield the title compound (227 mg, 0.73 mmol, 88%) as a colorless oil. TLC: R$_F$=0.81 (iso-hexane/TBME 1:1); HPLC: $^A$t$_{Ret}$=2.85; MS: m/z 313.2 [M+H]$^+$; $^1$H NMR (400 MHz, DMSO-d$_6$) δ 1.30 (t, J 7.1, 3H), 2.20 (s, 3H), 2.34 (s, 3H), 2.36 (s, 3H), 2.41 (s, 3H), 4.26 (q, J 7.1, 2H), 7.17 (m, 1H), 7.24 (br. s., 1H), 7.31 (m, 1H).

Step 4: 3-(2,4-Dimethyl-phenyl)-2,6-dimethyl-pyrazolo[5,1-b]oxazole-7-carboxylic acid A stirred mixture of 3-(2,4-dimethyl-phenyl)-2,6-dimethyl-pyrazolo[5,1-b]oxazole-7-carboxylic acid ethyl ester (224 mg, 0.72 mmol, 1 eq.) and lithium hydroxide monohydrate (150 mg, 3.59 mmol, 5 eq.) in EtOH (4 ml) and water (2 ml) is heated at 45° C. for 14 h. The reaction mixture is cooled to RT then concentrated under reduced pressure. The residue is dissolved in water and the resulting aqueous solution is neutralized using 2M HCl in water (1.8 ml). The resulting precipitate is filtered, washed with water and dried under vacuum to yield the title compound as a white solid. The crude compound is used without further purification. HPLC: $^A$t$_{Ret}$=2.12; MS: m/z 285.2 [M+H]$^+$. $^1$H NMR (400 MHz, DMSO-d$_6$) δ 2.20 (s, 3H), 2.33 (s, 3H), 2.36 (s, 3H), 2.39 (s, 3H), 7.16 (m, 1H), 7.24 (br. s., 1H), 7.31 (m, 1H), 12.30 (br. s., 1H).

Intermediate IBB 3-(2,4-Dichloro-phenyl)-2,6-dimethyl-pyrazolo[5,1-b]oxazole-7-carboxylic acid

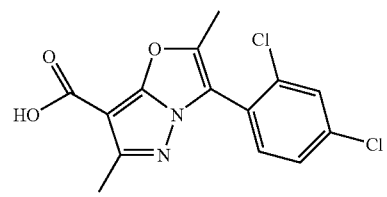

This compound is prepared analogously to Intermediate IB by replacing 2-bromo-1-(2,4-dimethyl-phenyl)-propan-1-one (Intermediate BA) with 2-bromo-1-(2,4-dichloro-phenyl)-propan-1-one (Intermediate AA): MS m/z 325.15 [M+H]$^+$

Intermediate IBC 3-(2,4-Dichloro-phenyl)-2,6-dimethyl-pyrazolo[5,1-b]oxazole-7-carbonyl chloride

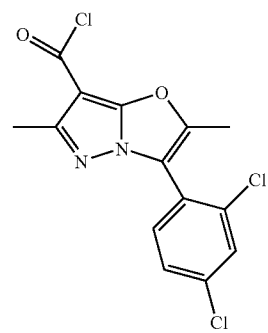

A mixture comprising 3-(2,4-dichloro-phenyl)-2,6-dimethyl-pyrazolo[5,1-b]oxazole-7-carboxylic acid (Intermediate IBB) (1 g, 3.08 mmol) and SOCl$_2$ (10 ml, 137 mmol) is heated at reflux for 2 hours. After cooling to room temperature excess SOCl$_2$ is removed under vacuum. The resulting solid is azeotroped with toluene until any remaining SOCl$_2$ is removed to afford the title compound as a solid; $^1$H NMR (400 MHz, CDCl$_3$) δ 2.48 (s, 3H), 2.53 (s, 3H), 7.48 (q, 1H), 7.52 (q, 1H), 7.62 (d, 1H).

Intermediate IC 3-(2,4-Dichloro-phenyl)-2,6-dimethyl-pyrazolo[5,1-b]oxazol-7-ol

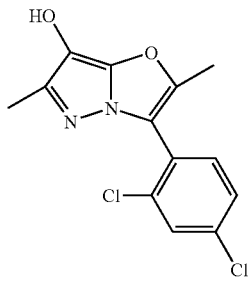

Step 1: 3-(2,4-Dichloro-phenyl)-2,6-dimethyl-pyrazolo[5,1-b]oxazole-7-carbaldehyde:

To DMF (12 ml) is added POCl$_3$ (1.326 ml, 14.23 mmol) dropwise at RT. After 10 mins 3-(2,4-dichloro-phenyl)-2,6-dimethyl-pyrazolo[5,1-b]oxazole (Intermediate HE) (2.00 g, 7.11 mmol) is added. The reaction is stirred at RT for 16 hours. On cooling to 0° C. the reaction mixture is quenched with 1M HCl and added in portions to sat. Na$_2$CO$_3$ (100 ml). The product is extracted with EtOAc (2×100 ml) and the combined organics are washed with brine, dried over MgSO$_4$ and concentrated in vacuo. The resulting solid is recrystallised from EtOAc/iso-hexane to afford the title compound as a pale yellow solid. MS: m/z 309.10 [M+H]$^+$ Step 2: 3-(2,4-Dichloro-phenyl)-2,6-dimethyl-pyrazolo[5,1-b]oxazol-7-ol 3-(2,4-Dichloro-phenyl)-2,6-dimethyl-pyrazolo[5,1-b]oxazole-7-carbaldehyde (750 mg, 2.426 mmol) and m-CPBA (897 mg, 3.64 mmol) are stirred in DCM (10.5 ml) at RT for 3 hours, whereupon the reaction mixture is diluted with DCM (120 ml). The organic phase is washed with sat. NaHCO$_3$ (70 ml) and the phases separated via a phase separator. Back extraction of the aqueous phase with DCM (50 ml) is carried out and the combined organic phases are concentrated in vacuo. The resultant yellow gum is dissolved in MeOH (16.80 ml) and K$_2$CO$_3$ (1676 mg, 12.13 mmol) is added. The reaction is stirred at RT for 30 mins before the MeOH is removed in vacuo. The resulting solid is diluted with water (~100 ml) and the product is extracted into EtOAc (2×100 ml). The combined organic extracts are washed with brine, dried over MgSO$_4$ and concentrated in vacuo. The crude product is isolated as a light orange solid which is dissolved DCM (15 ml), cooled to 0° C. and the resultant solid collected by filtration to afford the title compound as a pale yellow solid. MS: m/z 297.15 [M+H]$^+$.

Intermediate ID 3-(2,4-Dichloro-phenyl)-2,6-dimethyl-pyrazolo[5,1-b]oxazol-7-ylamine

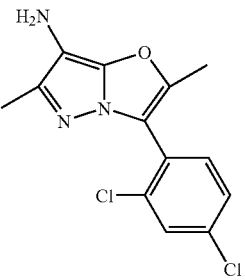

Step 1: 3-(2,4-Dichloro-phenyl)-2,6-dimethyl-7-nitro-pyrazolo[5,1-b]oxazole:

To a solution of 3-(2,4-dichloro-phenyl)-2,6-dimethyl-pyrazolo[5,1-b]oxazole (Intermediate HE) (768 mg, 2.73 mmol) in MeCN (13 ml) is added nitronium tetrafluoroborate (0.5M solution in sulfolane, 6.6 ml, 3.3 mmol, 1.2 eq.). The dark orange reaction mixture is stirred at RT for 3 h then diluted into Et$_2$O (150 ml) and washed successively with Na$_2$CO$_3$ 1M in water (100 ml), water (100 ml) and brine (50 ml). The organic layer is dried over Na$_2$SO$_4$, filtered and concentrated to dryness under reduced pressure. The resulting crude residue is purified by Combi-Flash Companion™ (Isco Inc.) column chromatography (SiO$_2$; gradient elution, heptane/TBME 95:5→7:3) to yield the title compound as a greenish solid. TLC: R$_F$=0.27 (heptane/TBME 3:1); HPLC: $^A$t$_{Ret}$=2.73; MS: m/z 325.8 [M+H]$^+$; 1H NMR (400 MHz, CDCl$_3$) δ 2.49 (s, 3H), 2.66 (s, 3H), 7.47 (dd, J 8.3, 2.0, 1H), 7.52 (d, J 8.3, 1H), 7.64 (d, J 2.0, 1H).

Step 2: 3-(2,4-Dichloro-phenyl)-2,6-dimethyl-pyrazolo[5,1-b]oxazol-7-ylamine

To a stirred suspension of black nickel boride (prepared in situ from 0.50 g, 2.15 mmol nickel (II) chloride hexahydrate and (0.080 g, 2.15 mmol sodium borohydride) in MeOH (15 ml) at RT is added a solution of 3-(2,4-dichloro-phenyl)-2,6-dimethyl-7-nitro-pyrazolo[5,1-b]oxazole (1.40 g, 4.29 mmol) in MeOH (55 ml). Further sodium borohydride (0.74 g, 19.5 mmol) is added in portions and the reaction is stirred at RT for 1 hour. The reaction is quenched by the addition of water (200 ml) and reduced in vacuo to remove the MeOH. EtOAc is added and the mixture passed through a Celite® (filter material) 521 pad. The crude product is extracted with EtOAc (2×125 ml) and the combined extracts are then extracted using 0.2N HCl (2×120 ml). The aqueous portions are combined and basified with 1N NaOH to pH10 to yield the title compound as a solid, which is filtered off and dried in vacuo; MS: m/z 296.1 [M+H]$^+$ Alternatively, 3-(2,4-dichloro-phenyl)-2,6-dimethyl-pyrazolo[5,1-b]oxazol-7-yl amine can been prepared from 3-(2,4-dichloro-phenyl)-2,6-dimethyl-7-nitro-pyrazolo[5,1-b]oxazole using the following method:

A suspension of 3-(2,4-dichloro-phenyl)-2,6-dimethyl-7-nitro-pyrazolo[5,1-b]oxazole (24.1 g, 73.9 mmol) in EtOH (300 ml) and water (60 ml) is heated to 50° C. and treated with ammonium chloride (7.91 g, 148 mmol). The resulting mixture is heated to 80° C. and iron (20.63 g, 369 mmol) is added. The reaction mixture is heated at reflux for 1 hour and then allowed to cool to RT.

The mixture is filtered through Celite® 521 (filter material) and washed with EtOAc (500 ml until eluant clear). The reaction mixture is evaporated to a small volume and partitioned between EtOAc (500 ml) and 1M NaOH (300 ml). The organic portion is separated and the aqueous is further extracted with EtOAc (3×100 ml). The combined organic extracts are washed with brine (250 ml), dried $Na_2SO_4$, filtered and concentrated in vacuo to yield a the title compound as a purple oil; MS m/z 296.1 [M+H]$^+$ The intermediates shown in the following Table are prepared analogously using the appropriate starting compounds:

TABLE 8

| Ex. | Structure | [M + H]$^+$ | Name |
|---|---|---|---|
| IE | 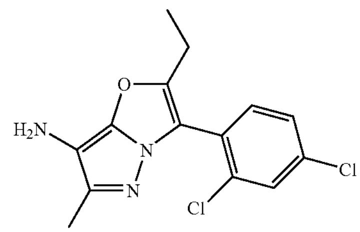 | 310.2 | 3-(2,4-Dichloro-phenyl)-2-ethyl-6-methyl-pyrazolo[5,1-b]oxazol-7-ylamine |
| IF | 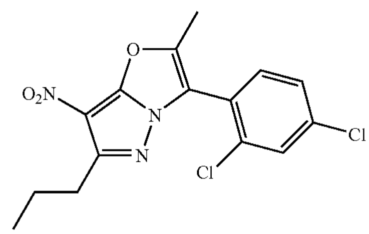 | 354.0 | 3-(2,4-Dichloro-phenyl)-2-methyl-7-nitro-6-propyl-pyrazolo[5,1-b]oxazole |
| IG | 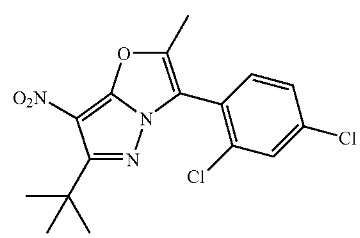 | 368.0 | 6-tert-Butyl-3-(2,4-dichloro-2-methyl-7-nitro-pyrazolo[5,1-b]oxazole |
| IH | 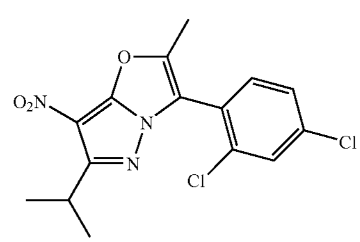 | 354.0 | 3-(2,4-Dichloro-phenyl)-6-isopropyl-2-methyl-7-nitro-pyrazolo[5,1-b]oxazole |
| II | 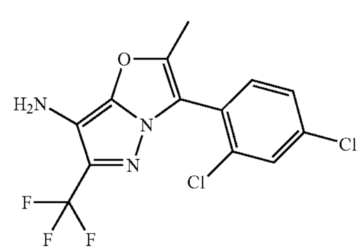 | 350.1 | 3-(2,4-Dichloro-phenyl)-2-methyl-6-trilfuoromethyl-pyrazolo[5,1-b]oxazol-7-ylamine |

TABLE 8-continued

| Ex. | Structure | [M + H]+ | Name |
|---|---|---|---|
| IJ | 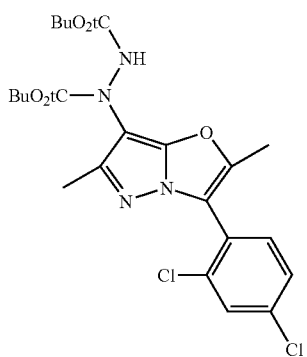 | 310 | 3-(2,4-Dichloro-phenyl)-6-ethyl-2-methyl-pyrazolo[5,1-b]oxazol-7-ylamine |

Intermediate JA

N'-[3-(2,4-Dichloro-phenyl)-2,6-dimethyl-pyrazolo[5,1-b]oxazol-7-yl]-N'-tert-butoxycarbonyl-hydrazinecarboxylic acid tert-butyl ester Step 1: 7-Bromo-3-(2,4-dichloro-phenyl)-2,6-dimethyl-pyrazolo[5,1-b]oxazole:

To a solution of 3-(2,4-dichloro-phenyl)-2,6-dimethyl-pyrazolo[5,1-b]oxazole (Intermediate HE) (0.755 g, 2.69 mmol) in DMF (10 ml) is added NBS (0.502 g, 2.82 mmol). The reaction is stirred at RT for 30 mins and then partitioned between $Na_2CO_3$ and EtOAc. The mixture is extracted with EtOAc (×2) and the combined organic phases are dried over $Na_2SO_4$, filtered and evaporated to dryness under reduced pressure. This resulting solid is recrystallised from hot EtOAc/iso-hexane to yield the title compound. MS: m/z 360.99 [M+H]+

Step 2: N'-[3-(2,4-Dichloro-phenyl)-2,6-dimethyl-pyrazolo[5,1-b]oxazol-7-yl]-N'-tert-butoxycarbonyl-hydrazinecarboxylic acid tert-butyl ester To a stirring solution of 7-bromo-3-(2,4-dichloro-phenyl)-2,6-dimethyl-pyrazolo[5,1-b]oxazole (710 mg, 1.972 mmol) in THF (15.5 ml) under $N_2$ at −78° C. is added n-butyllithium (0.789 ml, 1.972 mmol) dropwise; the temperature is maintained below −70° C. for the addition and then the reaction mixture is stirred for 5 mins at −78° C. before the addition of di-tert-butyl azodicarboxylate (545 mg, 2.366 mmol) in THF (1.5 ml); the temperature is maintained below −60° C. for the period of the addition. After stirring at −78° C. for 30 mins, the reaction is quenched with sat. ammonium chloride solution and allowed to warm to RT. Ammonium chloride solution (sat.) is added and the mixture is extracted with EtOAc (2×100 ml). The combined organics extracts are washed with brine, dried over $MgSO_4$ and concentrated in vacuo. The crude product is purified ISCO chromatography eluting (0 to 100%) EtOAc/iso-hexane on a 40 g $SiO_2$ cartridge to give the title compound as an orange solid; MS: m/z 511.22 [M+H]+

The intermediates shown in the following Table are prepared analogously to 7-bromo-3-(2,4-dichloro-phenyl)-2,6-dimethyl-pyrazolo[5,1-b]oxazole (Intermediate J step 1) using the appropriate starting compounds:

TABLE 9

| Ex. | Structure | [M + H]+ | Name |
|---|---|---|---|
| JB | 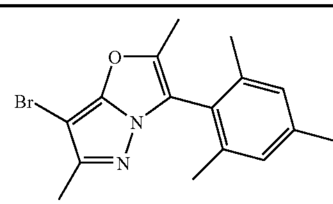 | 333.2 | 7-Bromo-2,6-dimethyl-3-(2,4,6-trimethyl-phenyl)-pyrazolo[5,1-b]oxazole |
| JC | 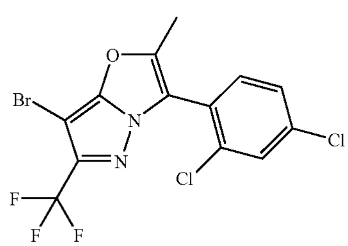 | 414.7 | 7-Bromo-3-(2,4-dichloro-phenyl)-2-methyl-6-trifluoromethyl-pyrazolo[5,1-b]oxazole |

TABLE 9-continued

| Ex. | Structure | [M + H]+ | Name |
|---|---|---|---|
| JD | 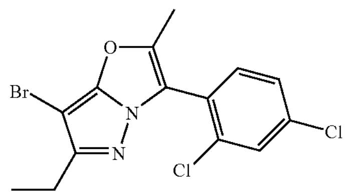 | 375.0 | 7-Bromo-3-(2,4-dichloro-phenyl)-6-ethyl-2-methyl-pyrazolo[5,1-b]oxazole |

Intermediate KA

5'-Methyl-3-trifluoromethyl-2'H-[1,4']bipyrazolyl-3'-ol

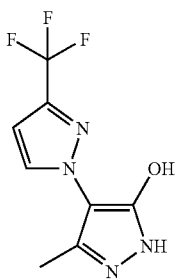

Step 1: 2-Bromo-3-oxo-butyric acid benzyl ester: prepared according to the procedure of Tanemura, K. et al. Chem. Commun., 470-471, 2004.

To a stirring dispersion of benzyl acetoacetate (3 ml, 17.37 mmol) and NBS (3.25 g, 18.24 mmol) in Et$_2$O (174 ml) is added ammonium acetate (0.134 g, 1.737 mmol). The reaction mixture is stirred at RT for 4 hours and then filtered. The filtrate is washed with water, brine, dried over MgSO$_4$ and concentrated in vacuo to yield the title compound as an oil. $^1$H NMR (400 MHz, CDCl$_3$) δ 7.39 (5H, m), 5.29 (2H, s), 4.82 (1H, s), 2.42 (3H, s).

Step 2: 3-Oxo-2-(3-trifluoromethyl-pyrazol-1-yl)-butyric acid benzyl ester:

To a stirring solution of 3-trifluoromethylpyrazole (0.703 g, 5.16 mmol) in THF (36.9 ml) is added NaH (0.199 g, 4.98 mmol). The reaction mixture is stirred at RT for 10 mins and then treated with 2-bromo-3-oxo-butyric acid benzyl ester (1.0 g, 3.69 mmol). After stirring at 40° C. for 30 mins, the mixture is diluted with water (50 ml) and extracted with EtOAc (2×50 ml). The combined organics are washed with brine, dried over MgSO$_4$ and concentrated in vacuo. The crude product is purified by ISCO combiflash chromatography, eluting with 0 to 100% (iso-hexane/EtOAc) on a 24 g SiO$_2$-column to afford the title compound; MS: m/z 327.22 [M+H]$^+$ Step 3: 5'-Methyl-3-trifluoromethyl-2'H-[1,4']bipyrazolyl-3'-ol 3-Oxo-2-(3-trifluoromethyl-pyrazol-1-yl)-butyric acid benzyl ester (800 mg, 2.452 mmol), EtOH (12.30 ml) and hydrazine (0.231 ml, 7.36 mmol) are stirred at 50° C. for hour. The volatiles are removed in vacuo yielding a wet solid which is added to ammonium chloride (sat. aq. 100 ml) and the product is extracted into EtOAc (2×100 ml). The combined organic extracts are washed with brine, dried over Na$_2$SO$_4$, and concentrated in vacuo to give a pale yellow solid. The crude product is purified by ISCO combiflash chromatography, eluting with 0 to 100% (EtOAc/Iso-hexane) on a 24 g SiO2-column to afford the title compound as an orange oil; MS: m/z 233.09 [M+H]$^+$.

The intermediates shown in the following Table 10 are prepared analogously to 5'-methyl-3-trifluoromethyl-2'H-[1,4']bipyrazolyl-3'-ol (Intermediate KA) using the appropriate starting compounds:

TABLE 10

| Ex. | Structure | NMR or MS Data [M + H]+ | Name |
|---|---|---|---|
| KB | 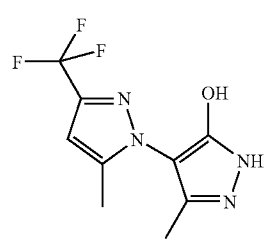 | 274.14 | 5,5'-Dimethyl-3-trifluoromethyl-2'H-[1,4']bi pyra zolyl-3'-ol |

TABLE 10-continued

| Ex. | Structure | NMR or MS Data [M + H]+ | Name |
|---|---|---|---|
| KC | 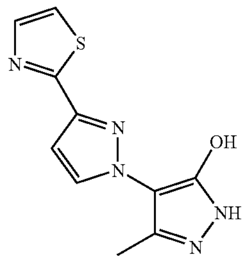 | 248.12 | 5'-Methyl-3-thiazol-2-yl-2'H-[1,4']bipyrazolyl-3'-ol |
| KD | 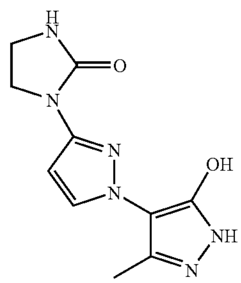 | 249.16 | 1-(5'-Hydroxy-3'-methyl-1'H-[1,4']bipyrazolyl-3-yl)-imidazolidin-2-one |
| KE | 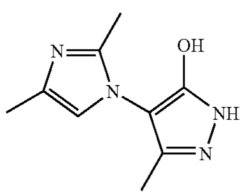 | (400MHz, DMSO-d$_6$) δ 11.68 (1 H, br s), 10.06 (1 H, br s), 6.70 (1 H, s), 2.07 (6 H, s), 1.99 (3 H, s) | 4-(2,4-Dimethyl-imidazol-1-yl)-5-methyl-2H-pyrazol-3-ol |
| KF | 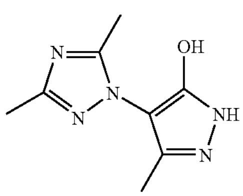 | 195.39 | 4-(3,5-Dimethyl-[1,2,4]triazol-1-yl)-5-methyl-2H-pyrazol-3-ol |
| KG | 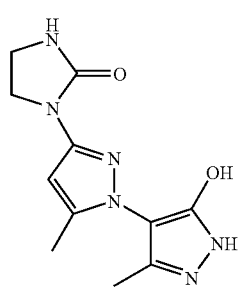 | 263.0 | 1-(5'-Hydroxy-5,3'-dimethyl-1'H-[1,4']bipyrazolyl-3-yl)-imidazolidin-2-one |
| KH | 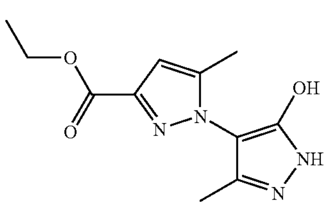 | 251.0 | 5'-Hydroxy-5,3'-dimethyl-1'H-[1,4']bipyrazolyl-3-carboxylic acid ethyl ester |

TABLE 10-continued

| Ex. | Structure | NMR or MS Data [M + H]+ | Name |
|---|---|---|---|
| KI | 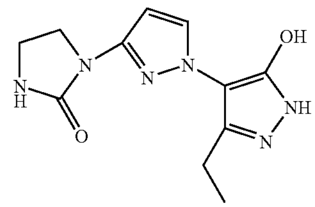 | 263.0 | 1-(3'-Ethyl-5'-hydroxy-1'H-[1,4']bipyrazolyl-3-yl)-imidazolidin-2-one |
| KJ | 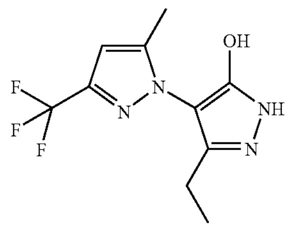 | 261.0 | 5'-Ethyl-5-methyl-3-trifluoromethyl-2'H-[1,4']bipyrazolyl-3'-ol |
| KK | 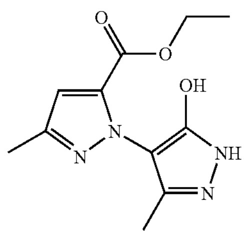 | 251.0 | 5'-Hydroxy-3,3'-dimethyl-1'H-[1,4']bipyrazolyl-5-carboxylic acid ethyl ester |
| KL | 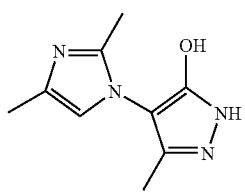 | 192.9 | 4-(2,4-Dimethyl-imidazol-1-yl)-5-methyl-2H-pyrazol-3-ol |
| KM | 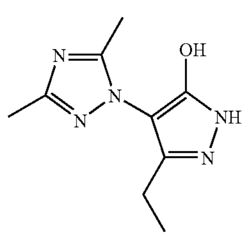 | 208.0 | 4-(3,5-Dimethyl-[1,2,4]triazol-1-yl)-5-ethyl-2H-pyrazol-3-ol |

Intermediate KN

5-Methyl-4-(5-methyl-3-trifluoromethyl-[1,2,4]triazol-1-yl)-2H-pyrazol-3-ol

Step 1: 2-(5-Methyl-3-trifluoromethyl-[1,2,4]triazol-1-yl)-3-oxo-butyric acid ethyl ester:

To a stirring solution of 5-methyl-3-(trifluoromethyl)-1H-1,2,4-triazole (2 g, 13.24 mmol) in THF (60 ml) is added $K_2CO_3$ (3.66 g, 26.5 mmol). The mixture is allowed to stir for 20 minutes at 40° C. before adding ethyl 2-chloro-3-oxobutanoate (2.61 g, 15.88 mmol) and leaving to stir. The reaction mixture is filtered to remove solids, before concentrating under vacuum to yield a dark orange/red oil. The oil is taken up in 2% MeOH in DCM and purified on silica eluting with 2% MeOH in DCM to afford the title compound as a pale yellow oil. MS m/z 280.0 [M+H]+

Step 2: 5-Methyl-4-(5-methyl-3-trifluoromethyl-[1,2,4]triazol-1-yl)-2H-pyrazol-3-ol To a solution of 2-(5-methyl-3-trifluoromethyl-[1,2,4]triazol-1-yl)-3-oxo-butyric acid ethyl ester (890 mg, 3.19 mmol) in EtOH (15 ml) is added hydrazine (0.500 ml, 15.94 mmol) and the mixture left to stir at 50° C. overnight. The solvent is removed in vacuo and trituration of the resulting pale yellow oil with ether and EtOAc affords the title compound as a fine white solid.

MS m/z 248.0 [M+H]+ 1H NMR (400 MHz, DMSO-d6,) δ 12.05 (s, 1H), 10.40 (s, 1H), 2.35 (s, 3H), 2.05 (s, 3H).

Intermediate L

1-[4-Methoxy-2-(2-methoxy-ethoxy)-phenyl]-propan-1-one

A solution of 1-(2-hydroxy-4-methoxyphenyl)propan-1-one (1 g, 5.55 mmol) in DMF (50 ml) is treated with potassium carbonate (0.920 g, 6.66 mmol) and stirred at RT for approximately 10 mins. 1-Bromo-2-methoxyethane (0.771 g, 5.55 mmol) is added and the mixture is stirred at RT overnight. The solvent is removed in vacuo and the residue is partitioned between in EtOAc/H$_2$O. The organic phase is separated and washed with sat Na$_2$CO$_3$, 1M HCl, brine, dried (MgSO$_4$) and concentrated in vacuo to afford a dark green/brown oil. Purification by chromatography on silica gel (50 g+70 g) eluting with 20% EtOAc/iso-hexane affords the title compound; MS m/z 239.2 [M+H]$^+$.

Intermediate MA

2-Bromo-1-(4-bromo-2-methyl-phenyl)-propan-1-one

Step 1: 4-Bromo-2-methyl-benzoyl chloride:

DMF (1 drop) and oxalyl chloride (0.44 ml, 5.0 mmol) are added to a stirred suspension of 4-bromo-2-methylbenzoic acid (0.90 g, 4.19 mmol) in dry DCM (10 ml). The reaction is stirred for 3 h at RT when a clear solution is obtained. The solvent is removed in vacuo to give the title product as an oil which crystallised. This is used in the next step without purification.

Step 2: 4-Bromo-N-methoxy-2,N-dimethyl-benzamide:

Triethylamine (1.3 ml, 10.04 mmol) is added to a stirred suspension of N,O-dimethylhydroxylamine hydrochloride (0.45 g, 4.6 mmol) in toluene (15 ml). After 30 minutes at RT the solution is cooled to 0° C. and a solution of 4-bromo-2-methylbenzoyl chloride (0.977 g, 4.81 mmol) in toluene (5 ml) is slowly added. The reaction is stirred at RT for 2 h at 0° C. and then diluted with ethyl acetate. The mixture is washed with 0.1M aq. HCl solution followed by brine. The organic extract is separated, dried over (MgSO$_4$) and concentrated in vacuo to afford a colourless oil. Purification by chromatography on silica, eluting with ethyl acetate:iso-hexane (1:1) yields the title product as a colourless oil. MS m/z 258.0 [M+H]$^{+1}$H NMR (400 MHz, CDCl$_3$) δ 2.32 (3H, s), 3.0 (3H, br s), 3.50 (3H, br s), 7.15 (1H, d), 7.35 (1H, d), 7.37 (1H, s).

Step 3: 1-(4-Bromo-2-methyl-phenyl)-propan-1-one:

Ethylmagnesium bromide (2.35 ml of 3M in diethyl ether, 7.05 mmol) is added slowly to a stirred solution of 4-bromo-N-methoxy-N,2-dimethylbenzamide (0.91 g, 3.53 mmol) in dry THF (40 ml) at 0° C. The reaction is stirred at 0° C. for 1 h followed by RT for 18 h. The reaction mixture is poured into saturated ammonium chloride solution to quench the reaction and concentrated in vacuo to remove most of the THF. The product is extracted with diethyl ether and the combined organic extracts are dried (MgSO$_4$). The solvent is removed in vacuo and the resulting oil is purified by chromatography on silica eluting with iso-hexane:ethyl acetate (3:1) give the title product as a colourless oil. MS m/z 227.0 [M+H]$^{+1}$H NMR (400 MHz, CDCl$_3$) δ 1.18 (3H, t), 2.45 (3H, s), 2.88 (2H, d), 7.40 (1H, d), 7.43 (1H, s), 7.50 (1H, d).

Step 4: 2-Bromo-1-(4-bromo-2-methyl-phenyl)-propan-1-one:

This compound is prepared from 1-(4-bromo-2-methyl-phenyl)-propan-1-one (step 3) analogously to 2-bromo-1-(2,4-dichloro-phenyl)-propan-1-one (Intermediate AA). $^1$H NMR (400 MHz, CDCl$_3$) δ 1.78 (3H, d), 2.98 (3H, s), 5.12 (1H, q), 7.45 (3H, m).

Intermediate MB

2-Bromo-1-(4-bromo-2-chloro-phenyl)-propan-1-one

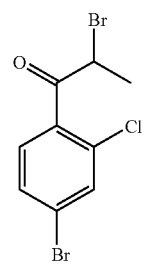

This compound is prepared from 4-bromo-2-chloro-benzoic acid analgously to 2-bromo-1-(4-bromo-2-methyl-phenyl)-propan-1-one (Intermediate MA). $^1$H NMR (400 MHz, CDCl$_3$) δ 1.90 (2H, d), 5.21 (1H, q), 7.40 (1H, d), 7.50 (1H, d), 7.62 (1H, s).

Intermediate MC

2-Bromo-1-(2-chloro-4-[1,2,4]triazol-1-yl-phenyl)-butan-1-one

This compound is prepared from 2-chloro-4-[1,2,4]triazol-1-yl-benzoic acid analgously to 2-bromo-1-(4-bromo-2-methyl-phenyl)-propan-1-one (Intermediate MA) by replacing ethylmagnesium bromide with the appropriate alkyl magnesium bromide.

Intermediate N

1-(2-Methoxy-4-methyl-phenyl)-propan-1-one

Step 1: 1-(2-Methoxy-4-methyl-phenyl)-propan-1-ol:

To a stirring solution of 2-methoxy-4-methylbenzaldehyde (1 g, 6.66 mmol) in diethyl ether (35 ml) at 0° C. is added EtMgBr (2.220 ml, 6.66 mmol). The mixture is stirred for 2 hours and then added to sat ammonium chloride solution. The mixture is extracted with ethyl acetate and the combined organic portions are washed with NaHCO$_3$, water and brine dried (MgSO$_4$) and reducing under vacuum to yield the title product as a clear oil. $^1$H NMR (400 MHz, CDCl$_3$) δ 7.18 (d, 1H), 6.78 (d, 1H), 6.72 (s, 1H), 4.77 (t, 1H), 3.85 (s, 3H), 2.37 (s, 3H), 1.83 (m, 2H), 0.96 (t, 3H).

Step 2: 1-(2-Methoxy-4-methyl-phenyl)-propan-1-one:

Dess-Martin periodinane (2.89 g, 6.82 mmol) and H$_2$O (0.123 ml, 6.82 mmol) are added to DCM (20 ml) and left to stir for 10 minutes. This mixture is treated with 1-(2-methoxy-4-methyl-phenyl)-propan-1-ol (step 1) (1.17 g, 6.49 mmol) in DCM (15 ml) and stirred for 1 hour. The reaction mixture is diluted with DCM and washed with Na$_2$S$_2$O$_3$, NaHCO$_3$, water, brine, dried (MgSO$_4$) and concentrated under vacuum to yield the title product as a clear oil; $^1$H NMR (400 MHz, CDCl$_3$) δ 7.64 (d, 1H), 6.82 (d, 1H), 6.77 (s, 1H), 3.90 (s, 3H), 3.00 (q, 2H), 2.39 (s, 3H), 1.17 (t, 3H).

Intermediate O 1-(5-Chloro-3-methyl-2-phenyl-3H-imidazol-4-yl)-propan-1-one

The title compound is prepared from 5-chloro-3-methyl-2-phenyl-3H-imidazole-4-carbaldehyde analogously to 1-(2-methoxy-4-methyl-phenyl)-propan-1-one (Intermediate N).

Intermediate P

Benzofuran-5-carboxylic acid methoxy-methyl-amide

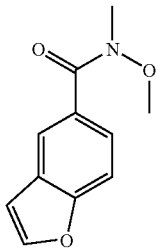

The title compound is prepared from the appropriate starting compound analogously to 4-bromo-N-methoxy-2,N-dimethyl-benzamide (Example MA, step 2) to yield the title compound as an oil; MS m/z=206.1 [M+H]$^+$; H NMR 400.13 MHz (CDCl3)-7.9 (s, 1H), 7.4 (m, 2H), 7.4 (d, 1H), 6.7 (s, 1H), 3.5 (s, 3H), 3.3 (s, 3H).

Intermediate Q 2,3-Dihydro-benzofuran-5-carboxylic acid methoxy-methyl-amide

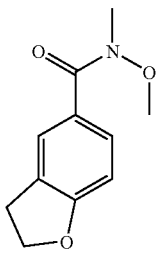

A solution of benzofuran-5-carboxylic acid methoxy-methyl-amide (Intermediate P, 235 mg, 1.145 mmol) in ethanol (20 ml) is hydrogenated over 10% Pd on carbon (30×4 mm CatCart®) at 40° C. and 30 bar using the H-Cube Hydrogenator. After 6 hrs the reaction is complete and the reaction mixture is concentrated in vacuo to give an oil; MS m/z=208.1 [M+H]$^+$; H NMR 400.13 MHz (CDCl3)-7.6 (1H, s), 7.55 (1H, d), 7.8 (1H, d), 4.6 (2H, t), 3.6 (3H, s), 3.35 (3H, s), 3.25 (2H, t).

Intermediate R 1-(2,3-Dihydro-benzofuran-5-yl)-propan-1-one

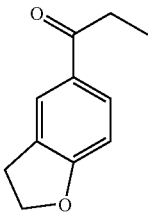

The title compound is prepared from 2,3-dihydro-benzofuran-5-carboxylic acid methoxy-methyl-amide (Intermediate Q) analogously to 1-(4-bromo-2-methyl-phenyl)-propan-1-one (Example MA, step 3) to afford the title compound as a solid; MS m/z=177.0 [M+H]$^+$;

Intermediate S

2-Bromo-1-(2,3-dihydro-benzofuran-5-yl)-propan-1-one

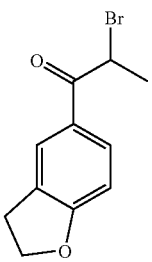

The title compound is made analogously to Intermediate GB (Br2& 48% HBr/H2O) to give an oil; MS m/z=257.0 [M+H]$^+$; which is taken on crude without further purification.

Intermediate T

2-Methyl-4-methylsulfanyl-benzonitrile

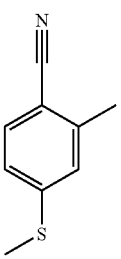

To a solution of 4-bromo-2-methylbenzonitrile (2 g, 10.20 mmol) in DMF (50 ml) is added NaSMe (1.260 g, 17.98 mmol) and the reaction left stirring at RT overnight. After this time the contents are diluted with water before extracting into EtOAc. The organic moiety is separated and washed with H2O, NaHCO3, Brine, dried (MgSO4) and evaporated down to give a pale yellow solid; MS m/z=164.0 [M+H]$^+$; H NMR 400.13 MHz (CDCl3) –7.50 (1H, d), 7.12 (1H, s), 7.09 (1H, d), 2.51 (6H, s).

Intermediate U 1-(2-Methyl-4-methylsulfanyl-phenyl)-propan-1-one

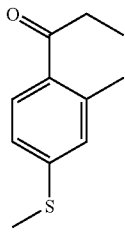

To a solution of EtMgBr (11.90 ml, 35.72 mmol) in toluene (40 ml) at 0° C. is added 2-Methyl-4-methylsulfanyl-benzonitrile (2.43 g, 14.89 mmol) in toluene dropwise over 30 mins. The reaction is then left to reach RT overnight with stirring. After this time, the contents are poured into ice, conc. $H_2SO_4$ (3 ml) is added and the contents are vigorously stirred for 4 hrs at RT. The misture is extracted into EtOAc, washed with $H_2O$, brine, dried ($MgSO_4$) and concentrated in vacuo to give a yellow solid; MS m/z=195.1 [M+H]$^+$; H NMR 400.13 MHz (CDCl3) −7.09 (2H, m), 2.41 (2H, q), 2.52 (6H, s), 1.20 (3H, t).

Biological Data

| Example | CRF-1 IC$_{50}$ (μM) | $^1$H NMR | Structure |
|---|---|---|---|
| 2.2 | 0.005 | (400 MHz, CDCl$_3$) δ 7.60 (1 H, s), 7.48 (2 H, d), 7.40 (2 H, dd), 3.79 (1 H, m), 2.32 (3 H, s), 2.30 (3 H, s), 1.70 (4 H, m), 1.04 (6 H, t). | 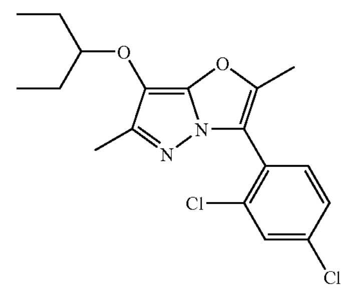 |
| 6.3 | 0.006 | (400 MHz, CDCl$_3$) δ 7.60 (3 H, m), 7.44 (1 H, dd), 5.95 (1 H, s), 2.63 (2 H, q), 2.32 (3 H, s), 2.30 (3 H, s), 2.20 (3 H, s), 1.10 (3 H, t). | 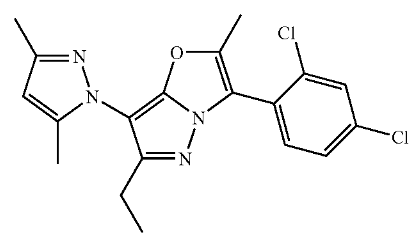 |
| 3.1 | 0.014 | (400 MHz, DMSO-d$_6$) δ 7.88 (1 H, d), 7.71 (1 H, d), 7.62 (1 H, dd), 2.81 (4 H, t), 2.30 (3 H, s), 2.14 (3 H, s), 1.35 (4 H, m), 0.86 (6 H, t). | 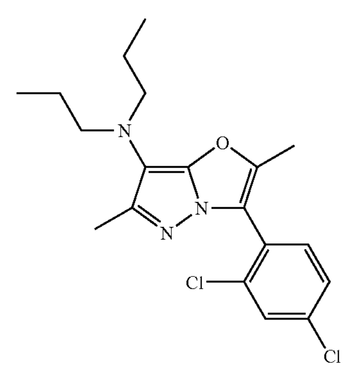 |

-continued

| Example | CRF-1 IC$_{50}$ (μM) | $^1$H NMR | Structure |
|---|---|---|---|
| 2.1 | 0.017 | (400 MHz, CDCl$_3$) δ 7.52 (2 H, m), 7.35 (6 H, m), 4.58 (1 H, t), 2.25 (3 H s), 2.20 (3 H, s), 2.15 (1 H, m), 1.94 (1 H, m), 1.05 (3 H, t). | 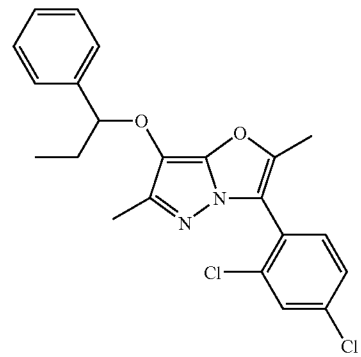 |
| 6.1 | 0.021 | (400 MHz, CDCl$_3$) δ 7.60 (2 H, m), 7.44 (1 H, d), 6.01 (1 H, s), 2.38 (3 H, s), 2.33 (3 H, s), 2.27 (3 H, s), 2.22 (3 H, s) | 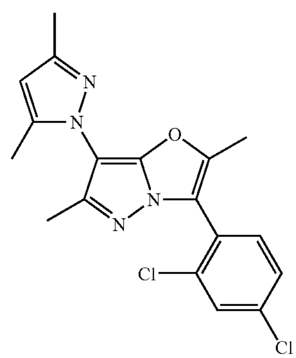 |
| 6.16 | 0.023 | (400 MHz, DMSO-d$_6$) δ 7.95 (1 H, d), 7.69 (1 H, dd), 7.53 (1 H, d), 2.49 (2 H, m), 2.35 (3 H, s), 2.29 (3 H, s), 2.27 (3 H, s), 1.03 (3 H, t). | 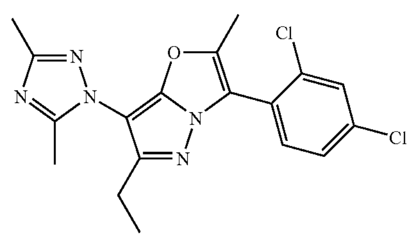 |
| 2.3 | 0.024 | (400 MHz, CDCl$_3$) δ 7.58 (2 H, m), 7.41 (1 H, dd), 4.03 (1 H, m), 3.58 (2 H, m), 3.44 (3 H, s), 2.33 (3 H, s), 2.30 (3 H, s), 1.76 (2 H, m), 1.57 (2 H, m), 1.00 (3 H, t) | 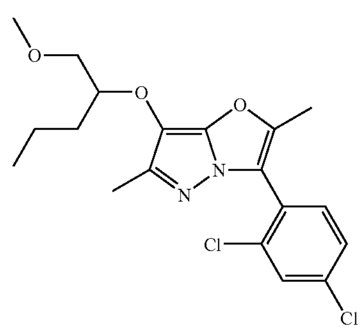 |

-continued

| Example | CRF-1 IC$_{50}$ (μM) | $^1$H NMR | Structure |
|---|---|---|---|
| 4.0 | 0.026 | (400 MHz, DMSO-d$_6$) δ 7.90 (1 H, d), 7.75 (1 H, d), 7.64 (1 H, dd), 3.79 (1 H, br s), 3.18 (1 H, br s), 2.33 (3 H, s), 2.12 (3 H, s), 2.04 (2 H, q), 1.45 (2 H, m), 0.92 (3 H, t), 0.85 (3 H, t). | 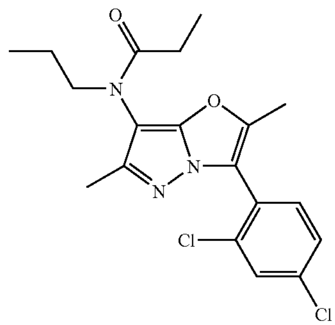 |
| 1.1 | 0.028 | (400 MHz, DMSO-d$_6$) δ 7.92 (1 H, d), 7.72 (1 H, d), 7.66 (1 H, dd), 3.47 (2 H, m), 3.31 (2 H, m), 2.35 (3 H, s), 2.29 (3 H, s), 1.61 (2 H, m), 1.04 (1 H, m), 0.84 (3 H, t), 0.49 (2 H, m), 0.21 (2 H, m). | 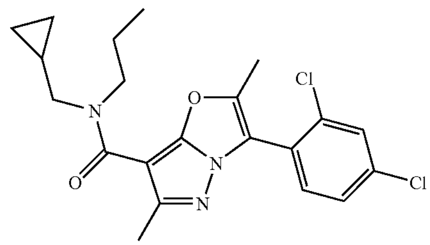 |
| 1.3 | 0.031 | (400 MHz, DMSO-d$_6$) δ 7.92 (1 H, d), 7.74 (1 H, d), 7.67 (1 H, dd), 3.37 (4 H, m), 2.35 (3 H, s), 2.29 (3 H, s), 1.58 (4 H, m), 0.84 (6 H, m). | 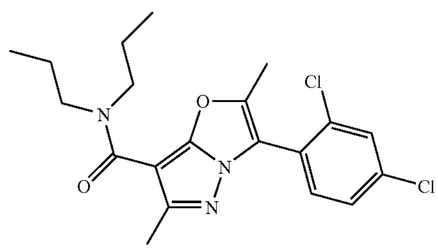 |
| 5.17 | 0.035 | (400 MHz, DMSO-d$_6$) δ 7.06 (s, 2 H) 4.35 (m, 2 H), 2.96-3.18 (m, 4 H), 2.32 (s, 3 H), 2.29 (s, 3 H), 2.23 (s, 3 H), 2.08 (s, 6 H), 1.74-1.84 (m, 2 H), 1.15-1.26 (m, 1 H), 0.97 (t, 3 H), 0.70 (m, 2 H), 0.44 (m, 2 H). | 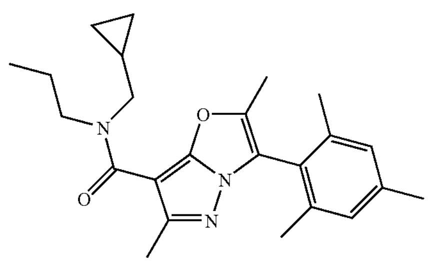 |
| 6.10 | 0.037 | (400 MHz, MeOD) δ 7.78 (1 H, d), 7.67 (1 H, d), 7.59 (1 H, dd), 6.83 (1 H, s), 2.39 (3 H, s), 2.25 (3 H, s), 2.21 (3 H, s), 2.19 (3 H, s). | 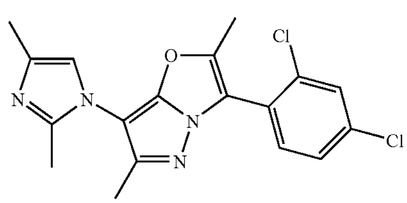 |
| 6.29 | 0.042 | (400 MHz, CDCl$_3$) δ 7.30 (d, 1 H), 6.91 (d, 1 H), 6.88 (dd, 1 H), 3.88 (s, 3 H), 2.53 (s, 3 H), 2.35 (s, 3 H), 2.31 (s, 3 H), 2.26 (s, 3 H) | 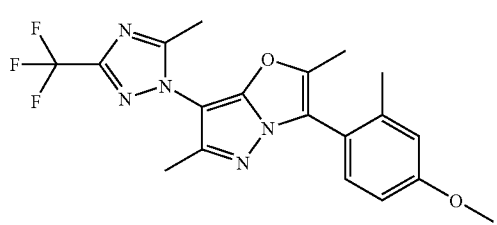 |

-continued

| Example | CRF-1 IC$_{50}$ (μM) | $^1$H NMR | Structure |
|---|---|---|---|
| 4.5 | 0.048 | (400 MHz, DMSO-d$_6$,) δ 7.90 (d, 1 H), 7.72 (d, 1 H), 7.64 (dd, 1 H), 3.46 (t, 2 H), 3.32 (m, 2 H), 2.51 (t, 3 H), 2.31 (s, 3 H), 2.09 (s, 3 H), 1.52 (m, 2 H), 0.89 (t, 3 H) | 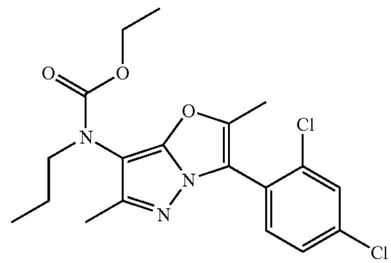 |
| 6.37 | 0.048 | (400 MHz, CDCl3) δ 7.15 (s, 1 H), 6.8 (s, 1 H), 3.9 (s, 3 H), 2.45 (s, 3 H), 2.40 (s, 3 H), 2.3 (s, 3 H), 2.25 (s, 3 H), 2.2 (s, 3 H), 2.2 (s, 3 H) | 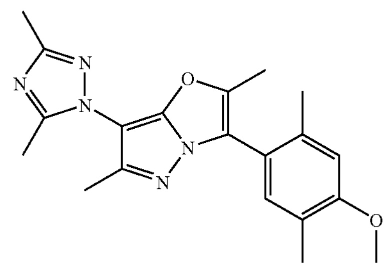 |
| 4.4 | 0.056 | (400 MHz, CDCl$_3$) δ 7.60 (2 H, m), 7.45 (1 H, m), 4.59 (1 H, m), 4.05 (1 H, m), 2.39 (3 H, s), 2.25 (5 H, m), 1.13 (3 H, t). | 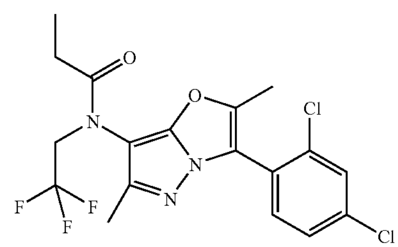 |
| 5.2 | 0.065 | (400 MHz, DMSO-d$_6$) δ 7.93 (1 H, m) 7.68 (2 H, m), 4.34 (2 H, m), 2.96-3.05 (4 H, m), 2.68 (2 H, q), 2.30 (3 H, s), 1.73-1.83 (4 H, m), 1.22 (3 H, t), 0.96 (6 H, t). | 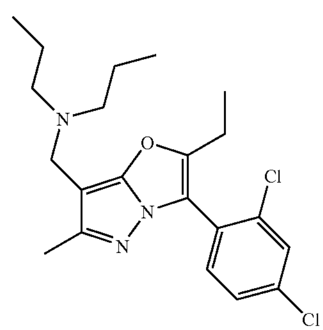 |
| 1.24 | 0.068 | (400 MHz, CDCl$_3$) δ 7.50 (1 H, d), 7.29 (1 H, q), 7.27 (1 H, q), 7.15-7.20 (5 H, m), 4.82 (2 H, s), 4.0 (2 H, q), 2.46 (3 H, s), 2.29 (3 H, s). | 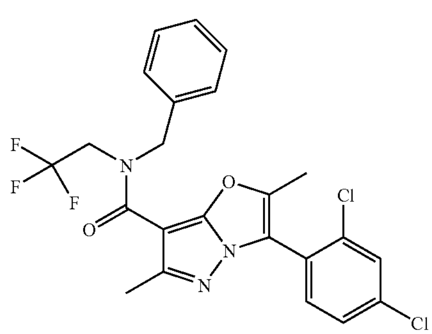 |

-continued

| Example | CRF-1 IC$_{50}$ (μM) | $^1$H NMR | Structure |
|---|---|---|---|
| 7.1 | 0.070 | (400 MHz, DMSO-d$_6$) δ 7.77 (1 H, d), 7.59 (1 H, d), 7.51 (1 H, dd), 4.94 (1 H, d), 4.85 (1 H, d), 2.30 (3 H, t), 2.18 (3 H, s), 2.14 (3 H, s), 1.35 (2 H, m), 0.79 (3 H, t) | 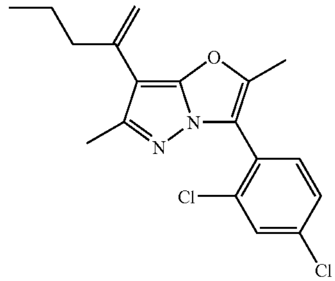 |
| 1.0 | 0.072 | (400 MHz, DMSO-d$_6$) δ 7.90 (1 H, d), 7.73 (1 H, d), 7.65 (1 H, dd), 3.46 (2 H, t), 3.30 (2 H, s), 2.70 (2 H, q), 2.34 (3 H, s), 1.60 (2 H, m), 1.11 (3 H, t), 1.02 (1 H, m), 0.63 (3 H, m), 0.48 (2 H, m), 0.20 (2 H, m). | 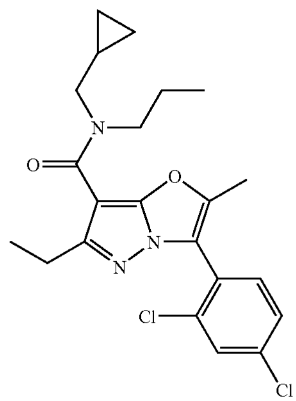 |
| 6.12 | 0.070 | (400 MHz, DMSO-d$_6$) δ 7.39 (1 H, d), 7.01 (1 H, d), 6.94 (1 H, dd), 3.83 (3 H, s), 2.30 (6 H, s), 2.26 (6 H, s), 2.11 (3 H, s) | 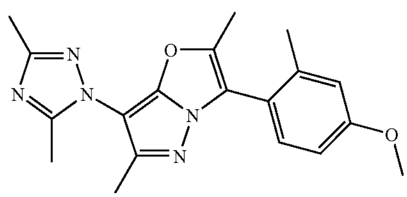 |
| 6.11 | 0.070 | (400 MHz, CDCl3) δ 7.52 (d, 1 H), 7.13 (d,1 H), 6.99 (dd, 1 H), 3.89 (s, 3 H), 2.43 (s, 3 H), 2.42 (s, 3 H), 2.36 (s, 3 H), 2.27 (s, 3 H). | 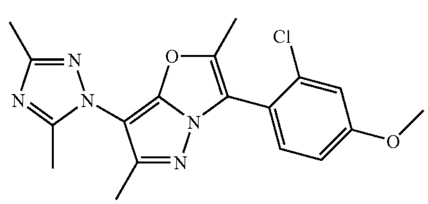 |
| 5.16 | 0.074 | (400 MHz, DMSO-d$_6$) δ 7.05 (s, 2 H) 4.32 (m, 2 H), 2.98-3.05 (m, 4 H), 2.32 (s, 3 H), 2.28 (s, 3 H), 2.23 (s, 3 H), 2.08 (s, 6 H), 1.72-1.82 (m, 4 H), 0.95 (t, 6 H). | 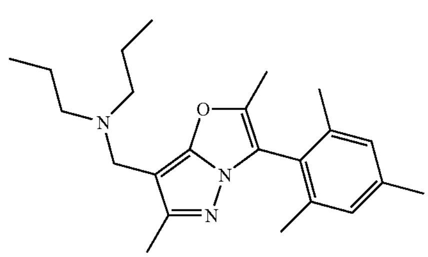 |

| Example | CRF-1 IC$_{50}$ (μM) | $^1$H NMR | Structure |
|---|---|---|---|
| 5.8 | 0.075 | (400 MHz, DMSO-d$_6$) δ 7.93 (1 H, d) 7.71 (1 H, d), 7.67 (1 H, dd), 4.33 (2 H, m), 3.00 (4 H, m), 2.37 (3 H, s), 2.31 (3 H, s), 1.77 (4 H, m), 0.95 (6 H, t). | 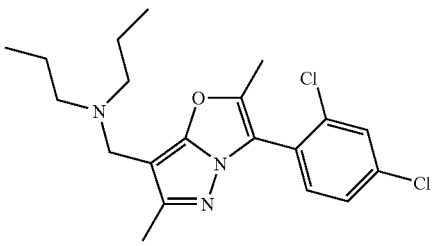 |
| 6.8 | 0.078 | (400 MHz, DMSO-d$_6$) δ 7.95 (1 H, d), 7.77 (1 H, d), 7.69 (1 H, d), 2.38 (3 H, s), 2.30 (3 H, s), 2.28 (3 H, s), 2.12 (3 H, s). | 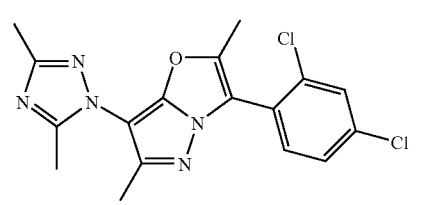 |
| 6.43 | 0.101 | (400 MHz, DMSO-d6) δ 7.82 (1 H, d), 6.43 (1 H, d), 3.93 (3 H, s), 3.91 (3 H, s), 2.37 (3 H, s), 2.35 (3 H, s), 2.27 (3 H, s), 2.17 (3 H, s) | 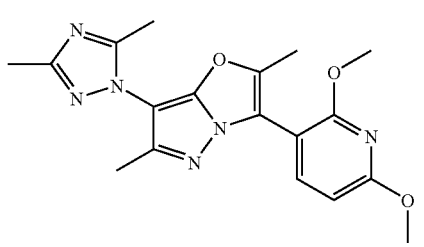 |
| 3.7 | 0.104 | (400 MHz, DMSO-d$_6$) δ 7.94 (1 H, d), 7.77 (1 H, d), 7.68 (1 H, dd), 2.88 (4 H, m), 2.40 (3 H, s), 1.39 (4 H, m), 0.85 (6 H, t). | 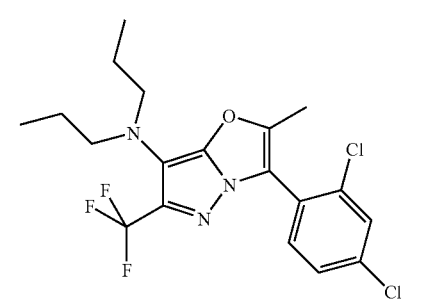 |
| 5.28 | 0.106 | (400 MHz, DMSO-d$_6$) δ 8.32-8.37 (2 H, m), 8.00 (1 H, m), 4.29-4.48 (2 H, m), 2.96-3.17 (4 H, m), 2.30 (3 H, s), 2.28 (3 H, s) 1.72-1.85 (2 H, m), 1.13-1.26 (1 H, m), 0.96 (3 H, t), 0.70 (2 H, m), 0.44 (2 H, m). | 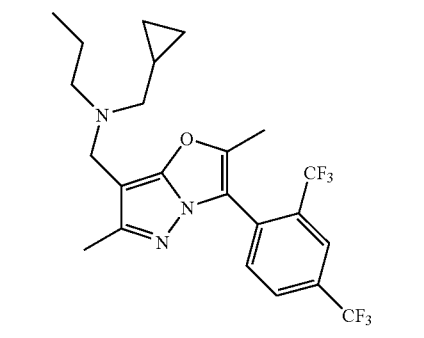 |
| 4.2 | 0.134 | (400 MHz, CDCl$_3$) δ 7.61 (2 H, m), 7.45 (1 H, dd), 3.95 (1 H, br s), 3.48 (1 H, br s), 2.38 (3 H, s), 2.25 (3 H, s), 2.17 (2 H, m), 1.20 (3 H, t), 1.10 (3 H, t). | 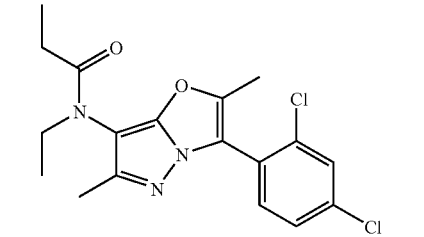 |

| Example | CRF-1 IC$_{50}$ (μM) | $^1$H NMR | Structure |
|---|---|---|---|
| 6.40 | 0.149 | (400 MHz, CDCl3) δ 7.45 (d, 1 H), 7.25 (s,1 H), 7.2 (d, 1 H), 2.45 (s, 3 H), 2.45 (s, 3 H), 2.35 (s, 3 H), 2.35 (s, 3 H) | 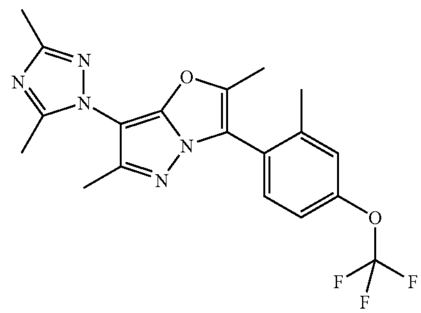 |
| 4.9 | 0.164 | (400 MHz, CDCl3) δ 1.03 (m, 3 H), 1.22 (m, 2 H), 2.08 (s, 3 H), 2.37 (s, 3 H), 3.56 & δ4.00 (d, 2 H), 7.70 (m, 3 H), 7.40 (m, 3 H), 7.50 (m, H), 7.56 (d, H). | 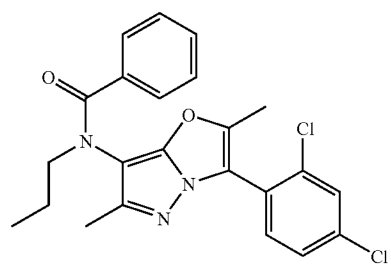 |
| 7.3 | 0.199 | (400 MHz, DMSO-d$_6$) δ 7.89 (1 H, d), 7.68 (1 H, d), 7.63 (1 H, dd), 4.90 (1 H, d), 4.73 (1 H, m), 2.32 (3 H, s), 2.22 (3 H, s), 1.49 (3 H, d). | 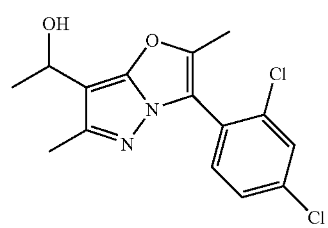 |
| 6.39 | 0.227 | (400 MHz, CDCl3) δ 7.2 (d, 1 H), 6.85 (d, 1 H), 3.9 (s, 3 H), 2.45 (s, 3 H), 2.45 (s, 3 H), 2.3 (s, 3 H), 2.25 (s, 3 H), 2.20 (s, 3 H) | 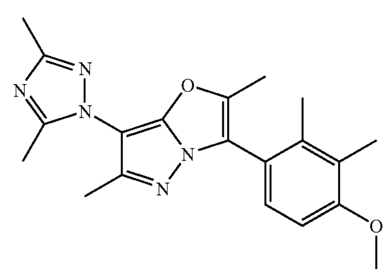 |
| 6.32 | 0.252 | (400 MHz, DMSO-d6) δ 7.5 (d, 1 H), 6.75 (s, 1 H), 6.7 (d, 1 H), 3.85 (s, 3 H), 3.825 (s, 3 H), 2.3 (s, 3 H), 2.275 (s, 3 H), 2.5 (s, 3 H), 2.1 (s, 3 H). | 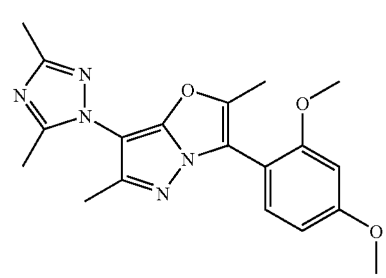 |

-continued

| Example | CRF-1 IC$_{50}$ (μM) | $^1$H NMR | Structure |
|---|---|---|---|
| 6.44 | 0.260 | (400 MHz, CDCl$_3$) δ 6.74 (m, 2 H), δ3.84 (s, 3 H), δ2.45 (s, 6 H), δ2.24 (s, 6 H), δ2.19 (s, 6 H) | 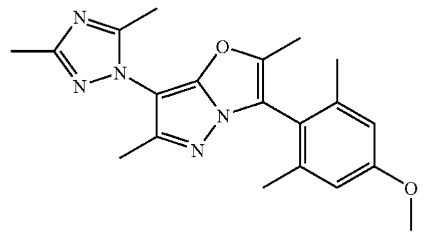 |
| 6.6 | 0.261 | (400 MHz, DMSO-d$_6$) δ 7.93 (1 H, d), 7.86 (1 H, d), 7.74 (1 H, d), 7.68 (1 H, dd), 6.97 (1 H, s), 6.70 (1 H, d), 3.84 (2 H, t), 3.43 (2 H, t), 2.35 (3 H, s), 2.20 (3 H, s). | 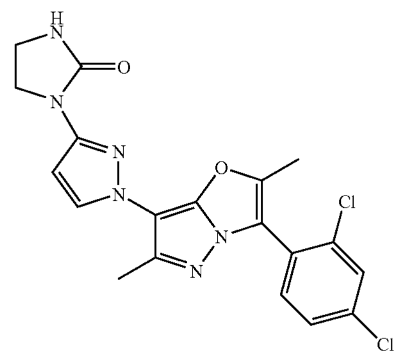 |
| 8.0 | 0.278 | (400MHz, CDCl3) δ 7.28 (1 H, d), 6.45 (1 H, s), 6.34 (1 H, d), 3.88 (4 H, t), 2.29-2.39 (8 H, m), 2.25 (3 H, s), 2.16 (3 H, s) | 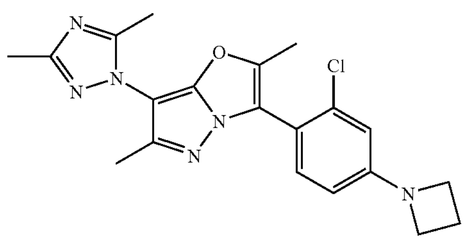 |
| 1.15 | 0.328 | (400 MHz, DMSO-d$_6$) δ 7.91 (1 H, d), 7.73 (1 H, d), 7.66 (1 H, dd), 7.35 (2 H, m), 7.28 (3 H, m), 4.71 (2 H, s), 3.42 (2 H, q), 2.76 (2 H, q), 2.32 (3 H, s), 1.13 (6 H, m). | 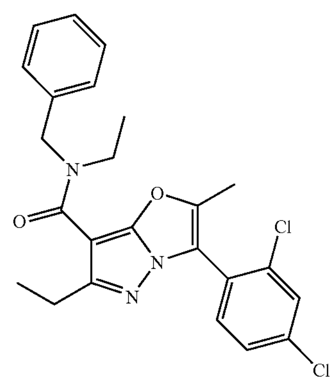 |
| 6.5 | 0.394 | (400 MHz, DMSO-d$_6$) δ 8.22 (1 H, d), 7.93 (2 H, m), 7.76 (2 H, m), 7.69 (1 H, m), 7.01 (1 H, d), 2.38 (3 H, s), 2.28 (3 H, s). | 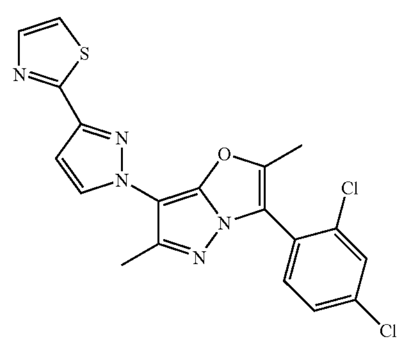 |

| Example | CRF-1 IC$_{50}$ (μM) | $^1$H NMR | Structure |
|---|---|---|---|
| 9.0 | 0.415 | (400 MHz, CDCl3) δ 2.25 (3 H, s), 2.37 (3 H, s), 2.42 (9 H, m), 6.50 (1 H, m), 7.45 (2 H, d), 7.65 (2 H, d), 7.75 (2 H, s), 7.98 (1 H, s) | 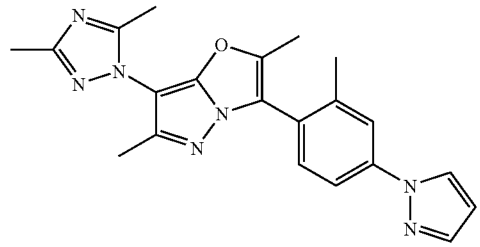 |
| 1.18 | 0.617 | (400 MHz, CDCl$_3$) δ 7.60 (1 H, d), 7.55 (q, 1 H), 7.42 (1 H, q), 3.65 (4 H, s), 2.50 (3 H, s), 2.38 (3 H, s), 1.7 (6 H, m). | 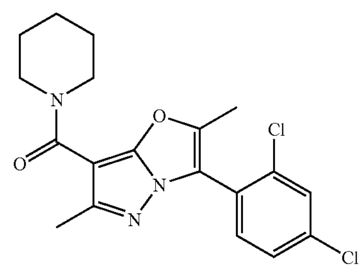 |
| 7.4 | 0.850 | (400 MHz, DMSO-d$_6$) δ 7.88 (1 H, d), 7.68 (1 H, d), 7.62 (1 H, dd), 7.46 (2 H, d), 7.35 (2 H, t), 7.25 (1 H, t), 5.71 (2 H, m), 2.25 (3 H, s), 2.20 (3 H, s). | 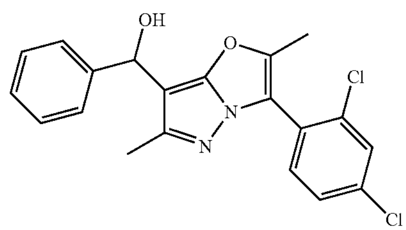 |
| 6.2 | 1.050 | (400 MHz, CDCl$_3$) δ 7.69 (1 H, dd), 7.60 (1 H, d), 7.54 (1 H, d), 7.43 (1 H, dd), 6.72 (1 H, d), 2.37 (3 H, s), 2.35 (3 H, s). | 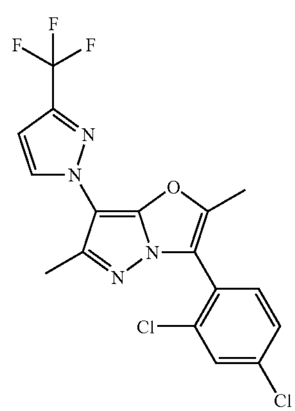 |
| 6.38 | 1.059 | (400 MHz, CDCl3) δ 7.7 (s, 1 H), 7.65 (d, 1 H), 7.55 (d, 1 H), 2.4 (s, 3 H), 2.4 (s, 3 H), 2.4 (s, 3 H), 2.35 (s, 3 H), 2.25 (s, 3 H) | 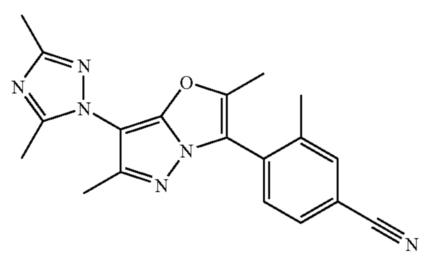 |

-continued

| Example | CRF-1 IC$_{50}$ (μM) | $^1$H NMR | Structure |
|---|---|---|---|
| 6.55 | 1.40 | (400 MHz, CDCl3) δ 7.5 (1 H, d), 7.2 (1 H, d), 2.6 (3 H, s), 2.5 (3 H, s), 2.45 (6 H, m), 2.35 (3 H, s), 2.25 (3 H, s). | 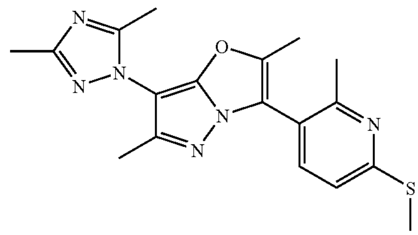 |
| 6.45 | 1.535 | (400 MHz, CDCl3) δ 2.27 (3 H, s), 2.40 (6 H, s), 2.47 (3 H, s), 3.78 (3 H, s) 7.5 (3 H, m), 7.7 (2 H, m) | 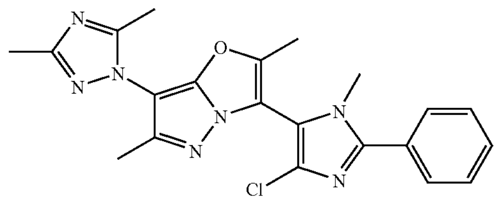 |
| 5.4 | 9.32 | (400 MHz, MeOD) δ 7.74 (1 H, d), 7.63 (2 H, m), 7.54 (1 H, dd), 3.98 (2 H, s), 2.68 (2 H, m), 2.56 (2 H, m), 2.39 (3 H, s), 1.69 (2 H, m), 1.05 (1 H, m), 0.96 (3 H, t), 0.64 (2 H, m), 0.27 (2 H, m). | 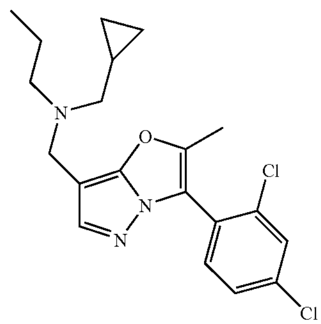 |

The invention claimed is:

1. A compound of formula I

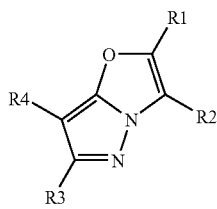

I in which R$^1$ and R$^3$, which may be the same or different, are each hydrogen, alkyl C1 to 6 or halo alkyl C1 to 6;

R$^2$ is phenyl, a 5- or 6-membered heteroaryl or a bicyclic heteroaryl system, each of which may optionally be substituted by one or more of alkyl C1 to 6, alkoxy C1 to 6, halo, haloalkyl C1 to 6, thioalkyl C1 to 6, —NR$^5$R$^6$, —CN, haloalkoxy C1 to 6, —O(CH$_2$)$_x$O(CH$_2$)$_y$—, aryl or -Het;

Het is a 5- or 6-membered heteroaryl or a 4, 5- or 6-membered heterocycle;

R$^4$ is alkylene C2 to 10, hydroxy alkyl C1 to 10, each of which may optionally be substituted by aryl, or is —OR$^7$, —(CH$_2$)$_m$NR$^8$R$^9$, —COR$^{10}$, a 5- or 6-membered heteroaryl or a 5- or 6-membered heterocycle, the 5- or 6-membered heteroaryl or 5- or 6-membered heterocycle being optionally substituted by one or more substituents selected from the group alkyl C1 to 10, haloalkyl C1 to 10, hydroxyalkyl C1 to 10, alkoxy(C1 to 3)alkyl(C1 to 3), halo, —CO$_2$R$^{19}$, —CONR$^{20}$R$^{21}$, aryl or a 5- or 6-membered heterocycle or heteroaryl;

R$^5$ and R$^6$, which may be the same or different, are each hydrogen or alkyl C1 to 6 or R$^5$ and R$^6$, together with the nitrogen to which they are attached, form an optionally substituted saturated or unsaturated cyclic group;

R$^7$ is alkyl C1 to 10, cycloalkyl C3 to 10, optionally fused to an aryl, alkyl(C1 to 6)-cycloalkyl(C3 to 6)-, hydroxy alkyl C1 to 10, hydroxyalkyl(C1 to 6)-(haloalkyl C1 to 6), alkyl(C1 to 6)-oxy-alkyl(C1 to 6), —(CH$_2$)$_q$COOR$^{22}$ or a 5- or 6-membered heterocycle; each of which is optionally substituted by one or more of alkyl C1 to 10, alkoxy C1 to 10, hydroxyalkyl C1 to 10, aryl or a 5- or 6-membered heteroaryl, the aryl or a 5- or 6-membered heteroaryl being optionally substituted by alkyl C1 to 10;

R$^8$ and R$^9$, which may be the same or different, are each hydrogen, alkyl C1 to 10, halo alkyl C1 to 10, alkyl(C1 to 6)-oxy-alkyl(C1 to 6), —COOR$^{11}$, —COR$^{12}$ or arylalkyl C1 to 6 or together with the nitrogen to which they are attached R$^8$ and R$^9$ form a 5- or 6-membered heterocycle, optionally substituted by one or more of alkyl C1 to 6;

m is an integer 0 or 1;

q is an integer from 1 to 6;

x and y, which may be the same or different, are each an integer from 1 to 6;

$R^{10}$ is hydrogen, alkyl C1 to 6, —$NR^{13}R^{14}$, hydroxy or alkoxy C1 to 6;

$R^{12}$ is alkyl C1 to 10, aryl or is a 5- or 6-membered unsaturated heterocyclic ring;

$R^{13}$ and $R^{14}$, which may be the same or different, are each alkyl C1 to 10, cycloalkyl C3 to 10, cycloalkyl(C3 to 6)alkyl(C1 to 6)-, alkoxy C1 to 10, haloalkyl C1 to 10, aryl, a 5- or 6-membered heterocycle or heteroaryl comprising 1, 2 or 3 heteroatoms; each of which may be optionally substituted by aryl or heteroaryl, or $R^{13}$ and $R^{14}$ together with the nitrogen to which they are attached form a 5- or 6-membered heterocycle comprising 1, 2 or 3 heteroatoms, which may optionally be fused to a phenyl group, said heterocycle and optionally fused phenyl group being optionally substituted by one or more of alkoxy C1 to 10;

$R^{22}$ is hydrogen or alkyl C1 to 6;

$R^{11}$ is alkyl C1 to 6 or aryl;

$R^{19}$ is hydrogen or alkyl C1 to 10;

$R^{20}$ and $R^{21}$, which may be the same or different, are each alkyl C1 to 10; and and diasteromers and enantiomers thereof, in free form or as a pharmaceutically acceptable salt.

2. A compound according to claim 1 wherein the compound is of formula II

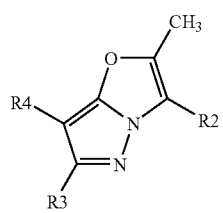

and diasteromers and enantiomers thereof;

in free form or as a pharmaceutically acceptable salt.

3. A compound according to claim 1 wherein the compound is of formula III

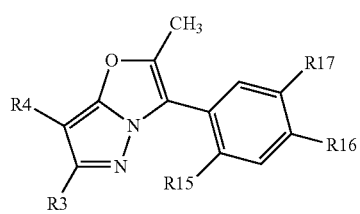

$R^{15}$ and $R^{16}$, which may be the same or different, are each alkyl C1 to 6, alkoxy C1 to 6, halo, haloalkyl C1 to 6, haloalkoxy C1 to 6 or —$NR^5R^6$; and $R^{17}$ is hydrogen, alkyl C1 to 6, alkoxy C1 to 6, halo, haloalkyl C1 to 6, haloalkoxy C1 to 6 or —$NR^5R^6$;

and diasteromers and enantiomers thereof;

in free form or as a pharmaceutically acceptable salt.

4. A compound according to claim 1 wherein the compound is of formula IV

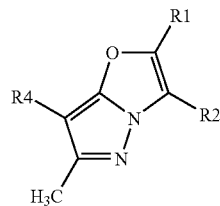

and diasteromers and enantiomers thereof;

in free form or as a pharmaceutically acceptable salt.

5. A compound according to claim 1 wherein the compound is of formula V

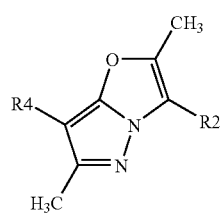

and diasteromers and enantiomers thereof;

in free form or as a pharmaceutically acceptable salt.

6. A compound of formula I according to claim 1

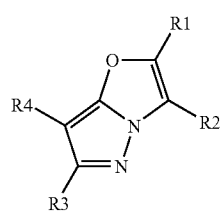

in which $R^4$ is a 5- or 6-membered heteroaryl being optionally substituted by one or more substituents selected from the group alkyl C1 to 10, haloalkyl C1 to 10, hydroxyalkyl C1 to 10, alkoxy(C1 to 3)alkyl(C1 to 3), —$CO_2R^{19}$, —$CONR^{20}R^{21}$, or a 5- or 6-membered heterocycle or heteroaryl;

and diasteromers and enantiomers thereof;

in free form or as a pharmaceutically acceptable salt.

7. A compound of formula I according to claim 1

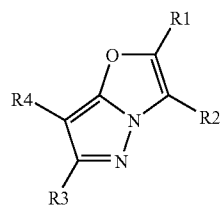

in which $R^4$ is a triazole being optionally substituted by one or more substituents selected from the group alkyl C1 to 10, haloalkyl C1 to 10, hydroxyalkyl C1 to 10, alkoxy (C1 to 3)alkyl(C1 to 3), —$CO_2R^{19}$, —$CONR^{20}R^{21}$, or a 5- or 6-membered heterocycle or heteroaryl;

and diasteromers and enantiomers thereof;
in free form or as a pharmaceutically acceptable salt.

8. A compound according to claim 1 which is selected from the group consisting of:

3-(2,4-Dichloro-phenyl)-6-ethyl-2-methyl-pyrazolo[5,1-b]oxazole-7-carboxylic acid cyclopropyl methyl-propyl-amide;
3-(2,4-Dichloro-phenyl)-2,6-dimethyl-pyrazolo[5,1-b]oxazole-7-carboxylic acid cyclopropyl methyl-propyl-amide;
3-(2,4-Dichloro-phenyl)-2,6-dimethyl-pyrazolo[5,1-b]oxazole-7-carboxylic acid diethylamide;
3-(2,4-Dichloro-phenyl)-2,6-dimethyl-pyrazolo[5,1-b]oxazole-7-carboxylic acid dipropylamide;
3-(2,4-Dimethyl-phenyl)-2,6-dimethyl-pyrazolo[5,1-b]oxazole-7-carboxylic acid dipropylamide;
3-(2,4-Dichloro-phenyl)-2,6-dimethyl-pyrazolo[5,1-b]oxazole-7-carboxylic acid propyl-(tetrahydro-pyran-4-yl)-amide;
3-(2,4-Dimethyl-phenyl)-6-methyl-pyrazolo[5,1-b]oxazole-7-carboxylic acid cyclopropyl methyl-propyl-amide;
3-(2,4-Dimethyl-phenyl)-2,6-dimethyl-pyrazolo[5,1-b]oxazole-7-carboxylic acid cyclopropyl methyl-propyl-amide;
3-(2,4-Dichloro-phenyl)-6-methyl-pyrazolo[5,1-b]oxazole-7-carboxylic acid dipropyl amide;
6-Methyl-3-(2,4,6-trimethyl-phenyl)-pyrazolo[5,1-b]oxazole-7-carboxylic acid dipropyl amide;
[3-(2,4-Dichloro-phenyl)-6-ethyl-2-methyl-pyrazolo|5,1-b]oxazol-7-yl]-pyrrolidin-1-yl-methanone;
3-(2,4-Dichloro-phenyl)-6-ethyl-2-methyl-pyrazolo[5,1-b]oxazole-7-carboxylic acid benzyl-methyl-amide;
[3-(2,4-Dichloro-phenyl)-6-ethyl-2-methyl-pyrazolo|5,1-b]oxazol-7-yl]-piperidin-1-yl-methanone;
3-(2,4-Dichloro-phenyl)-2,6-dimethyl-pyrazolo[5,1-b]oxazole-7-carboxylic acid cyclopropyl -(tetrahydro-pyran-4-yl)-amide;
[3-(2,4-Dichloro-phenyl)-6-ethyl-2-methyl-pyrazolo|5,1-b]oxazol-7-yl]-morpholin-4-yl-methanone;
3-(2,4-Dichloro-phenyl)-6-ethyl-2-methyl-pyrazolo[5,1-b]oxazole-7-carboxylic acid benzyl-ethyl-amide;
3-(2,4-Dichloro-phenyl)-6-ethyl-2-methyl-pyrazolo[5,1-b]oxazole-7-carboxylic acid ethyl-phenyl-amide;
3-(2,4-Dichloro-phenyl)-2,6-dimethyl-pyrazolo[5,1-b]oxazole-7-carboxylic acid benzyl-ethyl-amide;
[3-(2,4-Dichloro-phenyl)-2,6-dimethyl-pyrazolo[5,1-b]oxazol-7-yl]-piperidin-1-yl-methanone;
3-(2,4-Dichloro-phenyl)-2,6-dimethyl-pyrazolo[5,1-b]oxazole-7-carboxylic acid phenyl-propyl-amide;
[3-(2,4-Dichloro-phenyl)-2,6-dimethyl-pyrazolo[5,1-b]oxazol-7-yl]-(6,7-dimethoxy-3,4-dihydro-1H-isoquinolin-2-yl)-methanone;
[3-(2,4-Dichloro-phenyl)-2,6-dimethyl-pyrazolo[5,1-b]oxazol-7-yl]-(3,4-dihydro-1H-isoquinolin -2-yl)-methanone;
[3-(2,4-Dichloro-phenyl)-2,6-dimethyl-pyrazolo[5,1-b]oxazol-7-yl]-(3,4-dihydro-2H-quinolin-1-yl)-methanone;
3-(2,4-Dichloro-phenyl)-2,6-dimethyl-pyrazolo[5,1-b]oxazol-7-yl]-(2,3-dihydro-indol-1-yl)-methanone;
3-(2,4-Dichloro-phenyl)-2,6-dimethyl-pyrazolo[5,1-b]oxazole-7-carboxylic acid benzyl-(2,2,2-trifluoro-ethyl)-amide;
(±)-3-(2,4-Dichloro-phenyl)-2,6-dimethyl-7-(1-phenyl-propoxy)-pyrazolo[5,1-b]oxazole;
3-(2,4-Dichloro-phenyl)-7-(1-ethyl-propoxy)-2,6-dimethyl-pyrazolo[5,1-b]oxazole;
3-(2,4-Dichloro-phenyl)-7-(1-methoxymethyl-butoxy)-2,6-dimethyl-pyrazolo[5,1-b]oxazole;
7-Benzyloxy-3-(2,4-dichloro-phenyl)-2,6-dimethyl-pyrazolo[5,1-b]oxazole;
3-(2,4-Dichloro-phenyl)-2,6-dimethyl-7-(1-propyl-butoxy)-pyrazolo[5,1-b]oxazole;
7-Cyclopentyloxy-3-(2,4-dichloro-phenyl)-2,6-dimethyl-pyrazolo[5,1-b]oxazole;
3-(2,4-Dichloro-phenyl)-7-(furan-2-ylmethoxy)-2,6-dimethyl-pyrazolo[5,1-b]oxazole;
3-(2,4-Dichloro-phenyl)-2,6-dimethyl-7-(tetrahydro-furan-3-yloxy)-pyrazolo[5,1-b]oxazole;
3-(2,4-Dichloro-phenyl)-2,6-dimethyl-7-(3-methyl-cyclopentyloxy)-pyrazolo[5,1-b]oxazole;
7-Cyclohexyloxy-3-(2,4-dichloro-phenyl)-2,6-dimethyl-pyrazolo[5,1-b]oxazole;
3-(2,4-Dichloro-phenyl)-2,6-dimethyl-7-(thiazol-4-ylmethoxy)-pyrazolo[5,1-b]oxazole;
3-(2,4-Dichloro-phenyl)-2,6-dimethyl-7-(thiophen-3-ylmethoxy)-pyrazolo[5,1-b]oxazole;
(±)-2-[3-(2,4-Dichloro-phenyl)-2,6-dimethyl-pyrazolo[5,1-b]oxazol-7-yloxy]-2-phenyl-ethanol;
3-(2,4-Dichloro-phenyl)-2,6-dimethyl-7-((R)-1-phenyl-ethoxy)-pyrazolo[5,1-b]oxazole;
3-(2,4-Dichloro-phenyl)-2,6-dimethyl-7-((S)-1-phenyl-ethoxy)-pyrazolo[5,1-b]oxazole;
3-(2,4-Dichloro-phenyl)-2,6-dimethyl-7-(2-methyl-benzyloxy)-pyrazolo[5,1-b]oxazole;
3-(2,4-Dichloro-phenyl)-2,6-dimethyl-7-(pyridin-2-ylmethoxy)-pyrazolo[5,1-b]oxazole;
3-(2,4-Dichloro-phenyl)-2,6-dimethyl-7-(pyridin-3-ylmethoxy)-pyrazolo[5,1-b]oxazole;
3-(2,4-Dichloro-phenyl)-7-(indan-1-yloxy)-2,6-dimethyl-pyrazolo[5,1-b]oxazole;
3-(2,4-Dichloro-phenyl)-2,6-dimethyl-7-(3-methyl-benzyloxy)-pyrazolo[5,1-b]oxazole;
3-(2,4-Dichloro-phenyl)-2,6-dimethyl-7-(pyridin-4-ylmethoxy)-pyrazolo[5,1-b]oxazole;
3-(2,4-Dichloro-phenyl)-2,6-dimethyl-7-(4-methyl-benzyloxy)-pyrazolo[5,1-b]oxazole;
(±)-3-(2,4-Dichloro-phenyl)-7-(1,2-dimethyl-propoxy)-2,6-dimethyl-pyrazolo[5,1-b]oxazole;
7-((S)-sec-Butoxy)-3-(2,4-dichloro-phenyl)-2,6-dimethyl-pyrazolo[5,1-b]oxazole;
3-(2,4-Dichloro-phenyl)-7-(furan-3-ylmethoxy)-2,6-dimethyl-pyrazolo[5,1-b]oxazole;
7-((R)-sec-Butoxy)-3-(2,4-dichloro-phenyl)-2,6-dimethyl-pyrazolo[5,1-b]oxazole;
7-Benzyloxy-3-(2,4-dichloro-phenyl)-6-ethyl-2-methyl-pyrazolo[5,1-b]oxazole;
7-(4-Chloro-benzyloxy)-3-(2,4-dichloro-phenyl)-2,6-dimethyl-pyrazolo[5,1-b]oxazole;
(±)-3-(2,4-Dichloro-phenyl)-2,6-dimethyl-7-(2-methyl-cyclopentyloxy)-pyrazolo[5,1-b]oxazole;
(±)-[3-(2,4Dichloro-phenyl)-2,6-dimethyl-pyrazolo[5,1-b]oxazol-7-yloxy]-phenyl-acetic acid methyl ester;
3-(2,4-Dichloro-phenyl)-2,6-dimethyl-7-(1-methyl-1H-pyrazol-3-ylmethoxy)-pyrazolo [5,1-b]oxazole;
(±)-3-(2,4-Dichloro-phenyl)-7-(2-methoxy-1-methyl-ethoxy)-2,6-dimethyl-pyrazolo[5,1-b]oxazole;
2-[3-(2,4-Dichloro-phenyl)-2,6-dimethyl-pyrazolo[5,1-b]oxazol-7-yloxy]-2-phenyl-ethanol (Enantiomer 1);
2-[3-(2,4-Dichloro-phenyl)-2,6-dimethyl-pyrazolo[5,1-b]oxazol-7-yloxy]-2-phenyl-ethanol (Enantiomer 2);

2-[3-(2,4-Dichloro-phenyl)-2,6-dimethyl-pyrazolo[5,1-b]oxazol-7-yloxy]-3,3,3-trifluoro-propan-1-ol;
[3-(2,4-Dichloro-phenyl)-2,6-dimethyl-pyrazolo[5,1-b]oxazol-7-yl]-dipropyl-amine hydrochloride;
[3-(2,4-Dichloro-phenyl)-2,6-dimethyl-pyrazolo[5,1-b]oxazol-7-yl]-(1-propyl-butyl)-amine;
[3-(2,4-Dimethyl-phenyl)-2,6-dimethyl-pyrazolo[5,1-b]oxazol-7-yl]-(1-propyl-butyl)-amine;
[3-(2,4-Dichloro-phenyl)-2-ethyl-6-methyl-pyrazolo[5,1-b]oxazol-7-yl]-dipropyl-amine;
[3-(2,4-Bis-trifluoromethyl-phenyl)-2,6-dimethyl-pyrazolo[5,1-b]oxazol-7-yl]-dipropyl-amine;
[3-(2,4-Dichloro-phenyl)-6-isopropyl-2-methyl-pyrazolo[5,1-b]oxazol-7-yl]-dipropyl-amine;
[3-(2,4-Dichloro-phenyl)-2-methyl-6-trifluoromethyl-pyrazolo[5,1-b]oxazol-7-yl]-dipropyl-amine;
N-[3-(2,4-Dichloro-phenyl)-2,6-dimethyl-pyrazolo[5,1-b]oxazol-7-yl]-N-propyl-propionamide;
N-[3-(2,4-Dichloro-phenyl)-2,6-dimethyl-pyrazolo[5,1-b]oxazol-7-yl]-propionamide;
N-[3-(2,4-Dichloro-phenyl)-2,6-dimethyl-pyrazolo[5,1-b]oxazol-7-yl]-N-ethyl-propionamide;
N-[3-(2,4-Dichloro-phenyl)-2-ethyl-6-methyl-pyrazolo[5,1-b]oxazol-7-yl]-propionamide;
N-[3-(2,4-Dichloro-phenyl)-2,6-dimethyl-pyrazolo[5,1-b]oxazol-7-yl]-N-(2,2,2-trifluoro-ethyl)-propionamide;
Ethyl 3-(2,4-dichlorophenyl)-2,6-dimethylpyrazolo[5,1-b]oxazol-7-yl(propyl)carbamate;
N-(3-(2,4-dichlorophenyl)-2,6-dimethylpyrazolo[5,1-b]oxazol-7-yl)-N-propylacetamide;
N-(3-(2,4-dichlorophenyl)-2,6-dimethylpyrazolo[5,1-b]oxazol-7-yl)-N-propyliso butyramide;
N-[3-(2,4-Dichloro-phenyl)-2-ethyl-6-methyl-pyrazolo[5,1-b]oxazol-7-yl]-N-ethyl-propionamide;
N-(3-(2,4-dichlorophenyl)-2,6-dimethylpyrazolo[5,1-b]oxazol-7-yl)-N-propyl benzamide;
N-[3-(2,4-Dichloro-phenyl)-2-ethyl-6-methyl-pyrazolo[5,1-b]oxazol-7-yl]-N-(2,2,2-trifluoro-ethyl)-propionamide;
N-(3-(2,4-dichlorophenyl)-6-ethyl-2-methylpyrazolo[5,1-b]oxazol-7-yl)-N-propyl propionamide;
N-(3-(2,4-dichlorophenyl)-6-ethyl-2-methylpyrazolo[5,1-b]oxazol-7-yl)-N-ethyl propionamide;
N-(3-(2,4-dichlorophenyl)-6-ethyl-2-methylpyrazolo[5,1-b]oxazol-7-yl)-N-(2,2,2-trifluoroethyl) propionamide;
[3-(2,4-Dichloro-phenyl)-2-ethyl-6-methyl-pyrazolo[5,1-b]oxazol-7-ylmethyl]-dipropyl-amine;
[3-(2,4-Dimethyl-phenyl)-2,6-dimethyl-pyrazolo[5,1-b]oxazol-7-ylmethyl]-dipropyl-amine;
Bis-cyclopropylmethyl-[3-(2,4-dimethyl-phenyl)-2,6-dimethyl-pyrazolo[5,1-b]oxazol-7-yl methyl]-amine;
Cyclopropylmethyl-[3-(2,4-dichloro-phenyl)-2-methyl-pyrazolo[5,1-b]oxazol-7-yl methyl]-propyl-amine;
Cyclopropylmethyl-[3-(2,4-dimethyl-phenyl)-6-methyl-pyrazolo[5,1-b]oxazol-7-ylmethyl]-propyl-amine;
Cyclopropylmethyl-[3-(2,4-dimethyl-phenyl)-2,6-dimethyl-pyrazolo[5,1-b]oxazol-7-ylmethyl]-propyl-amine;
Cyclopropylmethyl-[3-(4-methoxy-2-methyl-phenyl)-2,6-dimethyl-pyrazolo[5,1-b]oxazol-7-ylmethyl]-propyl-amine;
[3-(2,4-Dichloro-phenyl)-2,6-dimethyl-pyrazolo[5,1-b]oxazol-7-ylmethyl]-dipropyl-amine;
[6-Methyl-3-(2,4,6-trimethyl-phenyl)-pyrazolo[5,1-b]oxazol-7-ylmethyl]-dipropyl-amine;
Cyclopropylmethyl-[3-(2,4-dichloro-phenyl)-2,6-dimethyl-pyrazolo[5,1-b]oxazol-7-ylmethyl]-propyl-amine;
Cyclobutylmethyl-[3-(2,4-dichloro-phenyl)-2,6-dimethyl-pyrazolo[5,1-b]oxazol-7-ylmethyl]-ethyl-amine;
Cyclobutylmethyl-[3-(2,4-dichloro-phenyl)-2,6-dimethyl-pyrazolo[5,1-b]oxazol-7-ylmethyl]-propyl-amine;
[3-(2,4-Dichloro-phenyl)-2,6-dimethyl-pyrazolo[5,1-b]oxazol-7-ylmethyl]-ethyl-(3,3,3-trifluoro-propyl)-amine;
[3-(2,4-Dichloro-phenyl)-2,6-dimethyl-pyrazolo[5,1-b]oxazol-7-ylmethyl]-propyl-(3,3,3-trifluoro-propyl)-amine;
Cyclopropylmethyl-[3-(2,4-dichloro-phenyl)-2,6-dimethyl-pyrazolo[5,1-b]oxazol-7-ylmethyl]-(2-methoxy-ethyl)-amine;
[2,6-Dimethyl-3-(2,4,6-trimethyl-phenyl)-pyrazolo[5,1-b]oxazol-7-ylmethyl]-dipropyl-amine;
Cyclopropylmethyl-[2,6-dimethyl-3-(2,4,6-trimethyl-phenyl)-pyrazolo[5,1-b]oxazol-7-ylmethyl]-propyl-amine;
Cyclopropylmethyl-[3-(2,4-dichloro-phenyl)-2-ethyl-6-methyl-pyrazolo[5,1-b]oxazol-7-yl methyl]-propyl-amine;
(±)-7-(2-Ethyl-piperidin-1-ylmethyl)-2,6-dimethyl-3-(2,4,6-trimethyl-phenyl)-pyrazolo[5,1-b]oxazole;
2,6-Dimethyl-7-piperidin-1-ylmethyl-3-(2,4,6-trimethyl-phenyl)-pyrazolo[5,1-b]oxazole;
[3-(2-Chloro-4-methoxy-phenyl)-2,6-dimethyl-pyrazolo[5,1-b]oxazol-7-ylmethyl]-cyclopropyl methyl-propyl-amine;
[3-(4-Chloro-2-methyl-phenyl)-2,6-dimethyl-pyrazolo[5,1-b]oxazol-7-ylmethyl]-dipropyl-amine;
[3-(4-Chloro-2-methyl-phenyl)-2,6-dimethyl-pyrazolo[5,1-b]oxazol-7-ylmethyl]-cyclopropyl methyl-propyl-amine;
[3-(2-Chloro-4-methoxy-phenyl)-2,6-dimethyl-pyrazolo[5,1-b]oxazol-7-ylmethyl]-dipropyl-amine;
[3-(2-Chloro-4-methoxy-phenyl)-2,6-dimethyl-pyrazolo[5,1-b]oxazol-7-ylmethyl]-cyclopropyl methyl-propyl-amine;
[3-(2,4-Dichloro-phenyl)-6-ethyl-2-methyl-pyrazolo[5,1-b]oxazol-7-ylmethyl]-dipropyl-amine;
Cyclopropylmethyl-[3-(2,4-dichloro-phenyl)-6-ethyl-2-methyl-pyrazolo[5,1-b]oxazol-7-yl methyl]-propyl-amine;
[3-(2,4-Bis-trifluoromethyl-phenyl)-2,6-dimethyl-pyrazolo[5,1-b]oxazol-7-ylmethyl]-cyclo propylmethyl-propyl-amine;
[3-(6-Chloro-4-methyl-pyridin-3-yl)-2,6-dimethyl-pyrazolo[5,1-b]oxazol-7-ylmethyl]-cyclo propylmethyl-propyl-amine;
4-Chloro-5-{7-[(cyclopropylmethyl-propyl-amino)-methyl]-2,6-dimethyl-pyrazolo[5,1-b]oxazol-3-yl}-pyridin-2-yl)-dimethyl-amine;
Cyclopropylmethyl-[3-(2,4-dimethoxy-phenyl)-6-ethyl-2-methyl-pyrazolo[5,1-b]oxazol-7-yl methyl]-propyl-amine;
Cyclopropylmethyl-[3-(6-methoxy-4-methyl-pyridin-3-yl)-2,6-dimethyl-pyrazolo[5,1-b]oxazol-7-ylmethyl]-propyl-amine;
Cyclopropylmethyl-[3-(6-methoxy-2-methyl-pyridin-3-yl)-2,6-dimethyl-pyrazolo[5,1-b]oxazol-7-ylmethyl]-propyl-amine;
[3-(2,4-Dichloro-phenyl)-2,6-dimethyl-pyrazolo[5,1-b]oxazol-7-ylmethyl]-diethyl-amine;

Cyclopropylmethyl-[3-(2,4-dichloro-phenyl)-2-isopropyl-6-methyl-pyrazolo[5,1-b]oxazol-7-yl methyl]-propyl-amine;

[6-Cyclopropyl-3-(2,4-dichloro-phenyl)-2-methyl-pyrazolo[5,1-b]oxazol-7-ylmethyl]-cyclo propylmethyl-propyl-amine;

Cyclopropylmethyl-[3-(2,4-dimethoxy-phenyl)-2,6-dimethyl-pyrazolo[5,1-b]oxazol-7-ylmethyl]-propyl-amine;

Cyclopropylmethyl-[3-(2,4-dichloro-phenyl)-6-methyl-2-propyl-pyrazolo[5,1-b]oxazol-7-yl methyl]-propyl-amine;

Cyclopropylmethyl-[3-(2,4-dichloro-phenyl)-2,6-dimethyl-pyrazolo[5,1-b]oxazol-7-ylmethyl]-propyl-amine;

[3-(2,4-Dichloro-phenyl)-6-methyl-pyrazolo[5,1-b]oxazol-7-ylmethy]-dipropyl-amine;

Cyclopropylmethyl-[3-(2,4-dichloro-phenyl)-2-methyl-6-propyl-pyrazolo[5,1-b]oxazol-7-yl methyl]-propyl-amine;

[2-Butyl-3-(2,4-dichloro-phenyl)-6-methyl-pyrazolo|5,1-b]oxazol-7-ylmethyl]-cyclopropyl methyl-propyl-amine;

3-(6-Chloro-2-methyl-pyridin-3-yl)-2,6-dimethyl-pyrazolo[5,1-b]oxazol-7-ylmethyl]-cyclo propylmethyl-propyl-amine;

(5-{7-[(Cyclopropyl methyl-propyl-amino)-methyl]-2,6-dimethyl-pyrazolo[5,1-b]oxazol-3-yl}-6-methyl-pyridin-2-yl)-dimethyl-amine;

3-(2-Chloro-phenyl)-2,6-dimethyl-pyrazolo[5,1-b]oxazol-7-ylmethyl]-cyclopropyl methyl-propyl-amine;

[3-(4-Chloro-phenyl)-2,6-dimethyl-pyrazolo [5,1-b]oxazol-7-ylmethy]-cyclopropyl methyl -propyl-amine;

3-(2,4-Dichloro-phenyl)-7-(3,5-dimethyl-pyrazol-1-yl)-2,6-dimethyl-pyrazolo[5,1-b]oxazole;

3-(2,4-Dichloro-phenyl)-7-(3-trifluoromethyl-pyrazol-1-yl)-2,6-dimethyl-pyrazolo[5,1-b]oxazole;

3-(2,4-Dichloro-phenyl)-7-(3,5-dimethyl-pyrazol-1-yl)-6-ethyl-2-methyl-pyrazolo[5,1-b]oxazole;

3-(2,4-Dichloro-phenyl)-2,6-dimethyl-7-(3-methyl-5-trifluoromethyl-pyrazol-1-yl)-pyrazolo[5,1-b]oxazole;

3-(2,4-Dichloro-phenyl)-2,6-dimethyl-7-(3-thiazol-2-yl-pyrazol-1-yl)-pyrazolo[5,1-b]oxazole;

1-{1-[3(2,4-Dichloro-phenyl)-2,6-dimethyl-pyrazolo[5,1-b]oxazol-7-yl]-1H-pyrazol-3-yl}-imidazolidin-2-one;

3-(2,4-Dichloro-phenyl)-2,6-dimethyl-7-(5-methyl-3-trifluoromethyl-pyrazol-1-yl)-pyrazolo[5,1-b]oxazole;

3-(2,4-Dichloro-phenyl)-7-(3,5-dimethyl-[1,2,4]triazol-1-yl)-2,6-dimethyl-pyrazolo[5,1-b]oxazole;

1-{1-[3-(2,4-Dichloro-phenyl)-2,6-dimethyl-pyrazolo[5,1-b]oxazol-7-yl]-5-methyl-1H-pyrazol-3-yl}-imidazolidin-2-one;

3-(2,4-Dichloro-phenyl)-7-(2,4-dimethyl-imidazol-1-yl)-2,6-dimethyl-pyrazolo[5,1-b]oxazole;

3-(2-Chloro-4-methoxy-phenyl)-7-(3,5-dimethyl-[1,2,4]triazol-1-yl)-2,6-dimethyl-pyrazolo[5,1-b]oxazole;

7-(3,5-Dimethyl-[1,2,4]triazol-1-yl)-3-(4-methoxy-2-methyl-phenyl)-2,6-dimethyl-pyrazolo[5,1-b]oxazole;

3-(2,4-Dichloro-phenyl)-7-(3,5-dimethyl-[1,2,4]triazol-1-yl)-2-ethyl-6-methyl-pyrazolo[5,1-b]oxazole;

2-[3-(2,4-Dichloro-phenyl)-2,6-dimethyl-pyrazolo[5,1-b]oxazol-7-yl]-5-methyl-2H-pyrazole-3-carboxylic acid ethyl ester;

1[3-(2,4-Dichloro-phenyl)-2,6-dimethyl-pyrazolo[5,1-b]oxazol-7-yl]-5-methyl-1H-pyrazole-3-carboxylic acid ethyl ester;

3-(2,4-Dichloro-phenyl)-7-(3,5-dimethyl-[1,2,4]triazol-1-yl)-6-ethyl-2-methyl-pyrazolo[5,1-b]oxazole;

1-{1-[6-Ethyl-3-(4-methoxy-2-methyl-phenyl)-2-methyl-pyrazolo[5,1-b]oxazol-7-yl]-1H-pyrazol -3-yl}-imidazolidin-2-one;

{1-[3-(2-Chloro-4-methoxy-phenyl)-6-ethyl-2-methyl-pyrazolo[5,1-b]oxazol-7-yl]-1H-pyrazol-3-yl}-imidazolidin-2-one;

1-{1[3-(4-Chloro-2-methyl-phenyl)-6-ethyl-2-methyl-pyrazolo[5,1-b]oxazol-7-yl]-1H-pyrazol-3-yl}-imidazolidin-2-one;

3-(2-Chloro-4-methoxy-phenyl)-6-ethyl-2-methyl-7-(5-methyl-3-trifluoromethyl-pyrazol-1-yl) -pyrazolo[5,1-b]oxazole;

3-(4-Chloro-2-methyl-phenyl)-6-ethyl-2-methyl-7-(5-methyl-3-trifluoromethyl-pyrazol-1-yl) -pyrazolo[5,1-b]oxazole;

3-(2-Chloro-4-methoxy-phenyl)-6-ethyl-2-methyl-7-(5-methyl-3-trifluoromethyl-pyrazol-1-yl) -pyrazolo[5,1-b]oxazole;

2-[3-(2,4-Dichloro-phenyl)-2,6-dimethyl-pyrazolo[5,1-b]oxazol-7-yl]-5-methyl-2H-pyrazole-3-carboxylic acid;

{2-[3-(2,4-Dichloro-phenyl)-2,6-dimethyl-pyrazolo[5,1-b]oxazol-7-yl]-5-methyl-2H-pyrazol-3-yl}-methanol;

{1-[3-(2,4-Dichloro-phenyl)-2,6-dimethyl-pyrazolo[5,1-b]oxazol-7-yl]-5-methyl-1H-pyrazol-3-yl}-methanol;

2[3-(2,4-Dichloro-phenyl)-2,6-dimethyl-pyrazolo[5,1-b]oxazol-7-yl]-5-methyl-2H-pyrazole-3-carboxylic acid dimethylamide;

1-{1-[3(2,4-Dichloro-phenyl)-6-ethyl-2-methyl-pyrazolo[5,1-b]oxazol-7-yl]-1H-pyrazol-3-yl}-imidazolidin-2-one;

3-(2,4-dichlorophenyl)-2-ethyl-6-methyl-7-(5-methyl -3-(trifluoromethyl)-1H-1,2,4-triazol-1-yl)pyrazolo[5,1-b]oxazole;

3-(4-methoxy-2-methylphenyl)-2,6-dimethyl-7-(5-methyl-3-(trifluoromethyl)-1H-1,2,4-triazol-1-yl)pyrazolo[5,1-b]oxazole;

3-(2,4-dichlorophenyl)-2,6-dimethyl-7-(5-methyl-3-(trifluoromethyl)-1H-1,2,4-triazol-1-yl) pyrazolo[5,1-b]oxazole;

3-(2-Chloro-4-methoxyphenyl)-2,6-dimethyl-7-(5-methyl-3-(trifluoromethyl)-1H-1,2,4-triazol-1-yl)pyrazolo[5,1-b]oxazole;

3-(2,4-Dimethoxy-phenyl)-7-(3,5-dimethyl-[1,2,4]triazol-1-yl)-2,6-dimethyl-pyrazolo[5,1-b]oxazole;

7-(3,5-Dimethyl-1H-1,2,4-triazol-1-yl)-2-ethyl-3-(4-methoxy-2-methylphenyl)-6-methyl pyrazolo[5,1-b]oxazole;

7-(3,5-Dimethyl-[1,2,4]triazol-1-yl)-3-[4-methoxy-2-(2-methoxy-ethoxy)-phenyl]-2,6-dimethyl -pyrazolo[5,1-b]oxazole;

2-Ethyl-3-(4-methoxy-2-methylphenyl)-6-methyl-7-(5-methyl-3-(trifluoromethyl)-1H-1,2,4-triazol-1-yl)pyrazolo[5,1-b]oxazole;

3-(2-Chloro-4-(1H-1,2,4-triazol-1-yl)phenyl)-7-(3,5-dimethyl-1H-1,2,4-triazol-1-yl)-2-ethyl-6-methylpyrazolo[5,1-b]oxazole;

7-(3,5-Dimethyl-[1,2,4]triazol-1-yl)-3-(4-methoxy-2,5-dimethyl-phenyl)-2,6-dimethyl-pyrazolo [5,1-b]oxazole;

4-(7-(3,5-Dimethyl-1H-1,2,4-triazol-1-yl)-2,6-dimethylpyrazolo[5,1-b]oxazol-3-yl)-3-methyl benzonitrile;

7-(3,5-Dimethyl-[1,2,4]triazol-1-yl)-3-(4-methoxy-2,3-dimethyl-phenyl)-2,6-dimethyl-pyrazolo [5,1-b]oxazole;

7-(3,5-Dimethyl-[1,2,4]triazol-1-yl)-2,6-dimethyl-3-(2-methyl-4-trifluoromethoxy-phenyl) -pyrazolo[5,1-b]oxazole;

3-(4-Bromo-2-methylphenyl)-7-(3,5-dimethyl-1H-1,2,4-triazol-1-yl)-2,6-dimethylpyrazolo[5,1-b]oxazole;

3-(4-Bromo-2-chlorophenyl)-7-(3,5-dimethyl-1H-1,2,4-triazol-1-yl)-2,6-dimethylpyrazolo[5,1-b]oxazole;

3-(2,6-Dimethoxy-pyridin-3-yl)-7-(3,5-dimethyl-[1,2,4]triazol-1-yl)-2,6-dimethyl-pyrazolo[5,1-b]oxazole;

7-(3,5-Dimethyl-[1,2,4]triazol-1-yl)-3-(4-methoxy-2,6-dimethyl-phenyl)-2,6-dimethyl -pyrazolo[5,1-b]oxazole;

3-(5-Chloro-3-methyl-2-phenyl-3H-imidazol-4-yl)-7-(3,5-dimethyl-[1,2,4]triazol-1-yl)-2,6-dimethyl-pyrazolo[5,1-b]oxazole;

7-(3,5-dimethyl-1H-1,2,4-triazol-1-yl)-3-(2-methoxy-4-methylphenyl)-2,6-dimethylpyrazolo[5,1-b]oxazole;

7-(3,5-dimethyl-1H-1,2,4-triazol-1-yl)-2,6-dimethyl-3-(7-methyl-2,3-dihydrobenzo[b][1,4]dioxin -6-yl)pyrazolo[5,1-b]oxazole;

7-(3,5-Dimethyl-[1,2,4]triazol-1-yl)-3-(2-methoxy-5-methyl-phenyl)-2,6-dimethyl-pyrazolo[5,1-b]oxazole;

7-(3,5-Dimethyl-[1,2,4]triazol-1-yl)-3-(6-methoxy-2-methyl-pyridin-3-yl)-2,6-dimethyl -pyrazolo[5,1-b]oxazole;

7-(3,5-Dimethyl-1H-1,2,4-triazol-1-yl)-3-(1,3-dimethyl-1H-indol-2-yl)-2,6-dimethyl pyrazolo[5,1-b]oxazole;

7-(3,5-Dimethyl-1H-1,2,4-triazol-1-yl)-3-(5-methoxy-2-methylphenyl)-2,6-dimethylpyrazolo[5,1-b]oxazole;

3-(4-Cyclobutoxy-2-methylphenyl)-7-(3,5-dimethyl-1H-1,2,4-triazol-1-yl)-2,6-dimethylpyrazolo [5,1-b]oxazole;

7-(3,5-Dimethyl-1H-1,2,4-triazol-1-yl)-3-(4-ethoxy-2-methylphenyl)-2,6-dimethylpyrazolo[5,1-b]oxazole;

3-(6-Chloro-2-methyl-pyridin-3-yl)-7-(3,5-dimethyl-[1,2,4]triazol-1-yl)-2,6-dimethyl -pyrazolo[5,1-b]oxazole;

7-(3,5-Dimethyl-[1,2,4]triazol-1-yl)-2,6-dimethyl-3-(2-methyl-6-methylsulfanyl-pyridin-3-yl) -pyrazolo[5,1-b]oxazole;

7-(3,5-Dimethyl-1H-1,2,4-triazol-1-yl)-2,6-dimethyl-3-(2-methyl-4-(methylthio)phenyl)pyrazolo [5,1-b]oxazole;

3-(2,3-Dihydrobenzofuran-5-yl)-7-(3,5-dimethyl-1H-1,2,4-triazol-1-yl)-2,6-dimethyl pyrazolo[5,1-b]oxazole;

3-(2,4-Dichloro-phenyl)-2,6-dimethyl-7-(1-methylene-butyl)-pyrazolo[5,1-b]oxazole;

4-[3-(2,4-Dichloro-phenyl)-2,6-dimethyl-pyrazolo[5,1-b]oxazol-7-yl]-heptan-4-ol;

1-[3-(2,4-Dichloro-phenyl)-2,6-dimethyl-pyrazolo[5,1-b]oxazol-7-yl]-ethanol;

[3-(2,4-Dichloro-phenyl)-2,6-dimethyl-pyrazolo[5,1-b]oxazol-7-yl]-phenyl-methanol;

7-((E)-But-1-enyl)-3-(2,4-dichloro-phenyl)-2,6-dimethyl-pyrazolo[5,1-b]oxazole;

3-(2,4-Dichloro-phenyl)-7-[1-eth-(Z)-ylidene-butyl]-2,6-dimethyl-pyrazolo[5,1-b]oxazole;

3-(2,4-Dichloro-phenyl)-2,6-dimethyl-7-(1-methylene-butyl)-pyrazolo[5,1-b]oxazole;

7-(3,5-Dimethyl-[1,2,4]triazol-1-yl)-2,6-dimethyl-3-(2-methyl-4-pyrazol-1-yl-phenyl)-pyrazolo [5,1-b]oxazole;

7-(3,5-Dimethyl-[1,2,4]triazol-1-yl)-2,6-dimethyl-3-(2-methyl-4-trideuteriomethoxy-phenyl) -pyrazolo[5,1-b]oxazole;

3-(4-(1H-imidazol-1-yl)-2-methylphenyl)-7-(3,5-dimethyl-1H-1,2,4-triazol-1-yl)-2,6-dimethyl pyrazolo[5,1-b]oxazole; and 3-(Benzofuran-5-yl)-7-(3,5-dimethyl-1H-1,2,4-triazol-1-yl)-2,6-dimethylpyrazolo[5,1-b]oxazole;

and diasteromers and enantiomers thereof, in free form or as a pharmaceutically acceptable salt.

9. A pharmaceutical composition comprising a compound according to claim 1 in free form or in pharmaceutically acceptable salt form, in association with a pharmaceutically acceptable adjuvant, diluent or carrier.

10. A pharmaceutical composition comprising a compound of formula I according to claim 1 in free form or in pharmaceutically acceptable salt form, in combination with another therapeutically active ingredient, optionally in association with a pharmaceutically acceptable adjuvant, diluent or carrier.

* * * * *